US012529064B2

(12) United States Patent
Long et al.

(10) Patent No.: US 12,529,064 B2
(45) **Date of Patent: *Jan. 20, 2026**

(54) TRANSGENIC PLANTS WITH INCREASED PHOTOSYNTHESIS EFFICIENCY AND GROWTH

(71) Applicants: The Board of Trustees of the University of Illinois, Urbana, IL (US); The Regents of the University of California, Oakland, CA (US)

(72) Inventors: Stephen P. Long, Urbana, IL (US); Johannes Kromdijk, Cambridge (GB); Katarzyna Glowacka, Lincoln, NE (US); Krishna K. Niyogi, Oakland, CA (US); Laurie Beth Leonelli, Oakland, CA (US); Stephane T. Gabilly, Walnut Creek, CA (US)

(73) Assignees: The Board of Trustees of the University of Illinois, Urbana, IL (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/057,190

(22) Filed: Nov. 18, 2022

(65) Prior Publication Data

US 2023/0183731 A1 Jun. 15, 2023

Related U.S. Application Data

(63) Continuation of application No. 16/304,633, filed as application No. PCT/US2017/034840 on May 26, 2017, now Pat. No. 11,572,569.

(60) Provisional application No. 62/342,248, filed on May 27, 2016.

(51) Int. Cl.
*C12N 15/82* (2006.01)
*C07K 14/415* (2006.01)
*C12N 9/02* (2006.01)

(52) U.S. Cl.
CPC .. *C12N 15/8269* (2013.01); *C12Y 110/99003* (2013.01); *C12Y 114/1309* (2013.01); *C07K 14/415* (2013.01); *C12N 9/0073* (2013.01)

(58) Field of Classification Search
CPC ........ C12N 15/8269; C12Y 110/99003; C12Y 114/1309
See application file for complete search history.

(56) References Cited

U.S. PATENT DOCUMENTS

| | | | |
|---|---|---|---|
| 5,268,463 | A | 12/1993 | Jefferson |
| 5,399,680 | A | 3/1995 | Zhu et al. |
| 5,466,785 | A | 11/1995 | de Framond |
| 5,519,164 | A | 5/1996 | Mullner et al. |
| 5,569,597 | A | 10/1996 | Grimsley et al. |
| 5,604,121 | A | 2/1997 | Hilder et al. |
| 5,608,142 | A | 3/1997 | Barton et al. |
| 5,608,144 | A | 3/1997 | Baden et al. |
| 5,608,149 | A | 3/1997 | Barry et al. |
| 5,639,949 | A | 6/1997 | Ligon et al. |
| 5,641,876 | A | 6/1997 | McElroy et al. |
| 5,659,026 | A | 8/1997 | Baszczynski et al. |
| 5,723,765 | A | 3/1998 | Oliver et al. |
| 5,789,156 | A | 8/1998 | Bujard et al. |
| 5,814,618 | A | 9/1998 | Bujard et al. |
| 6,072,050 | A | 6/2000 | Bowen et al. |
| 6,077,697 | A | 6/2000 | Hadlaczky et al. |
| 6,177,611 | B1 | 1/2001 | Rice |
| 6,232,526 | B1 | 5/2001 | McElroy et al. |
| 6,426,446 | B1 | 7/2002 | McElroy et al. |
| 6,429,362 | B1 | 8/2002 | Crane |
| 6,437,217 | B1 | 8/2002 | McElroy et al. |
| 11,220,694 | B1 | 1/2022 | Cermak et al. |
| 11,572,569 | B2 * | 2/2023 | Long ................ C12Y 114/1309 |
| 11,739,313 | B2 | 8/2023 | Gao et al. |
| 12,054,727 | B2 | 8/2024 | Long et al. |
| 2006/0143732 | A1 | 6/2006 | Perez et al. |
| 2006/0150283 | A1 | 7/2006 | Alexandrov et al. |
| 2006/0246586 | A1 | 11/2006 | Perkins et al. |
| 2007/0006346 | A1 | 1/2007 | Alexandrov et al. |

(Continued)

FOREIGN PATENT DOCUMENTS

| | | | |
|---|---|---|---|
| CA | 2300692 | A1 | 8/2000 |
| CA | 2302828 | A1 | 10/2000 |

(Continued)

OTHER PUBLICATIONS

Savojardo et al (Finding functional motifs in protein sequences with deep learning and natural language models. Current Opinion in Structural Biology, 81: p. 1-12, 2023) (Year: 2023).*
Zhang et al (Global Analysis of Gene Expression Profiles in Physic Nut (*Jatropha curcas* L.) Seedlings Exposed to Salt Stress. PLOS One. p. 1-9, 2014) (Year: 2014).*

(Continued)

*Primary Examiner* — Wayne Zhong
(74) *Attorney, Agent, or Firm* — Christian S. Hans; Bozicevic, Field & Francis LLP

(57) ABSTRACT

The present disclosure provides a transgenic plant comprising one or more nucleotide sequences encoding polypeptides selected from photosystem II subunit S (PsbS), zeaxanthin epoxidase (ZEP), and violaxanthin de-epoxidase (VDE), operably linked to at least one expression control sequence. Expression vectors for making transgenic plants, and methods for increasing biomass production and/or carbon fixation and/or growth in a plant comprising increasing expression of at least one of PsbS, ZEP and VDE polypeptides are also provided.

20 Claims, 52 Drawing Sheets

Specification includes a Sequence Listing.

(56) References Cited

U.S. PATENT DOCUMENTS

| | | | |
|---|---|---|---|
| 2010/0229256 A1 | 9/2010 | Somleva et al. |
| 2011/0179511 A1 | 7/2011 | Thilmony et al. |
| 2012/0060413 A1 | 3/2012 | Somleva et al. |
| 2019/0161765 A1 | 5/2019 | Long et al. |
| 2020/0199604 A1 | 6/2020 | Lippman et al. |
| 2020/0283788 A1 | 9/2020 | Long et al. |
| 2023/0323480 A1 | 10/2023 | Patel et al. |
| 2024/0368616 A1 | 11/2024 | Haas et al. |
| 2024/0417746 A1 | 12/2024 | Long et al. |

FOREIGN PATENT DOCUMENTS

| | | | |
|---|---|---|---|
| CN | 109207508 A | 1/2019 |
| EP | 1033405 A2 | 9/2000 |
| EP | 1059354 A2 | 12/2000 |
| WO | WO-9717447 A2 | 5/1997 |
| WO | WO-1999043838 A1 | 9/1999 |
| WO | WO-0040695 A2 | 7/2000 |
| WO | WO-2008069496 A1 | 6/2008 |
| WO | WO-2009117555 A1 | 9/2009 |
| WO | WO-2011041499 A2 | 4/2011 |
| WO | WO-2015089427 A1 | 6/2015 |
| WO | WO-2016030885 A1 | 3/2016 |
| WO | WO-2017205834 A1 | 11/2017 |
| WO | WO-2023067574 A1 | 4/2023 |

OTHER PUBLICATIONS

Hieber et al (Significance of the Lipid Phase in the Dynamics and Functions of the Xanthophyll Cycle as Revealed by PsbS Overexpression in Tobacco and In-vitro De-epoxidation in Monogalactosyldiacylglycerol Micelles. Plant Cell Physiol. 45(1): 92-102, 2004) (Year: 2004).*

Lambrev et al (On the relationship between non-photochemical quenching and photoprotection of Photosystem II. / Biochimica et Biophysica Acta 1817:760-769, 2012) (Year: 2012).*

Kromdijk et al (Improving photosynthesis and crop productivity by accelerating recovery from photoprotection. Science. 354:857-861. Nov. 2016) (Year: 2016).*

Pinnola et al (Zeaxanthin Binds to Light-Harvesting Complex Stress-Related Protein to Enhance Nonphotochemical Quenching in Physcomitrella patens. The Plant Cell, vol. 25: 3519-3534, 2013). (Year: 2013).*

Coesel et al (Evolutionary Origins and Functions of the Carotenoid Biosynthetic Pathway in Marine Diatoms. PLOS One. p. 1-16, 2008) (Year: 2008).*

Xu et al (Genetic Diversity and Molecular Evolution of a Violaxanthin De-epoxidase Gene in *Maize*. Frontiers in Genetics, Jul. 1-11, 2016) (Year: 2016).*

Ali, S. B. et al., "Genetic and Epigenetic Characterization of the cry1Ab Coding Region and its 3' Flanking Genomic Region in MON810 Maize using Next-Generation Sequencing", European Food Research and Technology, 2018, vol. 244, pp. 1473-1485.

Anderson, J. et al., "Antagonistic Interaction Between Abscisic Acid and Jasmonate-ethylene Signaling Pathways Modulates Defense Gene Expression and Disease Resistance in *Arabidopsis*", The Plant cell, Dec. 2004, vol. 16, No. 12, pp. 3460-3479.

Arnoux, P. et al., "A Structural Basis for the pH-dependent Xanthophyll Cycle in *Arabidopsis thaliana*", The Plant cell, Jul. 2009, vol. 21, No. 7, pp. 2036-2044.

AU Office Action dated Oct. 11, 2022, in Application No. AU2017270579.

Audran, C. et al., "Localisation and expression of zeaxanthin epoxidase mRNA in *Arabidopsis* in response to drought stress and during seed development", 2001, 28, pp. 1161-1173.

Barrero, J. et al., "A Mutational Analysis of the ABA1 Gene of *Arabidopsis thaliana* Highlights the Involvement of ABA in Vegetative Development", Journal of Experimental Botany, Aug. 2005, vol. 56, No. 418, pp. 2071-2083.

Barrero, J. M. et al., "The ABA1 Gene and Carotenoid Biosynthesis are Required for Late Skotomorphogenic Growth in *Arabidopsis thaliana*", Plant, Cell and Environment, Feb. 2008, vol. 31, No. 2, pp. 227-234.

BR Office Action dated Sep. 19, 2022 in Application No. BR20181174094 with English translation.

Bugos, R. C. et al., "Xanthophyll Cycle Enzymes are Members of The Lipocalin Family, The First Identified from Plants", The Journal of Biological Chemistry, Jun. 19, 1998, vol. 273, No. 25, pp. 15321-15324.

Busch (2014) "Opinion: the red-light response of stomatal movement is sensed by the redox state of the photosynthetic electron transport chain," Photosynth. Res., 119:131-140 [11 pages], Epub Mar. 13, 2013, doi: 10.1007/s11120-013-9805-6.

Cheng, C. et al., "Araport11: A Complete Reannotation of the *Arabidopsis thaliana* Reference Genome", Feb. 2017, vol. 89, No. 4, pp. 789-804.

CN Office Action dated Aug. 3, 2022 in Application No. CN201780045867 with English translation.

Coesel et al. (2008) "Evolutionary Origins and Functions of the Carotenoid Biosynthetic Pathway in Marine Diatoms." PLOS One 3: 1-16.

EP Office Action dated Jan. 15, 2020 issued in EP 17729973.2.

EP Office Action dated Nov. 19, 2021, in Application No. EP17729973.2.

EP Office Action dated Oct. 29, 2020 issued in EP 17729973.2.

Glowacka et al. (2018) "Photosystem II Subunit S overexpression increases the efficiency of water use in a field-grown crop," Nat. Commun., 9: 868 [9 pages], doi: 10.1038/s41467-018-03231-x.

Hall, M. et al., "Thioredoxin Targets of The Plant Chloroplast Lumen and their Implications for Plastid Function", Proteomics, Mar. 2010, vol. 10, No. 5, pp. 987-1001.

Havaux, M. et al., "Photodamage of The Photosynthetic Apparatus and its Dependence on the Leaf Developmental Stage in The npq1 *Arabidopsis* Mutant Deficient in the Xanthophyll Cycle Enzyme Violaxanthin De-epoxidase", Plant Physiology, Sep. 2000, vol. 124, No. 1, pp. 273-284.

Havaux, M. et al., "The Effect of Zeaxanthin as the Only Xanthophyll on the Structure and Function of the Photosynthetic Apparatus in *Arabidopsis thaliana*", The Journal of Biological Chemistry, Apr. 2, 2004, vol. 279, No. 14, pp. 13878-13888.

Hieber, A. D. et al., "Overexpression of Violaxanthin De-epoxidase: Properties of C-terminal Deletions on Activity and pH-dependent Lipid Binding", Planta, Jan. 2002, vol. 214, No. 3, pp. 476-483.

Hieber, D. et al., "Significance of the lipid phase in the dynamics and functions of the xanthophyll cycle as revealed by PsbS overexpression in tobacco and in-vitro de-epoxidation in monogalactosyldiacylglycerol micelles," Plant Cell Physiology, 2004, vol. 45, No. 1, pp. 92-102.

Huang et al. (2019) "The *Arabidopsis* Transcriptome Responds Specifically and Dynamically to High Light Stress" Cell Reports, 29: 4186-99.

Iuchi et al. (2000) "A Stress-Inducible Gene for 9-cis-Epoxycarotenoid Dioxygenase Involved in Abscisic Acid Biosynthesis under Water Stress in Drought-Tolerant Cowpea." Plant Physiol., 123: 553-562.

Izumi et al. (2012) "RBCS1A and RBCS3B, two major members within the *Arabidopsis* RBCS multigene family, function to yield sufficient Rubisco content for leaf photosynthetic capacity." Journal of Experimental Botany, 63(5): 2159-2170.

Jakab, G. et al., "Enhancing Arabidopsis Salt and Drought Stress Tolerance by Chemical Priming for its Abscisic Acid Responses", Plant Physiology, Sep. 2005, vol. 139, No. 1, pp. 267-274.

JP Office Action dated Jun. 22, 2021 issued in JP 2018-561589.

Kalituho, L. et al., "The Transiently Generated Nonphotochemical Quenching of Excitation Energy in *Arabidopsis* Leaves Is Modulated by Zeaxanthin", Plant Physiology, Apr. 2007, vol. 143, pp. 1861-1870.

Kayoko, Y. et al., "Empirical Analysis of Transcriptional Activity in the *Arabidopsis* Genome", Science, Oct. 31, 2003, vol. 302, No. 5646, pp. 842-846.

(56) References Cited

OTHER PUBLICATIONS

Koornneef, M. et al., "In Vivo Inhibition of Seed Development and Reserve Protein Accumulation in Recombinants of Abscisic Acid Biosynthesis and Responsiveness Mutants in *Arabidopsis thaliana*", Plant Physiology, Jun. 1989, vol. 90, No. 2, pp. 463-469.
KR Office Action dated Apr. 1, 2022, in Application No. KR1020187037434 with English translation.
KR Office Action dated Aug. 30, 2022, in Application No. KR1020187037434 with English translation.
Kromdijk et al. (2016) "Improving photosynthesis and crop productivity by accelerating recovery from photoprotection." Science, 354: 857-861.
Lambrev et al. (2012) "On the relationship between non-photochemical quenching and photoprotection of Photosystem II." Biochimica et Biophysica Acta, 1817: 760-769.
Liu et al. (2014) "Comparative analysis of carotenoid accumulation in two goji (*Lycium barbarum* L. and L. *ruthenicum* Murr.) fruits." Plant Biology 14:269 (14 pages).
Lu, Y. et al., "Identification of Potential Targets for Thylakoid Oxidoreductase AtVKOR/LTO1 in Chloroplasts", Protein and Peptide Letters, 2015, vol. 22, No. 3, pp. 219-225.
Merlot, S. et al., "Use of Infrared Thermal Imaging to Isolate *Arabidopsis* Mutants Defective in Stomatal Regulation", The Plant Journal : for Cell and Molecular Biology, Jun. 2002, vol. 30, No. 4, pp. 601-609.
Müller et al. (2001) "Non-photochemical quenching. A response to excess light energy." Plant Physiol., 125: 1558-1566, doi: 10.1104/pp. 125.4.1558.
Müller-Mouré, P. et al., "Ascorbate Deficiency Can Limit Violaxanthin De-epoxidase Activity in Vivo", Plant Physiology, Mar. 2002, vol. 128, No. 3, pp. 970-977.
Morillon, R. et al., "The Role of ABA and the Transpiration Stream in the Regulation of the Osmotic Water Permeability of Leaf Cells", Proceedings of the National Academy of Sciences of the United States of America, Nov. 20, 2001, vol. 98, No. 24, pp. 14138-14143.
Murchie, E.H. et al., "Manipulation of Photoprotection to Improve Plant Photosynthesis," Plant Physiology, 2011, vol. 155, No. 1, pp. 86-92.
Niyogi, K. et al., "*Arabidopsis* Mutants Define A Central Role for The Xanthophyll Cycle in the Regulation of Photosynthetic Energy Conversion", The Plant Cell, Jul. 1998, vol. 10, No. 7, pp. 1121-1134.
Nowicka, B. et al., "New Transgenic Line of *Arabidopsis thaliana* with Partly Disabled Zeaxanthin Epoxidase Activity Displays Changed Carotenoid Composition, Xanthophyll Cycle Activity and Non-photochemical Quenching Kinetics", Journal of Plant Physiology, 2009, vol. 166, pp. 1045-1056.
Park, H.Y et al., "Overexpression Of *Arabidopsis* Zep Enhances Tolerance to Osmotic Stress", Biochemical and Biophysical Research Communications, Oct. 10, 2008, vol. 375, No. 1, pp. 80-85.
PCT International Preliminary Report on Patentability dated Nov. 27, 2018 issued in PCT/US2017/034840.
PCT International Search Report and Written Opinion dated Jul. 26, 2017 issued in PCT/US2017/034840.
Pinnola et al. (2013) "Zeaxanthin Binds to Light-Harvesting Complex Stress-Related Protein to Enhance Nonphotochemical Quenching in Physcomitrella patens." The Plant Cell, 25: 3519-3534.
Raz, V. et al., "Sequential Steps for Developmental Arrest in *Arabidopsis* Seeds", Development (Cambridge, England), Jan. 2001, vol. 128, vol. 2, pp. 243-252.
Ruban (2016) "Nonphotochemical chlorophyll fluorescence quenching: mechanism and effectiveness in protecting plants from photodamage." Plant Physiol. 170: 1903-1916, doi: 10.1104/pp. 15.01935.
Sato, S. et al., "Structural analysis of Arabidopsis thaliana chromosome 5. X. Sequence features of the regions of 3,076,755 bp covered by sixty P1 and TAC clones". DNA Research, Feb. 28, 2000, vol. 7, No. 1, pp. 31-63.
Schubert, M. et al., "Proteome Map of The Chloroplast Lumen Of *Arabidopsis thaliana*", The Journal of Biological Chemistry, Mar. 8, 2002, vol. 277, No. 10, pp. 8354-8365.
Takahashi, N. et al., "Hydrotropism in Abscisic Acid, Wavy, and Gravitropic Mutants of *Arabidopsis thaliana*", Planta, Dec. 2002, vol. 216, No. 2, pp. 203-211.
Theologis, A. et al., "Sequence and Analysis of Chromosome 1 of the Plant *Arabidopsis thaliana*", Nature, Dec. 2000, vol. 408, No. 6814, pp. 816-820.
Ton, J. et al., "Beta-amino-butyric Acid-induced Resistance Against Necrotrophic Pathogens is Based on ABA-dependent Priming for Callose", The Plant journal : for cell and molecular biology, Apr. 2004, vol. 38, No. 1, pp. 119-130.
Ton, J. et al., "Dissecting the Beta-aminobutyric Acid-induced Priming Phenomenon in *Arabidopsis*", Mar. 2005, vol. 17, No. 3, pp. 987-999.
U.S. Notice of Allowance dated Sep. 23, 2022 in U.S. Appl. No. 16/304,633.
U.S Advisory Action dated Feb. 22, 2023 in U.S. Appl. No. 16/808,881.
US Final Office Action dated Apr. 27, 2021 issued in U.S. Appl. No. 16/304,633.
U.S. Final Office Action dated Oct. 7, 2022 in U.S. Appl. No. 16/808,881.
U.S. Non Final office Action dated Apr. 8, 2022 in U.S. Appl. No. 16/808,881.
U.S. Non-Final Office Action dated Dec. 21, 2021, in U.S. Appl. No. 16/304,633.
US Office Action dated Sep. 9, 2020 issued in U.S. Appl. No. 16/304,633.
US Office Action [Restriction Requirement] dated Feb. 20, 2020 issued in U.S. Appl. No. 16/304,633.
U.S. Restriction Requirement dated Oct. 7, 2021, in U.S. Appl. No. 16/808,881.
Vogl et al. (2015) "A Toolbox of Diverse Promoters Related to Methanol Utilization: Functionally Verified Parts for Heterologous Pathway Expression in Pichia pastoris." ACS Synth. Biol., 5: 172-186.
Willing, E. M. et al., "Genome Expansion of Arabis Alpina Linked with Retrotransposition and Reduced Symmetric DNA Methylation", Nature plants, Feb. 2, 2015, vol. 1, No. 14023, pp. 1-7.
Xiong, L. et al., "Regulation of Osmotic Stress-responsive Gene Expression by the LOS6/ABA1 Locus in *Arabidopsis*", The Journal of Biological Chemistry, Mar. 8, 2002, vol. 277, No. 10, pp. 8588-8596.
Yamamoto, H. Y. "Functional Roles of the Major Chloroplast Lipids in the Violaxanthin Cycle", Planta, Aug. 2006, vol. 224, No. 3, pp. 719-724.
Zhang et al. (2015) "MsZEP, a novel zeaxanthin epoxidase gene from alfalfa (*Medicago saliva*), confers drought and salt tolerance in transgenic tobacco." Plant Cell Rep 35:439-453 (published online Nov. 2015).
Zhang, L. et al., "Global Analysis of Gene Expression Profiles in Physic Nut (*Jatropha Curcas* L.) Seedlings Exposed to Salt Stress", PLoS One, May 16, 2014, vol. 9, No. 5, pp. 1-9.
Zhu, X. et al., "The Slow Reversibility of Photosystem Ii Thermal Energy Dissipation on Transfer From High to Low Light May Cause Large Losses in Carbon Gain by Crop Canopies: a Theoretical Analysis," Journal of Experimental Botany, 2004, vol. 55, No. 400, pp. 1167-1175.
Zia, A. et al., "Acclimation- and mutation-induced enhancement of PsbS levels affects the kinetics of non-photochemical quenching in *Arabidopsis thaliana*," Planta, 2011, vol. 233, No. 6, pp. 1253-1264.
Alboresi et al., (2010) "Physcomitrella patens mutants affected on heat dissipation clarify the evolution of photoprotection mechanisms upon land colonization", Proc Natl Acad Sci, 107(24):11128-11133.
Couso et al., (2012) "Efficient heterologous transformation of Chlamydomonas reinhardtii npq2 mutant with the zeaxanthin epoxidase gene isolated and characterized from Chlorella zofingiensis", Mar Drugs, 10(9):1955-1976.
Girolomoni et al., (2020) "Evolutionary divergence of photoprotection in the green algal lineage: a plant-like violaxanthin de-epoxidase enzyme activates the xanthophyll cycle in the green alga *Chlorella vulgaris* modulating photoprotection", New Phytol., 228(1):136-150.

(56) References Cited

OTHER PUBLICATIONS

Kim et al., (2018) "Loss of Function in Zeaxanthin Epoxidase of Dunaliella tertiolecta Caused by a Single Amino Acid Mutation within the Substrate-Binding Site", Marine Drugs, 16(11):1-14.
Lee et al., (2024) "Leaky mutations in the zeaxanthin epoxidase in Capsicum annuum result in bright-red fruit containing a high amount of zeaxanthin", Plant J., 118(2):469-487.
Leonelli et al., (2016) "Transient expression in Nicotiana benthamiana for rapid functional analysis of genes involved in non-photochemical quenching and carotenoid biosynthesis", Plant J., 88(3):375-386.
Li et al., (2016) "Evolution of an atypical de-epoxidase for photoprotection in the green lineage", Nat. Plants, 2:16140.
Lou et al., (2018) "Expression and functional analysis of two PsbS genes in bamboo (*Phyllostachys edulis*)", Physiol Plant., 163(4):459-471.
Lou et al., (2022) "PeVDE, a violaxanthin de-epoxidase gene from moso bamboo, confers photoprotection ability in transgenic *Arabidopsis* under high light", Front Plant Sci., 13:1-13.
Niyogi et al., (1997) "Chlamydomonas Xanthophyll Cycle Mutants Identified by Video Imaging of Chlorophyll Fluorescence Quenching", Plant Cell., 9(8):1369-1380.
Park et al., (2019) "Chlorophyll-carotenoid excitation energy transfer and charge transfer in Nannochloropsis oceanica for the regulation of photosynthesis", Proc Natl Acad Sci USA, 116(9):3385-3390.
Sun et al., (2019) "Overexpression of the ChVDE gene, encoding a violaxanthin de-epoxidase, improves tolerance to drought and salt stress in transgenic *Arabidopsis*", 3 Biotech. 9(5):1-10.
Abebe et al., (2006, published online 2005). "The Lem2 gene promoter of barley directs cell- and development-specific expression of gfp in transgenic plants," Plant Biotechnol. J., 4:35-44.
Affer et al., (2014). "Promiscuous MYC locus rearrangements hijack enhancers but mostly super-enhancers to dysregulate MYC expression in multiple myeloma," Leukemia, 28:1725-1735, 25 pages.
Aggarwal et al., (2016). "Biotechnological Approaches for the Improvement of Eucalyptus," Plant Tissue Culture: Propagation, Conservation and Crop Improvement, 219-244.
Ai et al., (2022). "Making Use of Plant uORFs to Control Transgene Translation in Response to Pathogen Attack," Biodesign Research, vol. 2022, 14 pages.
Extended European Search Report and Written Opinion received for European Patent Application No. 24184579.1 mailed on Oct. 23, 2024, 7 pages.
International Search Report and Written Opinion received for International Patent Application No. PCT/US2024/027800 mailed on Oct. 7, 2024, 20 pages.
Ariizumi et al., (2002). "Comparative study of promoter activity of three anther-specific genes encoding lipid transfer protein, xyloglucan endotransglucosylase/hydrolase and polygalacturonase in transgenic Arabidopsis thaliana," Plant Cell Rep., 21:90-96.
Bai et al., (2008). "Excision of a selective marker in transgenic rice using a novel Cre/loxP system controlled by a floral specific promoter," Transgenic Res, 17:1035-1043.
Bai et al., (2011). "In vivo O2 measurement inside single photosynthetic cells," Biotechnol. Lett., 33:1675-1681.
Bustos et al., (1989). "Regulation of β-Glucuronidase Expression in Transgenic Tobacco Plants by an A/T-Rich, cis-Acting Sequence Found Upstream of a French Bean β—Phaseolin Gene," Plant Cell, 1:839-853.
Canevascini et al., (1996). "Tissue-specific expression and promoter analysis of the tobacco Itp1 gene," Plant Physiol, 112:513-524.
Carlson et al., (2007). "Meiotic Transmission of an In Vitro-Assembled Autonomous Maize Minichromosome," PLoS Genet., 3(10):e179, 1965-1974.
Cerdán et al., (1997). "A 146 bp fragment of the tobacco Lhcb1*2 promoter confers very-low-fluence, low-fluence and high-irradiance responses of phytochrome to a minimal CaMV 35S promoter," Plant Mol. Biol. 33:245-255.
Chetty et al., (2013). "Empowering biotechnology in southern Africa: establishment of a robust transformation platform for the production of transgenic industry-preferred cassava," New Biotechnology, 30(2):136-143.
Christensen et al., (1989). "Sequence analysis and transcriptional regulation by heat shock of polyubiquitin transcripts from maize," Plant Mol. Biol., 12:619-632.
Chumakov et al., (2006). "Agrobacterium-mediated in planta transformation of maize via pistil filaments," Russian J. Genetics, 42(8):893-897.
Chung et al., (2000). "Floral spray transformation can efficiently generate Arabidopsis transgenic plants," Transgenic Res., 9:471-476.
Clough et al., (1998). "Floral dip: a simplified method for Agrobacterium-mediated transformation of Arabidopsis thaliana," The Plant J., 16(6):735-743.
Corpet (1988). "Multiple sequence alignment with hierarchical clustering" Nucleic Acids Res, 16(22):10881-10890.
Curtis et al., (2001). "Transgenic radish (Raphanus sativus L. longipinnatus Bailey) by floral-dip method—plant development and surfactant are important in optimizing transformation efficiency," Transgenic Res., 10:363-371.
Das et al., (2021). "Chapter 8: Genome Editing of Rice by CRISPR-Cas: End-to-End Pipeline for Crop Improvement," Rice Genome Engineering and Gene Editing: Methods and Protocols, 2238:115-134.
Desfeux et al., (2000). "Female reproductive tissues are the primary target of Agrobacterium-mediated transformation by the Arabidopsis floral-dip method," Plant Physiol, 123:895-904.
Ding et al., (2021). "Targeting Cis-Regulatory Elements for Rice Grain Quality Improvement," Frontiers in Plant Science, 12:705834, 9 pages.
Engelken et al., (2010). "Taxonomic distribution and origins of the extended LHC (light- harvesting complex) antenna protein superfamily," BMC Evol Biol 10:233, 15 pages.
Fejes et al., (1990). "A 268 bp upstream sequence mediates the circadian clock-regulated transcription of the wheat Cab-1 gene in transgenic plants," Plant Mol. Biol. 15:921-932.
Feldmann et al., (1987). "Agrobacterium-mediated transformation of germinating seeds of Arabidopsis thaliana: A non-tissue culture approach," Mol. Gen. Genet. 208:1-9.
Feng et al., (2011). "Gene Decay in Shigella as an Incipient Stage of Host-Adaptation," PLoS ONE 6(11):e27754, 6 pages.
Fu et al., (2021, published online 2020). "The coordination of OsbZIP72 and OsMYBS2 with reverse roles regulates the transcription of OsPsbS1 in rice," New Phytologist, 229(1):370-387.
Gasser et al., (1989). "Genetically engineering plants for crop improvement," Science, 244:1293-1299.
Gatz et al., (1991). "Regulation of a modified CaMV 35S promoter by the Tn10-encoded Tet repressor in transgenic tobacco," Mol. Gen. Genet., 227:229-237.
Genty et al., (1989). "The Relationship between the Quantum Yield of Photosynthetic Electron Transport and Quenching of Chlorophyll Fluorescence," Biochimica et Biophysica Acta, 990:87-92.
Gong et al., (2015). "13CO2/12CO2 exchange fluxes in a clamp-on leaf cuvette: disentangling artefacts and flux components," Plant, Cell and Environment, 38:2417-2432.
Goss et al., (2015). "Biodiversity of NPQ," Journal of Plant Physiology, 172,13-32.
Gotor et al., (1993). "Analysis of three tissue-specific elements from the wheat Cab-1 enhancer," Plant J., 3(4):509-518.
Green et al., (1988). "Binding site requirements for pea nuclear protein factor GT-1 correlate with sequences required for light-dependent transcriptional activation of the rbcS-3A gene," EMBO J, 7:4035-4044.
Guevara-Garcia et al., (1993). "Tissue-specific and wound-inducible pattern of expression of the mannopine synthase promoter is determined by the interaction between positive and negative cis-regulatory elements," Plant J., 4:495-505.
Guo et al., (2015). "Sorghum (Sorghum bicolor)," Methods Mol Biol, 1223:181-188.

(56) References Cited

OTHER PUBLICATIONS

Hansen et al., (1997). "Wound-inducible and organ-specific expression of ORF13 from Agrobacterium rhizogenes 8196 T-DNA in transgenic tobacco plants," Mol. Gen. Genet., 254:337-343.
Higgins et al. (1989). "Fast and sensitive multiple sequence alignments on a microcomputer," CABIOS, 5(2):151-153.
Higgins et al., (1988). "CLUSTAL: a package for performing multiple sequence alignment on a microcomputer," Gene, 73:237-244.
Howe et al., (2006). "Rapid and reproducible Agrobacterium-mediated transformation of sorghum," Plant Cell Rep, 25(8):784-791.
Huang et al., (1992). "Parallelization of a local similarity algorithm," CABIOS, 8(2):155-65.
Jordano et al., (1989). "A sunflower helianthinin gene upstream sequence ensemble contains an enhancer and sites of nuclear protein interaction," Plant Cell, 1:855-866.
Kasajima et al., (2011). "Molecular distinction in genetic regulation of nonphotochemical quenching in rice," PNAS, 108(33):13835-13840.
Kawamata et al., (1997). "Temporal and spatial pattern of expression of the pea phenylalanine ammonia-lyase gene1 promoter in transgenic tobacco," Plant Cell Physiol., 38(7):792-803.
Koziel et al., (1993). "Field Performance of Elite Transgenic Maize Plants Expressing an Insecticidal Protein Derived from Bacillus thuringiensis," Bio/technology, 11:194-200.
Koziol et al., (2007). "Tracing the evolution of the light-harvesting antennae in chlorophyll a/b-containing organisms," Plant Physiology, 143:1802-1816.
Kwon et al., (1994). "Identification of a Light-Responsive Region of the Nuclear Gene Encoding the B Subunit of Chloroplast Glyceraldehyde 3-Phosphate Dehydrogenase from Arabidopsis thaliana," Plant Physiol., 105:357-367.
Lam, (1994). "Chapter 8: Analysis of tissue-specific elements in the CaMV 35S promoter," Results Probl. Cell Differ., 20:181-196.
Liu et al., (2008). "Creation and analysis of a novel chimeric promoter for the complete containment of pollen- and seed-mediated gene flow," Plant Cell Rep., 27:995-1004.
Liu et al., (2011). "Characterization of a chalcone synthase (CHS) flower-specific promoter from Lilium orential 'Sorbonne'," Plant Cell Rep., 30:2187-2194.
Luan et al., (1992). "A rice cab gene promoter contains separate cis-acting elements that regulate expression in dicot and monocot plants," Plant Cell, 4:971-981.
Lùbberstedt et al., (1994). "Promoters from Genes for Plastid Proteins Possess Regions with Different Sensitivities toward Red and Blue Light," Plant Physiology, 104:997-1006.
Mamontova et al., (2010). "Agrobacterium-Mediated in planta Transformation of Maize Germ Cells," Russian J. Genetics, 46:501-504.
Matsuoka et al., (1993). "Tissue-specific light-regulated expression directed by the promoter of a C4 gene, maize pyruvate, orthophosphate dikinase, in a C3 plant, rice.," PNAS USA, 90:9586-9590.
McCormick et al., (1986). "Leaf disc transformation of cultivated tomato (L. esculentum) using Agrobacterium tumefaciens," Plant Cell Rep, 5:81-84.
McElroy et al., (1990). "Isolation of an efficient actin promoter for use in rice transformation," Plant Cell, 2:163-171.
McNellis et al., (1998). "Glucocorticoid-inducible expression of a bacterial avirulence gene in transgenic Arabidopsis induces hypersensitive cell death," Plant J., 14(2):247-257.
Medvecká et al., (2015). "Ch 16: Wheat (Triticum aestivum L.) Transformation Using Mature Embryos," Agrobacterium Protocols, 1:199-209.
Meier et al., (1991). "Elicitor-inducible and constitutive in vivo DNA footprints indicate novel cis-acting elements in the promoter of a parsley gene encoding pathogenesis-related protein 1," Plant Cell, 3:309-315.
Movahedi et al., (2014). "An efficient Agrobacterium-mediated transformation system for poplar," International Journal of Molecular Science, 15(6):10780-10793.
Myers et al., (1988). "Optimal alignments in linear space," CABIOS, 4(1):11-17.
Needleman et al., (1970). "A general method applicable to the search for similarities in the amino acid sequence of two proteins," J. Mol. Biol., 48:443-453.
Nilkens et al., (2010). "Identification of a slowly inducible zeaxanthin-dependent component of non-photochemical quenching of chlorophyll fluorescence generated under steady-state conditions in Arabidopsis," Biochimica et Biophysica Acta, 1797:466-475.
Kromdijk et al., (2022). "Relaxing non-photochemical quenching (NPQ) to improve photosynthesis in crops," Understanding and Improving Crop Photosynthesis, pp. 1-18.
Niyogi et al., (2013). "Evolution of flexible non-photochemical quenching mechanisms that regulate light harvesting in oxygenic photosynthesis," Curr Op Plant Biol, 16:307-314.
Odell et al., (1985). "Identification of DNA sequences required for activity of the cauliflower mosaic virus 35S promoter," Nature, 313:810-812.
Orozco et al., (1993). "Localization of light-inducible and tissue-specific regions of the spinach ribulose bisphosphate carboxylase/oxygenase (rubisco) activase promoter in transgenic tobacco plants," Plant Mol. Biol., 23:1129-1138.
Oxborough et al., (1997). "Resolving chlorophyll a fluorescence images of photosynthetic efficiency into photochemical and non-photochemical components—calculation of qP and Fv'/Fm' without measuring Fo'," Photosynthesis Research, 54:135-142.
Pearson et al., (1988). "Improved tools for biological sequence comparison," PNAS, 85:2444-2448.
Pearson et al., (1994). "Chapter 26: Using the FASTA program to search protein and DNA sequence databases," Meth. Mol. Biol., 24:307-331.
Perlak et al., (1991). "Modification of the coding sequence enhances plant expression of insect control protein genes," PNAS USA, 88:3324-3328.
Rinehart et al., (1996). "Tissue-Specific and Developmental Regulation of Cotton Gene FbL2A (Demonstration of Promoter Activity in Transgenic Plants)," Plant Physiol, 112:1331-1341.
Russell et al., (1997). "Tissue-specific expression in transgenic maize of four endosperm promoters from maize and rice," Transgenic Res., 6:157-168.
Schauer et al., (2009). "Intronic regulatory elements determine the divergent expression patterns of AGAMOUS-LIKE6 subfamily members in Arabidopsis," Plant J., 59:987-1000.
Schena et al., (1991). "A steroid-inducible gene expression system for plant cells," PNAS USA, 88:10421-10425.
Sharkey et al., (2007). "Fitting photosynthetic carbon dioxide response curves for C3 leaves," Plant Cell Environ., 30:1035-1040.
Shukla et al., (2009). "Precise genome modification in the crop species Zea mays using zinc-finger nucleases," Nature, 459:437-441.
Si et al., (2020). "Manipulating gene translation in plants by CRISPR-Cas9-mediated genome editing of upstream open reading frames," Nature Protocols, 15(2):338-363, 38 pages.
Silva et al., (2009). "Measuring seagrass photosynthesis: methods and applications," Aquatic Biology, 7:127-141.
Skadsen et al., (2002). "Cloning of the promoter for a novel barley gene, Lem1, and its organ-specific promotion of Gfp expression in lemma and palea," Plant Mol. Biol., 49:545-555.
Smith et al., (1981). "Comparison of biosequences," Adv. Appl. Math., 2:482-489.
Somleva et al., (2005). "The barley Lem 1 gene promoter drives expression specifically in outer floret organs at anthesis in transgenic wheat," Cereal Res. Comm, 33(4):665-671.
Taniguchi et al., (2000). "The Promoter for the Maize C4 Pyruvate, orthophosphate Dikinase Gene Directs Cell- and Tissue-Specific Transcription in Transgenic Maize Plants," Plant Cell Physiol., 41(1):42-48.
Thompson et al., (1989). "Structural elements regulating zein gene expression," BioEssays, 10:108-113.

(56) References Cited

OTHER PUBLICATIONS

Thompson et al., (1987). "Indolealkylamines of Desmanthus illinoensis and their growth inhibition activity," Journal of Agricultural and Food Chemistry, 35:361-365.
Timm et al., (2021). "Regulation of Central Carbon and Amino Acid Metabolism in Plants," Plants, 10(3):430, 4 pages.
Townsend et al., (2009). "High-frequency modification of plant genes using engineered zinc-finger nucleases," Nature, 459(7245):442-445, 12 pages.
Trieu et al., (2000). "Transformation of Medicago truncatula via infiltration of seedlings or flowering plants with Agrobacterium," Plant J., 22:531-541.
Truernit et al., (1995). "The promoter of the Arabidopsis thaliana SUC2 sucrose-H+ symporter gene directs expression of B-glucuronidase to the phloem: Evidence for phloem loading and unloading by SUC2," Planta, 196:564-570.
Van Camp et al., (1996). "Tissue-Specific Activity of Two Manganese Superoxide Dismutase Promoters in Transgenic Tobacco," Plant Physiol., 112:525-535.
Van Ex et al., (2009). "Evaluation of seven promoters to achieve germline directed Cre-Iox recombination in Arabidopsis thaliana," Plant Cell Rep., 28:1509-1520.
Verweire et al., (2007). "Marker-Free Transgenic Plants through Genetically Programmed Auto-Excision," Plant Physiol., 145:1220-1231.
Wang et al., (2001). "Transgenic Maize Plants Obtained by Pollen-mediated Transformation," Acta Botanica Sin., 43:275-279.
Wang et al., (2007). "Pollen-mediated transformation of Sorghum bicolor plants," Biotechnol. Appl. Biochem., 48:79-83.
Wang et al., (2017). "Genetic Architecture of Natural Variation in Rice Nonphotochemical Quenching Capacity Revealed by Genome-Wide Association Study," Frontiers in Plant Science, 8:1773, 13 pages.
Wong et al., (1992). "Arabidopsis thaliana small subunit leader and transit peptide enhance the expression of Bacillus thuringiensis proteins in transgenic plants," Plant Mol. Biol., 20:81-93.
Xu et al., (2017). "uORF-mediated translation allows engineered plant disease resistance without fitness costs," Nature, 545(7655):491-494, 21 pages.
Xue et al., (2023). "Tuning plant phenotypes by precise, graded downregulation of gene expression," Nat Biotechnol, 41(12): 1758-1764, 18 pages.
Yamamoto et al., (1994). "The Promoter of a Pine Photosynthetic Gene Allows Expression of a β-Glucuronidase Reporter Gene in Transgenic Rice Plants in a Light-Independent but Tissue-Specific Manner," Plant Cell Physiol., 35:773-778.
Yamamoto et al., (1997). "Light-responsive elements of the tobacco PSI-D gene are located both upstream and within the transcribed region," Plant J., 12(2):255-265.
Yang et al., (2011). "Petunia AGAMOUS Enhancer-Derived Chimeric Promoters Specify a Carpel-, Stamen-, and Petal-Specific Expression Pattern Sufficient for Engineering Male and Female Sterility in Tobacco," Plant Mol. Biol. Rep., 29:162-170.
Yu et al., (2006). "Telomere-mediated chromosomal truncation in maize," Pnas USA, 103(46): 17331-17336.
Yu et al., (2007). "Construction and behavior of engineered minichromosomes in maize," PNAS USA, 104(21):8924-8929.
Zale et al., (2009). "Evidence for stable transformation of wheat by floral dip in Agrobacterium tumefaciens," Plant Cell Rep., 28:903-913.
Zhang et al., (1996). "DNA Sequences That Activate Isocitrate Lyase Gene Expression during Late Embryogenesis and during Postgerminative Growth," Plant Physiology, 110:1069-1079.
Zhang et al., (2005). "Stability of inheritance of transgenes in maize (Zea mays L.) lines produced using different transformation methods," Euphytica, 144:11-22.
Zhang et al., (2011). "Expression of yeast Hem1 controlled by Arabidopsis HemA1 promoter enhances leaf photosynthesis in transgenic tobacco," Mol Biol Rep, 38:4369-4379.
Zhu et al., (2020). "Gain-of-function mutations: key tools for modifying or designing novel proteins in plant molecular engineering," Journal Of Experimental Botany, 71(4):1203-1205.
International Search Report and Written Opinion received for International Patent Application No. PCT/US2023/065633 mailed on Aug. 1, 2023, 17 pages.
Invitation to Pay Fees and Partial International Search Report and Written Opinion received for International Patent Application No. PCT/US2024/027800 mailed on Aug. 13, 2024, 16 pages.

* cited by examiner

Chlorophyll fluorescence of leaf discs

Chlorophyll fluorescence of young seedlings

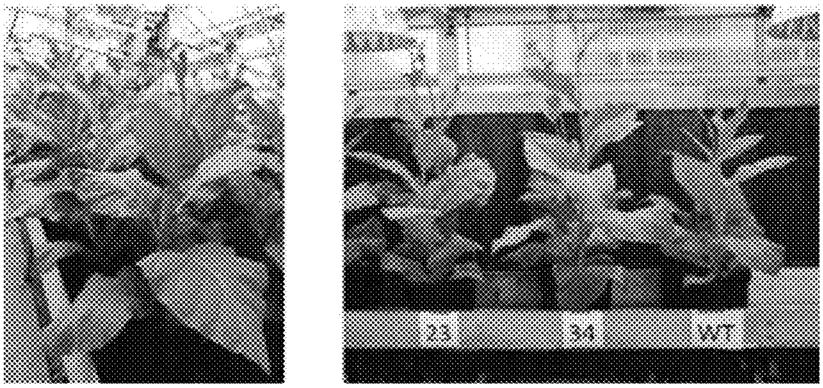
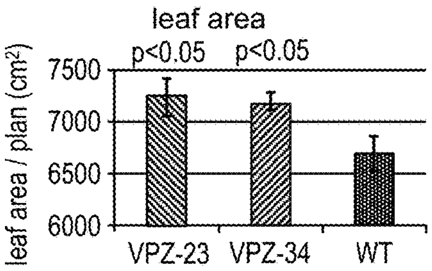
| | length | leaf area |
|---|---|---|
| ANOVA | <0.0001 | <0.0001 |
| WT<N2-23 | <0.05 | <0.05 |
| WT<N2-34 | <0.05 | <0.05 |
Error bars denote ± se, n=20
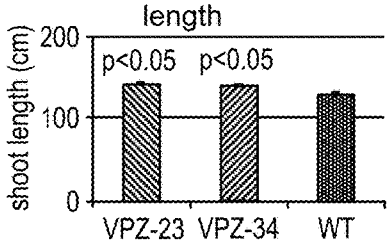
FIG. 12
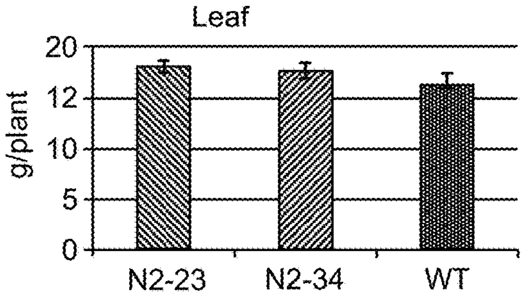
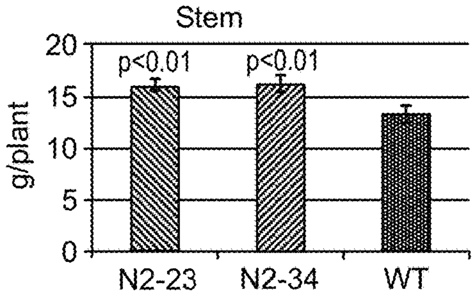
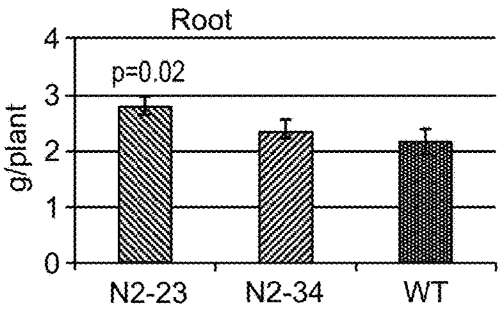
| | Stem (g) | Leaf (g) | Root (g) |
|---|---|---|---|
| ANOVA | <0.0001 | 0.0045 | 0.0025 |
| WT<N2-23 | <0.01 | ns | 0.02 |
| WT<N2-34 | <0.01 | ns | ns |
Error bars denote ± se, n=20
FIG. 13

Fitted time constants induction NPQ:

| NPQ | first induction (single exponential) | second induction (2-phase exponential) | | third induction (2-phase exponential) | |
|---|---|---|---|---|---|
| | $\tau$ (s) | $\tau_1$ (s) | $\tau_2$ (s) | $\tau_1$ (s) | $\tau_2$ (s) |
| N2-23 | 63.4 | 13.5 | 127.3 | 10.1 | 55.3 |
| N2-34 | 49.3 | 11.3 | 111.1 | 10.2 | 53.8 |
| N2-56 | 91.4 | 12.9 | 384.5 | 10.0 | 32.5 |
| WT | 82.7 | **5.5** | 115.3 | **4.3** | 37.2 |

Fitted time constants relaxation NPQ:

| | first relaxation (2-phase exponential) | | second relaxation (2-phase exponential) | | dark relaxation (2-phase exponential) | |
|---|---|---|---|---|---|---|
| | $\tau_1$ (s) | $\tau_2$ (s) | $\tau_1$ (s) | $\tau_2$ (s) | $\tau_1$ (s) | $\tau_2$ (s) |
| N2-23 | 1175.3 | 5.6 | 470.1 | 7.7 | 792.6 | 13.3 |
| N2-34 | 511.5 | 14.6 | 461.5 | 9.9 | 692.6 | 19.4 |
| N2-56 | 445.9 | 0.3 | 461.4 | 9.9 | 774.6 | 13.2 |
| WT | 564.9 | 10.4 | **886.4** | 9.2 | **2641.4** | 21.4 |

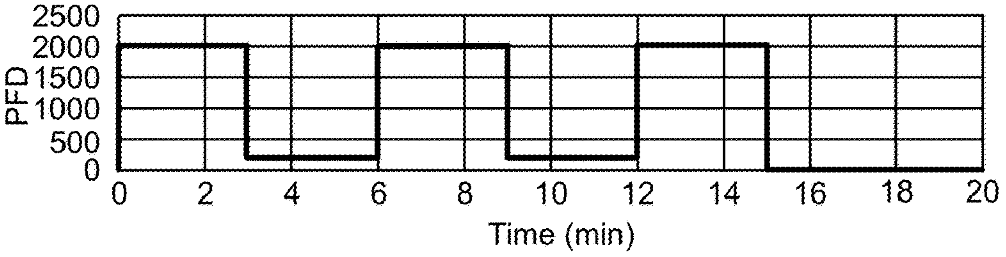

Fitted time constants dark relaxation $\phi_{PSII}$:

| | dark relaxation (2-phase exponential) | |
|---|---|---|
| | $\tau_1$ (s) | $\tau_2$ (s) |
| N2-23 | 20.4 | 103.0 |
| N2-34 | 14.2 | 85.6 |
| N2-56 | 7.9 | 70.3 |
| WT | 29.1 | **349.4** |

FIG. 16

This is Nb transient expression of co-inoculated leaf spots, as well as each singly inoculated. This is based on four biological replicates and error bars are standard error.

| Plants | Date of first coppicing (early flowering stage) | Wet weight (Grams) of 36 plants | Dry weight (Grams) of 36 plants | Percentage of wet weight |
|---|---|---|---|---|
| 515 (ZEP/PSBS) | Day1+19 | 5,791 | 311 (-0.6%) | 5.37 |
| 675 (ZEP/VDE) | Day1+19 | 6,823 | 399 (+27.5%) | 5.85 |
| 770 (PSBS) | Day1+19 | 5,463 | 306 (-2.2%) | 5.60 |
| null | Day1+19 | 5,623 | 313 | 5.56 |

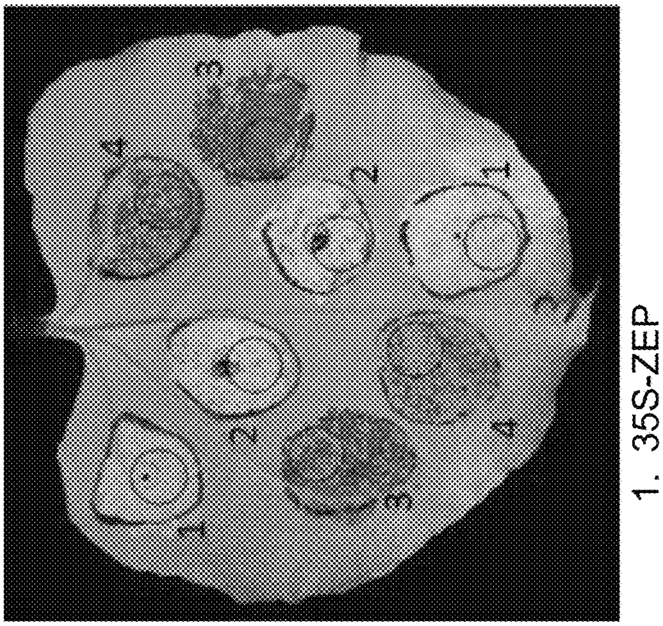
1. 35S-ZEP
2. Rbcs1a-ZEP
3. pEG301-RZGPFV
4. pEG100-35S-NbPsbs
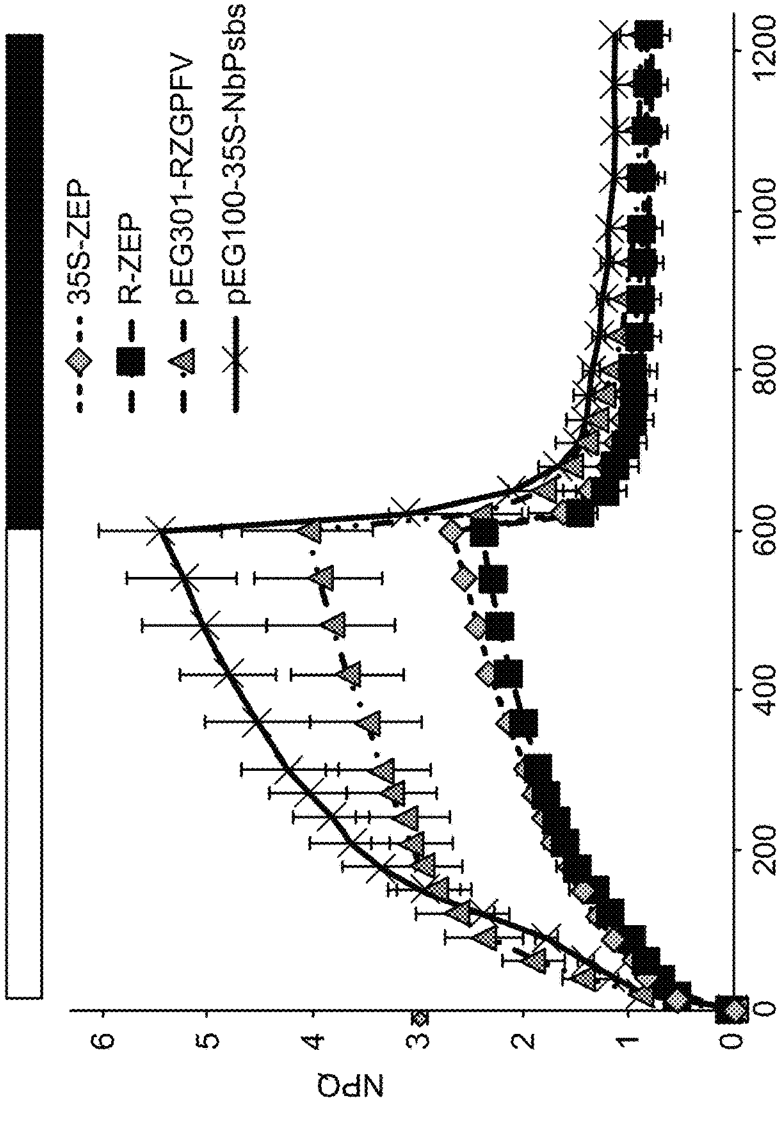
FIG. 23

```
Photosystem II subunit S (PSBS)
CLUSTAL O(1.2.4) multiple sequence alignment

(SEQ ID NO: 10) XP_008466710.1    MAAQTMLLTSGVCVGHGVCLKRELSLRP------NNNQFTRLFFNPLPNHSVSL-PARGF
(SEQ ID NO: 11) XP_004150442.1    MAAQTMLLTSGVCVGHGVCLKRELSLRP------NYTQFTRLFFNPLPSHSVSL-PPRGF
(SEQ ID NO: 12) XP_006393723.1    -MAQTMMLTSGVSANQFLRNKNPLAQ----------PKVHHLFLSGNSPVVIPS-RRQSL
(SEQ ID NO: 13) NP_175092.1       -MAQTMLLTSGVTAGHFLRNKSPLAQ----------PKVHHLFLSGNSPVALPS-RRQSF
(SEQ ID NO: 14) XP_002891292.1    -MAQTMLLTSGVSAGQFLRNKSPLAQ----------PKVHHLFLSGNSPVVLPS-RRQSF
(SEQ ID NO: 15) XP_010500150.1    -MAQTMLLTSGVSAGQFLRNKNPLAQ----------PKVHHLFLSGTSPVALPS-RRQSF
(SEQ ID NO: 16) XP_006304103.1    -MAQTMLLTSGVSAGQFLRNKNPLAQ----------PKVHQLFLSGTSPVALPS-RRQSF
(SEQ ID NO: 17) JAU12851.1        -MAQTMLLTSGVSANQFLRNKNPLAQ----------PKIQHLFLSGNSPVALPS-RRPSF
(SEQ ID NO: 18) XP_013681211.1    -MAQTMLLTSGISANHFLRNKNPLAQ----------PKVHHLFLSGNSPVTLPS-RIPSL
(SEQ ID NO: 19) XP_018447609.1    -MAQTMLLTSGISANHFLRNKNPLAQ----------PKVHHLFLSGNSPVTLPS-RRPSL
(SEQ ID NO: 20) XP_009109479.1    -MAQTMLLTSGISANHFLRNKNPLAQ----------PKVHHLFLSGNSPVTLPS-RRPSL
(SEQ ID NO: 21) XP_018467982.1    -MAQTMLLTSGVSANTFLRNKNPLAQ----------PKVHHLFLSGNSHVTLPS-RRPSL
(SEQ ID NO: 22) XP_013592876.1    -MAQTMLLTSGVSANQFLRNKNPLAQ----------PKVHHLFLSGNSHVVLPS-RRPSL
(SEQ ID NO: 23) XP_009123055.1    -MAQTMLLTSGVSANQFLRNKNPLAQ----------PKVHHFFLSGNSHVVLPS-RRPSL
(SEQ ID NO: 24) XP_008783427.1    -MVHAVFT--SGLGAHLPDSKREPLLQSQLRRLRPTPFSHLLLSQPSHKQLPSPSYSSYT
(SEQ ID NO: 25) JAT63827.1        -MAQSMLM--SSLGSRLVETKGEPLLQFQIRRLRPTPATHLLLPPPTRRHPLP---PSYA
(SEQ ID NO: 26) GAU40978.1        -MAQTMLLMSSVSSIYSVELKKDPLLQLQCQRLRSRI--SDVSFNPLSSNSKSL-SSRTF
(SEQ ID NO: 27) AKG94171.1        -MAQTMLLMSSVSSTYSVPLNKDPLLQLQCQRLKPRF--SDISFSPLSSNSKSF-SSRTF
(SEQ ID NO: 28) XP_010692414.1    -MAQAMLLMPSVSTTNTIDLKRNALLKIQIQKIKPKSSSSHLFFSPLSSSS-S--SSSTF
(SEQ ID NO: 29) GAV71974.1        -MAQTMLLMCGISTSHVVDLRRDPLFHVQIQKLRPKSF-SHLFFNPLSNNGFS--LAQKF
                                    .::::   .
```

FIG. 24A

```
(SEQ ID NO: 10) XP_008466710.1     TPLAVFKSRTKAPPKKV-EKPKQKVEDGIFGTSGGIGFTKQNELFVGRVAMIGFAASLLG
(SEQ ID NO: 11) XP_004150442.1     TTLAVFKSRTKAPPKKV-EKPKQKVEDGIFGTSGGIGFTKQNELFVGRVAMIGFAASILG
(SEQ ID NO: 12) XP_006393723.1     VPLALFKPKTKAAPKKV-EKVKPKVEDGIFGTSGGIGFTKANELFVGRVAMIGFAASLLG
(SEQ ID NO: 13) NP_175092.1        VPLALFKPKTKAAPKKV-EKPKSKVEDGIFGTSGGIGFTKANELFVGRVAMIGFAASLLG
(SEQ ID NO: 14) XP_002891292.1     VPLALFKPKTKAAPKKV-EKPKKKVEDGIFGTSGGIGFTKANELFVGRVAMIGFAASLLG
(SEQ ID NO: 15) XP_010500150.1     VPLALFKPKTKAAPKKV-VKPKDKVEDGIFGTSGGIGFTKANELFVGRVAMIGFAASLLG
(SEQ ID NO: 16) XP_006304103.1     VPLALFKPKTKAAPKKV-EKVKPKVEDGIFGTSGGIGFTKANELFVGRVAMIGFAASLLG
(SEQ ID NO: 17) JAU12851.1         VPLALFKPKTKAAPKKV-EKAKPKVEDGIFGTSGGIGFTKQNELFVGRVAMIGFAASLLG
(SEQ ID NO: 18) XP_013681211.1     VPLAIFKPKTKAAPKKV-EKVKPKVEDGIFGTSGGIGFTKQNELFVGRVAMIGFAASLLG
(SEQ ID NO: 19) XP_018447609.1     VPLAIFKPKTKAAPKKV-EKVKPKVEDGIFGTSGGIGFTKQNELFVGRVAMIGFAASLLG
(SEQ ID NO: 20) XP_009109479.1     VPLAIFKPKTKAAPKKV-EKVKPKVEDGIFGTSGGIGFTKQNELFVGRVAMIGFAASLLG
(SEQ ID NO: 21) XP_018467982.1     VPLAIFKPKTKAAPKKV-EKVKPKVEDGIFGTSGGIGFTKQNELFVGRVAMIGFAASLLG
(SEQ ID NO: 22) XP_013592876.1     VPLAIFKPKTKAAPKKV-EKVKPKVEDGIFGTSGGIGFTKQNELFVGRVAMIGFAASLLG
(SEQ ID NO: 23) XP_009123055.1     VPLAIFKPKTKAAPKKV-EKAKPKVEDGIFGTSGGIGFTKQNELFVGRVAMIGFAASLLG
(SEQ ID NO: 24) XP_008783427.1     PVLALFKSKTKAAPKKV-EKAKPKVEDGIFGTSGGIGFTKQNELFVGRVAMIGFAASLLG
(SEQ ID NO: 25) JAT63827.1         PTLAAFKSKTKAAPKKV-EKGNFKVEDGIFGTSGGIGFTKQNELFVGRVAMIGFAASLLG
(SEQ ID NO: 26) GAU40978.1         TTLALFKSKTKAPAKV-V-KPKPKVEDGIFGTSGGFGFTKQNELFVGRVAMIGFAASILG
(SEQ ID NO: 27) AKG94171.1         KTLALFKSKTKAPAKV-VPKQKPKVEDGVFGTSGGFGFTKQNELFVGRVAMIGFAASILG
(SEQ ID NO: 28) XP_010692414.1     KTLALFKPKTKAPVKKV-EKPKLKVEDGLFGTSGGIGFTKENELFVGRVAMIGFAASLLG
(SEQ ID NO: 29) GAV71974.1         NTLALFKSKTKAAPKKVATTAKPKVEDGLFGTSGGIGFTKQNELFVGRVAMIGFAASLLG
                                     ** ** :***  *    . : *****:******:**** ****************:**
```

FIG. 24A
(Continued)

```
(SEQ ID NO: 10) XP_008466710.1    EAITGKGILAQLNLETGIPITEAEPLLLFFILFTLLGAIGALGDRGKFIDDPEPATGLER
(SEQ ID NO: 11) XP_004150442.1    EAITGKGILAQLNLETGIPITEAEPLLLFFILFTLLGAIGALGDRGKFIDDPEPATGLER
(SEQ ID NO: 12) XP_006393723.1    EAVTGKGILAQLNLETGIPIYEAEPLLLFFILFTLLGAIGALGDRGKFVDDPPTPTGLEK
(SEQ ID NO: 13) NP_175092.1       EALTGKGILAQLNLETGIPIYEAEPLLLFFILFTLLGAIGALGDRGKFVDDPP--TGLEK
(SEQ ID NO: 14) XP_002891292.1    EALTGKGILAQLNLETGIPIYEAEPLLLFFILFTLLGAIGALGDRGQFVDDPP--TGLEK
(SEQ ID NO: 15) XP_010500150.1    EALTGKGILAQLNLETGIPIYEAEPLLLFFILFTLLGAIGALGDRGKFVDDPP--TGLEK
(SEQ ID NO: 16) XP_006304103.1    EAITGKGILAQLNLETGIPIYEAEPLLLFFILFTLLGAIGALGDRGKFVDDPP--TGLEK
(SEQ ID NO: 17) JAU12851.1        EALTGKGILAQLNLETGIPIYEAEPLLLFFILFTLLGAIGALGDRGKFVDDPP--TGLEK
(SEQ ID NO: 18) XP_013681211.1    EALTGKGILAQLNLETGIPIYEAEPLLLFFILFTLLGAIGALGDRGKFVDDPP--TGLEK
(SEQ ID NO: 19) XP_018447609.1    EALTGKGILAQLNLETGIPIYEAEPLLLFFILFTLLGAIGALGDRGKFVDDPP--TGLEK
(SEQ ID NO: 20) XP_009109479.1    EALTGKGILAQLNLETGIPIYEAEPLLLFFILFTLLGAIGALGDRGKFVDDPP--TGLEK
(SEQ ID NO: 21) XP_018467982.1    EALTGKGILAQLNLETGIPIYEAEPLLLFFILFTLLGAIGALGDRGKFVDDPP--TGLEK
(SEQ ID NO: 22) XP_013592876.1    EALTGKGILAQLNLETGIPIYEAEPLLLFFILFTLLGAIGALGDRGKFVDDPP--TGLEK
(SEQ ID NO: 23) XP_009123055.1    EALTGKGILAQLNLETGIPIYEAEPLLLFFILFTLLGAIGALGDRGKFVDDPP--TGLEK
(SEQ ID NO: 24) XP_008783427.1    EALTGKGILAQLNLETGIPIYEAEPLLLFFILFTLLGAIGALGDRGRFVDDPP--TGLEK
(SEQ ID NO: 25) JAT63827.1        EALTGKGILAQLNLETGIPIYEAEPLLLFFILFTLLGAIGALGDRGRFVDDPP--TGLEK
(SEQ ID NO: 26) GAU40978.1        EALTGKGILAQLNLETGIPIYEAEPLLLFFILFTLLGAIGALGDRGKFVDDEP--TT--G
(SEQ ID NO: 27) AKG94171.1        EGLTGKGILSQLNLETGIPIYEAEPLLLFFILFTLLGAIGALGDRGKFVDDEP--TT--G
(SEQ ID NO: 28) XP_010692414.1    EGLTGKGILAQLNLETGIPIYEAEPLLLFFILFTLLGAIGALGDRGRFVDDPP--TGLEK
(SEQ ID NO: 29) GAV71974.1        EAVTGKGILSQLNLETGIPIYEAEPLLLFFILFTLLGAIGALGDRGRFVDDEP--TGLEK
                                  *..:*****:********************:*************:*:**     *
```

FIG. 24A
(Continued)

```
(SEQ ID NO: 10) XP_008466710.1     AVIPPGKSFRSALGLKEGGPLFGFTKANELFVGRLAQLGFAFSLIGEIITGKGALAQLNI
(SEQ ID NO: 11) XP_004150442.1     AVIPPGKSFRSALGLKEGGPLFGFTKANELFVGRLAQLGFAFSLIGEIITGKGALAQLNI
(SEQ ID NO: 12) XP_006393723.1     AVIAPGKNVRSALGLKEQGPLFGFTKANELFVGRLAQLGIAFSLIGEIITGKGALAQLNI
(SEQ ID NO: 13) NP_175092.1        AVIAPGKNVRSALGLKEQGPLFGFTKANELFVGRLAQLGIAFSLIGEIITGKGALAQLNI
(SEQ ID NO: 14) XP_002891292.1     AVIAPGKNVRSALGLKEQGPLFGFTKANELFVGRLAQLGIAFSLIGEIITGKGALAQLNI
(SEQ ID NO: 15) XP_010500150.1     AVIPPGKGVRSALGLKEQGPLFGFTKANELFVGRLAQLGIAFSLIGEIITGKGALAQLNI
(SEQ ID NO: 16) XP_006304103.1     AVIPPGKGVRSALGLKEQGPLFGFTKANELFVGRLAQLGIAFSLIGEIITGKGALAQLNI
(SEQ ID NO: 17) JAU12851.1         AVIPPGKGVRSALGLKEQGPLFGFTKSNELFVGRLAQLGIAFSLIGEIITGKGALAQLNI
(SEQ ID NO: 18) XP_013681211.1     AVIPPGKGVRSALGLKEQGPLFGFTKANELFVGRLAQLGIAFSLIGEIITGKGALAQLNI
(SEQ ID NO: 19) XP_018447609.1     AVIPPGKGVRSALGLKEQGPLFGFTKANELFVGRLAQLGIAFSLIGEIITGKGALAQLNI
(SEQ ID NO: 20) XP_009109479.1     AVIPPGKGVRSALGLKEQGPLFGFTKANELFVGRLAQLGIAFSLIGEIITGKGALAQLNI
(SEQ ID NO: 21) XP_018467982.1     AVIPPGKGVRSALGLKEQGPLFGFTKANELFVGRLAQLGIAFSLIGEIITGKGALAQLNI
(SEQ ID NO: 22) XP_013592876.1     AVIPPGKGVRSALGLKEQGPLFGFTKANELFVGRLAQLGIAFSLIGEIITGKGALAQLNI
(SEQ ID NO: 23) XP_009123055.1     AVIPPGKGVRSALGLKEQGPLFGFTKANELFVGRLAQLGIAFSLIGEIITGKGALAQLNI
(SEQ ID NO: 24) XP_008783427.1     AVIPPGKGIRSALGLKEGGPLFGFTKSNELFVGRLAQLGIAFSIIGEIVTGKGALAQLNI
(SEQ ID NO: 25) JAT63827.1         AVVPPGKGFRSSLGLKEGGPLFGFTKSNELFVGRLAQLGIAFSIIGEIITGKGALAQLNI
(SEQ ID NO: 26) GAU40978.1         GVIPPGKGFRAALGLREGGPLFGFTKSNELFVGRLAQLGFVFSLIGEIVTGKGALAQLNV
(SEQ ID NO: 27) AKG94171.1         GVIPPGKGFRQALGLSEGGPLFGFTKSNELFVGRLAQLGFAFSLIGEIITGKGALAQLNI
(SEQ ID NO: 28) XP_010692414.1     AVIPPGKNVRSALGLREGGPLFGFTKSNELFVGRLAQLGFAFSIIGEIITGKGALAQLNI
(SEQ ID NO: 29) GAV71974.1         AVIPPGKGIRGALGLREGGPLFGFTKSNELFVGRLAQLGIAFSIIGEIITGKGALAQLNI
                                   .*: ***..* :*** * ********:************:.**:****:**********:
```

FIG. 24A
(Continued)

```
(SEQ ID NO: 10) XP_008466710.1    ETGVPINEIEPLVLLNVVFFFIAAVNPGTGKFVTDEEDDE
(SEQ ID NO: 11) XP_004150442.1    ETGVPINEIEPLVLLNVVFFFIAAVNPGTGKFVTDEEDDE
(SEQ ID NO: 12) XP_006393723.1    ETGIPIQDIEPLVLLNVAFFFFAAINPGNGKFITDEGEDM
(SEQ ID NO: 13) NP_175092.1       ETGIPIQDIEPLVLLNVAFFFFAAINPGNGKFITDDGEES
(SEQ ID NO: 14) XP_002891292.1    ETGIPIQDIEPLVLLNVAFFFFAAINPGNGKFITDDGEES
(SEQ ID NO: 15) XP_010500150.1    ETGIPIQDIEPLVLLNVAFFFFAAINPGNGKFITDDGEES
(SEQ ID NO: 16) XP_006304103.1    ETGIPIQDIEPLVLLNVAFFFFAAINPGNGKFITDDGEES
(SEQ ID NO: 17) JAU12851.1        ETGIPIQDIEPLVLLNVAFFFFAAINPGNGKFITDDGEES
(SEQ ID NO: 18) XP_013681211.1    ETGIPIQDIEPLVLLNVAFFFFAAINPGNGKFITDDGEES
(SEQ ID NO: 19) XP_018447609.1    ETGIPIQDIEPLVLLNVAFFFFAAINPGNGKFITDDGEES
(SEQ ID NO: 20) XP_009109479.1    ETGIPIQDIEPLVLLNVAFFFFAAINPGNGKFITDDGEES
(SEQ ID NO: 21) XP_018467982.1    ETGIPIQDIEPLVLLNVAFFFFAAINPGNGKFITDDGEES
(SEQ ID NO: 22) XP_013592876.1    ETGIPIQDIEPLVLLNVAFFFFAAINPGNGKFITDDGEES
(SEQ ID NO: 23) XP_009123055.1    ETGIPIQDIEPLVLLNVAFFFFAAINPGNGKFITDDGEER
(SEQ ID NO: 24) XP_008783427.1    ETGVPINEIEPLVLFNVIFFFIAALNPGNGKFVTDVDEEE
(SEQ ID NO: 25) JAT63827.1        ETGVPISDIEPLVLLNVVFFFLAALNPGTGQFVTDDGED-
(SEQ ID NO: 26) GAU40978.1        ETGVPITEIEPLVLFNVIFFFLAALNPGTGTFVTDEEED-
(SEQ ID NO: 27) AKG94171.1        ETGVPINEIEPLVLFNVAFFFIAALNPGTGKFVTDEEED-
(SEQ ID NO: 28) XP_010692414.1    ETGVPVNEIEPLVLLNVLFFFIAAINPGTGKFITDEEE--
(SEQ ID NO: 29) GAV71974.1        ETGIPINEIEPLVLFNVIFFFFAALNPGTGKFVTDEEAED
                                  ***:*: :******:** *** **:***.* *:**
```

FIG. 24A
(Continued)

Zeaxanthin epoxidase (ZEP)
CLUSTAL O(1.2.4) multiple sequence alignment

```
(SEQ ID NO: 30) XP_010547517.1    ------------------MGSTLFCSPVNPSLSKLDFSRTHLLSPADKHFFLDLPSFMGK
(SEQ ID NO: 31) KFK28343.1        ------------------MGSTPFCYTINPSPSKLDFTKTHL----AKQFYLDLSSFTGK
(SEQ ID NO: 32) XP_010444704.1    ------------------MGSTPFCYSINPSPSKLDFTRTHVFSPVSKQFYLDLSSFTGK
(SEQ ID NO: 33) XP_010484561.1    ------------------MGSTPFCYSINPSPSKLDFTRTHVFSPVSKQFYLDLSSFTGK
(SEQ ID NO: 34) XP_006280131.1    ------------------MGSTPFCYSINPSPSKLDFTRTHVFSPVAKQFYLDLSSFTGK
(SEQ ID NO: 35) NP_851285.1       ------------------MGSTPFCYSINPSPSKLDFTRTHVFSPVSKQFYLDLSSFSGK
(SEQ ID NO: 36) XP_002865032.1    ------------------MGSTLFCYSINPSPSKLDFTRTHVVSPVAKQFYLDLSSFSGK
(SEQ ID NO: 37) XP_018441511.1    -----------------MGSSTLFCYSINPSPSKLDFTKTHVFSPVAKQFYLDFPSFAA-
(SEQ ID NO: 38) CDY01444.1        MKCTSHIKLPLRASRIEMGSSTPFCYSINPSPSKLDFTRTHAFSPVAKQFYLDLPSFAGK
(SEQ ID NO: 39) XP_009103460.1    -----------------MGCSTPFCYSINPSPSKLDFTKTHAFSPVAKQFYLDLPSFAGK
(SEQ ID NO: 40) ACM68704.1        -----------------MGCSTPFCYSINPSPSKLDFTKTHAFSPVAKQFYLDLPSFAGK
(SEQ ID NO: 41) JAU06164.1        ------------------MGSTPFCYSTNPSPSKLDFTRTHAFSPLAKQFYLDLSSLAGK
(SEQ ID NO: 42) XP_006393901.1    ------------------MGSTPFCYSINPSPSKLDFTRTHVFSPVAKQFYLDLSSCAGK
(SEQ ID NO: 43) AAV85824.1        ------------------MGSTPFCYSINPSPSKLDFTRTHVFSPVAKQFYLDLSSCAGK
(SEQ ID NO: 44) KGN61963.1        ------------------MALTRFHNPFNLSSSS--LSRTCFPVPAFREYLVEISPCQRI
(SEQ ID NO: 45) NP_001268202.1    ------------------MASAVFYSSVQ--PSI--FSRTHIPIPISKDSFEEFGHSINY
(SEQ ID NO: 46) CMP01999.1        ------------------MATTL----FQNPSTF--FTGTQFPVSIPKYVPTESSACLHC
(SEQ ID NO: 47) XP_011043539.1    -----------------MASSTLFGNTL---TAV--SSRTHFPTPIFNNS-LELLSSTHS
(SEQ ID NO: 48) XP_002523587.1    -----------------MASSAFFCNSINPSTSV--FSRTHFSFPIFSTSTVEFSSFAQY
(SEQ ID NO: 49) XP_012079233.1    -----------------MASSTLFCNLINPSISV--FSRTHLPFPIVSSSSMELSSSAHC
                                                       :          :    : *            :
```

FIG. 24B

```
(SEQ ID NO: 30) XP_010547517.1    VR---GKSSVMSRRRVVGVKATAAVE--------EE-RRETAAEKEKLRVLVAGGGIGGL
(SEQ ID NO: 31) KFK28343.1        S--GAGLSGIKNRRGVVGVKASATAL-----V-EEEKRETVTEKKKKSRVLVAGGGIGGL
(SEQ ID NO: 32) XP_010444704.1    SAGGG--GGFRSRRALVGVKAATALV-----EEKRES---GTEKKKKSRVLVAGGGIGGL
(SEQ ID NO: 33) XP_010484561.1    SGVGA--GGFRSLRALVGVKAATALV-----EEEQKRESVTDKTKKKSRVLVAGGGIGGL
(SEQ ID NO: 34) XP_006280131.1    SGVGGGLSGFRSRRTLVGVKAATALV-----EEEQKPGEVT-ERKKKSRVLVAGGGIGGL
(SEQ ID NO: 35) NP_851285.1       P--G-GVSGFRSRRALLGVKAATALV-----EKEEKREAVT-EKKKKSRVLVAGGGIGGL
(SEQ ID NO: 36) XP_002865032.1    S--GGGLSGFRSRKTLVGVKAATALV-----EKEEKREAVT-EKKKKSRVLVAGGGIGGL
(SEQ ID NO: 37) XP_018441511.1    -----GKLRLRKRRALVGAKAET---------LLEEKRETVTEKKKKPRVLVAGGGIGGL
(SEQ ID NO: 38) CDY01444.1        S--GGGLSGLRKRRTLIGVKAAAATL-----VAEEEKRETVTESKKKPRVLVAGGGIGGL
(SEQ ID NO: 39) XP_009103460.1    S--GGGLSGLRKRRALVGVKA--ATL-----LAEEEKRETVTESKKKPRVLVAGGGIGGL
(SEQ ID NO: 40) ACM68704.1        S--GGGLSGLRKRRALVGVKA--ATL-----LAEEEKRETVTESKKKPRVLVAGGGIGGL
(SEQ ID NO: 41) JAU06164.1        S--GGGLSGFRSPRTLVGVKAAAATA-----LVEEEKREVV-AEKKKSRVLVAGGGIGGL
(SEQ ID NO: 42) XP_006393901.1    S--GGGLSGFRSRRALVGVRA--ATA-----LVEEEKREIA-KEKKKPRVLVAGGGIGGL
(SEQ ID NO: 43) AAV85824.1        S--GGGLSGFRSRRALVGVRA--ATA-----LVEEEKREIA-KEKKKPRVLVAGGGIGGL
(SEQ ID NO: 44) KGN61963.1        GCNFGGKSACGRRKKLTQVKAAVTEAPPAEGAAG---EISRSLPTKNVRILVAGGGIGGL
(SEQ ID NO: 45) NP_001268202.1    KHYFRSNPCG-QKKRVAQVKATLAEATPAPP--------APSLPSKKVRILVAGGGIGGL
(SEQ ID NO: 46) CMP01999.1        NYHFRGKASK-QKKRFLQVKATVAGTQSDSKSDEKNKVDANQQEKKKARILVAGGGIGGL
(SEQ ID NO: 47) XP_011043539.1    NYNFKTKTSTS--AKKLKVEAVVTETPAVSKS------EGKQSEQRKLKVLVAGGGIGGL
(SEQ ID NO: 48) XP_002523587.1    NFHFKTKKSDHQNKRFTQVKAVVTESPTVAES------NGKLSEQKKLRILVAGGGIGGL
(SEQ ID NO: 49) XP_012079233.1    NFHFRSKKSE-QNKKLTQVKAVVTESTSVAQS------DEKQPEQRKPRILVAGGGIGGL
                                                    ..*                        .: ::**********
```

FIG. 24B
(Continued)

```
(SEQ ID NO: 30) XP_010547517.1    VFALAAKRKGFDVAVFEKDLSAIRGEGQYRGPIQIQSNALAALEAIDMGVAEEVMEAGCI
(SEQ ID NO: 31) KFK28343.1        VFALAAKKKGFDVLVFEKDLSAIRGEGQYRGPIQIQSNALAALEAIDIAVAEEVMEAGCI
(SEQ ID NO: 32) XP_010444704.1    VFALAAKKKGFDVLVFEKDLSAIRGEGQYRGPIQIQSNALAALEAIDTDVAEQVMEAGCI
(SEQ ID NO: 33) XP_010484561.1    VFALAAKKKGFDVLVFEKDLSAIRGEGQYRGPIQIQSNALAALEAIDTDVAEQVMVAGCI
(SEQ ID NO: 34) XP_006280131.1    VFALAAKKKGFDVLVFEKDLSAIRGEGQYRGPIQIQSNALAALEAIDNDVAEQVMEAGCI
(SEQ ID NO: 35) NP_851285.1       VFALAAKKKGFDVLVFEKDLSAIRGEGKYRGPIQIQSNALAALEAIDIEVAEQVMEAGCI
(SEQ ID NO: 36) XP_002865032.1    VFALAAKKKGFDVVVFEKDLSAIRGEGQYRGPIQIQSNALAALEAIDTDVAEQVMEAGCI
(SEQ ID NO: 37) XP_018441511.1    VFALAAKKKGFDVLVFEKDLSAIRGEGQYRGPIQIQSNALAALEAIDTDVAEQVMEAGCI
(SEQ ID NO: 38) CDY01444.1        VFALAAKKKGFDVLVFEKDLSAIRGEGQYRGPIQIQSNALAALEAIDTGVAEEVMEAGCI
(SEQ ID NO: 39) XP_009103460.1    VFALAAKKKGFDVLVFEKDLSAIRGEGQYRGPIQIQSNALAALEAIDIGVAEEVMEAGCI
(SEQ ID NO: 40) ACM68704.1        VFALAAKKKGFDVLVFEKDLSAIRGEGQYRGPIQIQSNALAALEAIDIGVAEEVMEAGCI
(SEQ ID NO: 41) JAU06164.1        VFALAAKKKGFDVLVFEKDLSAIRGEGQYRGPIQIQSNALAALEAIDTDVAEEVMEAGCI
(SEQ ID NO: 42) XP_006393901.1    VFALAAKKKGFDVLVFEKDLSAIRGEGQYRGPIQIQSNALAALEAIDIDVAEEVMEAGCI
(SEQ ID NO: 43) AAV85824.1        VFALAAKKKGFDVLVFEKDLSAIRGEGQYRGPIQIQSNALAALEAIDIDVAEEVMEAGCI
(SEQ ID NO: 44) KGN61963.1        VFALAAKRKGFDVVVFEKDISAIRGEGQYRGPIQIQSNALAALEAIDLDVAEEVMRVGCI
(SEQ ID NO: 45) NP_001268202.1    VLALAAKKKGFDVVVFEKDMSAIRGEGQYRGPIQIQSNALAALEAVDMEVAEEVMRAGCI
(SEQ ID NO: 46) CMP01999.1        VFALAAKNKGFDVVVFEKDLSAIRGEGQYRGPIQIQSNALAALEAIDMEVAEKVMEAGCI
(SEQ ID NO: 47) XP_011043539.1    VFALAAKNKGFDVMVFEKDLSAVRGEGQYRGPIQIQSNALAALEAIDLDVAEEVMRAGCI
(SEQ ID NO: 48) XP_002523587.1    VFALAAKRKGFEVLVFEKDLSAIRGEGQYRGPIQVQSNALAALEAIDLEVAEEVMRAGCI
(SEQ ID NO: 49) XP_012079233.1    VFALAAKRKGFEVLVFEKDLSAVRGEGQYRGPIQIQSNALAALEAIDLEVAEEVMEAGCI
                                  *:*****.***:* *****:**:****:******:**********:*  ***:** .***
```

FIG. 24B
(Continued)

```
(SEQ ID NO: 30) XP_010547517.1    TGDRINGLVDGVSGSWYVKFDTFTPAAERGLPVTRVISRMTLQQILARAVGEDVIQNESN
(SEQ ID NO: 31) KFK28343.1        TGDRINGLVDGVSGTWYVKFDTFTPAASRGLPVTRVISRMTLQQILARAVGEEVIRNESN
(SEQ ID NO: 32) XP_010444704.1    TGDRINGLVDGISGTWYVKFDTFTPAASRGLPVTRVISRMTLQQILARAVGEEVIRNESN
(SEQ ID NO: 33) XP_010484561.1    TGDRINGLVDGISGTWYVKFDTFTPAASRGLPVTRVISRMTLQQILARAVGEELIRNESN
(SEQ ID NO: 34) XP_006280131.1    TGDRINGLVDGVSGTWYVKFDTFTPAASRGLPVTRVISRMTLQQILARAVGEEVIRNESN
(SEQ ID NO: 35) NP_851285.1       TGDRINGLVDGISGTWYVKFDTFTPAASRGLPVTRVISRMTLQQILARAVGEDVIRNESN
(SEQ ID NO: 36) XP_002865032.1    TGDRINGLVDGVSGSWYVKFDTFTPAASRGLPVTRVISRMTLQQILARAVGEDVIRNESN
(SEQ ID NO: 37) XP_018441511.1    TGDRINGLVDGVSGTWYVKFDTFTPAASRGLPVTRVISRMTLQQILARAVGEEIIRNESN
(SEQ ID NO: 38) CDY01444.1        TGDRINGLVDGVSGTWYVKFDTFTPAASRGLPVTRVISRMTLQQILARAVGEEIIRNESN
(SEQ ID NO: 39) XP_009103460.1    TGDRINGLVDGVSGTWYVKFDTFTPAASRGLPVTRVISRMTLQQILARAVGEEIIRNESN
(SEQ ID NO: 40) ACM68704.1        TGDRINGLVDGVSGTWYVKFDTFTPAASRGLPVTRVISRMTLQQILARAVGEEIIRNESN
(SEQ ID NO: 41) JAU06164.1        TGDRINGLVDGVSGTWYVKFDTFTPAASRGLPVTRVISRMTLQQILARAVGEEIIRNESN
(SEQ ID NO: 42) XP_006393901.1    TGDRINGLVDGVSGTWYVKFDTFTPAASRGLPVIRVISRMTLQQILARAVGEEVIRNESN
(SEQ ID NO: 43) AAV85824.1        TGDRINGLVDGVSGTWYVKFDTFTPAASRGLPVTRVISRMTLQQILARAVGEEVIRNESN
(SEQ ID NO: 44) KGN61963.1        TGDRINGLVDGVSGNWYIKFDTFTPAAERGLPVTRVISRMSLQQILARAVGDDVIINDSN
(SEQ ID NO: 45) NP_001268202.1    TGDRINGLVDGVSGDWYVKFDTFTPAAERGLPVTRVISRMTLQQILARAVGEDIIMNGSN
(SEQ ID NO: 46) CMP01999.1        TGDRINGLVDGVSGSWYIKFDTFTPAAERGLPVTRVISRMTLQQILARAVGEDIIFNESN
(SEQ ID NO: 47) XP_011043539.1    TGDRINGLVDGISGTWYVKFDTFTPAAERGLPVTRVISRMTLQQILARSVGDDTILNDSN
(SEQ ID NO: 48) XP_002523587.1    TGDRINGLVDGVSGTWYCKFDTFTPAAERGLPVTRVISRMTLQQILACAVGEDVIMNASN
(SEQ ID NO: 49) XP_012079233.1    TGDRINGLVDGVSGTWYVKFDTFTPAAERGLPVTRVISRMTLQQILALAVGEDVIRNESN
                                  ***********:** ** *********.***********:****** :**:: * * **
```

FIG. 24B
(Continued)

```
(SEQ ID NO: 30) XP_010547517.1    VVSFSESEDKVTVVLENGECYQGDLLVGADGIWSKVRSQLFGHEEATYSGYTCYTGIADF
(SEQ ID NO: 31) KFK28343.1        VVDFEDSGDKVTVVLENGQRYEGDLLVGADGIWSKVRNNLFGRSEATYSGYTCYTGIADF
(SEQ ID NO: 32) XP_010444704.1    VVDFEDSGDKVTVVLENGERYEGDLLVGADGIWSKVRNNLFGRSEASYSGYTCYTGIADF
(SEQ ID NO: 33) XP_010484561.1    VVDFEDSGDKVTVVLENGERYEGDLLVGADGIWSKVRNNLFGRSEASYSGYTCYTGIADF
(SEQ ID NO: 34) XP_006280131.1    VVDFEDSGDKVTVVLENGQRYEGDLLVGADGIWSKVRNNLFGRSEAEYSGYTCYTGIADF
(SEQ ID NO: 35) NP_851285.1       VVDFEDSGDKVTVVLENGQRYEGDLLVGADGIWSKVRNNLFGRSEATYSGYTCYTGIADF
(SEQ ID NO: 36) XP_002865032.1    VVDFEDSGDKVTVVLENGQRYEGDLLVGADGIWSKVRNNLFGRSEATYSGYTCYTGIADF
(SEQ ID NO: 37) XP_018441511.1    VVDFQDSGDKVTVVLENGERYEGDLLVGADGIWSKVRNNLFGRSEATYSGYTCYTGIADF
(SEQ ID NO: 38) CDY01444.1        VVDFEDSGDKVTVVLENGQRYEGDLLVGADGIWSKVRNNLFGRSEATYSGYTCYTGIADF
(SEQ ID NO: 39) XP_009103460.1    VVDFEDSGDKVTVVLENGQRYEGDLLVGADGIWSKVRNNLFGRSEATYSGYTCYTGIADF
(SEQ ID NO: 40) ACM68704.1        VVDFEDSGDKVTVVLENGQRYEGDLLVGADGIWSKVRNNLFGRSEATYSGYTCYTGIADF
(SEQ ID NO: 41) JAU06164.1        VVDFEDSGDKVTVVLENGERYEGDLLVGADGIWSKVRNNLFGRSEATYSGYTCYTGIADF
(SEQ ID NO: 42) XP_006393901.1    VVDFEDSGDKVTVVLENGERYEGDLLVGADGIWSKVRNNLFGRSEATYSGYTCYTGIADF
(SEQ ID NO: 43) AAV85824.1        VVDFEDSGDKVTVVLENGERYEGDLLVGADGIWSKVRNNLFGRSEATYSGYTCYTGIADF
(SEQ ID NO: 44) KGN61963.1        VVDFEDSGEKVKVTLENGQQHEGDLLVGADGIWSKVRKNLFGHSEAVYSGYTCYTGIADF
(SEQ ID NO: 45) NP_001268202.1    VVDFEDDGNKVTVILENGQRYEGDLLIGADGIWSKVRKSLFGPKEATYSGYTCYTGIADF
(SEQ ID NO: 46) CMP01999.1        VVDFEDDGNKVSVVLENGKRFEGDLLVGADGIWSKVRKNLFGPKDAVYSGYTCYTGIADF
(SEQ ID NO: 47) XP_011043539.1    VVSFQDDGDKVTVVLENGQQYEGDLLVGADGIWSKVRKNLFGPKEAVYSGYTCYTGIADF
(SEQ ID NO: 48) XP_002523587.1    VINFQDNEDKVTVTLENGQQFEGDLLVGADGIWSKVRKNLFGPKEATYSGYTCYTGIADF
(SEQ ID NO: 49) XP_012079233.1    VVSFQDDGDKVTVTLENGQHFEGDLLVGADGIWSKVRKNLFGPKDATYSDYTCYTGIADF
                                  *:.*.:. :**.* ****: .:****:**********..*** .:* **.**********
```

FIG. 24B
(Continued)

```
(SEQ ID NO: 30) XP_010547517.1    VPADIESVGYRVFLGHKQYFVSSDVGGGKMQWYAFHEEPAGGRDAPDGRKKRLLEIFQGW
(SEQ ID NO: 31) KFK28343.1        IPADIESVGYRVFLGHKQYFVSSDVGGGKMQWYAFYEEPAGGVDAPNGMKKRLFDIFEGW
(SEQ ID NO: 32) XP_010444704.1    IPADIESVGYRVFLGNKQYFVSSDVGGGKMQWYAFHEEPAGGADAPNGMKKRLFEIFDGW
(SEQ ID NO: 33) XP_010484561.1    IPADIESVGYRVFLGNKQYFVSSDVGGGKMQWYAFHEEPAGGADAPNGMKKRLFEIFDGW
(SEQ ID NO: 34) XP_006280131.1    IPADIESVGYRVFLGHKQYFVSSDVGGGKMQWYAFHEEPAGGTDAPNGMKKRLFEIFDGW
(SEQ ID NO: 35) NP_851285.1       IPADIESVGYRVFLGHKQYFVSSDVGGGKMQWYAFHEEPAGGADAPNGMKKRLFEIFDGW
(SEQ ID NO: 36) XP_002865032.1    VPADIESVGYRVFLGHKQYFVSSDVGGGKMQWYAFHEEPAGGVDAPNGMKKRLFEIFDGW
(SEQ ID NO: 37) XP_018441511.1    VPADIESVGYRVFLGHKQYFVSSDVGGGKMQWYAFHEEAAGGVDAPNGMKKRLFEIFEGW
(SEQ ID NO: 38) CDY01444.1        VPADIESVGYRVFLGHKQYFVSSDVGGGKMQWYAFHEEAAGGVDAPNGMKKRLFEIFEGW
(SEQ ID NO: 39) XP_009103460.1    VPADIESVGYRVFLGHKQYFVSSDVGGGKMQWYAFHEEAAGGVDAPNGMKKRLFDIFEGW
(SEQ ID NO: 40) ACM68704.1        VPADIESVGYRVFLGHKQYFVSSDVGGGKMQWYAFHEEAAGGVDAPNGMKKRLFDIFEGW
(SEQ ID NO: 41) JAU06164.1        VPADIESVGYRVFLGHKQYFVSSDVGGGKMQWYAFHEEPAGGVDAPNGMKKRLFDIFEGW
(SEQ ID NO: 42) XP_006393901.1    VPADIESVGYRVFLGHKQYFVSSDVGGGKMQWYAFHEEPAGGVDAPNGMKKRLFDIFEGW
(SEQ ID NO: 43) AAV85824.1        VPADIESVGYRVFLGHKQYFVSSDVGGGKMQWYAFHEEPAGGVDAPNGMKKRLFDIFEGW
(SEQ ID NO: 44) KGN61963.1        IPADIETVGYRVFLGHKQYFVSSDVGAGKMQWYAFHKEPPGGADAPNGKKERLFKIFEGW
(SEQ ID NO: 45) NP_001268202.1    VPADIDSVGYRVFLGHKQYFVSSDVGAGKMQWYAFYNEPAGGVDGPEGKKERLLKIFGGW
(SEQ ID NO: 46) CMP01999.1        VPADIDSVGYRVFLGHKQYFVSSDVGGGKMQWYAFHEEPAGGVDTPQGKKERLLKIFEGW
(SEQ ID NO: 47) XP_011043539.1    VPVDIETVGYRVFLGHKQYFVSSDVGAGKMQWYAFHKESPGGMDAPHGKKDRLLKIFEGW
(SEQ ID NO: 48) XP_002523587.1    VPVDIESVGYRVFLGHKQYFVSSDVGAGKMQWYAFHNEPPGGVDSPNGKKERLLKIFEGW
(SEQ ID NO: 49) XP_012079233.1    VPADIESVGYRVFLGHKQYFVSSDVGAGKMQWYAFHKEPPGGVDRPNGKKERLLKIFEGW
                                  .* **..********.********** ********..*  ** *    * * **. ** **
```

FIG. 24B
(Continued)

```
(SEQ ID NO: 30) XP_010547517.1    CDNVIDLLHATEEDAILRRDIYDRTPSFTWGKGRVTLLGDSIHAMQPNMGQGGCMAIEDS
(SEQ ID NO: 31) KFK28343.1        CDNVLDLLHATEEEAILRRDIYDRSPSFTWGKGRVTLLGDSIHAMQPNMGQGGCMAIEDS
(SEQ ID NO: 32) XP_010444704.1    CDNVLDLLHATEEDAILRRDIYDRNPSFTWGKGRVTLLGDSTHAMQPNMGQGGCMAIEDS
(SEQ ID NO: 33) XP_010484561.1    CDNVLDLLHATEEDAILRRDIYDRNPSFTWGKGRVTLLGDSIHAMQPNMGQGGCMAIEDS
(SEQ ID NO: 34) XP_006280131.1    CDNVLDLLHATEEDAILRRDIYDRSPSFTWGKGRVTLLGDSIHAMQPNMGQGGCMAIEDS
(SEQ ID NO: 35) NP_851285.1       CDNVLDLLHATEEEAILRRDIYDRSPGGTWGKGRVTLLGDSIHAMQPNMGQGGCMAIEDS
(SEQ ID NO: 36) XP_002865032.1    CDNVLDLLHATEEDAILRRDIYDRSPSFTWGKGRVTLLGDSIHAMQPNMGQGGCMAIEDS
(SEQ ID NO: 37) XP_018441511.1    CDNVLDLLQATEEEAILRRDIYDKSPSFTWGKGRVTLLGDSIHAMQPNMGQGGCMAIEDS
(SEQ ID NO: 38) CDY01444.1        CDNVLDLLQATEEEAILRRDIYDRSPSFTWGKGRVTLLGDSIHAMQPNMGQGGCMAIEDS
(SEQ ID NO: 39) XP_009103460.1    CDNVLDLLQATEEEAILRRDIYDRSPSFTWGKGRVTLLGDSIHAMQPNMGQGGCMAIEDS
(SEQ ID NO: 40) ACM68704.1        CDNVLDLLQATEEEAILRRDIYDRSPSFTWGKGRVTLLGDSIHAMQPNMGQGGCMAIEDS
(SEQ ID NO: 41) JAU06164.1        CDNVLDLLHATEEDAILRRDIYDRTPSFTWGKGRVTLLGDSIHAMQPNMGQGGCMAIEDS
(SEQ ID NO: 42) XP_006393901.1    CDNVLDLLHATEEEAILRRDIYDRTPSFNWGKGRVTLLGDSIHAMQPNMGQGGCMAIEDS
(SEQ ID NO: 43) AAV85824.1        CDNVLDLLHATEEEAILRRDIYDRTPSFNWGKGRVTLLGDSIHAMQPNMGQGGCMAIEDS
(SEQ ID NO: 44) KGN61963.1        CDNVTDLIQATDEDSVLRRDIYDRTPIFTWGKGRVTLLGDSVHAMQPNMGQGGCMAIEDG
(SEQ ID NO: 45) NP_001268202.1    CDNVIDLILATDEEAILRRDIYDRTPTFTWGRGRVTLLGDSVHAMQPNMGQGGCMAIEDS
(SEQ ID NO: 46) CMP01999.1        CDNVIDLLLATDEEAILRRDIYDRTPSLTWGKGRVTLLGDSIHAMQPNLGQGGCMAIEDG
(SEQ ID NO: 47) XP_011043539.1    CDNVIDLLLTTDEDSILRRDIYDREPIITWGKGRVTLLGDSVHAMQPNMGQGGCMAIEDS
(SEQ ID NO: 48) XP_002523587.1    CDNVIDLLHATDEDAILRRDIYDREPVFTWGKGRVTLLGDSIHAMQPNMGQGGCMAIEDS
(SEQ ID NO: 49) XP_012079233.1    CDNVIDLLLATDEDAILRRDIYDRTPTLTWGRGRVTLLGDSVHAMQPNMGQGGCMAIEDG
                                  **** **: :*:*:::*******: * :.**:*********:******:*********.
```

FIG. 24B
(Continued)

```
(SEQ ID NO: 30) XP_010547517.1    YQLAWELEHAWRRSVETDKPIDIVSSLRSYEEARKLRVAIIHGMARMAAIMASTYKGYLG
(SEQ ID NO: 31) KFK28343.1        YQLASELEDAWKQSVDTNRPVDVVSSLKRYEESRRLRVAIIHGMARMAAIMASTYKAYLG
(SEQ ID NO: 32) XP_010444704.1    FQLALELDEAWKQSVETKTPVDVVSSLKRYEESRRLRVALIHGMARMAAIMASTYKAYLG
(SEQ ID NO: 33) XP_010484561.1    FQLALELDEAWKQSVKTKTPVDVVSSLKRYEESRRLRVALIHGMARMAAIMASTYKAYLG
(SEQ ID NO: 34) XP_006280131.1    FQLALELEEAWKQSVETNTSVDVVSSLKKYEESRRLRVAIIHGMARMAAIMASTYKAYLG
(SEQ ID NO: 35) NP_851285.1       FQLALELDEAWKQSVETTTPVDVVSSLKRYEESRRLRVAIIHAMARMAAIMASTYKAYLG
(SEQ ID NO: 36) XP_002865032.1    FQLALELEEAWKQSVGTNTPVDVVSSLKRYEESRRLRVAIIHGMARMAAIMASTYKAYLG
(SEQ ID NO: 37) XP_018441511.1    FQLGLELEAAWKQSVETNTPVDVVSSLRRYEESRRLRCAIIHGMARMAAIMASTYKAYLG
(SEQ ID NO: 38) CDY01444.1        FQLGLELEQAWKQSVETNTPVDVVSSLRRYEESRRLRVAIIHGMARMAAIMASTYKAYLG
(SEQ ID NO: 39) XP_009103460.1    FQLGLELEQAWKQSVETNTPVDVVSSLRRYEESRRLRVAIIHGMARMAAIMASTYKAYLG
(SEQ ID NO: 40) ACM68704.1        FQLGLELEQAWKQSVETNTPVDVVSSLRRYEESRRLRVAIIHGMARMAAIMASTYKAYLG
(SEQ ID NO: 41) JAU06164.1        YQLAMELEGAWKQSVETNTPVDVVSSLKKYEESRRLRVAIIHGMARMAAIMASTYKAYLG
(SEQ ID NO: 42) XP_006393901.1    YQLALELEEAWERSVETNAPVDVVSSLRRYEESRRLRVAIIHGMARMAAIMASTYKAYLG
(SEQ ID NO: 43) AAV85824.1        YQLALELEEAWERSVETNAPVDVVSSLRRYEESRRLRVAIIHGMARMAAIMASTYKAYLG
(SEQ ID NO: 44) KGN61963.1        YQLALELDKAWNESVASGSPIDIVSSLKSYESSRRIRVAVIHGMARMAALMASTYKAYLG
(SEQ ID NO: 45) NP_001268202.1    YQLAMELDKAWEQSIKSGTPIDVVSCLKSYEKARRIRVAVIHGMARMAAIMASTYKAYLG
(SEQ ID NO: 46) CMP01999.1        YQLALELDKAWKQSVESGTPIDVVSSLRSYESARRLRVAIIHGMARMAAIMASTYKAYLG
(SEQ ID NO: 47) XP_011043539.1    YQLASELERAWKQSIESGTPVDVLSSLRSYENARRLRVAIIHGMARMAAIMASTYKAYLG
(SEQ ID NO: 48) XP_002523587.1    YQLALELDKAWKQSIESGYPVDVVSSLKSYERTRRLRVAIIHGMARMAAIMASTYKAYLG
(SEQ ID NO: 49) XP_012079233.1    YQLALEIEKAWKQSIESGTPIDIVSSLKSYERARRLRVAIIHGMARMAAIMASTYKAYLG
                                  :**. *:: **..*: :   :*::*.*: ** :*::***:**.******:******.***
```

FIG. 24B
(Continued)

```
(SEQ ID NO: 30) XP_010547517.1    VGLGPLSFLTMLRIPHPGTVGGRFFIDVAMPLMLNWVLGGNSSKLEGRLPCCRLSDKADD
(SEQ ID NO: 31) KFK28343.1        VGLGPLSFLTKFRVPHPGRVGGRFFIDIAMPLMLNWVLGGNSEKLEGRAPSCRLTDRADD
(SEQ ID NO: 32) XP_010444704.1    VGLGPLSFLTKFRVPHPGRVGGRFFIDIAMPMMLNWVLGGNSEKLEGRSPSCRLTDKADD
(SEQ ID NO: 33) XP_010484561.1    VGLGPLSFLTKFRVPHPGRVGGRFFIDIAMPMMLNWVLGGNSEKLEGRSPSCRLTDKADD
(SEQ ID NO: 34) XP_006280131.1    VGLGPLSFLTKFRVPHPGRVGGRFFIDIAMPLMLNWVLGGNSEKLEGRPPSCRLTDKADD
(SEQ ID NO: 35) NP_851285.1       VGLGPLSFLTKFRVPHPGRVGGRFFVDIAMPSMLDWVLGGNSEKLQGRPPSCRLTDKADD
(SEQ ID NO: 36) XP_002865032.1    VGLGPLSFLTKFRVPHPGRVGGRFFVDIAMPLMLDWVLGGNSEKLEGRPPSCRLTDKADD
(SEQ ID NO: 37) XP_018441511.1    VGLGPLSFLTKFRVPHPGRVGGRFFIDIAMPLMLNWVLGGNSEKLEGRPPSCRLTDKADD
(SEQ ID NO: 38) CDY01444.1        VGLGPLSFLTKFRVPHPGRVGGRFFIDIAMPLMLNWVLGGNSEKLEGRPPSCRLTDKADD
(SEQ ID NO: 39) XP_009103460.1    VGLGPLSFLTKFRVPHPGRVGGRFFIDIAMPLMLNWVLGGNSEKLEGRPPSCRLTDKADD
(SEQ ID NO: 40) ACM68704.1        VGLGPLSFLTKFRVPHPGRVGGRFFIDIAMPLMLNWVLGSNSEKLEGRPPSCRLTDKADD
(SEQ ID NO: 41) JAU06164.1        VGLGPLSFLTKFRVPHPGRVGGRFFIDIAMPLMLNWVLGGNSEKLEGRSPSCRLTDKADD
(SEQ ID NO: 42) XP_006393901.1    VGLGPLSFLTKFRVPHPGRVGGRFFIDIAMPLMLNWVLGGNSEKLEGRPPSCRLTDKADD
(SEQ ID NO: 43) AAV85824.1        VGLGPLSFLTKFRVPHPGRVGGRFFIDIAMPLMLNWVLGXNSEKLEGRPPSCRLTDKADD
(SEQ ID NO: 44) KGN61963.1        VGLGPLSFLTQFRIPHPGTFGGRFFIDLAMPLMLNWVLGGNSSKLEGRPPACRLSDKAND
(SEQ ID NO: 45) NP_001268202.1    VGLGPLSFLTKLRIPHPGRVGGRFFIDIAMPLMLSWVLGGNSSKLEGRPPSCRLSDKAND
(SEQ ID NO: 46) CMP01999.1        VGLGPLSFLTKYRIPHPGRVGGRFFIDIAMPLMLSWVLGGNSSKLEGRSLTCRLSDKASD
(SEQ ID NO: 47) XP_011043539.1    VGLGPLSFLTNFRIPHPGRVGGRFFIDIAMPVMLDWVLGGNSSKLEGRSLSCRLSDKASD
(SEQ ID NO: 48) XP_002523587.1    VGLGPLSFLTKYRIPHPGRVGGRFFIDIAMPVMLNWVLGGNSSKLEGRPLSCRLSDKASD
(SEQ ID NO: 49) XP_012079233.1    VGLGPLSFLTKYRIPHPGRVGGRFFIDIAMPVMLSWVLGGNSSKLEGRSQCCRLSDKASD
                                  **********  *:****  .*****:*:***  **.****  **.**:**    ***:*:*.*
```

FIG. 24B
(Continued)

```
(SEQ ID NO: 30) XP_010547517.1    QLQRWFQDNDALERTVIGDWYLIPYGNDSIVSETVRLDKDEDQPCIIGSEPDEDFPGMRI
(SEQ ID NO: 31) KFK28343.1        RLREWFDDNEALERTISGEWYLIPQGDDCCVSETLCLTKDEDQPCIIGSEPDKDFPGMHI
(SEQ ID NO: 32) XP_010444704.1    RLREWREDDDALERTIKGEWYLIPHGDDCCISETLCLTKDEDQPCIIGSEPDQDLPGKHI
(SEQ ID NO: 33) XP_010484561.1    RLREWFEDDDALERTIKGEWYLIPHGDECCISETLCLTKDEDQPCIIGSKPDQDLPGKHI
(SEQ ID NO: 34) XP_006280131.1    RLREWFENDDALERTINGEWYLIPHGDECCVSETLCLTKDEDQPCIVGSEPDQDLPGKHI
(SEQ ID NO: 35) NP_851285.1       RLREWFEDDDALERTIKGEWYLIPHGDDCCVSETLCLTKDEDQPCIVGSEPDQDFPGMRI
(SEQ ID NO: 36) XP_002865032.1    RLREWFEDDDALERTIKGEWYLIPHGEDCCVSETLCLTNDEDQPCIVGSEPDQDFPGMRI
(SEQ ID NO: 37) XP_018441511.1    RLREWFEDDEALERTINGEWYLIPHGNECSVSETLRLTKDEEQPCIVGSEPDQDFPGTHI
(SEQ ID NO: 38) CDY01444.1        RLREWFEDDEALERTINGEWYLIPHGNECSVSETLRLTKDEDQPCIVGSEPDQDFPGMHI
(SEQ ID NO: 39) XP_009103460.1    RLREWFEDDEALERTINGEWYLIPHGNECSVSETLRLTKDEEQPCIVGSEPDQDFPGTHI
(SEQ ID NO: 40) ACM68704.1        RLREWFEDDEALERTINGEWYLIPHGNECSVSETLRLTKDEEQPCIVGSEPDQDFPGTHI
(SEQ ID NO: 41) JAU06164.1        RLREWFEDNDALERTINGEWYLIPHGDDSSVKETISLTKDEDQPCIIGSEPDQDLPGMHI
(SEQ ID NO: 42) XP_006393901.1    RLREWFEDDDALERTINGEWYLIPYGNECSVSETLCLTKDEDQPCIIGSEPDQDFPGMHI
(SEQ ID NO: 43) AAV85824.1        RLREWFEDDDALERTINGEWYLIPYGNECSVSETLCLTKDEDQPCIIGSEPDQDFPGMHI
(SEQ ID NO: 44) KGN61963.1        QLRKWFEDDDALERAINGDWFLLPQGGEASVSQPICLRKDENQPCLIGSVEKEVDSGLSV
(SEQ ID NO: 45) NP_001268202.1    QLRRWFEDDDALERAIGGEWFLLPSGES--GLQPICLSKDENKPCIIGSVSHTDFPGIST
(SEQ ID NO: 46) CMP01999.1        QLREWFEDNDALERAISGEWFLFPAGDG-VSSQPICLSRDENNPFMIGSEKKEDFPGTSV
(SEQ ID NO: 47) XP_011043539.1    QLRRWFVDDDALERSLNGEWFLLPCGNDAVASQPIGLSRDENKPCVVGSYSQEDFPGMSI
(SEQ ID NO: 48) XP_002523587.1    QLQTWFEDDNALERALNGEWFLLPFGDDA-VQEPICLSRDENIPCMVGSESQEDFPGKSI
(SEQ ID NO: 49) XP_012079233.1    QLRTWFEDDDALERALNAEWFLLPLGNKVVVSEPICLSRNENTPCVVGKVSHKDFPGMSI
                                  :*: ** :::****:: .:*:*:* *      : : * .:*: * ::*.  .    *
```

FIG. 24B
(Continued)

```
(SEQ ID NO: 30) XP_010547517.1    EIPSSQVSKVHARIIYKDGAFFVMDLRSEYGTYITDNEGRRYRVTPNFPARFRPSDIIEL
(SEQ ID NO: 31) KFK28343.1        VIPSSQVSKMHARIIYKDGAFFVMDLRSEHGTYVVDNEGGRYRATPNFPARFRPSDILEF
(SEQ ID NO: 32) XP_010444704.1    VIPSSQVSKMHARVIYKDGAFFLMDLRSEHGTYVTDNEGRRYRATPNSPARFRTSDIIEF
(SEQ ID NO: 33) XP_010484561.1    VIPSSQVSKMHARVIYKDGAFFLMDLRSEHGTYVTDNEGRRYRATPNSPARFRTSDIIEF
(SEQ ID NO: 34) XP_006280131.1    VIPSSQVSKMHARVIYKDGAFFLMDLGSEHGTFVTDNEGRRYRATPNFPGRFRSSDIIEF
(SEQ ID NO: 35) NP_851285.1       VIPSSQVSKMHARVIYKDGAFFLMDLRSEHGTYVTDNEGRRYRATPNFPARFRSSDIIEF
(SEQ ID NO: 36) XP_002865032.1    VIPSSQVSKMHARVIYKDGVFFLMDLRSEHGTYVTDNEGRRYRATPNFPARFRSSDIIEF
(SEQ ID NO: 37) XP_018441511.1    VIPSPQVSKMHARVIYKDGAFFLMDLRSEHGTYLTDNEGGKYRVTPNFPTRFRSSDIIEF
(SEQ ID NO: 38) CDY01444.1        VIPSPQVSKMHARVIYKDGAFFVMDLRSEHGTYLTDNEGGKYRVTPNFPARFRPSDIIEF
(SEQ ID NO: 39) XP_009103460.1    VIPSPQVSKMHARVIYKDGAFFVMDLRSEHGTYLTDNEGGKYRVTPNFPARFRPSDIIEF
(SEQ ID NO: 40) ACM68704.1        VIPSPQVSKMHARVIYKDGAFFVMDLRSEHGTYLTDNEGGKYRVTPNFPARFRPSDIIEF
(SEQ ID NO: 41) JAU06164.1        VIPSSQVSKMHARVTYKDGAFFLMDLGSEHGTYVVDNEGRRYRASPNYPARFRSSDIIEF
(SEQ ID NO: 42) XP_006393901.1    VIPAPQVSKMHARVTYKDGAFFLMDLRSEHGTYVTDNEGRRYRVTPNFPARFRSSDIIEF
(SEQ ID NO: 43) AAV85824.1        VIPAPQVSKMHARVTYKDGAFFLMDLRSEHGTYVTDNEGRRYRVTPNFPARFRSSDIIEF
(SEQ ID NO: 44) KGN61963.1        AIPLPQVSEKHARIYYKDGAFFLTDLRSEHGTWLSDHEGRRYRAPPNFPVRFHQSDLIEF
(SEQ ID NO: 45) NP_001268202.1    VIPSPKVSKMHARISCKDGAFFLTDLQSEHGTWITDNVGRRQRVSPNFPTRFHPSEVIDF
(SEQ ID NO: 46) CMP01999.1        VIPSSQVSKTHAQITYKDGAFFVTDLQSEHGTYIINQEGKKSRVTPNVPTRIRPSDVIEF
(SEQ ID NO: 47) XP_011043539.1    VIPAPQVSKTHARITCKDGAFYLIDLRSEHGTFITDIEGRRYRAPPNFPTRFHPSDMIEF
(SEQ ID NO: 48) XP_002523587.1    VISSPQVSKMHARISYKDGGFYVIDLQSEHGTFITDNDGRRSRVPPNFPTLFHPSEAIEF
(SEQ ID NO: 49) XP_012079233.1    VIPSPQVSEMHARISYKDGAFYVIDLQSEHGTYISDADGRRYRVPQNSPTRFHPSDVIEF
                                   *   :**: **::  *** *:: ** **:**:: :  * : *.  * *  :: *: :::
```

FIG. 24B
(Continued)

```
(SEQ ID NO: 30) XP_010547517.1    GSDKKAAFRVKVIRKTPKMTRRDDRESSSKLLQAA-
(SEQ ID NO: 31) KFK28343.1        GSDKKAAFKVKVIRKTPKSTSKNESNG--KLLQAA-
(SEQ ID NO: 32) XP_010444704.1    GSDKKAAFRVKVIRTTPKSTRKNESND--KLLQ-AA
(SEQ ID NO: 33) XP_010484561.1    GSDKKAAFRVKVIRTTPKSTRKNESND  KLLQ AA
(SEQ ID NO: 34) XP_006280131.1    GSDKKAAFRVKVIRKTPKATRKNESND--K-LLQAA
(SEQ ID NO: 35) NP_851285.1       GSDKKAAFRVKVIRKTPKSTRKNESNN--DKLLQTA
(SEQ ID NO: 36) XP_002865032.1    GSDKKAAFRVKVIRKTPKSTRKNESND---KLLQTA
(SEQ ID NO: 37) XP_018441511.1    GSDKKAAFRVKVIRTTPKLTRRDEKSD--GKLLQAA
(SEQ ID NO: 38) CDY01444.1        GSDKKAAFRVKVIRTTPKLTRRDEKSD--GKLLQAA
(SEQ ID NO: 39) XP_009103460.1    GSDKKAAFRVKVIRTTPKLTRRDEKSD--GKLLQAA
(SEQ ID NO: 40) ACM68704.1        GSDKKAAFRVKVIRTTPKLTRRDEKSD--GKLLQAA
(SEQ ID NO: 41) JAU06164.1        GSDKKAAFRVKVIRTTPKSTSKN-ESN--GKLLQAA
(SEQ ID NO: 42) XP_006393901.1    GSDKKAAFRVKVIRTTPKSTSKNKESN--GKLLQAV
(SEQ ID NO: 43) AAV85824.1        GSDKKAAFRVKVIRTTPKSTSKNKESN--GKLLQAV
(SEQ ID NO: 44) KGN61963.1        GSDKKARFRVKVIRSSVENDREKVEMNS--------
(SEQ ID NO: 45) NP_001268202.1    GSE-KASFRVKVVRTPPDNAAKNEESKLFQAV----
(SEQ ID NO: 46) CMP01999.1        GSDKKAAFRVKAIKSAPKIAEKEGSGVLQAA-----
(SEQ ID NO: 47) XP_011043539.1    GSDKKVIFRVKVMRSPPKISEKKDEGQVLQSV----
(SEQ ID NO: 48) XP_002523587.1    GSAGKAKFRVKVMKSPAKIKEKGGN-EILQSV----
(SEQ ID NO: 49) XP_012079233.1    GSDEKAKFRVKVMKSPSRIKEKEGS-EILQSV----
                                  **  *. *:**.::.      .
```

FIG. 24B
(Continued)

```
Violaxanthin de-epoxidase (VDE)
CLUSTAL O(1.2.4) multiple sequence alignment

(SEQ ID NO: 50) XP_010043341.1    -----------MASMAAGSICLFRDESIGAASIAVTILANRSSHMAKLLCYRGKARATMW
(SEQ ID NO: 51) XP_010528777.1    -------------------------------------MAVAVQSFSSP-CYRD---TQFI
(SEQ ID NO: 52) XP_010475655.1    -------------------------------------MAVATHCFTSP-CHDR---IRFF
(SEQ ID NO: 53) XP_006307456.1    -------------------------------------MAVATHCFTSP-CHDR---IRFF
(SEQ ID NO: 54) NP_172331.1       -------------------------------------MAVATHCFTSP-CHDR---IRFF
(SEQ ID NO: 55) XP_002889702.1    -------------------------------------MAVATHCFTSP-CHGR---IRFF
(SEQ ID NO: 56) XP_013641072.1    -------------------------------------MSVSTHCFTSP-CHDR---TRFF
(SEQ ID NO: 57) XP_009148110.2    MSYPKGISSHPYISLFLFSLYLPP---LLPAELSVSSMSVSTHCFTSP-CHDR---TRFF
(SEQ ID NO: 58) JAU20005.1        LS--LSLSLSLSLSLLPAELSIFG---IASGRLATESMSVATHCFTSPTCHDR---IRFF
(SEQ ID NO: 59) XP_006417674.1    -------------------------------------MAVATYCFTSP-CHDR---IRFF
(SEQ ID NO: 60) AIZ75647.1        ------------MALAGRSIFLSHNDSIG--NT----------C--------------IR
(SEQ ID NO: 61) XP_009379699.1    ------------MAFAGRSVFLSHKESIG--NA----------C--------------IR
(SEQ ID NO: 62) AMJ39491.1        ------------MALAPHST---------------------------------------H
(SEQ ID NO: 63) EOY10737.1        ------------MAQAARSLCFSHDKSVQ--VP----------C--------------RT
(SEQ ID NO: 64) XP_017627747.1    ------------MAEAARLICFSHGKSVK--VP----------C--------------RT
(SEQ ID NO: 65) XP_016673034.1    ------------MAEAARLICFSHGKSVK--VP----------C--------------RT
(SEQ ID NO: 66) XP_002319136.2    ------------MALAANPFCLSQEQYIISSSS----------V--------------AK
(SEQ ID NO: 67) OAY41983.1        ------------MAISANSVCLSHEESIC--SS----------Y--------------FR
(SEQ ID NO: 68) XP_012092715.1    ------------MALAANSIYLSHEESIS--SS----------Y--------------IK
```

FIG. 24C

```
(SEQ ID NO: 50) XP_010043341.1    MGIKTTRRLAMK------------CSLESHCRSESSCSGFP----------------L--
(SEQ ID NO: 51) XP_010528777.1    SGNRSNR--KLLRKRMVDSDTIVLVKICSGARGKIHCS----------------------
(SEQ ID NO: 52) XP_010475655.1    SSDDGIGRLGISRKRINGT---FLVKILPPIQNVDLRT----------------------
(SEQ ID NO: 53) XP_006307456.1    SSDDGIARLGISRKRINGT---FLVKILSPIQSADLRT----------------------
(SEQ ID NO: 54) NP_172331.1       SSDDGIGRLGITRKRINGT---FLLKILPPIQSADLRT----------------------
(SEQ ID NO: 55) XP_002889702.1    SSDD--GRLGITRKRINGT---FLLKILPPIQN---------------------------
(SEQ ID NO: 56) XP_013641072.1    SG--DDG-NKLLRKRIKGT---FLVKILPSSQNAYLRI----------------------
(SEQ ID NO: 57) XP_009148110.2    SG--DDG-NKLLRKRIKGT---FLVKILPSSQNAYLRV----------------------
(SEQ ID NO: 58) JAU20005.1        SRITSDD-GRLVRKRINGT---FLLKILPPSQNAHLRT----------------------
(SEQ ID NO: 59) XP_006417674.1    SGVTSFD-GRLLRKRINGT---FLVKILPPSQNADLRT----------------------
(SEQ ID NO: 60) AIZ75647.1        LGITSDE--GFQKRRMVGFHVVV--KFPSNRRKS-RYSQFIRSKRNFCVLGSKCSSLLSS
(SEQ ID NO: 61) XP_009379699.1    LGLKSDE--RLQKGRMVGFHVVV--KFSSQRRKS-RYCQFISAKRNFSGLGSKRSSLLSS
(SEQ ID NO: 62) AMJ39491.1        FSELTGR--RFLSRKVVHLHGMVLLRIQSSDRKSR-YSKSINPYRNHIVSKLRCSDQLSE
(SEQ ID NO: 63) EOY10737.1        SGLTSNE--RFHRRQIAHFHGIMLVKIQSSGRKAR-YSQLNKSNPNYSASDLRCSNQLSR
(SEQ ID NO: 64) XP_017627747.1    SGFTRKE--RFHRRLVAHFHGMMLLKLQSSCRNSR-YSQLIKPNMNYSASKLRCSHQLSR
(SEQ ID NO: 65) XP_016673034.1    SGFTRKE--RFHRRLVAHFHGMMLLKLQSSCRNSR-YSQLIKPNMNYSASKLRCSHQFSR
(SEQ ID NO: 66) XP_002319136.2    SGLASDG--RFHRRQRLHFHGAVLSQFWPNSRKLR-YIQSIRSHRHHYGGVIRCSNQLSD
(SEQ ID NO: 67) OAY41983.1        PGIASYE--RIHGRRGLNYQSIVVLNFWPNSRKSR-YVQLMRTHKNYHGIKLRCSHGFSG
(SEQ ID NO: 68) XP_012092715.1    SGI---E--RFHGRKGLHFRSIVVLKILPNSRKSRRHVQLIRSYRNYCGLVLRCSHQFSG
```

FIG. 24C
(Continued)

```
(SEQ ID NO: 50) XP_010043341.1    -PRKEEVTSSRG-SRSGVPKVTE--SAREIFHLVREWSQRRVIQLAALAACTFLIIPSAD
(SEQ ID NO: 51) XP_010528777.1    -LKARFSSPSSG-YKSGLSKGRPPFEALTLWNKLKEQSRQSLLKLVGILACTFLIVPSVD
(SEQ ID NO: 52) XP_010475655.1    -N-GRSSRPLSA-FRSGISKGVFDILSLPSKDELKELSTPLLLKLVGVFACAFLIVPSAE
(SEQ ID NO: 53) XP_006307456.1    -S-GRSSRPLSA-FRSGFSKRVFDIVSLPSKNELKELSTPLLLKLVGVLACAFLIVPSAE
(SEQ ID NO: 54) NP_172331.1       -TGGRSSRPLSA-FRSGFSKGIFDIVPLPSKNELKELTAPLLLKLVGVLACAFLIVPSAD
(SEQ ID NO: 55) XP_002889702.1    -AGGRSSRPISA-FRSGFSKGIFDIVALPSKNELKELTTPLLLKLVFVLACAFLIVPSAD
(SEQ ID NO: 56) XP_013641072.1    -TAKSSRPLS-G-FRSGISKGVFDIVALTSKNALKELTTPLMLKLVGVVACAFLIVPSAD
(SEQ ID NO: 57) XP_009148110.2    -TAKSSRPLS-G-FRSGISKGVFDIVALTSKNALKELSTPLMLKLVGVVACAFLIVPSAD
(SEQ ID NO: 58) JAU20005.1        -TLRSSRPLSAG-FRSGISKGVIDIVALTSRNALKELSTPLLLKLVGVLACAFLIVPSAD
(SEQ ID NO: 59) XP_006417674.1    -TSRSSRPLS-G-FRSGTSKGVFDIVALTSRNALKELSTPMVLKLVGVLACAFLIVPSAD
(SEQ ID NO: 60) AIZ75647.1        KTEEAFSKCSTR-TSEPEMKRVISFLLEEASSCIKEWSQLHFMKVAGLLACTFMIMPSAN
(SEQ ID NO: 61) XP_009379699.1    RTEEAFSERSTK-TSEPEMGRAIDLMIEEVLSVIKEWSQLHFMKVAGLLLCTFMVMPSAN
(SEQ ID NO: 62) AMJ39491.1        GTHNISSTCSSNTRRKHEAKEGFEFVVPNLPNILRKWSQLQIMKVAGVLACALLVIPSAS
(SEQ ID NO: 63) EOY10737.1        RKDRNFSSCSCNRR-RPKAEEAFAFLVPTISNVLKEWSQSKIVKVVGLLACAYLVIPSAS
(SEQ ID NO: 64) XP_017627747.1    RKERKFSSSSSNER-TPK--------IPTISNLLEQWSQSQTVKLVGLLACAYLVIPSAA
(SEQ ID NO: 65) XP_016673034.1    RKERKFSSSSSNER-TPKAEEVFSFQIPTISNLLEQWSQSQTVKLVGLLACAYLVIPSAA
(SEQ ID NO: 66) XP_002319136.2    WTKKFSSLCSSSSRSMPKAIERLNFVVLSVTNALKERNNLECLKLAGILLCALLVIPSAD
(SEQ ID NO: 67) OAY41983.1        WTKKFSSFCRTG-ANVTKAKEVLNFLMFSVSNNLKEKSHLQFLKVASILACVLLFIPSAD
(SEQ ID NO: 68) XP_012092715.1    WTNKFPSFSSTA-ASINKAKEVLNFLMLSVSNNLKEKGQLQFLKVAGILACALLVIPSAD
                                                                   :.:      :::..:  *. :.:**.
```

FIG. 24C
(Continued)

```
(SEQ ID NO: 50) XP_010043341.1    AVDALKTCACLLKECRIELAKCVANPSCAANVACLQTCNNRPDETECQ---IKCGDLFEN
(SEQ ID NO: 51) XP_010528777.1    AVDALKTCACLLKECRIELAKCISNPSCAANVACLQTCNNRPDETECQ---IKCGDLFEN
(SEQ ID NO: 52) XP_010475655.1    AVDALKTCACLLKGCRIELAKCISNPACAANIACLQTCNNRPDETECQ---IKCGDIFEN
(SEQ ID NO: 53) XP_006307456.1    AVDALKTCACLLEGCRIELAKCIANPACAANVACLQTCNNRPDETECQ---IKCGDLFEN
(SEQ ID NO: 54) NP_172331.1       AVDALKTCACLLKGCRIELAKCIANPACAANVACLQTCNNRPDETECQ---IKCGDLFEN
(SEQ ID NO: 55) XP_002889702.1    AVDALKTCACLLKGCRIELAKCIANPACAANVACLQTCNNRPDETECQ---IKCGDLFEN
(SEQ ID NO: 56) XP_013641072.1    AVDALKTCACLLKGCRIELAKCIANPSCAANVACLQTCNNRPDETECQ---IKCGDLFEN
(SEQ ID NO: 57) XP_009148110.2    AVDALKTCACLLKGCRIELAKCIANPSCAANVACLQTCNNRPDETECQ---IKCGDLFEN
(SEQ ID NO: 58) JAU20005.1        AVDALKTCACLLKECRIELAKCIANPSCAANVACLQTCNNRPDETECQ---IKCGDLFAN
(SEQ ID NO: 59) XP_006417674.1    AVDALKTCACLLKGCRIELAKCIANPSCAANVACLQTCNNRPDETECQ---IKCFDLFEN
(SEQ ID NO: 60) AIZ75647.1        AADALKTCACLLKECRVELAKCIGNPSCAANIACLQTCNNRPDETECQ---IKCGDLFEN
(SEQ ID NO: 61) XP_009379699.1    AVDALKTCACLLKECRVELAKCIGNPSCAANIACLQTCNNRPDETECQ---IKCGDLFEN
(SEQ ID NO: 62) AMJ39491.1        AVDALKTCTCLLKECRIELAKCIANPSCAANVACLQTCNNRPDETECQ---IKCGDLFEN
(SEQ ID NO: 63) EOY10737.1        AVDALKTCTCLLKECRIELAKCIANPSCAANIACLQTCNDRPDETECQ---IKCGDLFEN
(SEQ ID NO: 64) XP_017627747.1    AVDALKTCTCLLKECRIELAKCIANPSCAANVACLQTCNDRPDETECQ---IKCGDLFEN
(SEQ ID NO: 65) XP_016673034.1    AVDALKTCTCLLKECRIELAKCIANPSCAANVACLQTCNDRPDETECQ---IKCGDLFEN
(SEQ ID NO: 66) XP_002319136.2    AVDALKTCTCLLKECRLELAKCIANPSCAANVACLQTCNNRPDETECQASSIKCGDLFEN
(SEQ ID NO: 67) OAY41983.1        AVDALKTCTCLLKECRLELAKCIANPACAANIACLQTCNNRPDETECQ---IKCGDLFEN
(SEQ ID NO: 68) XP_012092715.1    AVDALKTCACLLKECRLELAKCIANPACAANIACLQTCNNRPDETECQ---IKCGDLFEN
                                  *.******:***: **:*****:.**:****:*******:********   *****:* *
```

FIG. 24C
(Continued)

```
(SEQ ID NO: 50) XP_010043341.1     SVVDEFNECAVSRKKCVPRKSDVGEFPVPDPAVLVKSFNMADFTGKWFISSGLNPTFDTF
(SEQ ID NO: 51) XP_010528777.1     SVVDEFNECAVSRKKCVPRKSDLGEFPAPDPAVLVKRFNIGDFSGKWYISSGLNPTFDTF
(SEQ ID NO: 52) XP_010475655.1     KVVDEFNECAVTRKKCVPKKSDLGEFPAPDPSVLVQNFNIGDFSGKWYITSGLNPTFDAF
(SEQ ID NO: 53) XP_006307456.1     SVVDEFNECAVSRKKCVPRKSDLGEFPAPDPSVLVQNFNIGDFNGKWYITSGLNPTFDAF
(SEQ ID NO: 54) NP_172331.1        SVVDEFNECAVSRKKCVPRKSDLGEFPAPDPSVLVQNFNISDFNGKWYITSGLNPTFDAF
(SEQ ID NO: 55) XP_002889702.1     SVVDEFNECAVSRKKCVPRKSDLGEFPAPDPSVLVQNFNISDFNGKWYITSGLNPTFDAF
(SEQ ID NO: 56) XP_013641072.1     SVVDEFNECAVSRKKCVPRKSDLGEFPAPDPSVLVKNFNINDFDGKWYITSGLNPTFDAF
(SEQ ID NO: 57) XP_009148110.2     SVVDEFNECAVSRKKCVPRKSDLGEFPAPDPSVLVKNFNVKDFDGKWYITSGLNPTFDAF
(SEQ ID NO: 58) JAU20005.1         SVVDEFNECAVSRKKCVPRKSDLGEFPVPDPSALVKNFNIQDFNGKWYITSGLNPTFDIF
(SEQ ID NO: 59) XP_006417674.1     KVVDEFNECAVSRKKCVPQKSDLGEFPVPDPSVLVKNFNISDFNGKWYITSGLNPTFDTF
(SEQ ID NO: 60) AIZ75647.1         SVVDEFNECAVSRKKCVPKKSDVGEFPIPDPAVLVKSFDIEKFNGKWFITSGLNPTFDAF
(SEQ ID NO: 61) XP_009379699.1     KVVDEFNECAVSRKKCVPMKSDVGEFPIPDPAALVKSFDMSKFNGKWFITSGLNPTFDVF
(SEQ ID NO: 62) AMJ39491.1         SVVDVFNECAVSRKKCVPQKSDVGEFAVPDPSVLVKNFNIADFSGKWYISSGLNPSFDTF
(SEQ ID NO: 63) EOY10737.1         SVVDEFNECAVSRKKCVPQKSDIGEFPVPSPAVLVKNFNIADFSGKWFISSGLNPTFDTF
(SEQ ID NO: 64) XP_017627747.1     SVVDEFNECAVSRKKCVPQKSDIGEFPVPDPAVLVENFNIADFTGKWFISSGLNPTFDTF
(SEQ ID NO: 65) XP_016673034.1     SVVDEFNECAVSRKKCVPQKSDIGEFPVPDPAVLVENFNIADFTGKWFISSGLNPTFDTF
(SEQ ID NO: 66) XP_002319136.2     SVVDEFNECAVSRKKCVPRKSDVGEFPVPDPAVLVENFNMADFSGKWFITSGLNPTFDTF
(SEQ ID NO: 67) OAY41983.1         TVVDEFNECAVSRKKCVPKKSDVGEFPVPDPAVLVKSFNIADFNGKWYITRGLNPTFDTF
(SEQ ID NO: 68) XP_012092715.1     NVVDEFNECAVSRKKCVPKKSDVGEFPVPDPAVLVKSFNIADFSGKWFITSGLNPTFDTF
                                   .*** ******:****** ***:***  *.*:.**: *:: .* ***:*: ****:** *
```

FIG. 24C
(Continued)

```
(SEQ ID NO: 50) XP_010043341.1    DCQLHEFHTES-NKLMGNLTWRIRTPDSGFFTRTAVQRFVQDPEQPGILYNHDNEYLHYQ
(SEQ ID NO: 51) XP_010528777.1    DCQLHEFHTES-DKLVGNLSWRIRTPDGGFFTRSTVQKFVQDPNQPGILYNHDNEYLHYQ
(SEQ ID NO: 52) XP_010475655.1    DCQLHEFHTEGENKLVGNISWRIKTLDSGFFTRSAVQTFVQDPNQPGVLYNHDNEYLHYQ
(SEQ ID NO: 53) XP_006307456.1    DCQLHEFHTEGDNKLVGNISWRIKTLDSGFFTRSAVQTFVQDPNQPGVLYNHDNAYLHYQ
(SEQ ID NO: 54) NP_172331.1       DCQLHEFHTEGDNKLVGNISWRIKTLDSGFFTRSAVQKFVQDPNQPGVLYNHDNEYLHYQ
(SEQ ID NO: 55) XP_002889702.1    DCQVHEFHTEGDNKLVGNISWRIKTLDSGFFTRSAVQKFVQDPNQPGVLYNHDNEYLHYQ
(SEQ ID NO: 56) XP_013641072.1    DCQLHEFHTED-GKLVGNISWRIKTPDSGFFTRSTVQKFVQDPNQPAVFYNHDNEYLHYQ
(SEQ ID NO: 57) XP_009148110.2    DCQLHEFHTED-GKLVGNISWRIKTPDSGFFTRSTVQKFVQDPNQPAVFYNHDNEYLHYQ
(SEQ ID NO: 58) JAU20005.1        DCQLHEFHVQG-NKLVGNISWRIKTPDTGFFTRSAVQTFKQDPNQPAVLYNHDNEYLHYQ
(SEQ ID NO: 59) XP_006417674.1    DCQRHEFHADG-DKLVGNISWRIKTLDSGFFTRSAVQKFVQDPNQPAILYNHDNEYLHYQ
(SEQ ID NO: 60) AIZ75647.1        DCQLHEFHTES-SKLVGNLSWRIRTPDGGFFTRSAVQKFVQDPNQPGILYNHDNDYLHYQ
(SEQ ID NO: 61) XP_009379699.1    DCQLHEFHTES-SKLVGNLSWRIKTPDGGFFTRSAVQKFVQDPNQPGILYNHDNEYLHYQ
(SEQ ID NO: 62) AMJ39491.1        DCQLHEFHTES-NKLVGNLSWRIRTPDGGFFTRSTLQKFVQDPKQPGILYNHDNEYLHYQ
(SEQ ID NO: 63) EOY10737.1        DCQLHEFHTEA-GKLVGNLSWRIGTPDGGFFTRSTLQRFVQDPNYPGILYNHDNEYLHYQ
(SEQ ID NO: 64) XP_017627747.1    DCQLHEFHIEG-GKLVGNLSWRIRTPDGGFFTRSATQRFVQDPNHPGILYNHDNEYLHYQ
(SEQ ID NO: 65) XP_016673034.1    DCQLHEFHIEG-GKLVGNLSWRIRTPDGGFFTRSATQRFLQDPNHPGILYNHDNEYLHYQ
(SEQ ID NO: 66) XP_002319136.2    DCQLHEFHTES-NKLVGNLSWRIKTPDTGFFTRSAVQRFVQDPVHPGILYNHDNEYLHYQ
(SEQ ID NO: 67) OAY41983.1        DCQLHEFHVES-NKLVGNISWRIRTPDSGFFTRSTVQRFVQDPMQPGILYNHDNEYLHYQ
(SEQ ID NO: 68) XP_012092715.1    DCQLHDFHRES-NRLVGNLSWRIRTPDGGFFTRSTVQKFVQDPLQPGILYNHDNEYLHYQ
                                  *** *:** :  .:*:**::*** * * *****:: * * ***  *.::***** *****
```

FIG. 24C
(Continued)

```
(SEQ ID NO: 50) XP_010043341.1    DDWYILSSKTENKPDDYVFVYYRGRNDAWDGYGGAVVYTRSAVLPDSIVPELERAAKSVG
(SEQ ID NO: 51) XP_010528777.1    DDWYILSSKVENGPDDYVFVYYRGRNDAWDGYGGAVVYTRSAVLPNNIVPELERAAKSVG
(SEQ ID NO: 52) XP_010475655.1    DDWYILSSKIENKPEDYIFVYYRGRNDAWDGYGGAVVYTRSSVLPNSIVPELEKAAKSIG
(SEQ ID NO: 53) XP_006307456.1    DDWYILSSKIENKPEDYIFVYYRGRNDAWDGYGGAVVYTRSSVLPNSIVPELEKAAKSIG
(SEQ ID NO: 54) NP_172331.1       DDWYILSSKIENKPEDYIFVYYRGRNDAWDGYGGAVVYTRSSVLPNSIVPELEKAAKSIG
(SEQ ID NO: 55) XP_002889702.1    DDWYILSSKIENKPDDYIFVYYRGRNDAWDGYGGAVVYTRSSVLPNSIIPELEKAAKSIG
(SEQ ID NO: 56) XP_013641072.1    DDWYILSSKIENKPEDYIFVYYRGRNDAWDGYGGAVVYTRSASLPNTIVPELEKAAKSIG
(SEQ ID NO: 57) XP_009148110.2    DDWYILSSKIENKPEDYIFVYYRGRNDAWDGYGGAVVYTRSASLPNTIVPELEKAAKSIG
(SEQ ID NO: 58) JAU20005.1        DDWYILSSKIENKPEDYIFVYYRGRNDAWDGYGGAVVYTRSNVLPNSIVPELEKAAKSIG
(SEQ ID NO: 59) XP_006417674.1    DDQYILSSKVENKPDDYIFVYYRGRNDAWDGYGGAVVYTRSAVLPNSIVPELEKAAKSIG
(SEQ ID NO: 60) AIZ75647.1        DDWYILSSKMENKPDDYIFVYYRGRNDAWDGYGGAVIYTRSSVLPASIVPDLEKAAASVG
(SEQ ID NO: 61) XP_009379699.1    DDWYILSSKIENTPEDYIFVYYRGRNDAWDGYGGAVVYTRSSVLPESIVPELERAAKSVG
(SEQ ID NO: 62) AMJ39491.1        DDWYILSSKIENKQDDYVFVYYRGRNDAWDGYGGAVVYTRSAVLPESIVPELERAAKCVG
(SEQ ID NO: 63) EOY10737.1        DDWYIISSKIENKQDDYIFVYYQGRNDAWDGYGGAVVYTRSAVLPESIVPELEKAAKNVG
(SEQ ID NO: 64) XP_017627747.1    DDWYIISSKIENKPDDYVFVYYRGRNDAWDGYGGAVVYTRSAVLPETIVPELKRAAQNVG
(SEQ ID NO: 65) XP_016673034.1    DDWYILSSKIENKPDDYVFVYYRGRNDAWDGYGGAVVYTRSAVLPETIVPELKRAAQNVG
(SEQ ID NO: 66) XP_002319136.2    DDWYILSSKIENKQDDYVFVYYQGRNDAWDGYGGAVVYTRSAVLPESIVPELEKAAKSVG
(SEQ ID NO: 67) OAY41983.1        DDWYILSSKVENKSDDYIFVYYRGRNDAWDGYGGAVVYTRSSVLPESIAPELERAAKSVG
(SEQ ID NO: 68) XP_012092715.1    DDWYILSSKLENSENDYIFVYYRGRNDAWDGYFFAVVYTRSAVLPESIIPELETAAKKVG
                                  *****:*** **  :**:****:*************:****  ** .* *:*: **  :*
```

FIG. 24C
(Continued)

```
(SEQ ID NO: 50) XP_010043341.1   RDFKDFIRTDNTCGPEPPLVERIEKTVEEGEKTIVREVEQIED----EVQKVGKTEMTLF
(SEQ ID NO: 51) XP_010528777.1   RDFSKFIRTDNTCGPEPPLVERIEKTVEEGERTIIREVEQIEG----EVAKVGETEMTLL
(SEQ ID NO: 52) XP_010475655.1   RDFSTFIRTDNTCGPEPPLVERLEKTVEEGERIIVKDREEIEEEVIKEVEKVGKTEMTLF
(SEQ ID NO: 53) XP_006307456.1   RDFSTFIKTDNTCGPEPPLVERLEKTVEEGERIIVKEVEEIEEEVEKEVEKVGKTEMTLF
(SEQ ID NO: 54) NP_172331.1      RDFSTFIRTDNTCGPEPALVERIEKTVEEGERIIVKEVEEIEEEVEKEVEKVGRTEMTLF
(SEQ ID NO: 55) XP_002889702.1   RDFSTFIRTDNTCGPEPPLVERIEKTVEEGERIIVKEVEEIEEEVEKEVEKVGKTEMTLF
(SEQ ID NO: 56) XP_013641072.1   REFSTFIKTDNTCGPEPPLVERLEKTVEEGEKIIVKEVEEIEEEVEKEVEKVGKTEMTLF
(SEQ ID NO: 57) XP_009148110.2   REFSTFIKTDNTCGPEPPLVERLEKTVEEGEKIIVKEVEEIEEEVEKEVEKVGKTEMTLF
(SEQ ID NO: 58) JAU20005.1       RDFNTFVRTDNTCGPEPPLVERLEKTVEEGEKMIEKEVEEIEEEVEKEVEKVGKTEMTLF
(SEQ ID NO: 59) XP_006417674.1   RDFSTFVRTDNTCGPEPPLVERFEKTVEEGEKIIVKEVEEIEEEVEKEVEKVGKTEMTLF
(SEQ ID NO: 60) AIZ75647.1       RDFSKFIRTDNTCGPEPPLVERLEKTLEEGERNIIEEVKQIEGEVE----KVEQTELTLL
(SEQ ID NO: 61) XP_009379699.1   RDFSKFIRTDNTCGPEPPLVERLEKTIEEGERTIIEEVKQIEGEVE----KVEQTELTLF
(SEQ ID NO: 62) AMJ39491.1       RDFNKFIKTDNTCGPEPPLVERLEKKVEEGEETIIREVEQLEGQVE----KVGKTEMTLF
(SEQ ID NO: 63) EOY10737.1       RDFNKFIRTDNTCGPEPPLVERLEKKVEEGEQTLIREVKEIEGEVEKEVKRVEKTEMTLF
(SEQ ID NO: 64) XP_017627747.1   RNFNKFIRTDNSCGPEPPLVERLEKKVEEGEQTLIREVEQIEGEVEKGVEKVEKTEQTLF
(SEQ ID NO: 65) XP_016673034.1   RNFNKFIRTDNSCGPEPPLVERLEKKVEEGEQTLIREVEQIEGEVEKGVEKVEKTEQTLF
(SEQ ID NO: 66) XP_002319136.2   RDFSKFIRTDNTCGPEPPLVERLEKTVEEGEKTIIKEVEEIEQKVE----KAGKTELSLF
(SEQ ID NO: 67) OAY41983.1       RDFSKFIRTDNTCGPEPPLVERLEKTVEEGEKSIIKEVQEIEGEVE----KVGKTEMTLF
(SEQ ID NO: 68) XP_012092715.1   RDFNKFIITDNTCGPEPPLAERIEKTVEEGEKTIIREVEEIEGNVE----KVGKTEMALF
                                 *:*. *: ***:***** *.**:**.:****. : .:.:::*        :. .** :*:
```

FIG. 24C
(Continued)

```
(SEQ ID NO: 50) XP_010043341.1    QRLTEGFRELRQDEENFLRRLSQEEMEVLNELKMEATEVEKLFGRALPIRKLR
(SEQ ID NO: 51) XP_010528777.1    QRLVEGFKELKQDEENFLQGLNKEEMELLSELKMEASEVEKLFGKALPIRKLR
(SEQ ID NO: 52) XP_010475655.1    QRLAEGFNELRKDEENFMRELSKEEMEFLDEIKMEANEVEKLFGKALPIRKVR
(SEQ ID NO: 53) XP_006307456.1    QRLAEGFNELKQDEENFVRELSKEEMEFLDEIKMEASEVEKLFGKALPIRKVR
(SEQ ID NO: 54) NP_172331.1       QRLAEGFNELKQDEENFVRELSKEEMEFLDEIKMEASEVEKLFGKALPIRKVR
(SEQ ID NO: 55) XP_002889702.1    QRLAEGFNELKQDEENFVREFSKEEMEFLDEIKMEASEIEKLFGKALPIRKVR
(SEQ ID NO: 56) XP_013641072.1    QRLAEGFEELKQDEENFLRGLSKEEMELLDELKMEANEVEKLFGKALPIRKFR
(SEQ ID NO: 57) XP_009148110.2    QRLAEGFEELKQDEENFLRGLSKEEMELLDELKMEANEVEKLFGKALPIRKFR
(SEQ ID NO: 58) JAU20005.1        QRLAEGFNELKQDEENFLRGLSEEEMALLDELKMEAGEVEKLFGKALPIRKFR
(SEQ ID NO: 59) XP_006417674.1    QRLAEGFNELKQDEENFLRGLSEEEMELLNELKMEASEVEKLFGKSLPIRKVR
(SEQ ID NO: 60) AIZ75647.1        QKLAEGFNELKQDEENFLRGLSKEEMDILSELKMEAGEVEKLFGQTLPLRKLR
(SEQ ID NO: 61) XP_009379699.1    QKLLEGFNVLKQDEENFLRGLSKEEMDLLSELKMEAGEVGKLFGKTLPLRKLR
(SEQ ID NO: 62) AMJ39491.1        QKLAEGFKELQKDEENFLEELSKEEMDVLSELKMEAREVEKLFGGALPLRKLR
(SEQ ID NO: 63) EOY10737.1        QKLAEGFKELQQDEENFLRGLSKEEMGLLNELKMEASEVEKLFGEALPLRKLR
(SEQ ID NO: 64) XP_017627747.1    QRLAEGFKELQQDEENFLRGLSKEEMELLNDLKMEASEVEKLFGEALPIRKLR
(SEQ ID NO: 65) XP_016673034.1    QRLAEGFKELQQDEENFLRGLSKEEMELLNDLKMEASEVEKLFGEALPIRKLR
(SEQ ID NO: 66) XP_002319136.2    QRLTEGFKEIQKDEENFLRELSKEETDLLNDLRMEAGEVEKLFGRALPIRKLR
(SEQ ID NO: 67) OAY41983.1        QRLAEGFKELQQDEEILLRKLSKEEMELFNDLKMEASEVEKLFGGALPLRKLR
(SEQ ID NO: 68) XP_012092715.1    QRLAEGFKELQQDEEFFVRELSKEEMDILNDLKMEAGEVEKLFGEALPLRKLR
                                  *:* ***. :::*** ::. :.:**  .:.:::*** *: **** :**:**.*
```

FIG. 24C
(Continued)

TRANSGENIC PLANTS WITH INCREASED PHOTOSYNTHESIS EFFICIENCY AND GROWTH

CROSS REFERENCE TO RELATED APPLICATIONS

This application is a continuation of U.S. application Ser. No. 16/304,633, filed Nov. 26, 2018, which is the § 371 U.S. National Stage of International Application No. PCT/US2017/034840, filed May 26, 2017, which was published in English under PCT Article 21(2), which claims the benefit of U.S. Provisional Application. No. 62/342,248, filed May 27, 2016, all of which are hereby incorporated by reference in their entireties.

SUBMISSION OF SEQUENCE LISTING AS AN XML FILE

This application contains references to nucleic acid sequences that have been submitted as the sequence listing ST26 format XML file "BERK-497CON_seqlist.xml, created Jul. 8, 2024, and has a file size of 94,140 bytes, which is incorporated by reference in its entirety pursuant to 37 C.F.R. § 1.52 (e) (5).

FIELD OF THE INVENTION

The present invention relates to a method of increasing plant photosynthetic efficiency and growth.

BACKGROUND

Light intensity in plant canopies is very dynamic and leaves routinely experience sharp fluctuations in levels of absorbed irradiance. Several photo-protective mechanisms are induced to protect the photosynthetic antenna complexes from over-excitation when light intensity is too high or increases too fast for photochemistry to utilize the absorbed energy. Excess excitation energy in the photosystem II (PSII) antenna complex is harmlessly dissipated as heat through an inducible protective process, which is observable and often named as non-photochemical quenching of chlorophyll fluorescence (NPQ; Müller et al. Plant Physiol. Vol 125, 1558-1566, 2000). Changes in NPQ can be fast but not instantaneous, and therefore lag behind fluctuations in absorbed irradiance. The rate of NPQ relaxation is considerably slower than the rate of induction, and this asymmetry is exacerbated by prolonged or repeated exposure to excessive light conditions. This relatively slow rate of recovery of PSII antennae from the quenched to the unquenched state may imply that photosynthetic quantum yield and associated $CO_2$ fixation are transiently limited by NPQ upon a change from high to low light intensity. When this hypothesis was tested in model simulations and integrated over a crop canopy, corresponding losses of $CO_2$ fixation were estimated to range between 7.5%-30% (Zhu et al. J. Exp. Bot. Vol 55, 1167-1175, 2004). Based on these computations, increasing the relaxation rate of NPQ suggests a possible strategy to improve photosynthetic efficiency, however experimental proof has so far been lacking.

While the exact NPQ quenching site and nature of the quenching mechanisms involved are still being elucidated, it is clear that for NPQ to occur, PSII-associated antennae need to undergo a conformational change to the quenched state, which can be induced by a number of different mechanisms with contrasting time constants. The predominant and universally present mechanism of NPQ in higher plants is so-called energy-dependent quenching (qE). Induction of qE requires low thylakoid lumen pH and is greatly aided by the presence of photosystem II subunit S (PsbS) and de-epoxidation of violaxanthin to antheraxanthin and zeaxanthin via the reversible xanthophyll pigment cycle.

Overexpression of PsbS strongly affects the amplitude of qE formation, and results in an increased rate of induction and relaxation of qE, but can compete with photosynthetic quantum yield under less stressful conditions. Thus, while the enhancement of qE via PsbS overexpression may offer increased photoprotection under high light or rapidly fluctuating conditions, the positive effects of PsbS overexpression alone on $CO_2$ fixation and plant growth, will depend greatly on the prevailing light environment. An alternative route of NPQ manipulation is to modify the reversible xanthophyll pigment cycle. A schematic representation of the pathway for the biosynthesis of carotenoids (carotenes and xanthophylls) from lycopene is shown in FIG. 17. Zeaxanthin accumulation is associated with several NPQ components (qE, qZ, and qI). The conversion of violaxanthin to zeaxanthin in excess light is catalyzed by the enzyme violaxanthin de-epoxidase (VDE). The conversion of zeaxanthin to violaxanthin is catalyzed by the enzyme zeaxanthin epoxidase (ZEP). *Arabidopsis* mutants with increased xanthophyll pigment pool size were shown to have slower rates of NPQ formation and relaxation while the amplitude of NPQ was unaffected. Interestingly, the rate of NPQ formation and relaxation in these mutants and the wild-type control plants appeared to be mainly controlled by the de-epoxidation state of the xanthophyll pigment pool. It was shown by Nilkens et al. Biochimica et Biophysica Acta 1797; 466-475 (2010) that in particular the kinetics of zeaxanthin epoxidation are strongly correlated with the rate of NPQ relaxation. Therefore, the rate of adjustment of xanthophyll cycle equilibrium also has control over the rate of NPQ formation and relaxation, and seems to be affected by the xanthophyll pool size relative to the rate of turn-over by violaxanthin de-epoxidase (VDE) and zeaxanthin epoxidase (ZEP).

It is yet to be determined whether NPQ can be manipulated to reduce transient competition with photosynthetic quantum yield at low light intensity, while maintaining photo-protection at high light intensity. Plants having improved quantum yield and $CO_2$ fixation under fluctuating light conditions could provide improved plant growth and crop yields.

BRIEF SUMMARY

One aspect of the present disclosure relates to a transgenic plant having one or more heterologous nucleotide sequences encoding PsbS, ZEP and/or VDE. In some embodiments, the nucleotide sequences are derived from a dicot plant. In some embodiments, the nucleotide sequences are derived from *Arabidopsis thaliana*. In some embodiments, the transgenic plant has one or more heterologous nucleotide sequences encoding PsbS, ZEP and VDE. In some embodiments, PsbS is encoded by the nucleotide sequence of SEQ ID NO: 1. In some embodiments, ZEP is encoded by the nucleotide sequence of SEQ ID NO: 2. In some embodiments, VDE is e encoded by the nucleotide sequence of SEQ ID NO: 3. In some embodiments, PsbS is encoded by a nucleotide sequence having at least 90% of sequence identity to SEQ ID NO: 1. In some embodiments, ZEP is encoded by a nucleotide sequence having at least 90% of sequence identity to SEQ ID NO: 2. In some embodiments, VDE is encoded by a nucleotide sequence having at least 90% of sequence identity to SEQ ID NO: 3. In some embodiments, PsbS is encoded by a nucleotide sequence having at least 70% of sequence identity to SEQ ID NO: 1. In some embodiments, ZEP is encoded by a nucleotide sequence having at least 70% of sequence identity to SEQ ID NO: 2. In some embodiments, VDE is encoded by a nucleotide sequence having at least 70% of sequence identity to SEQ ID NO: 3. In some embodiments, PsbS has the amino acid sequence of SEQ ID NO: 4. In some embodiments, ZEP has the amino acid sequence of SEQ ID NO:5. In some embodiments, VDE has the amino acid sequence of SEQ ID NO: 6. In some embodiments, PsbS has an amino acid sequence having at least 90% of sequence identity to SEQ ID NO: 4. In some embodiments, ZEP has an amino acid sequence having at least 90% of sequence identity to SEQ ID NO: 5. In some embodiments, VDE has an amino acid sequence having at least 90% of sequence identity to SEQ ID NO: 6. In some embodiments, PsbS has an amino acid sequence having at least 70% of sequence identity to SEQ ID NO: 4. In some embodiments, ZEP has an amino acid sequence having at least 70% of sequence identity to SEQ ID NO: 5. In some embodiments, VDE has an amino acid sequence having at least 70% of sequence identity to SEQ ID NO: 6. In some embodiments, PsbS further comprises a conserved domain of SEQ ID NO: 7. In some embodiments, ZEP further comprises a conserved domain of SEQ ID NO:8. In some embodiments, VDE further comprises a conserved domain of SEQ ID NO: 9. In some of the embodiments described above, the plant is a crop plant, a model plant, a monocotyledonous plant, a dicotyledonous plant, a plant with Crassulacean acid metabolism (CAM) photosynthesis, a plant with C3 photosynthesis, a plant with C4 photosynthesis, an annual plant, a greenhouse plant, a horticultural flowering plant, a perennial plant, a switchgrass plant, a maize plant, a biomass plant, or a sugarcane plant. In some of the embodiments described above, the plant is switchgrass, *Miscanthus, Medicago*, sweet sorghum, grain sorghum, sugarcane, energy cane, elephant grass, maize, cassava, cowpea, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, a vegetable crop, a forage crop, an industrial crop, a woody crop or a biomass crop. In some embodiments, the plant is *Nicotiana tabacum*. In some embodiments, the plant is *Zea mays*. In some embodiments, the plant is *Oryza sativa*. In some embodiments, the plant is *Sorghum bicolor*. In some embodiments, the plant is *Glycine max*. In some embodiments, the plant is *Vigna unguiculata*. In some embodiments, the plant is *Populus* spp. In some embodiments, the plant is *Eucalyptus* spp. In some embodiments, the plant is *Manihot esculenta*. In some embodiments, the plant is *Hordeum vulgare*. In some embodiments, the plant is *Solanum tuberosum*. In some embodiments, the plant is *Saccharum* spp. In some embodiments, the plant is *Medicago sativa*. In some of the embodiments described above, the plant has increased growth under fluctuating light conditions as compared to a control plant under fluctuating light conditions. In some of the embodiments described above, the plant has increased photosynthetic efficiency under fluctuating light conditions as compared to a control plant under fluctuating light conditions. In some of the embodiments described above, the plant has improved photoprotection efficiency under fluctuating light conditions as compared to a control plant under fluctuating light conditions. In some of the embodiments described above, the plant has improved quantum yield and $CO_2$ fixation under fluctuating light conditions as compared to a control plant under fluctuating light conditions. In some of the embodiments described above, the plant is an elite line or elite strain. In some of the embodiments described above, the plant further comprises expression of at least one additional polypeptide that provides herbicide resistance, insect or pest resistance, disease resistance, modified fatty acid metabolism, and/or modified carbohydrate metabolism.

Another aspect of the present disclosure relates to an expression vector having one or more heterologous nucleotide sequences that encode PsbS, ZEP and/or VDE. In some embodiments, the vector contains a promoter of Rbcs1A, GAPA-1 or FBA2. In some embodiments, the Rbcs1A promoter drives expression of ZEP, a GAPA-1 promoter drives expression of PsbS, and an FBA2 promoter drives expression of VDE. In some embodiments, the vector is a T-DNA. In some embodiments, the vector has a nucleotide sequence encoding polypeptide that provides antibiotic resistance. In some embodiments, the vector has a left border (LB) and right border (RB) domain flanking the expression control sequences and the nucleotide sequence encoding the PsbS, ZEP and VDE polypeptides. In some embodiments, PsbS is encoded by the nucleotide sequence of SEQ ID NO: 1. In some embodiments, ZEP is encoded by the nucleotide sequence of SEQ ID NO: 2. In some embodiments, VDE is e encoded by the nucleotide sequence of SEQ ID NO: 3. In some embodiments, PsbS is encoded by a nucleotide sequence having at least 90% of sequence identity to SEQ ID NO: 1. In some embodiments, ZEP is encoded by a nucleotide sequence having at least 90% of sequence identity to SEQ ID NO: 2. In some embodiments, VDE is encoded by a nucleotide sequence having at least 90% of sequence identity to SEQ ID NO: 3. In some embodiments, PsbS is encoded by a nucleotide sequence having at least 70% of sequence identity to SEQ ID NO: 1. In some embodiments, ZEP is encoded by a nucleotide sequence having at least 70% of sequence identity to SEQ ID NO: 2. In some embodiments, VDE is encoded by a nucleotide sequence having at least 70% of sequence identity to SEQ ID NO: 3. In some embodiments, PsbS has the amino acid sequence of SEQ ID NO: 4. In some embodiments, ZEP has the amino acid sequence of SEQ ID NO:5. In some embodiments, VDE has the amino acid sequence of SEQ ID NO: 6. In some embodiments, PsbS has an amino acid sequence having at least 90% of sequence identity to SEQ ID NO: 4. In some embodiments, ZEP has an amino acid sequence having at least 90% of sequence identity to SEQ ID NO: 5. In some embodiments, VDE has an amino acid sequence having at least 90% of sequence identity to SEQ ID NO: 6. In some embodiments, PsbS has an amino acid sequence having at least 70% of sequence identity to SEQ ID NO: 4. In some embodiments, ZEP has an amino acid sequence having at least 70% of sequence identity to SEQ ID NO: 5. In some embodiments, VDE has an amino acid sequence having at least 70% of sequence identity to SEQ ID NO: 6. In some embodiments, PsbS further comprises a conserved domain of SEQ ID NO: 7. In some embodiments, ZEP further comprises a conserved domain of SEQ ID NO:8. In some embodiments, VDE further comprises a conserved domain of SEQ ID NO: 9. In some embodiments, the expression vector is in a bacterial cell. In some of the embodiments described above, the expression vector is in an *Agrobacterium* cell. In some of the embodiments described above, the expression vector is used to produce a transgenic plant. In some of the embodiments described above, the transgenic plant produces a seed. In some of the embodiments described above, the seed further produces a progeny plant.

Other aspects of the present disclosure relate to methods of increasing photosynthesis and growth in a plant, the methods including increasing expression in the plant of two or more polypeptides described herein. In one aspect, the present disclosure relates to a method for increasing growth in a plant under fluctuating light conditions, including increasing expression in the plant of at least two polypeptides from PsbS, ZEP and VDE, thereby producing a plant with increased expression of the two or more polypeptides as compared to a control plant. In one aspect, the present disclosure relates to a method for increasing photosynthetic efficiency in a plant under fluctuating light conditions, including increasing expression in the plant of at least two polypeptides from PsbS, ZEP and VDE, thereby producing a plant with increased expression of the two or more polypeptides as compared to a control plant. In one aspect, the present disclosure relates to a method for increasing photoprotection efficiency in a plant under fluctuating light conditions, including increasing expression in the plant of at least two polypeptides from PsbS, ZEP and VDE, thereby producing a plant with increased expression of the two or more polypeptides as compared to a control plant. In one aspect, the present disclosure relates to a method for increasing quantum yield and $CO_2$ in a plant under fluctuating light conditions, including increasing expression in the plant of at least two polypeptides from PsbS, ZEP and VDE, thereby producing a plant with increased expression of the two or more polypeptides as compared to a control plant. In one aspect, the present disclosure relates to a method for increasing the rate of relaxation of non-photochemical quenching (NPQ) in a plant, including increasing expression in the plant of at least two polypeptides from PsbS, ZEP and VDE, thereby producing a plant with increased expression of the two or more polypeptides as compared to a control plant. In some embodiments, expression is increased in PsbS and ZEP. In some embodiments, expression is increased in PsbS and VDE. In some embodiments, expression is increased in VDE and ZEP. In some embodiments, expression is increased in PsbS, ZEP and VDE. In some embodiments, expression of PsbS, ZEP and/or VDE is increased by expressing one or more heterologous nucleotide sequences encoding PsbS, ZEP and/or VDE. In some embodiments, expression of PsbS, ZEP and/or VDE is increased by modifying the promoter region of PsbS, ZEP and/or VDE. In some embodiments, promoter modification is achieved by a genome editing system. In some embodiments, the genome editing system is CRISPR.

Another aspect of the present disclosure relates to a method of selecting a plant for improved growth characteristics under fluctuating light conditions, including the steps of providing a population of plants; modifying the population of plants to increase the activity of any of PsbS, ZEP and VDE; detecting the level of non-photochemical quenching (NPQ) under fluctuating light conditions in a plant; comparing the level of NPQ under fluctuating light conditions in a plant with the control level of NPQ under fluctuating light conditions; and selecting a plant having increased rate of NPQ relaxation when the plant is transitioned from under high light intensity to low light intensity. In some embodiments, the control level of NPQ is the lowest level of NPQ in the population. In some embodiments, the control level of NPQ is the median level of NPQ in the population. In some embodiments, the control level of NPQ is the mean level of NPQ in the population. In some embodiments, the control level of NPQ is the level of NPQ in a control plant. In some embodiments, the plants are modified by inducing one or more mutations in PsbS, ZEP and/or VDE with a mutagen. In some embodiments, the mutagen is ethane methyl sulfonate (EMS). In some embodiments, the plants are modified by introducing heterologous PsbS, ZEP and/VDE using transgenic techniques. In some embodiments, the plants are modified by modifying the respective native promoters of PsbS, ZEP and/VDE using a genome editing system. In some embodiments, the genome editing system is CRISPR. Another aspect of the present disclosure relates to a method of screening for a nucleotide sequence polymorphism associated with improved growth characteristics under fluctuating light conditions, including the steps of providing a population of plants; obtaining the nucleotide sequences regulating and/or encoding any of PsbS, ZEP and VDE in the population of plants; obtaining one or more polymorphisms in the nucleotide sequences regulating and/or encoding any of PsbS, ZEP and VDE in the population of plants; detecting the rate of non-photochemical quenching (NPQ) relaxation upon transition from high light intensity to low light intensity in the population of plants; performing statistical analysis to determine association of the polymorphism with the rate of NPQ relaxation in the population of plants; and selecting the polymorphism having statistically significant association with the rate of NPQ relaxation. In some embodiments, the polymorphism is a single nucleotide polymorphism (SNP). In some embodiments, the polymorphism is located in the promoter of PsbS, ZEP and/or VDE. In some embodiments, the polymorphism is detected by sequence determination. In some embodiments, the polymorphism is detected by gel electrophoresis. In some embodiments, the polymorphism is further used to screen a population of plants to select a plant having improved growth characteristics under fluctuating light conditions. In some embodiments, the polymorphism is further used as a target for genome editing in PsbS, ZEP and/or VDE to improve growth characteristics in a plant under fluctuating light conditions. In some of the embodiments described above, the improved growth characteristic is improved growth, improved photosynthetic efficiency, improved photoprotection efficiency, improved quantum yield and/or improved CO2 fixation. In some of the embodiments described above, NPQ in a plant is detected by measuring chlorophyll fluorescence.

In some of the embodiments described above, the improved growth characteristic is improved growth. In some embodiments, the improved growth characteristic is improved photosynthetic efficiency. In some embodiments, the improved growth characteristic is improved photoprotection efficiency. In some embodiments, the improved growth characteristic is improved quantum yield and $CO_2$ fixation. In some embodiments, the improved growth characteristic is increased rate of relaxation of non-photochemical quenching (NPQ). In some embodiments, NPQ is detected using chlorophyll fluorescence imaging.

In some embodiments that may be combined with any of the preceding embodiments, PsbS is encoded by the nucleotide sequence of SEQ ID NO: 1. In some embodiments that may be combined with any of the preceding embodiments, ZEP is encoded by the nucleotide sequence of SEQ ID NO: 2. In some embodiments that may be combined with any of the preceding embodiments, VDE is e encoded by the nucleotide sequence of SEQ ID NO: 3. In some embodiments that may be combined with any of the preceding embodiments, PsbS is encoded by a nucleotide sequence having at least 90% of sequence identity to SEQ ID NO: 1.

In some embodiments that may be combined with any of the preceding embodiments, ZEP is encoded by a nucleotide sequence having at least 90% of sequence identity to SEQ ID NO: 2. In some embodiments that may be combined with any of the preceding embodiments, VDE is encoded by a nucleotide sequence having at least 90% of sequence identity to SEQ ID NO: 3. In some embodiments that may be combined with any of the preceding embodiments, PsbS is encoded by a nucleotide sequence having at least 70% of sequence identity to SEQ ID NO: 1. In some embodiments that may be combined with any of the preceding embodiments, ZEP is encoded by a nucleotide sequence having at least 70% of sequence identity to SEQ ID NO: 2. In some embodiments that may be combined with any of the preceding embodiments, VDE is encoded by a nucleotide sequence having at least 70% of sequence identity to SEQ ID NO: 3. In some embodiments that may be combined with any of the preceding embodiments, PsbS has the amino acid sequence of SEQ ID NO: 4. In some embodiments that may be combined with any of the preceding embodiments, ZEP has the amino acid sequence of SEQ ID NO:5. In some embodiments that may be combined with any of the preceding embodiments, VDE has the amino acid sequence of SEQ ID NO: 6. In some embodiments that may be combined with any of the preceding embodiments, PsbS has an amino acid sequence having at least 90% of sequence identity to SEQ ID NO: 4. In some embodiments that may be combined with any of the preceding embodiments, ZEP has an amino acid sequence having at least 90% of sequence identity to SEQ ID NO: 5. In some embodiments that may be combined with any of the preceding embodiments, VDE has an amino acid sequence having at least 90% of sequence identity to SEQ ID NO: 6. In some embodiments that may be combined with any of the preceding embodiments, PsbS has an amino acid sequence having at least 70% of sequence identity to SEQ ID NO: 4. In some embodiments that may be combined with any of the preceding embodiments, ZEP has an amino acid sequence having at least 70% of sequence identity to SEQ ID NO: 5. In some embodiments that may be combined with any of the preceding embodiments, VDE has an amino acid sequence having at least 70% of sequence identity to SEQ ID NO: 6. In some embodiments that may be combined with any of the preceding embodiments, PsbS further comprises a conserved domain of SEQ ID NO: 7. In some embodiments that may be combined with any of the preceding embodiments, ZEP further comprises a conserved domain of SEQ ID NO:8. In some embodiments that may be combined with any of the preceding embodiments, VDE further comprises a conserved domain of SEQ ID NO: 9. In some embodiments that may be combined with any of the preceding embodiments, the plant is a crop plant, a model plant, a monocotyledonous plant, a dicotyledonous plant, a plant with Crassulacean acid metabolism (CAM) photosynthesis, a plant with C3 photosynthesis, a plant with C4 photosynthesis, an annual plant, a greenhouse plant, a horticultural flowering plant, a perennial plant, a switchgrass plant, a maize plant, a biomass plant, or a sugarcane plant. In some embodiments that may be combined with any of the preceding embodiments, the plant is switchgrass, *Miscanthus, Medicago*, sweet sorghum, grain sorghum, sugarcane, energy cane, elephant grass, maize, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, a vegetable crop, a forage crop, an industrial crop, a woody crop or a biomass crops. In some embodiments that may be combined with any of the preceding embodiments, the plant is *Nicotiana tabacum*. In some embodiments that may be combined with any of the preceding embodiments, the plant is *Zea mays*. In some embodiments that may be combined with any of the preceding embodiments, the plant is *Oryza sativa*. In some embodiments that may be combined with any of the preceding embodiments, the plant is *Sorghum bicolor*. In some embodiments that may be combined with any of the preceding embodiments, the plant is *Glycine max*. In some embodiments that may be combined with any of the preceding embodiments, the plant is *Vigna unguiculata*. In some embodiments that may be combined with any of the preceding embodiments, the plant is *Populus* spp. In some embodiments that may be combined with any of the preceding embodiments, the plant is *Eucalyptus* spp. In some embodiments that may be combined with any of the preceding embodiments, the plant is *Manihot esculenta*. In some embodiments that may be combined with any of the preceding embodiments, the plant is *Hordeum vulgare*. In some embodiments that may be combined with any of the preceding embodiments, the plant is *Solanum tuberosum*. In some embodiments that may be combined with any of the preceding embodiments, the plant is *Saccharum* spp. In some embodiments that may be combined with any of the preceding embodiments, the plant is *Medicago sativa*.

In some embodiments that may be combined with any of the preceding embodiments, the transcript level of VDE in the plant is increased 3-fold as compared to a control plant. In some embodiments that may be combined with any of the preceding embodiments, the transcript level of PsbS in the plant is increased 3-fold as compared to a control plant. In some embodiments that may be combined with any of the preceding embodiments, the transcript level of ZEP in the plant is increased 8-fold as compared to a control plant. In some embodiments that may be combined with any of the preceding embodiments, the transcript level of VDE in the plant is increased 10-fold as compared to a control plant. In some embodiments that may be combined with any of the preceding embodiments, the transcript level of PsbS in the plant is increased 3-fold as compared to a control plant. In some embodiments that may be combined with any of the preceding embodiments, the transcript level of ZEP in the plant is increased 6-fold as compared to a control plant. In some embodiments that may be combined with any of the preceding embodiments, the transcript level of VDE in the plant is increased 4-fold as compared to a control plant. In some embodiments that may be combined with any of the preceding embodiments, the transcript level of PsbS in the plant is increased 1.2-fold as compared to a control plant. In some embodiments that may be combined with any of the preceding embodiments, the transcript level of ZEP in the plant is increased 7-fold as compared to a control plant. In some embodiments that may be combined with any of the preceding embodiments, the protein level of VDE in the plant is increased 16-fold as compared to a control plant. In some embodiments that may be combined with any of the preceding embodiments, the protein level of PsbS in the plant is increased 2-fold as compared to a control plant. In some embodiments that may be combined with any of the preceding embodiments, the protein level of ZEP in the plant is increased 80-fold as compared to a control plant. In some embodiments that may be combined with any of the preceding embodiments, the protein level of VDE in the plant is increased 30-fold as compared to a control plant. In some embodiments that may be combined with any of the preceding embodiments, the protein level of PsbS in the plant is increased 4-fold as compared to a control plant. In some embodiments that may be combined with any of the preceding embodiments, the protein level of ZEP in the plant is increased 74-fold as compared to a control plant. In some embodiments that may be combined with any of the preceding embodiments, the protein level of VDE in the plant is increased 47-fold as compared to a control plant. In some embodiments that may be combined with any of the preceding embodiments, the protein level of PsbS in the plant is increased 3-fold as compared to a control plant. In some embodiments that may be combined with any of the preceding embodiments, the protein level of ZEP in the plant is increased 75-fold as compared to a control plant. In some embodiments that may be combined with any of the preceding embodiments, the increase of transcript level in the plant as compared to a control plant between VDE, PsbS and ZEP has a ratio of 3:3:8, 10:3:6, or 4:1.2:7. In some embodiments that may be combined with any of the preceding embodiments, the increase of protein level in the plant as compared to a control plant between VDE, PsbS and ZEP has a ratio of 16:2:80, 30:4:74, or 47:3:75. In some embodiments that may be combined with any of the preceding embodiments, the increase of transcript level of VDE in the plant as compared to a control plant is in the range of 3-fold to 10-fold. In some embodiments that may be combined with any of the preceding embodiments, the increase of transcript level of PsbS in the plant as compared to a control plant is from about 1.2-fold to about 3-fold. In some embodiments that may be combined with any of the preceding embodiments, the increase of transcript level of ZEP in the plant as compared to a control plant is from about 6-fold to about 8-fold. In some embodiments that may be combined with any of the preceding embodiments, the increase of protein level of VDE in the plant as compared to a control plant is in the range of 16-fold to 47-fold. In some embodiments that may be combined with any of the preceding embodiments, the increase of protein level of PsbS in the plant as compared to a control plant is from about 2-fold to about 4-fold. In some embodiments that may be combined with any of the preceding embodiments, the increase of protein level of ZEP in the plant as compared to a control plant is from about 74-fold to about 80-fold.

BRIEF DESCRIPTION OF THE DRAWINGS

The features, objects and advantages other than those set forth above will become more readily apparent when consideration is given to the detailed description below. Such detailed description makes reference to the following drawings, wherein:

FIG. 12. Growth experiment comparing VPZ-23 and VPZ-34 transgenic to wild type plants.

FIG. 13. Greenhouse experiment showing significantly increased growth in all lines.

FIG. 16. Time constants of NPQ in the first induction/relaxation.

FIG. 23. Transient overexpression of NbPsbS and Rbcs-laAtZEP+GapalAtPsbS+Fba2AtVDE constructs in *N. benthamiana*.

FIG. 24. Amino acid alignment of NPQ genes in representative plant species for (A) PsbS, (B) ZEP and (C) VDE.

DETAILED DESCRIPTION

Figure 1:
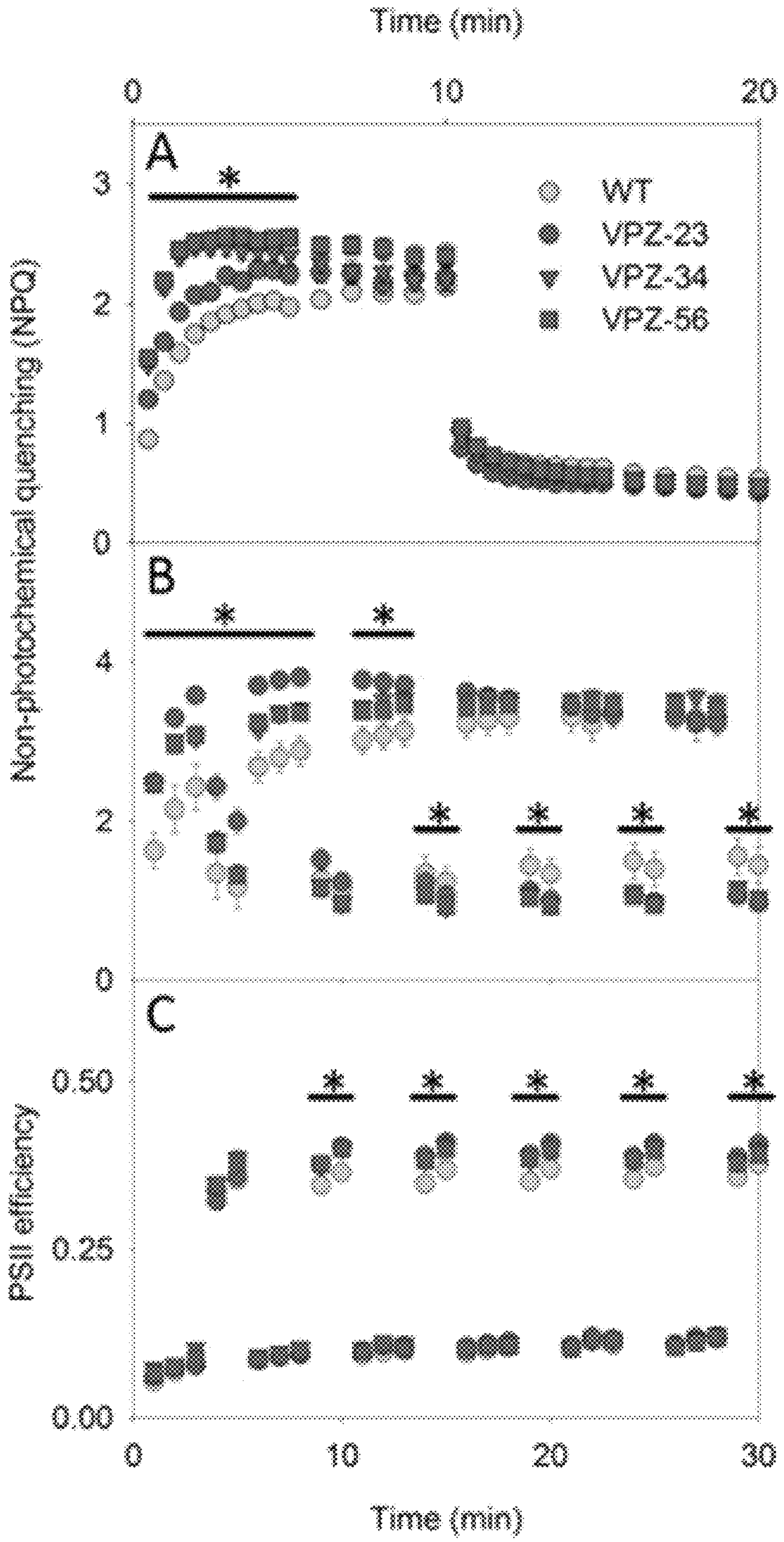
FIG. 1. (A) Non-photochemical quenching in young seedlings of wild-type and three (VDE-PsbS-ZEP) VPZ overexpressing lines during 10 min illumination with 1000 μmol $m^{-2}$ $s^{-1}$ PFD, followed by 10 min of dark relaxation. (B) Non-photochemical quenching and (C) PSII efficiency in young seedlings during repeated cycles of 3 min illumination with 2000 μmol $m^{-2}$ $s^{-1}$ PFD, followed by 2 min of 200 μmol $m^{-2}$ $s^{-1}$ PFD. Error bars indicate ±se (n=18), asterisks indicate significant differences between VPZ lines and wild-type (α=0.05).

The plants, vectors, and methods now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the plants, vectors, and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Definitions

Unless otherwise noted, technical terms are used according to conventional usage. Definitions of common terms in molecular biology may be found in Lewin, Genes VII, 2001 (Oxford University Press), The Encyclopedia of Molecular Biology, Kendrew et al, eds., 1999 (Wiley-Interscience) and Molecular Biology and Biotechnology, a Comprehensive Desk Reference, Robert A. Meyers, ed., 1995 (VCH Publishers. Inc), Current Protocols In Molecular Biology, F. M. Ausubel et al., eds., 1987 (Green Publishing), Sambrook and Russell, Molecular Cloning: A Laboratory Manual, 3rd edition, 2001.

The terms "polynucleotide", "nucleotide", "nucleotide sequence", "nucleic acid", "gene," and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, a "vector" is a replicon, such as a plasmid, phage, or cosmid, into which another DNA segment may be inserted so as to bring about the replication of the inserted segment. The vectors described herein can be expression vectors.

As used herein, an "expression vector" is a vector that includes one or more expression control sequences.

As used herein, an "expression control sequence" or "expression cassette" is a DNA sequence that controls and regulates the transcription and/or translation of another DNA sequence. The expression control sequence can comprise a heterologous or non-heterologous promoter.

As used herein, "operably linked" means incorporated into a genetic construct so that expression control sequences effectively control expression of a coding sequence of interest.

As used herein, "transformed" and "transfected" encompass the introduction of a nucleic acid (e.g., a vector) into a cell by a number of techniques known in the art.

"Plasmids" are designated by a lower case "p" preceded and/or followed by capital letters and/or numbers.

As used herein, the term "level of expression" refers to the measurable expression level of a given nucleic acid or polypeptide. The level of expression of a given nucleic acid or polypeptide is determined by methods well known in the art. The term "differentially expressed" or "differential expression" refers to an increase or decrease in the measurable expression level of a given a given nucleic acid or polypeptide. "Differentially expressed" or "differential expression" means a 1-fold, or more, up to and including 2-fold, 5-fold, 10-fold, 20-fold, 50-fold or more difference in the level of expression of a given nucleic acid or polypeptide in two samples used for comparison. A given nucleic acid or polypeptide is also said to be "differentially expressed" in two samples if one of the two samples contains no detectable expression of a given nucleic acid or polypeptide.

Polymorphism refers to variation in nucleotide sequences within a genome that may or may not have a functional consequence. These variants can be developed as genetic markers and used in all aspects of genetic investigation including the analysis of associating genetic differences with variation in traits of interest. As used herein, the term "polymorphism" includes, but is not limited to, single nucleotide polymorphism (SNP), insertion/deletion (InDel), simple sequence repeats (SSR), presence/absence variation (PAV), and copy number variation (CNV). Polymorphisms can be naturally occurring or artificially induced. The methods of inducing and detecting polymorphisms are well known in the art.

As used herein, the term "promoter" refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. As is well-known in the art, promoters can be categorized according to their strength and/or the conditions under which they are active, e.g., constitutive promoters, strong promoters, weak promoters, inducible/repressible promoters, tissue-specific/developmentally regulated promoters, cell-cycle dependent promoters, etc.

As used herein, the term "genome editing" is a type of genetic engineering in which DNA is inserted, replaced, or removed from a genome using artificially engineered nucleases, or "molecular scissors." It is a useful tool to elucidate the function and effect of a gene in a sequence specific manner, and to make alterations within a genome that result in desirable phenotypic changes. Genome editing systems include, but are not limited to, meganucleases, zinc finger nucleases (ZFN), transcription activator-like effector-based nucleases (TALEN), and the clustered regularly interspaced short palindromic repeats (CRISPR).

The term "plant" refers to any of various photosynthetic, eukaryotic multi-cellular organisms of the kingdom Plantae, characteristically producing embryos, containing chloroplasts, having cellulose cell walls and lacking locomotion. As used herein, a "plant" includes any plant or part of a plant at any stage of development, including seeds, suspension cultures, plant cells, embryos, meristematic regions, callus tissue, leaves, roots, shoots, gametophytes, sporophytes, pollen, microspores, and progeny thereof. Also included are cuttings, and cell or tissue cultures. As used in conjunction with the present disclosure, plant tissue includes, for example, whole plants, plant cells, plant organs, e.g., leafs, stems, roots, meristems, plant seeds, protoplasts, callus, cell cultures, and any groups of plant cells organized into structural and/or functional units.

The term "plant" is used in its broadest sense. It includes, but is not limited to, any species of woody, ornamental or decorative, crop or cereal, fruit or vegetable plant, and algae (e.g., *Chlamydomonas reinhardtii*). It also refers to a plurality of plant cells that is largely differentiated into a structure that is present at any stage of a plant's development. Such structures include, but are not limited to, a fruit, shoot, stem, leaf, flower petal, etc.

The term "control plant" or "wild type" as used herein refers to a plant cell, an explant, seed, plant component, plant tissue, plant organ, or whole plant used to compare against transgenic or genetically modified plant for the purpose of identifying an enhanced phenotype or a desirable trait in the transgenic or genetically modified plant. A "control plant" may in some cases be a transgenic plant line that comprises an empty vector or marker gene, but does not contain the recombinant polynucleotide of interest that is present in the transgenic or genetically modified plant being evaluated. A control plant may be a plant of the same line or variety as the transgenic or genetically modified plant being tested, or it may be another line or variety, such as a plant known to have a specific phenotype, characteristic, or known genotype. A suitable control plant would include a genetically unaltered or non-transgenic plant of the parental line used to generate a transgenic plant herein.

The term "plant tissue" includes differentiated and undifferentiated tissues of plants including those present in roots, shoots, leaves, inflorescences, anthers, pollen, ovaries, seeds and tumors, as well as cells in culture (e.g., single cells, protoplasts, embryos, callus, etc.). Plant tissue may be in planta, in organ culture, tissue culture, or cell culture.

The term "plant part" as used herein refers to a plant structure, a plant organ, or a plant tissue.

A "non-naturally occurring plant" refers to a plant that does not occur in nature without human intervention. Non-naturally occurring plants include transgenic plants, plants created through genetic engineering and plants produced by non-transgenic means such as traditional or market assisted plant breeding.

The term "plant cell" refers to a structural and physiological unit of a plant, comprising a protoplast and a cell wall. The plant cell may be in the form of an isolated single cell or a cultured cell, or as a part of a higher organized unit such as, for example, a plant tissue, a plant organ, or a whole plant. The term "plant cell culture" refers to cultures of plant units such as, for example, protoplasts, cells and cell clusters in a liquid medium or on a solid medium, cells in plant tissues and organs, microspores and pollen, pollen tubes, anthers, ovules, embryo sacs, zygotes and embryos at various stages of development.

The term "plant material" refers to leaves, stems, roots, inflorescences and flowers or flower parts, fruits, pollen, anthers, egg cells, zygotes, seeds, cuttings, cell or tissue cultures, or any other part or product of a plant.

A "plant organ" refers to a distinct and visibly structured and differentiated part of a plant, such as a root, stem, leaf, flower bud, inflorescence, spikelet, floret, seed or embryo.

The term "crop plant", means in particular monocotyledons such as cereals (wheat, millet, sorghum, rye, triticale, oats, barley, teff, spelt, buckwheat, fonio and quinoa), rice, maize (corn), and/or sugar cane; or dicotyledon crops such as beet (such as sugar beet or fodder beet); fruits (such as pomes, stone fruits or soft fruits, for example apples, pears, plums, peaches, almonds, cherries, strawberries, raspberries or blackberries); leguminous plants (such as beans, lentils, peas or soybeans); oil plants (such as rape, mustard, poppy, olives, sunflowers, coconut, castor oil plants, cocoa beans or groundnuts); cucumber plants (such as marrows, cucumbers or melons); fiber plants (such as cotton, flax, hemp or jute); citrus fruit (such as oranges, lemons, grapefruit or mandarins); vegetables (such as spinach, lettuce, cabbages, carrots, tomatoes, potatoes, cucurbits or paprika); lauraceae (such as avocados, cinnamon or camphor); tobacco; nuts; coffee; tea; vines; hops; durian; bananas; natural rubber plants; and ornamentals (such as flowers, shrubs, broad-leaved trees or evergreens, for example conifers). This list does not represent any limitation.

The term "woody crop" or "woody plant" means a plant that produces wood as its structural tissue. Woody crops include trees, shrubs, or lianas. Examples of woody crops include, but are not limited to, thornless locust, hybrid chestnut, black walnut, Japanese maple, eucalyptus, casuarina, spruce, fir, pine (e.g. *Pinus radiata* and *Pinus caribaea*), and flowering dogwood.

The term "improved growth" or "increased growth" is used herein in its broadest sense. It includes any improvement or enhancement in the process of plant growth and development. Examples of improved growth include, but are not limited to, increased photosynthetic efficiency, increased biomass, increased yield, increased seed number, increased seed weight, increased stem height, increased leaf area, and increased plant dry weight, By "quantum yield" it is meant the moles of $CO_2$ fixed per mole of quanta (photons) absorbed, or else the efficiency with which light is converted into fixed carbon. The quantum yield of photosynthesis is derived from measurements of light intensity and rate of photosynthesis. As such, the quantum yield is a measure of the efficiency with which absorbed light produces a particular effect. The amount of photosynthesis performed in a plant cell or plant can be indirectly detected by measuring the amount of starch produced by the transgenic plant or plant cell. The amount of photosynthesis in a plant cell culture or a plant can also be detected using a $CO_2$ detector (e.g., a decrease or consumption of $CO_2$ indicates an increased level of photosynthesis) or a 02 detector (e.g., an increase in the levels of 02 indicates an increased level of photosynthesis (see, e.g., the methods described in Silva et al., Aquatic Biology 7:127-141, 2009; and Bai et al., Biotechnol. Lett. 33:1675-1681, 2011). Photosynthesis can also be measured using radioactively labeled $CO_2$ (e.g., $14CO_2$ and $H_{14}CO_3$—) (see, e.g., the methods described in Silva et al., Aquatic Biology 7:127-141, 2009, and the references cited therein). Photosynthesis can also be measured by detecting the chlorophyll fluorescence (e.g., Silva et al., Aquatic Biology 7:127-141, 2009, and the references cited therein). Additional methods for detecting photosynthesis in a plant are described in Zhang et al., Mol. Biol. Rep. 38:4369-4379, 2011."

In the physical sciences, the term "relaxation" means the return of a perturbed system into equilibrium, usually from a high energy level to a low energy level. As used herein, the term "non-photochemical quenching relaxation" or "NPQ relaxation" refers to the process in which NPQ level decreases upon transition from high light intensity to low light intensity.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X."

Overview

Faced with a fast growing world population, further increases in food production are imperative for global political and societal stability, and as such, a two-fold increase of crop production has been projected necessary to meet this demand by 2050. A better understanding of physiological processes underlying important crop traits such as photosynthesis is hence key to ameliorating world's food security crisis. Photosynthesis is a process used by plants and green algae to convert light energy into chemical energy that can be later released to fuel the organisms' activities, during which atmospheric carbon dioxide ($CO_2$) is assimilated and oxygen is released. The ratio of the amount of $CO_2$ being fixed or assimilated over the amount of photon (quantum) absorbed, also known as quantum yield, is commonly used as a measure of the photosynthetic efficiency of a plant.

Although light is necessary for photosynthesis, damage can occur when leaves are exposed to high light intensity. To avoid this, plants have developed several photoprotective mechanisms. Non-photochemical quenching (NPQ) is one of those mechanisms, which allows excessive absorbed irradiance to be dissipated as heat. However, when a plant is transitioned from high to low light intensity, the quantum yield of photosynthesis is temporarily reduced, due to the fact that NPQ inhibits $CO_2$ fixation. In addition, NPQ turns on (induces) rapidly at high light intensity, but turns off (relaxes) more slowly upon a return to limiting irradiance. As a result, the photosynthetic efficiency and growth of plants under fluctuating light, a common occurrence under natural field conditions, are compromised.

The present disclosure provides a method to speed up the relaxation of NPQ after plants transition from high to low light intensity, thereby allowing a faster recovery of photosynthetic quantum yield of $CO_2$ fixation. This method includes increasing expression of one or more nucleotide sequences encoding photosystem II subunit S (PsbS), zeaxanthin epoxidase (ZEP), and violaxanthin de-epoxidase (VDE). Since this is achieved without reducing the amplitude of NPQ, normal photoprotection under high light intensity is not affected. Under fluctuating light conditions, where plants frequently undergo transitions from high to low light intensity, this method results in improved photoprotection efficiency and in turn photosynthetic efficiency and growth of plants.

The present disclosure further provides a method to genetically engineer plants for improved photosynthesis and growth. An expression vector comprising nucleotide sequences encoding PsbS, ZEP and VDE can be introduced into plants by currently available methods including, but not limited to, protoplast transformation, *Agrobacterium*-mediated transformation, electroporation, microprojectile bombardment. This method may be used to produce transgenic plants with improved photosynthesis and growth in plant species including, but not limited to, tobacco, wheat, maize, rice, soybean, sorghum, cassava, cowpea, poplar, and eucalyptus.

It is well known in the art that mechanisms underlying NPQ response and the associated xanthophyll cycle are highly conserved across plants and green algae. See, e.g. Niyogi K K, Truong T B (2013). Evolution of flexible non-photochemical quenching mechanisms that regulate light harvesting in oxygenic photosynthesis. Curr Op Plant Biol 16: 307-314, Koziol A G, Borza T, Ishida K-I, Keeling P, Lee R W, Durnford D G (2007). Tracing the evolution of the light-harvesting antennae in chlorophyll a/b-containing organisms. Plant Physiol 143: 1802-1816, Engelken J, Brinkmann H, Adamska I (2010). Taxonomic distribution and origins of the extended LHC (light-harvesting complex) antenna protein superfamily. BMC Evol Biol 10: 233, Brooks M D, Jansson S, Niyogi K K (2014). PsbS-dependent non-photochemical quenching. In: Non-photochemical quenching and energy dissipation in plants, algae and cyanobacteria. Demmig-Adams B, Garab G, Adams W W III, Govindjee eds. (Dordrecht: Springer), pp. 297-314, Kasajima I, Ebana K, Yamamoto T, Takahara K, Yano M, Kawai-Yamada M, Uchimiya H (2011). Molecular distinction in genetic regulation of nonphotochemical quenching in rice. Proc Natl Acad Sci USA 108:13835-13840, Alboresi A, Gerotto C, Giacometti G M, Bassi R, Morosinotto T (2010). *Physcomitrella patens* mutants affected on heat dissipation clarify the evolution of photoprotection mechanisms upon land colonization. Proc Natl Acad Sci USA 107:11128-11133, and Goss R, Lepetit B (2015). Biodiversity of NPQ. Journal of Plant Physiology, 172, 13-32. Therefore, methods disclosed in the present invention can be applied to all plants and green algae.

Unless otherwise indicated, the disclosure encompasses all conventional techniques of plant transformation, plant breeding, microbiology, cell biology and recombinant DNA, which are within the skill of the art. See, e.g., Sambrook and Russell, Molecular Cloning: A Laboratory Manual, 3rd edition, 2001; Current Protocols in Molecular Biology, F. M. Ausubel et al. eds., 1987; Plant Breeding: Principles and Prospects, M. D. Hayward et al., 1993; Current Protocols in Protein Science, Coligan et al, eds., 1995, (John Wiley & Sons, Inc.); the series Methods in Enzymology (Academic Press, Inc.): PCR 2: A Practical Approach, M. J. MacPherson, B. D. Hames and G. R. Taylor eds., 1995.

In one aspect, a transgenic plant, or a portion of a plant, or a plant material, or a plant seed, or a plant cell is provided, comprising one or more heterologous nucleotide sequences encoding polypeptides selected from PsbS, ZEP and VDE operably linked to an expression control sequence. In one embodiment, the PsbS polypeptide is encoded by the nucleotide sequence of SEQ ID NO: 1, the ZEP polypeptide is encoded by the nucleotide sequence of SEQ ID NO:2, and the VDE polypeptide is encoded by the nucleotide sequence of SEQ ID NO: 3. In another embodiment, the transgenic plant comprises nucleotide sequences encoding PsbS, ZEP and VDE. The transgenic plant may comprise any combination of at least two of PsbS, ZEP and VDE, or comprise only one of PsbS, ZEP and VDE. The nucleotide sequences may have at least 60%, 65%, 70%, 75%, 80%, 85%, 90%, 95%, or 99% sequence identity to SEQ ID NO: 1, SEQ ID NO:2, and/or SEQ ID NO:3. In another embodiment, the PsbS polypeptide has the amino acid sequence of SEQ ID NO: 4, the ZEP polypeptide has the amino acid sequence of SEQ ID NO:5, and the VDE polypeptide has the amino acid sequence of SEQ ID NO: 6. The polypeptides may be at least 60%, 65%, 70%, 75%, 80%, 85%, 90%, 95%, or 99% amino acid sequence identity to SEQ ID NO: 4, SEQ ID NO:5, or SEQ ID NO:6. Homologues of *Arabidopsis* PsbS, Zep and VDE nucleotides and the polypeptides encoded by the nucleotide sequences exist in most species of plants, and the plants listed below, and may be used in place of the *Arabidopsis* genes.

Enzymes having similar activity to PsbS, ZEP and VDE, or those having conserved domains could alternatively be used, including, but not limited to, homologues in switchgrass, *Miscanthus, Medicago*, sweet sorghum, grain sorghum, sugarcane, energy cane, elephant grass, maize, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, vegetable, forage, industrial, woody and biomass crops. PsbS has a conserved Chloroa_b-binding domain (SEQ ID NO: 7), ZEP comprises a NADB_Rossman and FHA superfamily domain (SEQ ID NO:8), and VDE has a Lipocalin domain (SEQ ID NO:9). Homologues having these domains could also be used.

In another embodiment, the transgenic plant, or a portion of a plant, or a plant material, or a plant seed, or a plant cell is a crop plant, a model plant, a monocotyledonous plant, a dicotyledonous plant, a plant with Crassulacean acid metabolism (CAM) photosynthesis, a plant with C3 photosynthesis, a plant with C4 photosynthesis, an annual plant, a greenhouse plant, a horticultural flowering plant, a perennial plant, a switchgrass plant, a maize plant, a biomass plant, or a sugarcane plant. In another embodiment, the plant is selected from switchgrass, *Miscanthus, Medicago*, sweet sorghum, grain sorghum, sugarcane, energy cane, elephant grass, maize, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, vegetable, forage, industrial, woody and biomass crops. In a further embodiment, the transgenic plant is *Nicotiana tabacum*. In another embodiment, the plant has improved quantum yield and/or $CO_2$ fixation under fluctuating light conditions, and/or improved growth. A balance of level of gene expression can play a role in plant improvements. In one embodiment, VDE and ZEP polypeptides are expressed at relatively similar levels.

In another embodiment, the transgenic plant, or a portion of a plant, or a plant material, or a plant seed, or a plant cell has additional characteristics, for example, herbicide resistance, insect or pest resistance, disease resistance, modified fatty acid metabolism, and/or modified carbohydrate metabolism.

Figure 9:
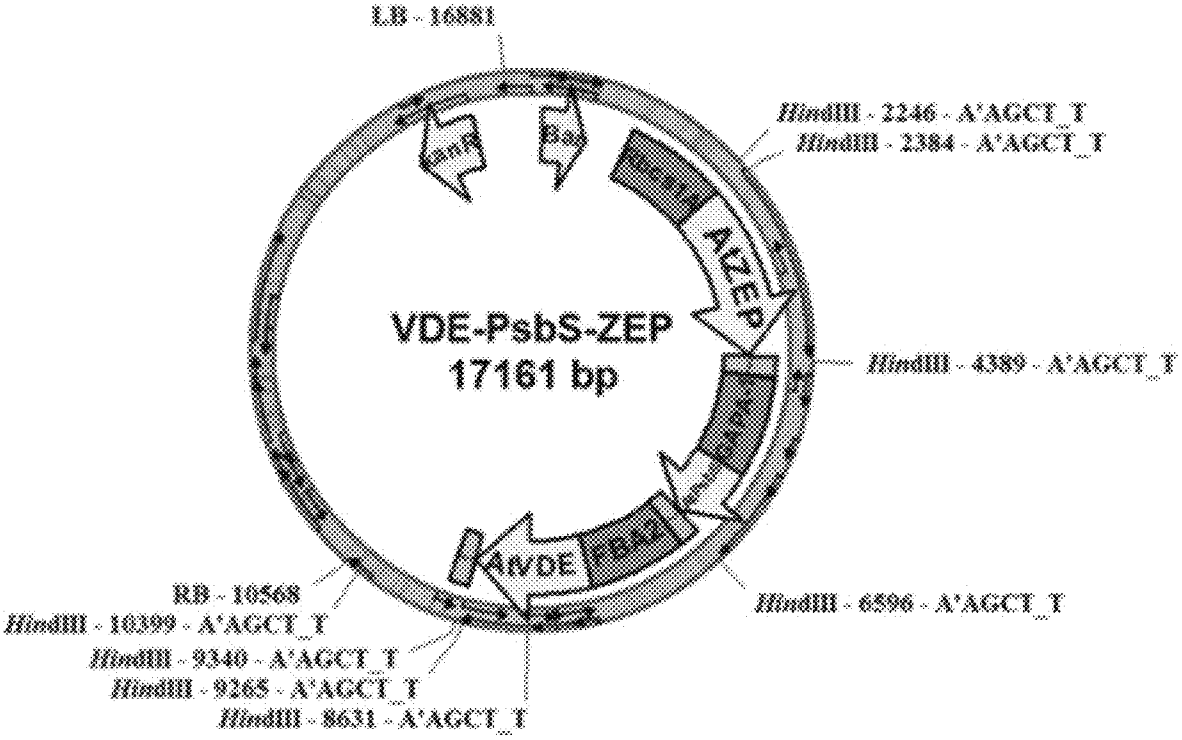
FIG. 9. Plasmid map of VDE-PsbS-ZEP construct.
Figure 10:
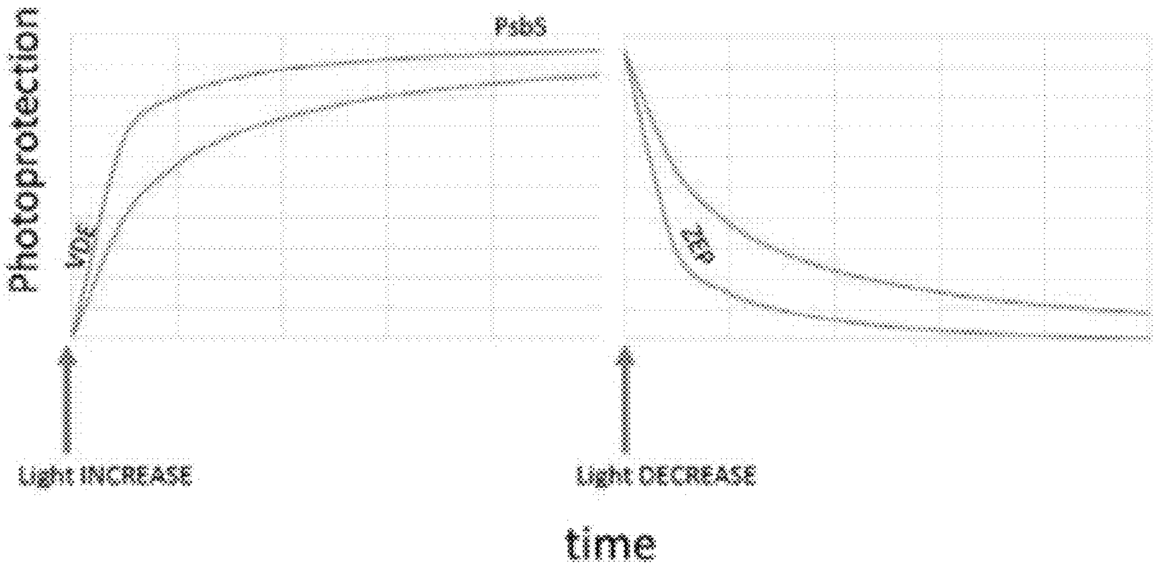
FIG. 10. The intended goal to increase speed in which photoprotection responds to changes in light intensity and the role VDE, PsbS and ZEP play in this process. Blue lines represent transgenic plants compared to orange lines (wild type).
Figure 11:
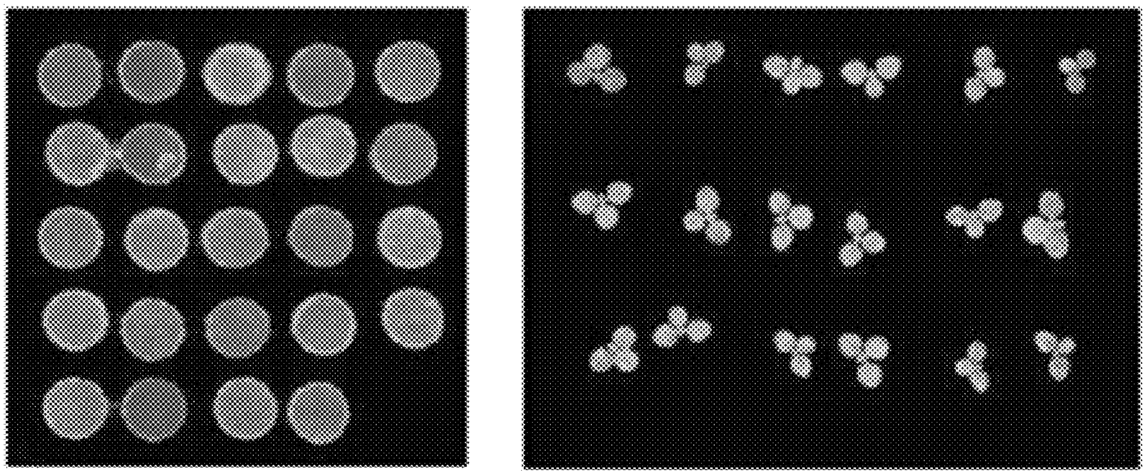
FIG. 11. Fast high throughput screening of phenotypes. Chlorophyll fluorescence of leaf discs (left) and chlorophyll fluorescence of young seedlings (right).

In another aspect, an expression vector is provided, the expression vector comprising at least one expression control sequence operably linked to at least one nucleotide sequence encoding one or more polypeptides selected from PsbS, ZEP and VDE. In one embodiment, the vector comprises at least one expression control sequence comprising a promoter capable of driving expression of the nucleotide sequence encoding one or more polypeptides selected from PsbS, ZEP and VDE, in a plant, a portion of a plant, or a plant material, or a plant seed, or a plant cell. In another embodiment, the promoter is selected from Rbcs1A, GAPA-1 and FBA2. In a further embodiment, the vector comprises an Rbcs1A promoter drives expression of ZEP, a GAPA-1 promoter drives expression of PsbS, and an FBA2 promoter drives expression of VDE. In another embodiment, the vector is a T-DNA. In another embodiment, the vector comprises a vector as shown in FIG. 9. In another embodiment, the vector can express the nucleotide sequence encoding the PsbS, ZEP and VDE polypeptides in a plant, a portion of a plant, or a plant material, or a plant seed, or a plant cell of a crop plant, a model plant, a monocotyledonous plant, a dicotyledonous plant, a plant with Crassulacean acid metabolism (CAM) photosynthesis, a plant with C3 photosynthesis, a plant with C4 photosynthesis, an annual plant, a greenhouse plant, a horticultural flowering plant, a perennial plant, a switchgrass plant, a maize plant, a biomass plant, or a sugarcane plant. In another embodiment, the plant is selected from switchgrass, *Miscanthus, Medicago*, sweet sorghum, grain sorghum, sugarcane, energy cane, elephant grass, maize, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, vegetable, forage, industrial, woody and biomass crops.

In another aspect, a transgenic plant, or a portion of a plant, or a plant material, or a plant seed is provided, comprising a recombinant vector as described herein.

In another aspect, methods of increasing biomass production and/or carbon fixation and/or growth in a plant, or a portion of a plant, or a plant material, or a plant seed, or a plant cell are provided, the method comprising introducing into the genome of the plant, plant tissue, plant seed, or plant cell one or more nucleotide sequences encoding polypeptides selected from PsbS, ZEP and VDE operably linked to one or more expression control sequences. It was found that incorporation of polypeptides encoded by the nucleotides SEQ ID NO: 1, SEQ ID NO: 2, and SEQ ID NO: 3 increased quantum yield, $CO_2$ fixation under fluctuating light conditions, and improved plant growth. In one embodiment, the method comprises a recombinant vector as described herein.

Transgenic Plants of the Disclosure

In one aspect, provided herein is a transgenic plant having one or more heterologous nucleotide sequences encoding one or more polypeptides PsbS, ZEP, or VDE. In some embodiments, the transgenic plant has one or more heterologous nucleotide sequences encoding PsbS. In some embodiments, the transgenic plant has one or more heterologous nucleotide sequences encoding ZEP. In some embodiments, the transgenic plant has one or more heterologous nucleotide sequences encoding VDE. In some embodiments, the transgenic plant has one or more heterologous nucleotide sequences encoding PsbS and ZEP. In some embodiments, the transgenic plant has one or more heterologous nucleotide sequences encoding PsbS and VDE. In some embodiments, the transgenic plant has one or more heterologous nucleotide sequences encoding ZEP and VDE. In some embodiments, the transgenic plant has one or more heterologous nucleotide sequences encoding PsbS, ZEP and VDE.

In some of the embodiments described above, the one or more heterologous nucleotide sequences are derived from a dicot. In some embodiments, the one or more heterologous nucleotide sequences are derived from a monocot. In some embodiments, the one or more heterologous nucleotide sequences are derived from *Arabidopsis thaliana*. In some embodiments, the one or more heterologous nucleotide sequences are derived from *Zea mays*. In some embodiments, the one or more heterologous nucleotide sequences are derived from *Oryza sativa*. In some embodiments, the one or more heterologous nucleotide sequences are derived from *Sorghum bicolor*. In some embodiments, the one or more heterologous nucleotide sequences are derived from *Glycine max*. In some embodiments, the one or more heterologous nucleotide sequences are derived from *Vigna unguiculata*. In some embodiments, the one or more heterologous nucleotide sequences are derived from *Populus* spp. In some embodiments, the one or more heterologous nucleotide sequences are derived from *Eucalyptus* spp. In some embodiments, the one or more heterologous nucleotide sequences are derived from *Manihot esculenta*. In some embodiments, the one or more heterologous nucleotide sequences are derived from *Hordeum vulgare*. In some embodiments, the one or more heterologous nucleotide sequences are derived from *Solanum tuberosum*. In some embodiments, the one or more heterologous nucleotide sequences are derived from *Saccharum* spp. In some embodiments, the one or more heterologous nucleotide sequences are derived from *Medicago sativa*. In some embodiments, the one or more heterologous nucleotide sequences are derived from switchgrass, *Miscanthus, Medicago*, sweet sorghum, grain sorghum, sugarcane, energy cane, elephant grass, maize, cassava, cowpea, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, a vegetable crop, a forage crop, an industrial crop, a woody crop or a biomass crop.

In some of the embodiments described above, the transcript level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 15-fold, at least about 20-fold, or at least about 30-fold, as compared to a control plant. In some embodiments, the protein level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, or at least about 100-fold, as compared to a control plant.

Photoprotection mechanism has a high degree of conservation among higher plants. The degree of conservation, or homology, can be analyzed through comparing sequences of nucleotides or amino acids of genes of interest. As used herein "sequence identity" refers to the percentage of residues that are identical in the same positions in the sequences being analyzed. Methods of alignment of sequences for comparison are well known to one of skill in the art, including, but not limited to, manual alignment and computer assisted sequence alignment and analysis. This latter approach is a preferred approach in the present disclosure, due to the increased throughput afforded by computer assisted methods. The determination of percent sequence identity between any two sequences can be accomplished using a mathematical algorithm. Examples of such mathematical algorithms are the algorithm of Myers and Miller, CABIOS 4:11-17 (1988); the local homology algorithm of Smith et al., Adv. Appl. Math. 2:482 (1981); the homology alignment algorithm of Needleman and Wunsch, J. Mol. Biol. 48:443-453 (1970); the search-for-similarity-method of Pearson and Lipman, Proc. Natl. Acad. Sci. 85:2444-2448 (1988); the algorithm of Karlin and Altschul, Proc. Natl. Acad. Sci. USA 87:2264-2268 (1990), modified as in Karlin and Altschul, Proc. Natl. Acad. Sci. USA 90:5873-5877 (1993). Computer implementations of these mathematical algorithms can be utilized for comparison of sequences to determine sequence identity and/or similarity. Such implementations include, for example: CLUSTAL in the PC/Gene program (available from Intelligenetics, Mountain View, Calif.); the AlignX program, version10.3.0 (Invitrogen, Carlsbad, CA) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. Gene 73:237-244 (1988); Higgins et al. CABIOS 5:151-153 (1989); Corpet et al., Nucleic Acids Res. 16:10881-90 (1988); Huang et al. CABIOS 8:155-65 (1992); and Pearson et al., Meth. Mol. Biol. 24:307-331 (1994). The BLAST programs of Altschul et al. J. Mol. Biol. 215:403-410 (1990) are based on the algorithm of Karlin and Altschul (1990) supra.

In some of the embodiments described above, PsbS is encoded by a nucleotide sequence having at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identity to SEQ ID NO: 1. In some embodiments, ZEP is encoded by a nucleotide sequence having at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identity to SEQ ID NO: 2. In some embodiments, VDE is encoded by a nucleotide sequence having at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identity to SEQ ID NO: 3. In some embodiments, PsbS has an amino acid sequence at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identical to SEQ ID NO: 4. In some embodiments, ZEP has an amino acid sequence at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identical to SEQ ID NO: 5. In some embodiments, VDE has an amino acid sequence at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identical to SEQ ID NO: 6. In some embodiments, PsbS further includes a conserved domain of SEQ ID NO: 7. In some embodiments, ZEP further includes a conserved domain of SEQ ID NO: 8. In some embodiments, VDE further includes a conserved domain of SEQ ID NO: 9.

In some of the embodiments described above, the transgenic plant contains an expression vector, wherein the expression vector contains one or more nucleotide sequences described herein. In some embodiments, the transgenic plant produces a seed containing an expression vector that has one or more heterologous nucleotide sequences encoding any of PsbS, ZEP or VDE. In some embodiments, the seed that is derived from the transgenic plant further produces a progeny plant.

In some of the embodiments described above, the transgenic plant has increased growth under fluctuating light conditions as compared to a control plant under fluctuating light conditions. In some embodiments, the transgenic plant has increased photosynthetic efficiency under fluctuating light conditions as compared to a control plant under fluctuating light conditions. In some embodiments, the transgenic plant has improved photoprotection efficiency under fluctuating light conditions as compared to a control plant under fluctuating light conditions. In some embodiments, the transgenic plant has improved quantum yield and $CO_2$ fixation under fluctuating light conditions as compared to a control plant under fluctuating light conditions. In some embodiments, the transgenic plant is an elite line or elite strain. In some embodiments, the transgenic plant further includes expression of at least one additional polypeptide that provides herbicide resistance, insect or pest resistance, disease resistance, modified fatty acid metabolism, and/or modified carbohydrate metabolism.

In some of the embodiments described above, the transcript level of VDE in the plant is increased 3-fold as compared to a control plant. In some of the embodiments described above, the transcript level of PsbS in the plant is increased 3-fold as compared to a control plant. In some of the embodiments described above, the transcript level of ZEP in the plant is increased 8-fold as compared to a control plant. In some of the embodiments described above, the transcript level of VDE in the plant is increased 10-fold as compared to a control plant. In some of the embodiments described above, the transcript level of PsbS in the plant is increased 3-fold as compared to a control plant. In some of the embodiments described above, the transcript level of ZEP in the plant is increased 6-fold as compared to a control plant. In some of the embodiments described above, the transcript level of VDE in the plant is increased 4-fold as compared to a control plant. In some of the embodiments described above, the transcript level of PsbS in the plant is increased 1.2-fold as compared to a control plant. In some of the embodiments described above, the transcript level of ZEP in the plant is increased 7-fold as compared to a control plant. In some of the embodiments described above, the protein level of VDE in the plant is increased 16-fold as compared to a control plant. In some of the embodiments described above, the protein level of PsbS in the plant is increased 2-fold as compared to a control plant. In some of the embodiments described above, the protein level of ZEP in the plant is increased 80-fold as compared to a control plant. In some of the embodiments described above, the protein level of VDE in the plant is increased 30-fold as compared to a control plant. In some of the embodiments described above, the protein level of PsbS in the plant is increased 4-fold as compared to a control plant. In some of the embodiments described above, the protein level of ZEP in the plant is increased 74-fold as compared to a control plant. In some of the embodiments described above, the protein level of VDE in the plant is increased 47-fold as compared to a control plant. In some of the embodiments described above, the protein level of PsbS in the plant is increased 3-fold as compared to a control plant. In some of the embodiments described above, the protein level of ZEP in the plant is increased 75-fold as compared to a control plant. In some of the embodiments described above, the increase of transcript level in the plant as compared to a control plant between VDE, PsbS and ZEP has a ratio of 3:3:8, 10:3:6, or 4:1.2:7. In some of the embodiments described above, the increase of protein level in the plant as compared to a control plant between VDE, PsbS and ZEP has a ratio of 16:2:80, 30:4:74, or 47:3:75. In some of the embodiments described above, the increase of transcript level of VDE in the plant as compared to a control plant is in the range of 3-fold to 10-fold. In some of the embodiments described above, the increase of transcript level of PsbS in the plant as compared to a control plant is from about 1.2-fold to about 3-fold. In some of the embodiments described above, the increase of transcript level of ZEP in the plant as compared to a control plant is from about 6-fold to about 8-fold. In some of the embodiments described above, the increase of protein level of VDE in the plant as compared to a control plant is in the range of 16-fold to 47-fold. In some of the embodiments described above, the increase of protein level of PsbS in the plant as compared to a control plant is from about 2-fold to about 4-fold. In some of the embodiments described above, the increase of protein level of ZEP in the plant as compared to a control plant is from about 74-fold to about 80-fold.

Expression Vectors of the Disclosure

In another aspect, the present disclosure relates to an expression vector having one or more nucleotide sequences encoding any of PsbS, ZEP, and VDE. In some embodiments, the expression vector has one or more nucleotide sequences encoding PsbS. In some embodiments, the expression vector has one or more nucleotide sequences encoding ZEP. In some embodiments, the expression vector has one or more nucleotide sequences encoding VDE. In some embodiments, the expression vector has one or more nucleotide sequences encoding PsbS and ZEP. In some embodiments, the expression vector has one or more nucleotide sequences encoding PsbS and VDE. In some embodiments, the expression vector has one or more nucleotide sequences encoding ZEP and VDE. In some embodiments, the expression vector has one or more nucleotide sequences encoding PsbS, ZEP and VDE.

In some of the embodiments described above, PsbS is encoded by a nucleotide sequence having at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identity to SEQ ID NO: 1. In some embodiments, ZEP is encoded by a nucleotide sequence having at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identity to SEQ ID NO: 2. In some embodiments, VDE is encoded by a nucleotide sequence having at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identity to SEQ ID NO: 3. In some embodiments, PsbS has an amino acid sequence at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identical to SEQ ID NO: 4. In some embodiments, ZEP has an amino acid sequence at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identical to SEQ ID NO: 5. In some embodiments, VDE has an amino acid sequence at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99%, or 100% identical to SEQ ID NO: 6. In some embodiments, PsbS further includes a conserved domain of SEQ ID NO: 7. In some embodiments, ZEP further includes a conserved domain of SEQ ID NO: 8. In some embodiments, VDE further includes a conserved domain of SEQ ID NO: 9.

In some of the embodiments described above, the vector includes one or more expression control sequences having a promoter capable of driving expression of the nucleotide sequence of PsbS, ZEP, or VDE, in a plant. In some embodiments, the promoter is an inducible promoter. In some embodiments, the promoter is a constitutive promoter. In some embodiments, the promoter is a weak promoter. In some embodiments, the promoter is a tissue-specific promoter. In some embodiments, the promoter is a seed- and/or embryo-specific promoter. In some embodiments, the promoter is a leaf-specific promoter. In some embodiments, the promoter is a temporal-specific promoter. In some embodiments, the promoter is an anther- and/or pollen-specific promoter. In some embodiments, the promoter is a floral-specific promoter. In some embodiments, a combination of promoters is used in the expression vector.

In some of the embodiments described above, the promoter is Rbcs1A, GAPA-1, or FBA2. In some embodiments, the Rbcs1A promoter drives expression of ZEP, a GAPA-1 promoter drives expression of PsbS, and an FBA2 promoter drives expression of VDE. In some embodiments, the vector is a T-DNA. In some embodiments, the expression vector further includes a nucleotide sequence encoding polypeptide that provides antibiotic resistance. In some embodiments, the expression vector further includes a left border (LB) and right border (RB) domain flanking the expression control sequences and the nucleotide sequence encoding the PsbS, ZEP and VDE polypeptides. In some embodiments, the expression vector is in a bacterial cell. In some embodiments, the expression vector is in an *Agrobacterium* cell.

Methods of the Disclosure

In certain other aspects, the present disclosure relates to methods of increasing photosynthesis and growth in a plant, including increasing expression in the plant of one or more polypeptides described herein.

In some embodiments, the increased expression is achieved by introducing to a plant one or more heterologous nucleotide sequences encoding any of PsbS, ZEP and VDE. In some embodiments, the increased expression is achieved by modifying expression of the endogenous nucleotide sequences encoding any of PsbS, ZEP and VDE. In some embodiments, the increased expression is achieved by modifying the promoter of the endogenous nucleotide sequences encoding any of PsbS, ZEP and VDE. In some embodiments, the increased expression is achieved by modifying transcription factors that regulate the transcription efficiency of any of PsbS, ZEP and VDE. In some embodiments, the increased expression is achieved by increasing the stability of the mRNA of any of PsbS, ZEP and VDE. In some embodiments, the increased expression is achieved by optimizing codon usage of any of PsbS, ZEP and VDE in a target plant. In some embodiments, the increased expression is achieved by altering epigenetics in a plant. In some embodiments, the increased expression is achieved by altering DNA methylation in a plant. In some embodiments, the increased expression is achieved by altering histone modification in a plant. In some embodiments, the increased expression is achieved by altering small RNAs (sRNA) in a plant. In some embodiments, the increased expression is achieved by increasing the translation efficiency of any of PsbS, ZEP and VDE. In some embodiments, genome-editing techniques including, but not limited to, ZFN, TALEN and CRISPR are used to modify the nucleotide sequences regulating the expression of any of PsbS, ZEP and VDE.

In some embodiments, the transcript level of VDE in the plant is increased 3-fold as compared to a control plant. In some embodiments, the transcript level of PsbS in the plant is increased 3-fold as compared to a control plant. In some embodiments, the transcript level of ZEP in the plant is increased 8-fold as compared to a control plant. In some embodiments, the transcript level of VDE in the plant is increased 10-fold as compared to a control plant. In some embodiments, the transcript level of PsbS in the plant is increased 3-fold as compared to a control plant. In some embodiments, the transcript level of ZEP in the plant is increased 6-fold as compared to a control plant. In some embodiments, the transcript level of VDE in the plant is increased 4-fold as compared to a control plant. In some embodiments, the transcript level of PsbS in the plant is increased 1.2-fold as compared to a control plant. In some embodiments, the transcript level of ZEP in the plant is increased 7-fold as compared to a control plant. In some embodiments, the protein level of VDE in the plant is increased 16-fold as compared to a control plant. In some embodiments, the protein level of PsbS in the plant is increased 2-fold as compared to a control plant. In some embodiments, the protein level of ZEP in the plant is increased 80-fold as compared to a control plant. In some embodiments, the protein level of VDE in the plant is increased 30-fold as compared to a control plant. In some embodiments, the protein level of PsbS in the plant is increased 4-fold as compared to a control plant. In some embodiments, the protein level of ZEP in the plant is increased 74-fold as compared to a control plant. In some embodiments, the protein level of VDE in the plant is increased 47-fold as compared to a control plant. In some embodiments, the protein level of PsbS in the plant is increased 3-fold as compared to a control plant. In some embodiments, the protein level of ZEP in the plant is increased 75-fold as compared to a control plant. In some embodiments, the increase of transcript level in the plant as compared to a control plant between VDE, PsbS and ZEP has a ratio of 3:3:8, 10:3:6, or 4:1.2:7. In some embodiments, the increase of protein level in the plant as compared to a control plant between VDE, PsbS and ZEP has a ratio of 16:2:80, 30:4:74, or 47:3:75. In some embodiments, the increase of transcript level of VDE in the plant as compared to a control plant is in the range of 3-fold to 10-fold. In some embodiments, the increase of transcript level of PsbS in the plant as compared to a control plant is from about 1.2-fold to about 3-fold. In some embodiments, the increase of transcript level of ZEP in the plant as compared to a control plant is from about 6-fold to about 8-fold. In some embodiments, the increase of protein level of VDE in the plant as compared to a control plant is in the range of 16-fold to 47-fold. In some embodiments, the increase of protein level of PsbS in the plant as compared to a control plant is from about 2-fold to about 4-fold. In some embodiments, the increase of protein level of ZEP in the plant as compared to a control plant is from about 74-fold to about 80-fold.

Methods for Increasing Growth Under Fluctuating Light Conditions

In one aspect, provided herein is a method for increasing growth in a plant under fluctuating light conditions, including increasing expression in the plant of PsbS, ZEP, and/or VDE, thereby producing a plant with increased expression of the one or more polypeptides as compared to a control plant. In some embodiments, the increased expression is in the form of increased transcript level. In some embodiments, the transcript level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 15-fold, at least about 20-fold, or at least about 30-fold, as compared to a control plant. In some embodiments, the increased expression is in the form of increased protein level. In some embodiments, the protein level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, or at least about 100-fold, as compared to a control plant. In some embodiments, the method includes increasing expression of PsbS. In some embodiments, the method includes increasing expression of ZEP. In some embodiments, the method includes increasing expression of VDE. In some embodiments, the method includes increasing expression of PsbS and ZEP. In some embodiments, the method includes increasing expression of PsbS and VDE. In some embodiments, the method includes increasing expression of ZEP and VDE. In some embodiments, the method includes increasing expression of PsbS, ZEP and VDE.

In some of the embodiments described above, PsbS is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 1. In some embodiments, ZEP is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 2. In some embodiments, VDE is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 3.

In some of the embodiments described above, PsbS has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 4. In some embodiments, ZEP has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 5. In some embodiments, VDE has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 6. In some embodiments, PsbS further includes a conserved domain of SEQ ID NO: 7. In some embodiments, ZEP further includes a conserved domain of SEQ ID NO:8. In some embodiments, VDE further includes a conserved domain of SEQ ID NO: 9.

In some of the embodiments described above, the plant is *Zea mays*. In some embodiments, the plant is *Oryza sativa*. In some embodiments, the plant is *Sorghum bicolor*. In some embodiments, the plant is *Glycine max*. In some embodiments, the plant is *Vigna unguiculata*. In some embodiments, the plant is *Populus* spp. In some embodiments, the plant is *Eucalyptus* spp. In some embodiments, the plant is *Manihot esculenta*. In some embodiments, the plant is *Hordeum vulgare*. In some embodiments, the plant is *Solanum tuberosum*. In some embodiments, the plant is *Saccharum* spp. In some embodiments, the plant is *Medicago sativa*. In some embodiments, the plant is switchgrass, *Miscanthus, Medicago*, sweet sorghum, grain sorghum, sugarcane, energy cane, elephant grass, maize, cassava, cowpea, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, a vegetable crop, a forage crop, an industrial crop, a woody crop or a biomass crop.

Methods for Increasing Photosynthetic Efficiency Under Fluctuating Light Conditions In another aspect, provided herein is a method for increasing photosynthetic efficiency in a plant under fluctuating light conditions, including increasing expression in the plant of any of PsbS, ZEP, or VDE, thereby producing a plant with increased expression of the one or more polypeptides as compared to a control plant. In some embodiments, the increased expression is in the form of increased transcript level. In some embodiments, the transcript level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 15-fold, at least about 20-fold, or at least about 30-fold, as compared to a control plant. In some embodiments, the increased expression is in the form of increased protein level. In some embodiments, the protein level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, or at least about 100-fold, as compared to a control plant. In some embodiments, the method includes increasing expression of PsbS. In some embodiments, the method includes increasing expression of ZEP. In some embodiments, the method includes increasing expression of VDE. In some embodiments, the method includes increasing expression of PsbS and ZEP. In some embodiments, the method includes increasing expression of PsbS and VDE. In some embodiments, the method includes increasing expression of ZEP and VDE. In some embodiments, the method includes increasing expression of PsbS, ZEP and VDE.

In some of the embodiments described above, PsbS is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 1. In some embodiments, ZEP is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 2. In some embodiments, VDE is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 3.

In some of the embodiments described above, PsbS has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 4. In some embodiments, ZEP has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 5. In some embodiments, VDE has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 6. In some embodiments, PsbS further includes a conserved domain of SEQ ID NO: 7. In some embodiments, ZEP further includes a conserved domain of SEQ ID NO:8. In some embodiments, VDE further includes a conserved domain of SEQ ID NO: 9.

In some of the embodiments described above, the plant is *Zea mays*. In some embodiments, the plant is *Oryza sativa*. In some embodiments, the plant is *Sorghum bicolor*. In some embodiments, the plant is *Glycine max*. In some embodiments, the plant is *Vigna unguiculata*. In some embodiments, the plant is *Populus* spp. In some embodiments, the plant is *Eucalyptus* spp. In some embodiments, the plant is *Manihot esculenta*. In some embodiments, the plant is *Hordeum vulgare*. In some embodiments, the plant is *Solanum tuberosum*. In some embodiments, the plant is *Saccharum* spp. In some embodiments, the plant is *Medicago sativa*. In some embodiments, the plant is switchgrass, *Miscanthus, Medicago*, sweet sorghum, grain sorghum, sugarcane, energy cane, elephant grass, maize, cassava, cowpea, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, a vegetable crop, a forage crop, an industrial crop, a woody crop or a biomass crop.

Methods for Increasing Photoprotection Efficiency Under Fluctuating Light Conditions In another aspect, provided herein is a method for increasing photoprotection efficiency in a plant under fluctuating light conditions, including increasing expression in the plant of PsbS, ZEP, and/or VDE, thereby producing a plant with increased expression of the one or more polypeptides as compared to a control plant. In some embodiments, the increased expression is in the form of increased transcript level. In some embodiments, the transcript level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 15-fold, at least about 20-fold, or at least about 30-fold, as compared to a control plant. In some embodiments, the increased expression is in the form of increased protein level. In some embodiments, the protein level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, or at least about 100-fold, as compared to a control plant. In some embodiments, the method includes increasing expression of PsbS. In some embodiments, the method includes increasing expression of ZEP. In some embodiments, the method includes increasing expression of VDE. In some embodiments, the method includes increasing expression of PsbS and ZEP. In some embodiments, the method includes increasing expression of PsbS and VDE. In some embodiments, the method includes increasing expression of ZEP and VDE. In some embodiments, the method includes increasing expression of PsbS, ZEP and VDE.

In some of the embodiments described above, PsbS is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 1. In some embodiments, ZEP is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 2. In some embodiments, VDE is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 3.

In some of the embodiments described above, PsbS has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 4. In some embodiments, ZEP has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 5. In some embodiments, VDE has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 6. In some embodiments, PsbS further includes a conserved domain of SEQ ID NO: 7. In some embodiments, ZEP further includes a conserved domain of SEQ ID NO:8. In some embodiments, VDE further includes a conserved domain of SEQ ID NO: 9.

In some of the embodiments described above, the plant is *Zea mays*. In some embodiments, the plant is *Oryza sativa*. In some embodiments, the plant is *Sorghum bicolor*. In some embodiments, the plant is *Glycine max*. In some embodiments, the plant is *Vigna unguiculata*. In some embodiments, the plant is *Populus* spp. In some embodiments, the plant is *Eucalyptus* spp. In some embodiments, the plant is *Manihot esculenta*. In some embodiments, the plant is *Hordeum vulgare*. In some embodiments, the plant is *Solanum tuberosum*. In some embodiments, the plant is *Saccharum* spp. In some embodiments, the plant is *Medicago sativa*. In some embodiments, the plant is switchgrass, *Miscanthus, Medicago*, sweet sorghum, grain sorghum, sugarcane, energy cane, elephant grass, maize, cassava, cowpea, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, a vegetable crop, a forage crop, an industrial crop, a woody crop or a biomass crop.

Methods for Increasing Quantum Yield and $CO_2$ Fixation Under Fluctuating Light Conditions In another aspect, provided herein is a method for increasing quantum yield and $CO_2$ fixation in a plant under fluctuating light conditions, including increasing expression in the plant of PsbS, ZEP, and/or VDE, thereby producing a plant with increased expression of the one or more polypeptides as compared to a control plant. In some embodiments, the increased expression is in the form of increased transcript level. In some embodiments, the transcript level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 15-fold, at least about 20-fold, or at least about 30-fold, as compared to a control plant. In some embodiments, the increased expression is in the form of increased protein level. In some embodiments, the protein level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, or at least about 100-fold, as compared to a control plant. In some embodiments, the method includes increasing expression of PsbS. In some embodiments, the method includes increasing expression of ZEP. In some embodiments, the method includes increasing expression of VDE. In some embodiments, the method includes increasing expression of PsbS and ZEP. In some embodiments, the method includes increasing expression of PsbS and VDE. In some embodiments, the method includes increasing expression of ZEP and VDE. In some embodiments, the method includes increasing expression of PsbS, ZEP and VDE.

In some of the embodiments described above, PsbS is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 1. In some embodiments, ZEP is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 2. In some embodiments, VDE is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 3.

In some of the embodiments described above, PsbS has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 4. In some embodiments, ZEP has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 5. In some embodiments, VDE has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 6. In some embodiments, PsbS further includes a conserved domain of SEQ ID NO: 7. In some embodiments, ZEP further includes a conserved domain of SEQ ID NO:8. In some embodiments, VDE further includes a conserved domain of SEQ ID NO: 9.

In some of the embodiments described above, the plant is *Zea mays*. In some embodiments, the plant is *Oryza sativa*. In some embodiments, the plant is *Sorghum bicolor*. In some embodiments, the plant is *Glycine max*. In some embodiments, the plant is *Vigna unguiculata*. In some embodiments, the plant is *Populus* spp. In some embodiments, the plant is *Eucalyptus* spp. In some embodiments, the plant is *Manihot esculenta*. In some embodiments, the plant is *Hordeum vulgare*. In some embodiments, the plant is *Solanum tuberosum*. In some embodiments, the plant is *Saccharum* spp. In some embodiments, the plant is *Medicago sativa*. In some embodiments, the plant is switchgrass, *Miscanthus, Medicago*, sweet sorghum, grain sorghum, sugarcane, energy cane, elephant grass, maize, cassava, cowpea, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, a vegetable crop, a forage crop, an industrial crop, a woody crop or a biomass crop.

Methods for Increasing the Rate of Relaxation of Non-Photochemical Quenching (NPQ) Under Fluctuating Light Conditions In another aspect, provided herein is a method for increasing the rate of relaxation of non-photochemical quenching (NPQ) in a plant, including increasing expression in the plant of PsbS, ZEP, and/or VDE, thereby producing a plant with increased expression of the one or more polypeptides as compared to a control plant. In some embodiments, the increased expression is in the form of increased transcript level. In some embodiments, the transcript level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 15-fold, at least about 20-fold, or at least about 30-fold, as compared to a control plant. In some embodiments, the increased expression is in the form of increased protein level. In some embodiments, the protein level of any of VDE, PsbS or ZEP is increased at least about 1-fold, at least about 2-fold, at least about 3-fold, at least about 4-fold, at least about 5-fold, at least about 6-fold, at least about at least about 7-fold, at least about 8-fold, at least about 9-fold, at least about 10-fold, at least about 20-fold, at least about 30-fold, at least about 40-fold, at least about 50-fold, at least about 60-fold, at least about 70-fold, at least about 80-fold, at least about 90-fold, or at least about 100-fold, as compared to a control plant. In some embodiments, the method includes increasing expression of PsbS. In some embodiments, the method includes increasing expression of ZEP. In some embodiments, the method includes increasing expression of VDE. In some embodiments, the method includes increasing expression of PsbS and ZEP. In some embodiments, the method includes increasing expression of PsbS and VDE. In some embodiments, the method includes increasing expression of ZEP and VDE. In some embodiments, the method includes increasing expression of PsbS, ZEP and VDE.

In some of the embodiments described above, PsbS is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 1. In some embodiments, ZEP is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 2. In some embodiments, VDE is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 3.

In some of the embodiments described above, PsbS has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 4. In some embodiments, ZEP has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 5. In some embodiments, VDE has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 6. In some embodiments, PsbS further includes a conserved domain of SEQ ID NO: 7. In some embodiments, ZEP further includes a conserved domain of SEQ ID NO:8. In some embodiments, VDE further includes a conserved domain of SEQ ID NO: 9.

In some of the embodiments described above, the plant is *Zea mays*. In some embodiments, the plant is *Oryza sativa*. In some embodiments, the plant is *Sorghum bicolor*. In some embodiments, the plant is *Glycine max*. In some embodiments, the plant is *Vigna unguiculata*. In some embodiments, the plant is *Populus* spp. In some embodiments, the plant is *Eucalyptus* spp. In some embodiments, the plant is *Manihot esculenta*. In some embodiments, the plant is *Hordeum vulgare*. In some embodiments, the plant is *Solanum tuberosum*. In some embodiments, the plant is *Saccharum* spp. In some embodiments, the plant is *Medicago sativa*. In some embodiments, the plant is switchgrass, *Miscanthus, Medicago*, sweet sorghum, grain sorghum, sugarcane, energy cane, elephant grass, maize, cassava, cowpea, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, a vegetable crop, a forage crop, an industrial crop, a woody crop or a biomass crop.

Methods for Selecting a Plant for Improved Growth Characteristics Under Fluctuating Light Conditions In another aspect, provided herein are methods of selecting a plant for improved growth characteristics under fluctuating light conditions, including the steps of providing a population of plants; modifying the population of plants to increase the activity of any of PsbS, ZEP and VDE; detecting the level of non-photochemical quenching (NPQ) under fluctuating light conditions in a plant; comparing the level of NPQ under fluctuating light conditions in a plant with the control level of NPQ under fluctuating light conditions; and selecting a plant having increased rate of NPQ relaxation when the plant is transitioned from under high light intensity to low light intensity. In some embodiments, the control level of NPQ is the lowest level of NPQ in the population. In some embodiments, the control level of NPQ is the median level of NPQ in the population. In some embodiments, the control level of NPQ is the mean level of NPQ in the population. In some embodiments, the control level of NPQ is the level of NPQ in a control plant. In some embodiments, the population includes plants expressing heterologous sequences of PsbS, ZEP and/or VDE or in which the genome has been edited in order to increase expression of PsbS, ZEP, and/or VDE. In some embodiments, the genome editing technique is ZFN. In some embodiments, the genome editing technique is TALEN. In some embodiments, the genome editing technique is CRISPR. In some embodiments, the promoter of PsbS is modified. In some embodiments, the promoter of ZEP is modified. In some embodiments, the promoter of VDE is modified. In some embodiments, the population includes plants that have been treated to induce mutations in PsbS, ZEP and/or VDE. In some embodiments, the mutagen is EMS.

In some of the embodiments described above, PsbS is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 1. In some embodiments, ZEP is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 2. In some embodiments, VDE is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 3.

In some of the embodiments described above, PsbS has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 4. In some embodiments, ZEP has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 5. In some embodiments, VDE has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 6. In some embodiments, PsbS further includes a conserved domain of SEQ ID NO: 7. In some embodiments, ZEP further includes a conserved domain of SEQ ID NO:8. In some embodiments, VDE further includes a conserved domain of SEQ ID NO: 9.

In some of the embodiments described above, the plant is *Zea mays*. In some embodiments, the plant is *Oryza sativa*. In some embodiments, the plant is *Sorghum bicolor*. In some embodiments, the plant is *Glycine max*. In some embodiments, the plant is *Vigna unguiculata*. In some embodiments, the plant is *Populus* spp. In some embodiments, the plant is *Eucalyptus* spp. In some embodiments, the plant is *Manihot esculenta*. In some embodiments, the plant is *Hordeum vulgare*. In some embodiments, the plant is *Solanum tuberosum*. In some embodiments, the plant is *Saccharum* spp. In some embodiments, the plant is *Medicago sativa*. In some embodiments, the plant is switchgrass, *Miscanthus, Medicago*, sweet sorghum, grain sorghum, sugarcane, energy cane, elephant grass, maize, cassava, cowpea, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, a vegetable crop, a forage crop, an industrial crop, a woody crop or a biomass crop.

Methods for Screening for a Polymorphism Associated with Improved Growth Characteristics Under Fluctuating Light Conditions In another aspect, provided herein are methods of screening for a nucleotide sequence polymorphism associated with improved growth characteristics under fluctuating light conditions, including the steps of providing a population of plants; obtaining the nucleotide sequences regulating and/or encoding any of PsbS, ZEP and VDE in the population of plants; obtaining one or more polymorphisms in the nucleotide sequences regulating and/or encoding any of PsbS, ZEP and VDE in the population of plants; detecting the rate of non-photochemical quenching (NPQ) relaxation upon transition from high light intensity to low light intensity in the population of plants; performing statistical analysis to determine association of the polymorphism with the rate of NPQ relaxation in the population of plants; and selecting the polymorphism having statistically significant association with the rate of NPQ relaxation. In some embodiments, the population is a collection of germplasm. In some embodiments, the population includes plants expressing heterologous sequences of PsbS, ZEP and/or VDE or in which the genome has been edited in order to increase expression of PsbS, ZEP, and/or VDE. In some embodiments, the population includes plants that have not been treated to induce mutations. In some embodiments, the population includes plants that have been treated to induce mutations in PsbS, ZEP and/or VDE. In some embodiments, the polymorphism is a single nucleotide polymorphism (SNP). In some embodiments, the polymorphism is an insertion/deletion (InDel). In some embodiments, the polymorphism is a simple sequence repeat (SSR). In some embodiments, the polymorphism is a presence/absence variation (PAV). In some embodiments, the polymorphism is a copy number variation (CNV). In some embodiments, the polymorphism is located in the promoter of PsbS. In some embodiments, the polymorphism is located in the promoter of ZEP. In some embodiments, the polymorphism is located in the promoter of VDE. In some embodiments, the polymorphism is detected by Sanger sequencing. In some embodiments, the polymorphism is detected by next-generation-sequencing. In some embodiments, the polymorphism is detected by agarose gel electrophoresis. In some embodiments, the polymorphism is detected by polyacrylamide gel electrophoresis. In some embodiments, the polymorphism is further used to screen a population different from the one from which the polymorphism is identified. In some embodiments, the polymorphism is further used as a target for genome editing in order to improve growth characteristics of a plant.

In some of the embodiments described above, the improved growth characteristic is improved growth. In some embodiments, the improved growth characteristic is improved photosynthetic efficiency. In some embodiments, the improved growth characteristic is improved photoprotection efficiency. In some embodiments, the improved growth characteristic is improved quantum yield and $CO_2$ fixation. In some embodiments, the improved growth characteristic is increased rate of relaxation of non-photochemical quenching (NPQ). In some embodiments, NPQ is detected using chlorophyll fluorescence imaging.

In some of the embodiments described above, PsbS is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 1. In some embodiments, ZEP is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 2. In some embodiments, VDE is encoded by a nucleotide sequence having at least about 65%, 70%, 75%, 80%, 85%, 90%, 91%, 92%, 93%, 94%, 95%, 96%, 97%, 98%, 99%, 99%, or 100% identity to SEQ ID NO: 3.

In some of the embodiments described above, PsbS has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 4. In some embodiments, ZEP has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 5. In some embodiments, VDE has an amino acid sequence at least about 65%, 70%, 75%, 80%, 85%, 90%, 91%, 92%, 93%, 94%, 95%, 96%, 97%, 98%, 99%, 99%, or 100% identical to SEQ ID NO: 6. In some embodiments, PsbS further includes a conserved domain of SEQ ID NO: 7. In some embodiments, ZEP further includes a conserved domain of SEQ ID NO:8. In some embodiments, VDE further includes a conserved domain of SEQ ID NO: 9.

In some of the embodiments described above, the plant is *Zea mays*. In some embodiments, the plant is *Oryza sativa*. In some embodiments, the plant is *Sorghum bicolor*. In some embodiments, the plant is *Glycine max*. In some embodiments, the plant is *Vigna unguiculata*. In some embodiments, the plant is *Populus* spp. In some embodiments, the plant is *Eucalyptus* spp. In some embodiments, the plant is *Manihot esculenta*. In some embodiments, the plant is *Hordeum vulgare*. In some embodiments, the plant is *Solanum tuberosum*. In some embodiments, the plant is *Saccharum* spp. In some embodiments, the plant is *Medicago sativa*. In some embodiments, the plant is switchgrass, *Miscanthus, Medicago*, sweet sorghum, grain sorghum, sugarcane, energy cane, elephant grass, maize, cassava, cowpea, wheat, barley, oats, rice, soybean, oil palm, safflower, sesame, tobacco, flax, cotton, sunflower, *Camelina, Brassica napus, Brassica carinata, Brassica juncea*, pearl millet, foxtail millet, other grain, rice, oilseed, a vegetable crop, a forage crop, an industrial crop, a woody crop or a biomass crop.

General Methods for Practice of the Embodiments Described Herein

Transformation of Plants with Nucleotide Sequences of Interest

Transgenic plants can be produced using conventional techniques to express any nucleotide sequence of interest in plants or plant cells (Methods in Molecular Biology, 2005, vol. 286, Transgenic Plants: Methods and Protocols, Pena L., ed., Humana Press, Inc. Totowa, NT). Typically, gene transfer, or transformation, is carried out using explants capable of regeneration to produce complete, fertile plants. Generally, a DNA or an RNA molecule to be introduced into the organism is part of a transformation vector. A large number of such vector systems known in the art may be used, such as plasmids. The components of the expression system can be modified, e.g., to increase expression of the introduced nucleic acids. For example, truncated sequences, nucleotide substitutions or other modifications may be employed. Expression systems known in the art may be used to transform virtually any plant cell under suitable conditions. A transgene comprising a DNA molecule encoding a gene of interest is preferably stably transformed and integrated into the genome of the host cells. Transformed cells are preferably regenerated into whole plants. Detailed description of transformation techniques are within the knowledge of those skilled in the art.

Genetic Constructs for Transformation

DNA constructs useful in the methods described herein include transformation vectors capable of introducing transgenes into plants. As used herein, "transgenic" refers to an organism in which a nucleic acid fragment containing a heterologous nucleotide sequence has been introduced. The transgenes in the transgenic organism are preferably stable and inheritable. The heterologous nucleic acid fragment may or may not be integrated into the host genome.

Several plant transformation vector options are available, including those described in Gene Transfer to Plants, 1995, Potrykus et al, eds., Springer-Verlag Berlin Heidelberg New York, Transgenic Plants: A Production System for Industrial and Pharmaceutical Proteins, 1996, Owen et al, eds., John Wiley & Sons Ltd. England, and Methods in Plant Molecular Biology: A Laboratory Course Manual, 1995, Maliga et al., eds., Cold Spring Laboratory Press, New York. Plant transformation vectors generally include one or more coding sequences of interest under the transcriptional control of 5' and 3' regulatory sequences, including a promoter, a transcription termination and/or polyadenylation signal, and a selectable or screenable marker gene. For the expression of two or more polypeptides from a single transcript, additional RNA processing signals and ribozyme sequences can be engineered into the construct (U.S. Pat. No. 5,519,164). This approach has the advantage of locating multiple transgenes in a single locus, which is advantageous in subsequent plant breeding efforts. In one embodiment, the vector comprises at least one expression control sequence comprising a promoter capable of driving expression of the nucleotide sequence encoding one or more polypeptides selected from PsbS, ZEP and VDE, in a plant, a portion of a plant, or a plant material, or a plant seed, or a plant cell. In another embodiment, the promoter is selected from Rbcs1A, GAPA-1 and FBA2. In another embodiment, the RbcslA promoter drives expression of ZEP, a GAPA-1 promoter drives expression of PsbS, and an FBA2 promoter drives expression of VDE. In another embodiment, the vector is a T-DNA. In another embodiment, the vector is as shown in FIG. 9. Particular promoters and vectors that work in one plant type may not work in another, as known by one of skill in the art. Methods of making transgenic plants are well known in the art, as described herein.

T-DNA

Methods for introducing transgenes into plants by an *Agrobacterium*-mediated transformation method generally involve a T-DNA (transfer DNA) that incorporates the genetic elements of at least one transgene and transfers those genetic elements into the genome of a plant. The transgene(s) are typically constructed in a DNA plasmid vector and are usually flanked by an *Agrobacterium* Ti plasmid right border DNA region (RB) and a left border DNA region (LB). During the process of *Agrobacterium*-mediated transformation, the DNA plasmid is nicked by an endonuclease, VirD2, at the right and left border regions. A single strand of DNA from between the nicks, called the T-strand, is transferred from the *Agrobacterium* cell to the plant cell. The sequence corresponding to the T-DNA region is inserted into the plant genome.

Integration of the T-DNA into the plant genome generally begins at the RB and continues to the end of the T-DNA, at the LB. However, endonucleases sometimes do not nick equally at both borders. When this happens, the T-DNA that is inserted into the plant genome often contains some or all of the plasmid vector DNA. This phenomenon is referred to as "read-through." A desired approach is often that only the transgene(s) located between the right and left border regions (the T-DNA) is transferred into the plant genome without any of the adjacent plasmid vector DNA (the vector backbone). Vector backbone DNA contains various plasmid maintenance elements, including, for example, origin of replications, bacterial selectable marker genes, and other DNA fragments that are not required to express the desired trait(s) in plants.

Engineered minichromosomes can also be used to express one or more genes in plant cells. Cloned telomeric repeats introduced into cells may truncate the distal portion of a chromosome by the formation of a new telomere at the integration site. Using this method, a vector for gene transfer can be prepared by trimming off the arms of a natural plant chromosome and adding an insertion site for large inserts (Yu et al., 2006, Proc. Natl. Acad. Sci. USA 103: 17331-17336; Yu et al., 2007, Proc. Natl. Acad. Sci. USA 104: 8924-8929).

An alternative approach to chromosome engineering in plants involves in vivo assembly of autonomous plant minichromosomes (Carlson et al., 2007, PLoS Genet. 3: 1965-74). Plant cells can be transformed with centromeric sequences and screened for plants that have assembled autonomous chromosomes de novo. Useful constructs combine a selectable marker gene with genomic DNA fragments containing centromeric satellite and retroelement sequences and/or other repeats.

Another approach useful to the described invention is Engineered Trait Loci ("ETL") technology (U.S. Pat. No. 6,077,697; US 2006/0143732). This system targets DNA to a heterochromatic region of plant chromosomes, such as the pericentric heterochromatin, in the short arm of acrocentric chromosomes. Targeting sequences may include ribosomal DNA (rDNA) or lambda phage DNA. The pericentric rDNA region supports stable insertion, low recombination, and high levels of gene expression. This technology is also useful for stacking of multiple traits in a plant (US 2006/0246586).

Zinc-finger nucleases (ZFN), TALEN and CRISPR-Cas9 are also useful for practicing the invention in that they allow double strand DNA cleavage at specific sites in plant chromosomes such that targeted gene insertion or deletion can be performed (Shukla et al., 2009, Nature 459: 437-441; Townsend et al, 2009, Nature 459: 442-445, WO 2015089427 A1).

Tissue Culture-Based Methods for Nuclear Transformation

Transformation protocols, as well as protocols for introducing nucleotide sequences into plants may vary depending on the type of plant or plant cell, i.e., monocot or dicot, targeted for transformation.

Suitable methods of introducing nucleotide sequences into plant cells and subsequent insertion into the plant genome are described in US 2010/0229256 A1 to Somleva & Ali and US 2012/0060413 to Somleva et al.

The transformed cells are grown into plants in accordance with conventional techniques. See, for example, McCormick et al., 1986, Plant Cell Rep. 5: 81-84. These plants may then be grown, and either pollinated with the same transformed variety or different varieties, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

In Planta Transformation Methods

Procedures for in planta transformation are not complex. Tissue culture manipulations and possible somaclonal variations are avoided and only a short time is required to obtain transgenic plants. However, the frequency of transformants in the progeny of such inoculated plants is relatively low and variable. At present, there are very few species that can be routinely transformed in the absence of a tissue culture-based regeneration system. Stable *Arabidopsis* transformants can be obtained by several in planta methods including vacuum infiltration (Clough & Bent, 1998, The Plant J. 16: 735-743), transformation of germinating seeds (Feldmann & Marks, 1987, Mol. Gen. Genet. 208: 1-9), floral dip (Clough and Bent, 1998, Plant J. 16: 735-743), and floral spray (Chung et al., 2000, Transgenic Res. 9: 471-476). Other plants that have successfully been transformed by in planta methods include rapeseed and radish (vacuum infiltration, Ian and Hong, 2001, Transgenic Res., 10: 363-371; Desfeux et al., 2000, Plant Physiol. 123: 895-904), *Medicago truncatula* (vacuum infiltration, Trieu et al., 2000, Plant J. 22: 531-541), camelina (floral dip, WO/2009/117555 to Nguyen et al.), and wheat (floral dip, Zale et al., 2009, Plant Cell Rep. 28: 903-913). In planta methods have also been used for transformation of germ cells in maize (pollen, Wang et al. 2001, Acta Botanica Sin., 43, 275-279; Zhang et al, 2005, Euphytica, 144, 11-22; pistils, Chumakov et al. 2006, Russian J. Genetics, 42, 893-897; Mamontova et al. 2010, Russian J. Genetics, 46, 501-504) and Sorghum (pollen, Wang et al. 2007, Biotechnol. Appl. Biochem., 48, 79-83)

Reporter Genes and Selectable Marker Genes

Reporter genes and/or selectable marker genes may be included in an expression control sequence (expression cassette) as described in US Patent Applications 20100229256 and 20120060413, incorporated by reference herein. An expression cassette including a promoter sequence operably linked to a heterologous nucleotide sequence of interest can be used to transform any plant by any of the methods described above. Useful selectable marker genes and methods of selection transgenic lines for a range of different crop species are described in the examples herein.

Nucleotide Sequence Expression in Plants

Plant promoters can be selected to control the expression of the nucleotide sequence in different plant tissues or organelles for all of which methods are known to those skilled in the art (Gasser & Fraley, 1989, Science 244: 1293-1299).

The choice of promoter(s) that can be used depends upon several factors, including, but not limited to, efficiency, selectability, inducibility, desired expression level, and/or preferential cell or tissue expression. It is a routine matter for one of skill in the art to modulate the expression of a nucleotide sequence by appropriately selecting and positioning promoters and other regulatory regions relative to that sequence. Examples of promoters that can be used are known in the art. Promoters that can be used include those present in plant genomes, as well as promoters from other sources. Some suitable promoters initiate transcription only, or predominantly, in certain cell types. Methods for identifying and characterizing promoter regions in plant genomic DNA include, for example, those described in Jordano, et al., *Plant Cell* 1:855-866, 1989; Bustos, et al., *Plant Cell* 1:839-854, 1989; Green, et al., *EMBO J.* 7:4035-4044, 1988; Meier et al., *Plant Cell* 3:309-316, 1991; and Zhang et al., *Plant Physiology* 110: 1069-1079, 1996.

Additional examples of promoters that can be used include ribulose-1,5-bisphosphate carboxylase (RbcS) promoters, such as the RbcS promoter from Eastern larch (*Larix laricina*), the pine cab6 promoter (Yamamoto et al., *Plant Cell Physiol.* 35:773-778, 1994), the Cab-1 gene promoter from wheat (Fejes et al., *Plant Mol. Biol.* 15:921-932, 1990), the CAB-1 promoter from spinach (Lubberstedt et al., *Plant Physiol.* 104:997-1006, 1994), the cab1R promoter from rice (Luan et al., *Plant Cell* 4:971-981, 1992), the GAPA-1 promoters from maize, the FBA2 promoter from *Saccharomyces cerevisiae*, the pyruvate orthophosphate dikinase (PPDK) promoter from maize (Matsuoka et al., *Proc. Natl. Acad. Sci. U.S.A.* 90:9586-9590, 1993), the tobacco Lhcb1*2 promoter (Cerdan et al., *Plant Mol. Biol.* 33:245-255, 1997), the *Arabidopsis thaliana* SUC2 sucrose-$H^+$ symporter promoter (Truernit et al., *Planta* 196:564-570, 1995), and thylakoid membrane protein promoters from spinach (psaD, psaF, psaE, PC, FNR, atpC, atpD, cab, and rbcS). Additional exemplary promoters that can be used to drive gene transcription in stems, leafs, and green tissue are described in U.S. Patent Application Publication No. 2007/0006346, herein incorporated by reference in its entirety. Additional promoters that result in preferential expression in plant green tissues include those from genes such as *Arabidopsis thaliana* ribulose-1,5-bisphosphate carboxylase (Rubisco) small subunit (Fischhoff et al., *Plant Mol. Biol.* 20:81-93, 1992), aldolase and pyruvate orthophosphate dikinase (PPDK) (Taniguchi et al., *Plant Cell Physiol.* 41(1): 42-48, 2000).

Inducible Promoters

Chemical-regulated promoters can be used to modulate the expression of a nucleotide sequence in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize ln2-2 promoter, which is activated by benzenesulfonamide herbicide safeners, the maize GST promoter, which is activated by hydrophobic electrophlic compounds that are used as pre-emergent herbicides, and the tobacco PR-1 promoter which is activated by salicylic acid. Other chemical-regulated promoters include steroid-responsive promoters [see, for example, the glucocorticoid-inducible promoter (Schena et al, 1991, Proc. Natl. Acad. Sci. USA 88: 10421-10425; McNellis et al., 1998, Plant 14:247-257) and tetracycline-inducible and tetracycline-repressible promoters (see, for example, Gatz et al., 1991, Mol. Gen. Genet. 227: 229-237; U.S. Pat. Nos. 5,814,618 and 5,789,156, herein incorporated by reference in their entirety). A three-component osmotically inducible expression system suitable for plant metabolic engineering has recently been reported (Feng et al, 2011, PLoS ONE 6: 1-9).

Constitutive Promoters

Constitutive promoters include, for example, the core promoter of the Rsyn7 promoter and other constitutive promoters disclosed in WO 99/43838 and U.S. Pat. No. 6,072,050, the core CaMV 35S promoter (Odell et al., 1985, Nature 313: 810-812), rice actin (McElroy et al., 1990, Plant Cell 2: 163-171), ubiquitin (Christensen et al., 1989, Plant Mol. Biol. 12: 619-632; Christensen et al, 1992, Plant Mol. Biol. 18: 675-689), pEMU (Last et al, 1991, Theor. Appl. Genet. 81: 581-588), MAS (Velten et al., 1984, EMBO J. 3: 2723-2730), and ALS promoter (U.S. Pat. No. 5,659,026). Other constitutive promoters are described in U.S. Pat. Nos. 5,608,149; 5,608,144; 5,604,121; 5,569,597; 5,466,785; 5,399,680; 5,268,463; and 5,608,142.

Weak Promoters

Where low level expression is desired, weak promoters may be used. Generally, the term "weak promoter" is intended to describe a promoter that drives expression of a nucleotide sequence at a low level. Where a promoter is expressed at unacceptably high levels, portions of the promoter sequence can be deleted or modified to decrease expression levels. Such weak constitutive promoters include, for example, the core promoter of the Rsyn7 promoter (WO 99/43838 and U.S. Pat. No. 6,072,050).

Tissue Specific Promoters

"Tissue-preferred" promoters can be used to target gene expression within a particular tissue. Compared to chemically inducible systems, developmentally and spatially regulated stimuli are less dependent on penetration of external factors into plant sells. Tissue-preferred promoters include those described by Van Ex et al., 2009, Plant Cell Rep. 28: 1509-1520; Yamamoto et al, 1997, Plant J. 12: 255-265; Kawamata et al., 1997, Plant Cell Physiol. 38: 792-803; Hansen et al., 1997, Mol. Gen. Genet. 254: 337-343; Russell et al., 199), Transgenic Res. 6: 157-168; Rinehart et al., 1996, Plant Physiol. 1 12: 1331-1341; Van Camp et al., 1996, Plant Physiol. 112: 525-535; Canevascini et al., 1996, Plant Physiol. 1 12: 513-524; Yamamoto et al., 1994, Plant Cell Physiol. 35: 773-778; Lam, 1994, Results Probl. Cell Differ. 20: 181-196, Orozco et al., 1993, Plant Mol. Biol. 23: 1 129-1 138; Matsuoka et al., 1993, Proc. Natl. Acad. Sci. USA 90: 9586-9590, and Guevara-Garcia et al, 1993, Plant J. 4: 495-505. Such promoters can be modified, if necessary, for weak expression.

Seed/Embryo Specific Promoters

"Seed-preferred" promoters include both "seed-specific" promoters (those promoters active during seed development such as promoters of seed storage proteins) as well as "seed-germinating" promoters (those promoters active during seed germination). See Thompson et al., 1989, BioEssays 10: 108-1 13, herein incorporated by reference. Such seed-preferred promoters include, but are not limited to, Cim1 (cytokinin-induced message), cZ19B1 (maize 19 kDa zein), milps (myo-inositol-1-phosphate synthase), and celA (cellulose synthase). Gamma-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, and globulin 1. The stage specific developmental promoter of the late embryogenesis abundant protein gene LEA has successfully been used to drive a recombination system for excision-mediated expression of a lethal gene at late embryogenesis stages in the seed terminator technology (U.S. Pat. No. 5,723,765 to Oliver et al.).

Leaf Specific Promoters

Leaf-specific promoters are known in the art. See, for example, WO/2011/041499 and U.S. Patent No. 2011/0179511 A1 to Thilmony et al.; Yamamoto et al., 1997, Plant J. 12: 255-265; Kwon et al., 1994, Plant Physiol. 105: 357-367; Yamamoto et al, 1994, Plant Cell Physiol. 35: 773-778; Gotor et al, 1993, Plant J. 3: 509-518; Orozco et al., 1993, Plant Mol. Biol. 23: 1 129-1 138, and Matsuoka et al, 1993, Proc. Natl. Acad. Sci. USA 90: 9586-9590.

Temporal Specific Promoters

Also contemplated are temporal promoters that can be utilized during the developmental time frame, for example, switched on after plant reaches maturity in leaf to enhance carbon flow.

Anther/Pollen Specific Promoters

Numerous genes specifically expressed in anthers and/or pollen have been identified and their functions in pollen development and fertility have been characterized. The specificity of these genes has been found to be regulated mainly by their promoters at the transcription level (Ariizumi et al., 2002, Plant Cell Rep. 21: 90-96 and references therein). A large number of anther- and/or pollen-specific promoters and their key ds-elements from different plant species have been isolated and functionally analyzed.

Floral Specific Promoters

Floral-preferred promoters include, but are not limited to, CHS (Liu et al., 201 1, Plant Cell Rep. 30: 2187-2194), OsMADS45 (Bai et al., 2008, Transgenic Res. 17: 1035-1043), PSC (Liu et al, 2008, Plant Cell Rep. 27: 995-1004), LEAFY, AGAMOUS, and API (Van Ex et al., 2009, Plant Cell Rep. 28: 1509-1520), API (Verweire et al, 2007, Plant Physiol. 145: 1220-1231), PtAGIP (Yang et al, 201 1, Plant Mol. Biol. Rep. 29: 162-170), Leml (Somleva & Blechl, 2005, Cereal Res. Comm. 33: 665-671; Skadsen et al, 2002, Plant Mol. Biol. 45: 545-555), Lem2 (Abebe et al., 2005, Plant Biotechnol. J. 4: 35-44), AGL6 and AGL13 (Schauer et al., 2009, Plant J. 59: 987-1000).

Combinations of Promoters

Certain embodiments use transgenic plants or plant cells having multi-gene expression constructs harboring more than one promoter. The promoters can be the same or different.

Any of the described promoters can be used to control the expression of one or more of the nucleotide sequences of the invention, their homologues and/or orthologues as well as any other genes of interest in a defined spatiotemporal manner.

Maize Promoters

Transgenic DNA constructs used for transforming plant cells will comprise the heterologous nucleotides which one desires to introduced into and a promoter to express the heterologous nucleotides in the host maize cells. As is well known in the art such constructs can further include elements such as regulatory elements, 3' untranslated regions (such as polyadenylation sites), transit or signal peptides and marker genes elements as desired. 1. Regulatory Elements A number of promoters that are active in plant cells have been described in the literature both constitutive and tissue specific promoters and inducible promoters. See the background section of U.S. Pat. No. 6,437,217 for a description of a wide variety of promoters that are functional in plants. Such promoters include the nopaline synthase (NOS) and octopine synthase (OCS) promoters that are carried on tumor-inducing plasmids of *Agrobacterium tumefaciens*, the caulimovirus promoters such as the cauliflower mosaic virus (CaMV) 19S and 35S promoters and the figwort mosaic virus (FMV) 35S promoter, the enhanced CaMV35S promoter (e35S), the light-inducible promoter from the small subunit of ribulose bisphosphate carboxylase (ssRUBISCO, a very abundant plant polypeptide). For instance, see U.S. Pat. No. 6,437,217 which discloses a maize RS81 promoter, 5,641,876 which discloses a rice actin promoter, 6,426,446 which discloses a maize RS324 promoter, 6,429,362 which discloses a maize PR-1 promoter, 6,232,526 which discloses a maize A3 promoter and 6,177,611 which discloses constitutive maize promoters, all of which are incorporated herein by reference.

Requirements for Construction of Plant Expression Cassettes

Nucleotide sequences intended for expression in transgenic plants are first assembled in expression cassettes behind a suitable promoter active in plants. The expression cassettes may also include any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be transferred to the plant transformation vectors described herein. The following is a description of various components of typical expression cassettes.

Transcriptional Terminators

A variety of transcriptional terminators are available for use in expression cassettes. These are responsible for the termination of transcription beyond the transgene and the correct polyadenylation of the transcripts. Appropriate transcriptional terminators are those that are known to function in plants and include the CaMV 35S terminator, the tml terminator, the nopaline synthase terminator and the pea rbcS E9 terminator. These are used in both monocotyledonous and dicotyledonous plants.

Sequences for the Enhancement or Regulation of Expression

Numerous sequences have been found to enhance gene expression from within the transcriptional unit and these sequences can be used in conjunction with the genes to increase their expression in transgenic plants. For example, various intron sequences such as introns of the maize Adhl gene have been shown to enhance expression, particularly in monocotyledonous cells. In addition, a number of non-translated leader sequences derived from viruses are also known to enhance expression, and these are particularly effective in dicotyledonous cells.

Coding Sequence Optimization

The coding sequence of the selected gene may be genetically engineered by altering the coding sequence for optimal expression in the crop species of interest. Methods for modifying coding sequences to achieve optimal expression in a particular crop species are well known (Perlak et al, 1991, Proc. Natl. Acad. Sci. USA 88: 3324 and Koziel et al., 1993, Biotechnology 11: 194-200).

Construction of Plant Transformation Vectors

Numerous vectors available for plant transformation are known to those of ordinary skill in the plant transformation arts. The genes pertinent to this disclosure can be used in conjunction with any such vectors. The choice of vector depends upon the selected transformation technique and the target species.

Many vectors are available for transformation using *Agrobacterium tumefaciens*. These typically carry at least one T-DNA sequence and include vectors such as pBIN19. Typical vectors suitable for *Agrobacterium* transformation include the binary vectors pCIB200 and pCIB2001, as well as the binary vector pCIB 10 and hygromycin selection derivatives thereof (See, for example, U.S. Pat. No. 5,639,949).

Transformation without the use of *Agrobacterium tumefaciens* circumvents the requirement for T-DNA sequences in the chosen transformation vector and consequently vectors lacking these sequences are utilized in addition to vectors such as the ones described above which contain T-DNA sequences. The choice of vector for transformation techniques that do not rely on *Agrobacterium* depends largely on the preferred selection for the species being transformed. Typical vectors suitable for non-*Agrobacterium* transformation include pCIB3064, pSOG 19, and pSOG35. (See, for example, U.S. Pat. No. 5,639,949).

Transformation and Selection of Cultures and Plants

Plant cultures can be transformed and selected using one or more of the methods described above which are well known to those skilled in the art.

Manipulation of Endogenous Promoters

Zinc-finger nucleases (ZFN), TALEN, and CRISPR-Cas9 are also useful for practicing the invention in that they allow double strand DNA cleavage at specific sites in plant chromosomes such that targeted gene insertion or deletion can be performed (Shukla et al., 2009, Nature 459: 437-441; Townsend et al, 2009, Nature 459: 442-445). This approach may be particularly useful for the present invention to modify the promoter of endogenous genes to modify expression of genes homologous to PsbS, ZEP and VDE, which are present in the genome of the plant of interest. In this case the ZFN, TALEN or CRISPR/Cas9 can be used to change the sequences regulating the expression of the TF of interest to increase the expression or alter the timing of expression beyond that found in a non-engineered or wild type plant.

EXAMPLES

The present disclosure will be more fully understood by reference to the following examples. It should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1. Transgenic *Nicotiana tabacum*

*Nicotiana tabacum* plants were transformed with a T-DNA cassette containing three *Arabidopsis thaliana* genes. *Arabidopsis* ZEP was overexpressed to increase the rate of xanthophyll epoxidation and corresponding NPQ relaxation, together with *Arabidopsis* PsbS overexpression to stimulate the amplitude of qE formation and *Arabidopsis* VDE to maintain critical levels of zeaxanthin for ROS scavenging. The resulting transgenic plants are shown to have modified NPQ kinetics leading to higher quantum yield and $CO_2$ fixation without loss of photo-protective efficiency under fluctuating light intensity and increased growth in two independent greenhouse experiments. These results confirm that photosynthetic efficiency is transiently limited by NPQ under fluctuating light intensity and provide the first proof of principle for improvement of photosynthetic efficiency and crop yield via changes in NPQ kinetics.

Example 2. NPQ and PSII Operating Efficiency in Young Seedlings

Transient NPQ was determined from chlorophyll fluorescence imaging on $T_1$ progeny of 20 independent transformation events with the vde-psbs-zep (VPZ) construct during 10 minutes of illumination with 1000 μmol quanta $m^{-2}$ $s^{-1}$, followed by 10 minutes of dark relaxation. Since the aim was to maintain similar non-photochemical quenching capacity, lines with maximum levels of NPQ similar to WT were selected for further investigation. This yielded eight lines from which two lines harboring a single T-DNA copy (VPZ-34 and 56) and one line with two T-DNA insertions (VPZ-23) were included in the present work. All results are reported for homozygous $T_2$ progeny. NPQ kinetic behavior showed substantial differences between the three VPZ lines and WT (FIG. 1A). NPQ in the VPZ lines rapidly increased, reaching the maximum NPQ level between two to four minutes, after which the level of NPQ stabilized (VPZ-23) or even slightly decreased (VPZ-34 and VPZ-56). In contrast, NPQ in the WT control continued to increase for seven minutes, after which the maximum level was retained for the remaining three minutes. As a result of these contrasting induction patterns, NPQ was significantly higher in all three transgenic lines during the initial five minutes of induction, but not in the final five minutes (FIG. 1A). After turning the lights off, NPQ relaxation was very rapid and very similar in both WT and VPZ lines.

Repetitive cycles of light intensity between 2000 (3 min) and 200 (2 min) μmol $m^{-2}$ $s^{-1}$ resulted in even more pronounced differences in NPQ between the VPZ lines and WT (FIG. 1B). NPQ in the VPZ lines increased rapidly during the high light phase of the first two cycles, reaching maximum levels during the second minute of the second cycle. In contrast, NPQ increased more slowly in the WT seedlings, only reaching maximum levels in the third minute of the fourth cycle. Interestingly, NPQ during the low light phase of the cycles showed the opposite pattern. In the first cycle, NPQ levels during the low light phase were higher in the VPZ lines, however NPQ levels in the second cycle were equal between the VPZ lines and WT, and were significantly lower in the VPZ lines in the final three cycles.

Photosystem II (PSII) operating efficiency, estimated in conjunction with NPQ, showed no differences between VPZ lines and WT in the first cycle (FIG. 1C). However, during the five following cycles, VPZ lines showed superior PSII operating efficiency during the low light phase of the cycles, whereas no differences were found during the high light phase. This pattern was established in the second cycle, and repeated throughout the remainder of the experiment.

Example 3. Transcription and Protein Expression

Figure 2:
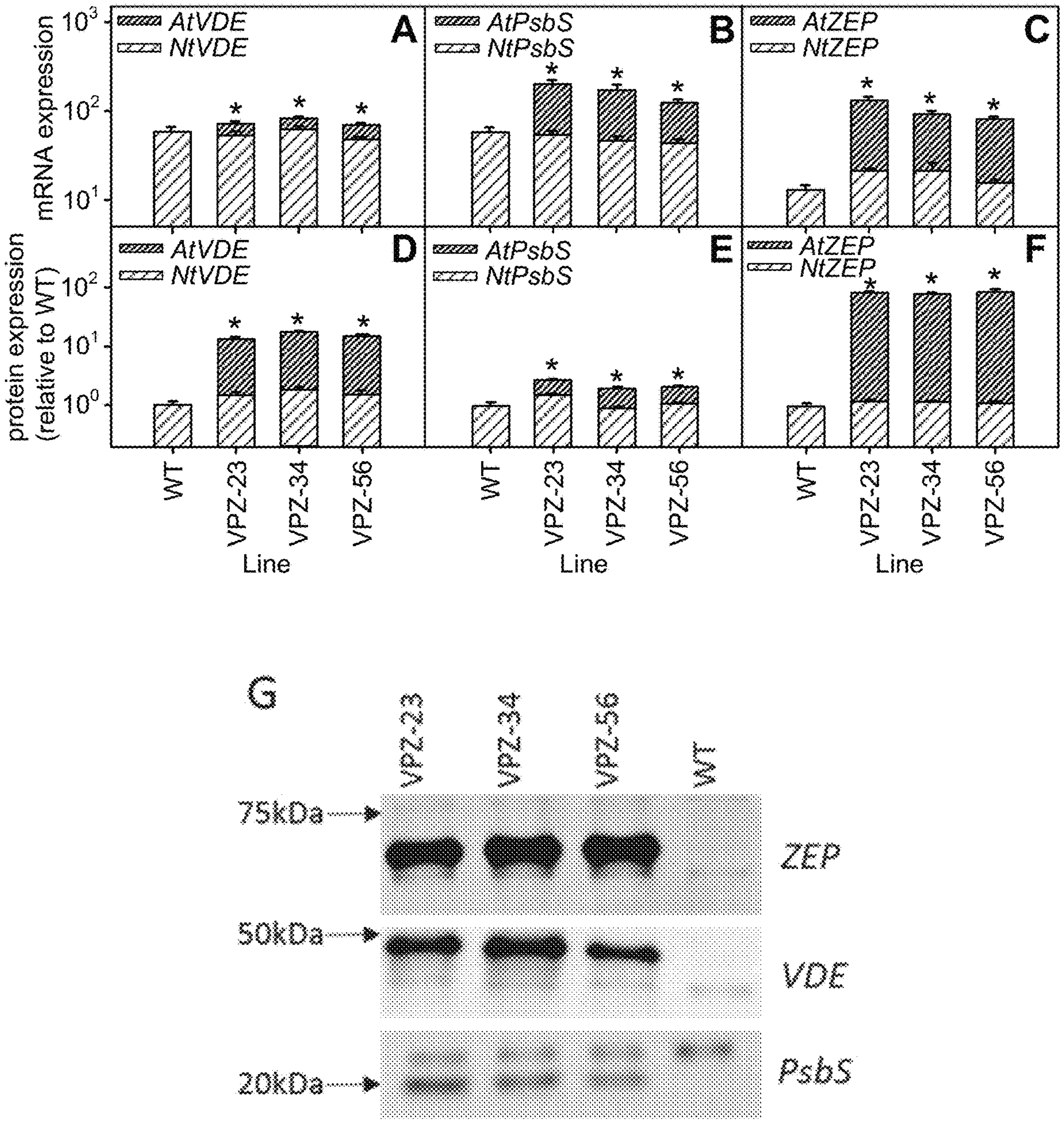
FIG. 2. mRNA and protein expression of native (Nt) and transgenic (At) violaxanthin de-epoxidase (VDE), photosystem II subunit S (PsbS) and zeaxanthin epoxidase (ZEP). (A-C) mRNA levels relative to actin and tubulin, (D-F) protein levels relative to wild-type, determined from densitometry on western blots, error bars indicate ±se (n=5) asterisks indicate significant differences between VPZ lines and wild-type (α=0.05), (G) Example of western blots for VDE, PsbS and ZEP.

All three VPZ-lines showed significant increases in combined transgenic (At) and native (Nt) transcript levels of VDE (3-fold), PsbS (3-fold) and ZEP (8-fold) relative to wild-type (FIGS. 2A, B and C). For PsbS the increase in transcript levels translated into approximately 2-fold higher PsbS protein level (FIG. 2E), as exemplified in two approximately equal density bands around 22 kDa (FIG. 2G, VPZ lanes), representing the native and transgenic protein. However, for VDE and ZEP the increase in transcript levels was amplified in the protein levels (FIG. 2G, labelled bands around 73 kDa for ZEP and 45 kDa for VDE), showing substantial increases of VDE (FIG. 2D) and ZEP (FIG. 2F) protein relative to WT (16 and 80-fold, respectively). Interaction between transgenic and native transcript and protein levels appeared to be negligible, since transcript and protein levels of the native proteins were similar in the VPZ lines and WT.

Example 4. Kinetics of NPQ in Young Seedlings Following Repeated Changes in Light Intensity To compare the kinetics of dynamic NPQ adjustment, time constants of a double exponential model were fitted to time-series of NPQ in young seedlings as a function of repeated changes in light intensity between 2000 and 200 μmol $m^{-2}$ $s^{-1}$ (Table 1). During the first 2000/200 cycle no consistent differences between WT and VPZ overexpression lines were observed. The time constant of NPQ induction varied between 49.3±1.9 (VPZ-34) to 91.8±6.2 (VPZ-56), and time constants of readjustment from 2000 to 200 μmol $m^{-2}$ $s^{-1}$ were also similar across WT and the three VPZ lines, averaging 10.2 s for $\tau_1$ and 669.9 s for $\tau_2$. During the second 2000/200 cycle, the effect of VPZ expression on NPQ kinetics became more apparent. The fast phase of NPQ increase in the WT was approximately 2.3 times faster than in the VPZ lines, with $\tau_1$ of 5.5 s in WT versus average $\tau_1$ of 12.6 s in the VPZ lines (Table 1). The second adjustment of NPQ to 200 μmol $m^{-2}$ $s^{-1}$ showed a pronounced difference in the slow component of NPQ decline. Estimated $\tau_2$ in the VPZ lines, was found to be 1.9 times faster than WT (464.3 versus 886.4 s). Thus, repeated light intensity changes resulted in faster build-up and slower relaxation of NPQ in the WT, but the time constants in the VPZ lines were relatively unaffected. This same trend continued in the final 3 min at 2000 μmol $m^{-2}$ $s^{-1}$ followed by 10 min of darkness. The fast phase of NPQ increase in the WT seedlings was approximately 2.4 times faster than the VPZ lines ($\tau_1$ of 4.3 versus 10.3 s) but final relaxation of NPQ during 10 min of darkness was 1.4 ($\tau_1$) and 3.5 times ($\tau_2$) faster in the VPZ lines relative to WT. In addition, $\tau_1$ and $\tau_2$ determined for recovery of PSII operating efficiency were 2.1 and 4.1 times faster in the VPZ lines, compared to WT.

TABLE 1

Time constants of NPQ adjustment to repeated changes in light intensity (value ± se). Asterisks indicate significant differences between VPZ lines and wild-type (a = 0.05).

| Experiment phase (HL = 2000, LL = 200 μmol $m^{-2}$ $s^{-1}$, D = dark) | Time constant(s) | WT | VPZ-23 | VPZ-34 | VPZ-56 |
|---|---|---|---|---|---|
| 1st HL | τ1[a] | 82.7 ± 3.2 | *63.4 ± 2.8 | *49.3 ± 1.9 | 91.8 ± 6.2 |
| 1st LL | τ1 | 10.4 ± 2.9 | 5.6 ± 1.9 | 14.6 ± 5.4 | n.d.[b] |
| | τ2 | 564.9 ± 48.1 | *1175.3 ± 130.8 | 511.5 ± 39.7 | 428.0 ± 20.9 |
| 2nd HL | τ1 | 5.5 ± 0.4 | 13.5 ± 3.5 | 11.3 ± 2.8 | *12.9 ± 3.2 |
| | τ2 | 115.3 ± 24.4 | 127.5 ± 150.1 | 111.2 ± 71.2 | 389.3 ± 1586.8 |
| 2nd LL | τ1 | 9.2 ± 0.6 | 7.7 ± 1.2 | 9.9 ± 1.4 | 9.9 ± 1.1 |
| | τ2 | 886.4 ± 101.9 | *470.1 ± 45.0 | *461.5 ± 60.3 | *461.4 ± 64.6 |
| 3rd HL | τ1 | 4.3 ± 0.3 | *10.1 ± 1.2 | *10.2 ± 1.4 | *10.6 ± 2.6 |
| | τ2 | 37.2 ± 4.8 | 55.4 ± 33.4 | 53.8 ± 28.2 | 35.5 ± 9.9 |
| D | τ1 | 21.4 ± 1.2 | *13.3 ± 1.3 | 19.4 ± 1.4 | *13.2 ± 1.0 |
| | τ2 | 2641.1 ± 821.2 | 792.6 ± 131.7 | *692.6 ± 77.9 | *774.9 ± 94.5 |
| D (PSII efficiency) | τ1 | 29.2 ± 2.0 | *20.6 ± 2.4 | *14.2 ± 1.0 | *7.7 ± 0.6 |
| | τ2 | 357.9 ± 480.0 | 106.3 ± 29.5 | 85.6 ± 5.8 | 68.3 ± 3.7 |

[a]Data in 1st HL phase didn't constrain two time constants, so the model was reduced to a single exponential function and only one time constant was fitted.
[b]Data resolution was not sufficient to properly constrain fast phase, only slow phase was fitted.

Example 5. NPQ, Linear Electron Transport and $CO_2$ Uptake in Steady State

Figure 3:
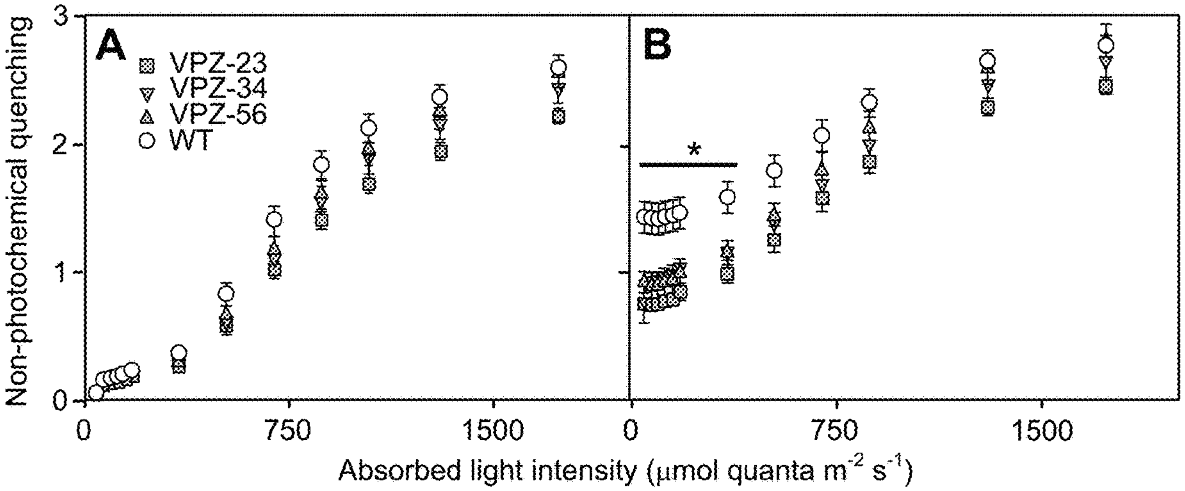
FIG. 3. Non-photochemical quenching during gas exchange as a function of absorbed light intensity in fully-expanded leaves of wild-type and VPZ-overexpressing lines. Light intensity was either increased from low to high PFD, while waiting for steady state at each step (A), or varied from high to low PFD with 4 min of 2000 μmol $m^{-2}$ $s^{-1}$ before each light intensity change (B). Error bars indicate ±se (n=6), asterisks indicate significant differences between VPZ lines and wild-type (α=0.05).
Figure 7:
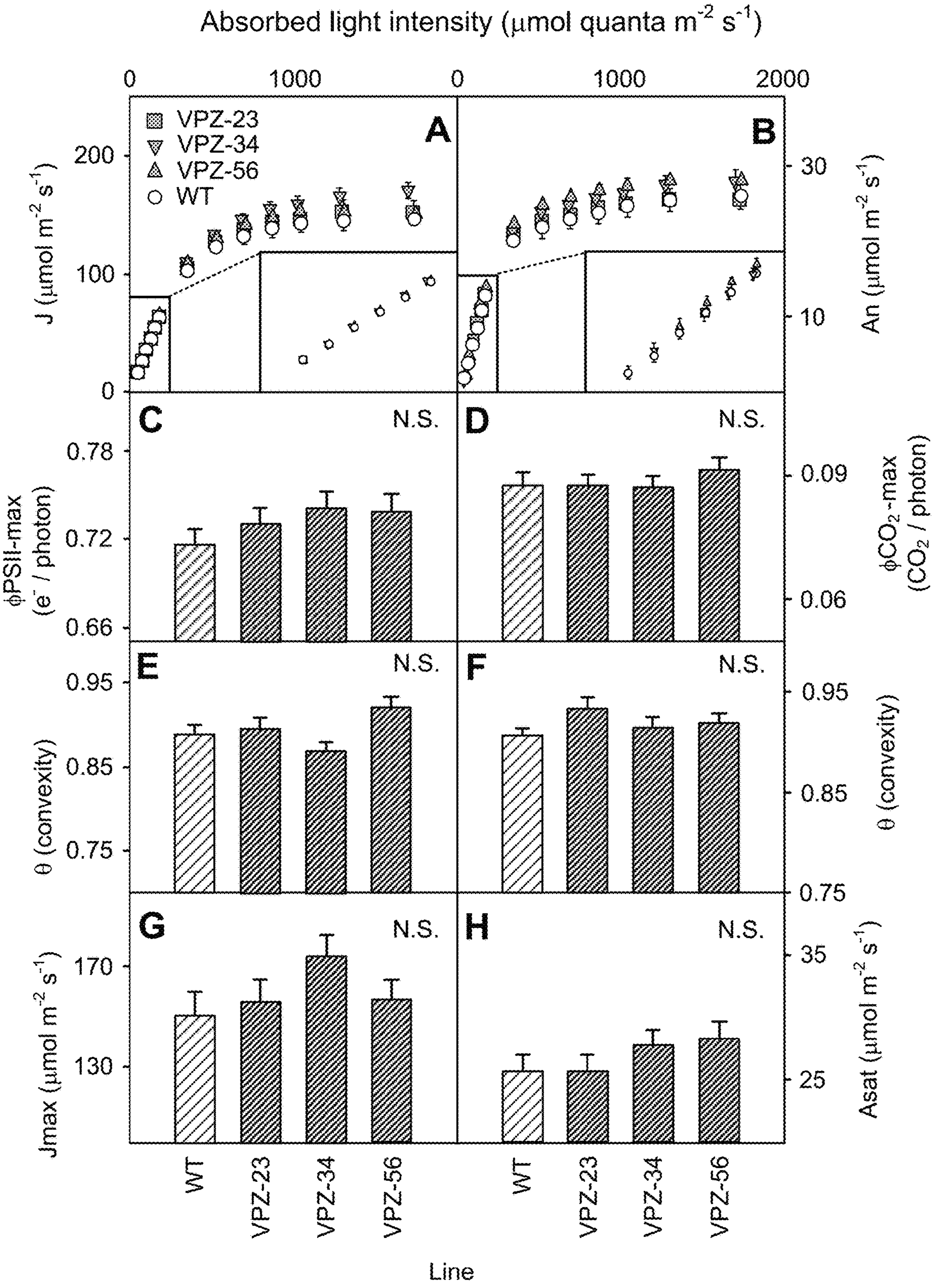
FIG. 7. Linear electron transport and net assimilation rate as a function of light intensity. Light intensity was varied from high to low PFD with 4 min of 2000 μmol $m^{-2}$ $s^{-1}$ PFD before each light intensity change. (A-B) Linear electron transport (J) and net assimilation rate (An) and corresponding parameter fits for initial slope (C-D), convexity (E-F) and asymptote (G-H). Error bars indicate ±se (n=6).
Figure 8:
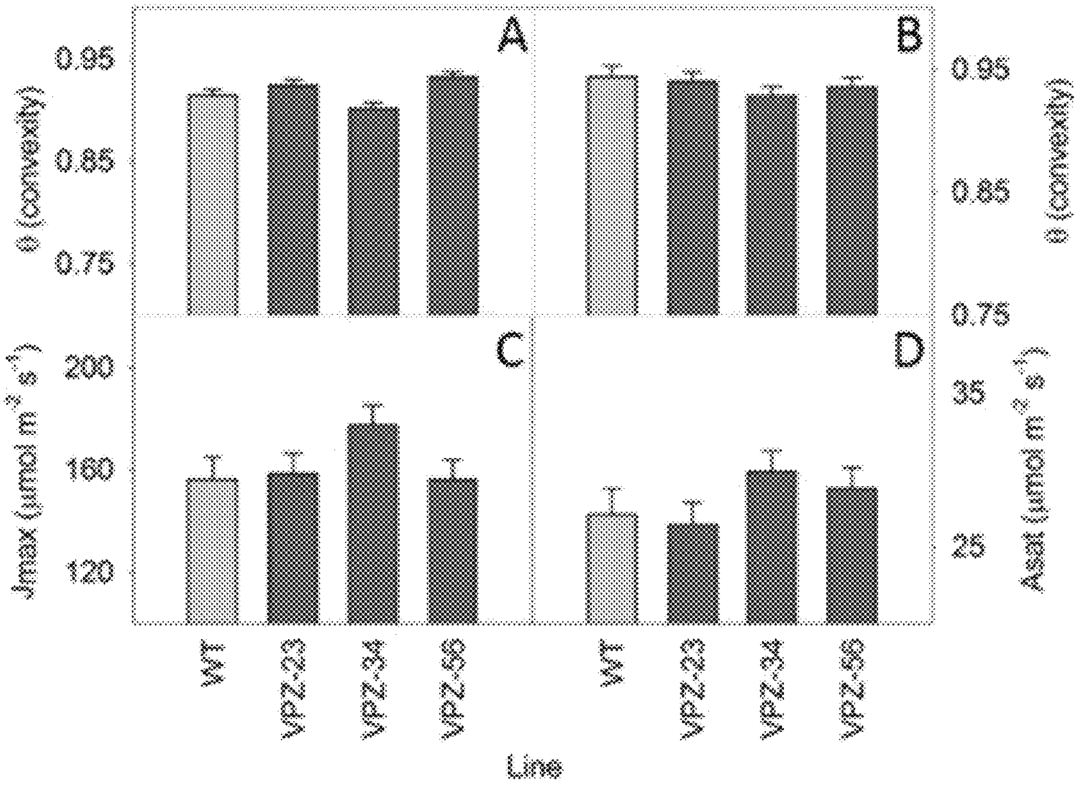
FIG. 8. Convexity (A-B) and asymptote (C-D) parameter fits to linear electron transport (J) and net assimilation rate (An) as a function of light intensity. Light intensity was varied from high to low PFD with 4 min of 2000 μmol $m^{-2}$ $s^{-1}$ PFD before each light intensity change. Error bars indicate ±se (n=6).

To measure steady state gas exchange and chlorophyll fluorescence in fully expanded leaves, light intensity was varied from low to high intensity, taking great care to allow gas exchange and fluorescence to fully stabilize at each intensity. NPQ was very similar between WT and VPZ lines, especially at light intensity below 400 μmol $m^{-2}$ $s^{-1}$ (FIG. 3A). Corresponding response curves of linear electron transport and net assimilation rate as a function of absorbed light intensity did not show significant differences between WT and VPZ lines (FIG. 7). Additionally, fitted parameter values $V_{cmax}$, J, TPU, and Rd derived from $CO_2$ response curves were also similar between WT and the VPZ lines (Table 2.)

Table 2. Parameter fits derived from $CO_2$ response curves. Maximal carboxylation capacity (Vcmax), maximal rate of linear electron transport (Jmax), mitochondrial respiration rate not associated with photorespiration ($R_d$) and maximal rate of triose phosphate utilization (TPU). Values ±se, n=10, no significant differences between wild-type and VPZ lines were found.

| | WT | VPZ-23 | VPZ-34 | VPZ-56 |
|---|---|---|---|---|
| Vcmax (μmol $m^{-2}$ $s^{-1}$) | 112.3 ± 4.5 | 108.2 ± 2.7 | 104.7 ± 3.7 | 121.8 ± 6.1 |
| Jmax (μmol $m^{-2}$ $s^{-1}$) | 146.0 ± 5.7 | 136.2 ± 3.4 | 137.8 ± 4.2 | 149.0 ± 3.8 |
| TPU (μmol $m^{-2}$ $s^{-1}$) | 11.1 ± 0.4 | 10.1 ± 0.3 | 10.5 ± 0.3 | 10.9 ± 0.3 |
| $R_d$ (μmol $m^{-2}$ $s^{-1}$) | 2.1 ± 0.3 | 1.8 ± 0.3 | 2.2 ± 0.2 | 2.3 ± 0.3 |

Figure 4:
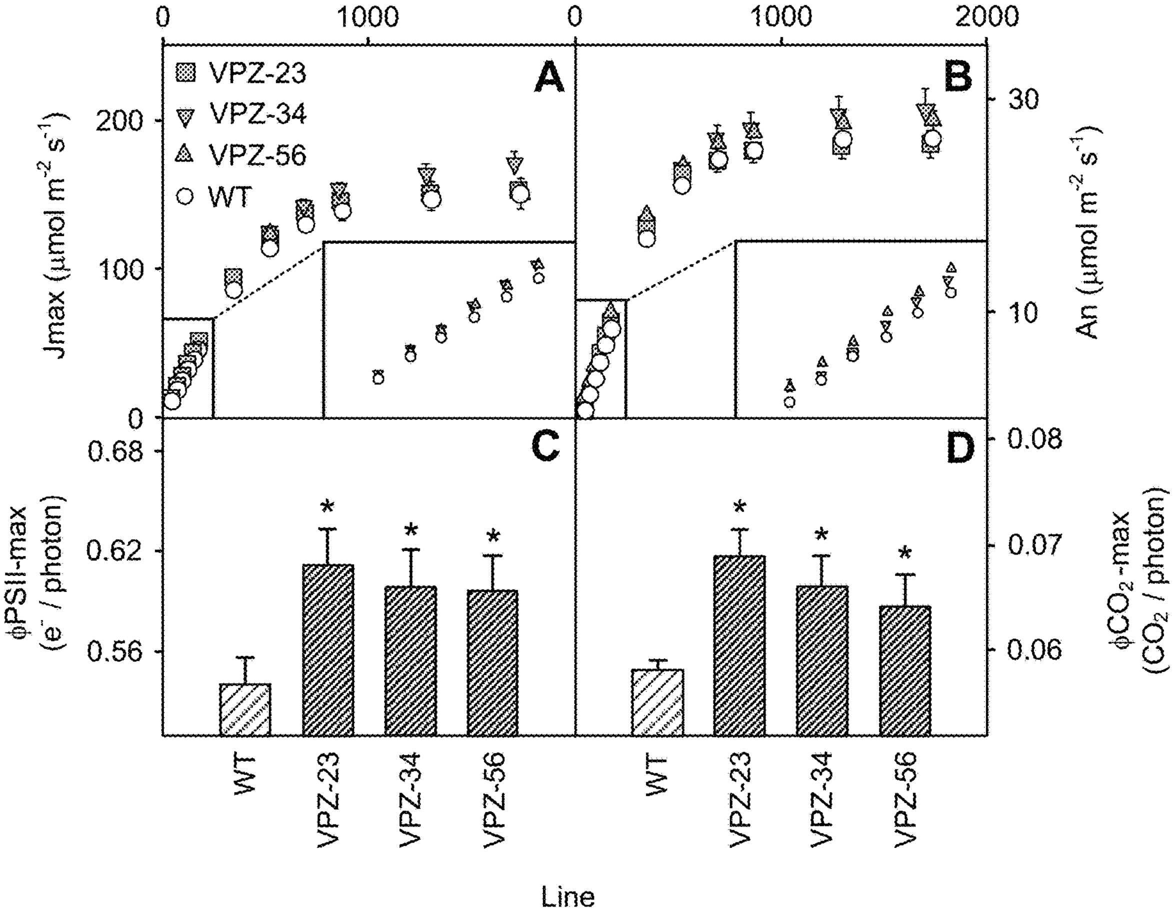
FIG. 4. (A-B) Linear electron transport (J) and net assimilation rate (An) as a function of light intensity and corresponding parameter fits for initial slope (C-D). Light intensity was varied from high to low PFD with 4 min of 2000 μmol $m^{-2}$ $s^{-1}$ PFD before each light intensity change. Error bars indicate ±se (n=6), asterisks indicate significant differences between VPZ lines and wild-type (α=0.05).

Example 6. NPQ, Electron Transport and $CO_2$ Fixation Under Fluctuating Light To evaluate the dynamic effect of VPZ overexpression on the shape of the light response curve, light intensity was varied in 4 min steps from high to low PFD with intermittent steps of 4 min of 2000 μmol $m^{-2}$ $s^{-1}$ before each light transition. NPQ in the VPZ lines was similar to WT at high light intensity, but significantly lower than WT at low light intensity (FIG. 3B). The resulting response curves of linear electron transport rate and net assimilation rate were distinctly different between WT and VPZ lines (FIGS. 4A and B). Fitted convexity and asymptote parameters were similar between WT and VPZ lines (FIG. 8A-D), but initial slopes were distinctly different (FIGS. 4C and D). Fluctuating intensity reduced ΦPSIImax to 0.541±0.012 in the WT plants (FIG. 4C), but VPZ lines maintained a less reduced ΦPSIImax of 0.612±0.021 (VPZ-23), 0.599±0.023 (VPZ-34) and 0.595±0.023 (VPZ-56). Similarly $\Phi CO_2$-max was reduced to 0.058±0.001 in the WT plants (FIG. 4D), whereas $\Phi CO_2$-max values in the VPZ lines were much less impacted by intermittent high light intensity, yielding 0.069±0.003 for VPZ-23, 0.066±0.003 for VPZ-34 and 0.064±0.003 for VPZ-56. Thus, under these fluctuating conditions, average ΦPSII-max and $ΦCO_2$-max of the VPZ lines were 11.3% and 14.0% higher than WT.

Example 7. Xanthophyll Cycle De-Epoxidation as a Function of Different Light Treatments To evaluate the effects of VPZ overexpression on the xanthophyll cycle, leaves were subjected to four different light treatments (Table 3). The combined pool size of violaxanthin, antheraxanthin, and zeaxanthin was similar between WT and VPZ lines. The xanthophyll pigment pool was completely epoxidated in dark-adapted leaves and no differences between WT and VPZ were observed. Exposure to PFD of 400 μmol $m^{-2}$ $s^{-1}$ resulted in almost no change in the xanthophyll composition and DES remained close to zero, but illumination with PFD of 2000 μmol $m^{-2}$ $s^{-1}$ led to considerable build-up of antheraxanthin and mainly zeaxanthin. VPZ lines retained significantly more violaxanthin and accumulated less zeaxanthin and antheraxanthin compared to WT, which led to xanthophyll DES in the VPZ lines to be almost two times lower than WT (25.5% versus 46.2%). The fluctuating light treatment showed the same trend as high light exposure, with even less xanthophyll de-epoxidation in the VPZ lines, relative to WT (17.8% versus 52.5%).

Table 3 Xanthophyll cycle pigment concentrations and de-epoxidation state (DES) in fully expanded leaves in either dark-adapted state or after exposure to constant 400 or 2000 μmol $m^{-2}$ $s^{-1}$ PFD or 3 cycles of 3 min 2000/3 min 200 μmol $m^{-2}$ $s^{-1}$ PFD. Pigment concentration (value±se, n=3-5) has been normalized per unit leaf area (g $m^{-2}$). DES (%)=(Zea+0.5Ant)/(Zea+Ant+Viola), n.d.=not detected. Asterisks indicate significant differences between VPZ lines and wild-type (α=0.05).

(FIG. 5B) was considerably less than after one hour, but VPZ seedlings were again found to be less photo-inhibited than WT. Residual NPQ after ten minutes of dark recovery tended to be lower in the VPZ seedlings (FIG. 5C). As a result of lower residual NPQ and higher photo-protection index, PSII efficiency in the VPZ seedlings also tended to be higher after 10 min of dark recovery (FIG. 5C).

Example 9. Plant Growth Under Greenhouse Conditions

Figure 6:
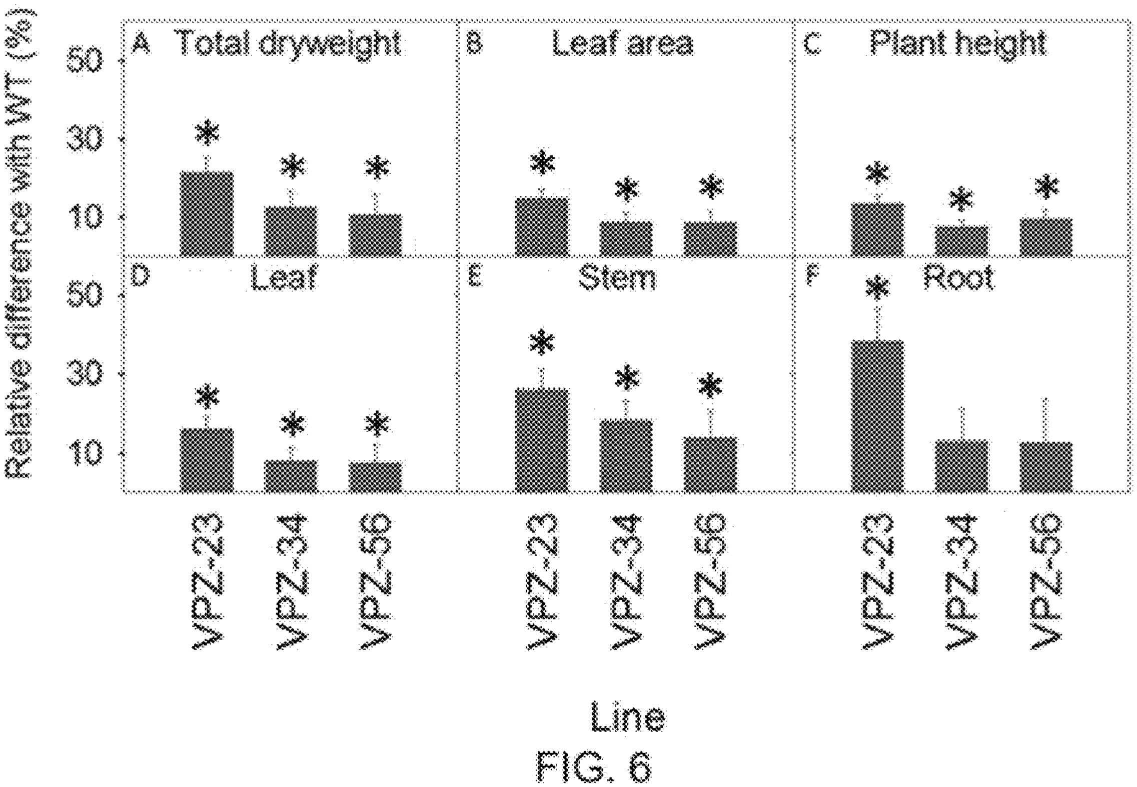
FIG. 6. Final plant size and weight in greenhouse experiments relative to WT. (A) Total dry-weight per plant, (B) leaf area per plant, (C) Plant height, (D) Leaf dry-weight per plant, (E) Stem dry-weight per plant, (F) Root dry-weight per plant. Error bars indicate ±se (n=20 and n=19 for experiment 1 and 2), asterisks indicate significant differences between VPZ lines and wild-type (α=0.05).

To investigate if the aforementioned differences in photosynthetic efficiency would affect growth, biomass accumulation was evaluated in two greenhouse experiments. Temperature was similar between both experiments and varied between 21 and 25° C. Peak light intensity exceeded 2000 μmol $m^{-2}$ $s^{-1}$ in the first experiment and 1600 μmol $m^{-2}$ $s^{-1}$ in the second experiment and daily light integrals averaged 21.3 and 19.3 mol $m^{-2}$ $d^{-1}$ in the first and second experiment, respectively. However, in the final week of the second experiment peak light intensity and daily light integral were decreasing substantially to 1037 μmol $m^{-2}$ $s^{-1}$ and 8.9 mol $m^{-2}$ $d^{-1}$, due to seasonal decline in light intensity. As a result, average plant dry weight was substantially higher in the first experiment, 35.6 g versus 22.5 g respectively. Across both trials, plants from VPZ lines exhibited increased plant height (FIG. 6C) and leaf area (FIG. 6B), relative to WT. Additionally, total dry weight per plant was between 10 to 21% higher in VPZ lines (FIG. 6A), mainly due to substantial increases in stem dry weight (14 to 26%, FIG. 6E) as well as increases in leaf (7.5 to 16%, FIG. 6D) and root (12.5 to 38.3%, FIG. 6F) dry weight.

Example 10. Additional Data

FIGS. 12 and 13 leaf, stem and root size, and growth, increase in transgenic plant lines N2-23 and N2-34 com-

| Light treatment | Pigment (g $m^{-2}$) | WT | VPZ-23 | VPZ-34 | VPZ-56 |
|---|---|---|---|---|---|
| Dark-adapted | Vio | 7.72 ± 0.37 | 6.64 ± 0.45 | 6.94 ± 0.64 | 6.70 ± 0.40 |
| | Ant | 0.01 ± 0.00 | 0.00 ± 0.00 | 0.00 ± 0.00 | 0.01 ± 0.00 |
| | Zea | n.d. | n.d. | n.d. | n.d. |
| | DES | 0.0 | 0.0 | 0.0 | 0.0 |
| Constant at 400 μmol $m^{-2}$ $s^{-1}$ PFD | Vio | 6.68 ± 0.62 | 7.29 ± 0.47 | 7.05 ± 0.48 | 7.07 ± 0.31 |
| | Ant | 0.03 ± 0.01 | 0.01 ± 0.00 | 0.02 ± 0.01 | 0.01 ± 0.00 |
| | Zea | 0.20 ± 0.10 | 0.00 ± 0.00 | 0.05 ± 0.05 | 0.00 ± 0.00 |
| | DES | 2.9 ± 1.4 | 0.1 ± 0.0 | 0.7 ± 0.6 | 0.1 ± 0.0 |
| Constant at 2000 μmol $m^{-2}$ $s^{-1}$ PFD | Vio | 4.47 ± 0.41 | 5.09 ± 0.52 | 3.63 ± 0.59 | 5.02 ± 0.09 |
| | Ant | 0.07 ± 0.00 | 0.08 ± 0.01 | 0.06 ± 0.00 | 0.09 ± 0.01 |
| | Zea | 3.81 ± 3.81 | *1.48 ± 0.48 | *1.23 ± 0.24 | *1.94 ± 0.49 |
| | DES | 46.2 ± 2.8 | *22.9 ± 7.5 | *26.2 ± 5.3 | *27.4 ± 5.1 |
| Fluctuating between 2000 and 200 μmol $m^{-2}$ $s^{-1}$ PFD | Vio | 4.20 ± 0.16 | *7.11 ± 0.57 | *5.72 ± 0.15 | *6.14 ± 0.34 |
| | Ant | 0.16 ± 0.02 | *0.08 ± 0.01 | 0.13 ± 0.03 | *0.08 ± 0.01 |
| | Zea | 4.70 ± 0.36 | *0.88 ± 0.08 | *2.29 ± 0.85 | *1.20 ± 0.21 |
| | DES | 52.5 ± 5.5 | *11.4 ± 0.9 | *25.5 ± 17.3 | *16.4 ±4.2 |

Example 8. Efficiency of Photo-Protection by Non-Photochemical Quenching

Figure 5:
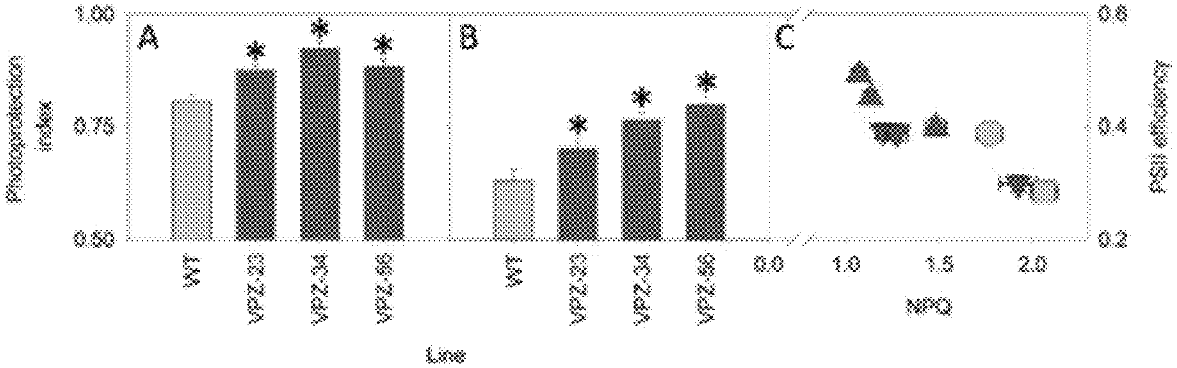
FIG. 5. Photo-protection index after exposure of (A) one hour or (B) two hours to 2000 μmol $m^{-2}$ $s^{-1}$ PFD ($\lambda_{max}$=470 nm) in seedlings of VPZ overexpression lines and wild-type. Index values less than one indicate occurrence of photoinhibition. (C) PSII efficiency plotted against residual NPQ in young seedlings after exposure to one hour (Upward pointing triangles—VPZ, Circle—WT) or two hours (Downward pointing triangles—VPZ, Square—WT) of 2000 μmol $m^{-2}$ $s^{-1}$ and 10 min of subsequent dark relaxation. Error bars indicate ±se (n=18), asterisks indicate significant differences between VPZ lines and wild-type (α=0.05).
Figure 14:
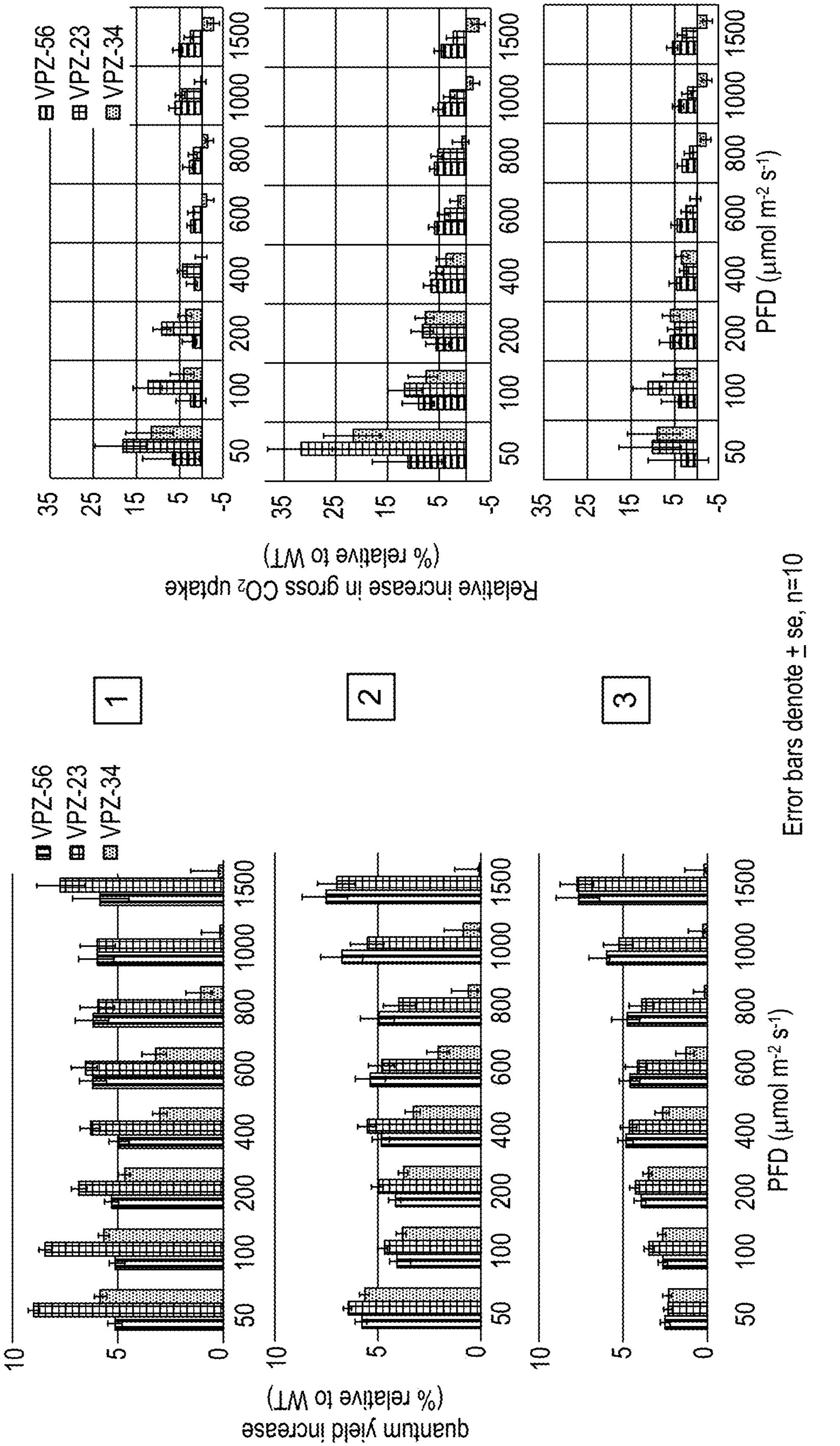
FIG. 14. Results of quantum yield and $CO_2$ fixation at various light intensities, after prior exposure of the leaf to 2000 μmol $m^{-2}s^{-1}$ PFD.
Figure 15:
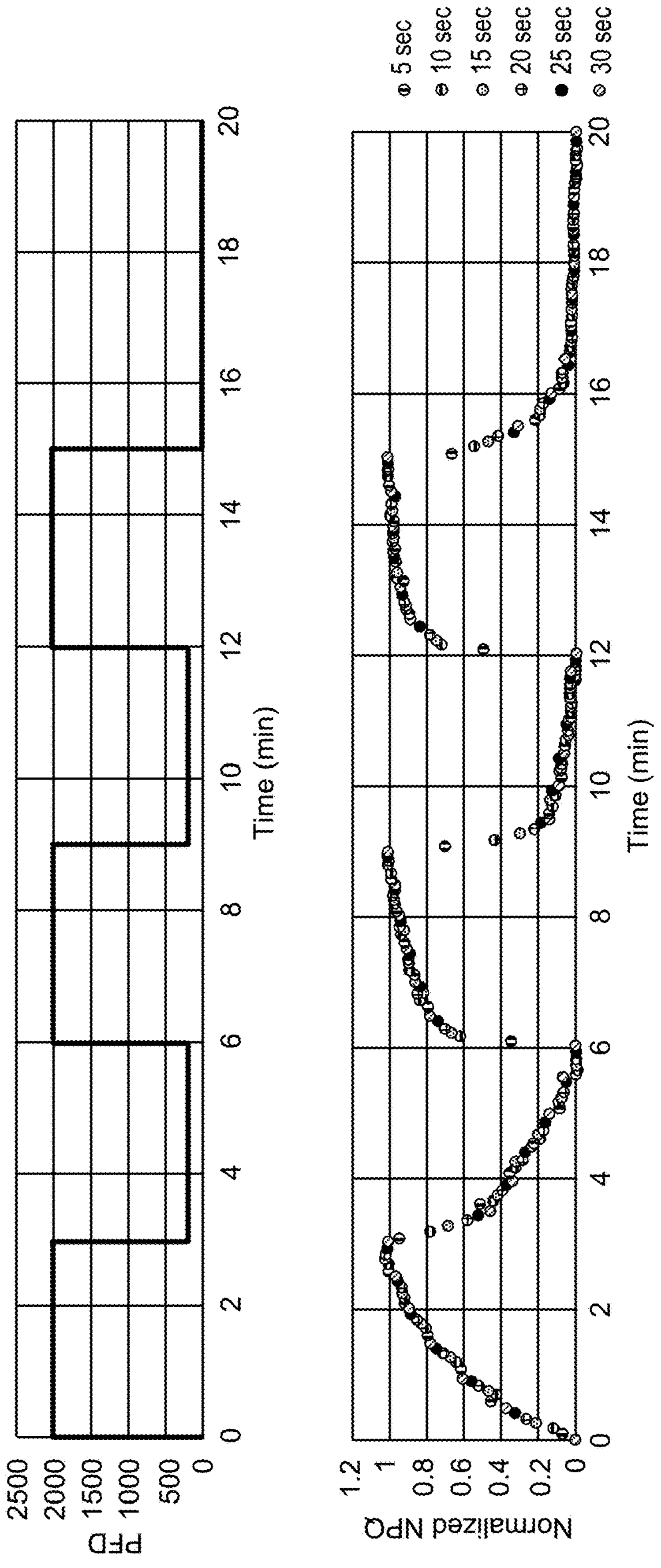
FIG. 15. NPQ kinetics under fluctuating light.
Figure 17:
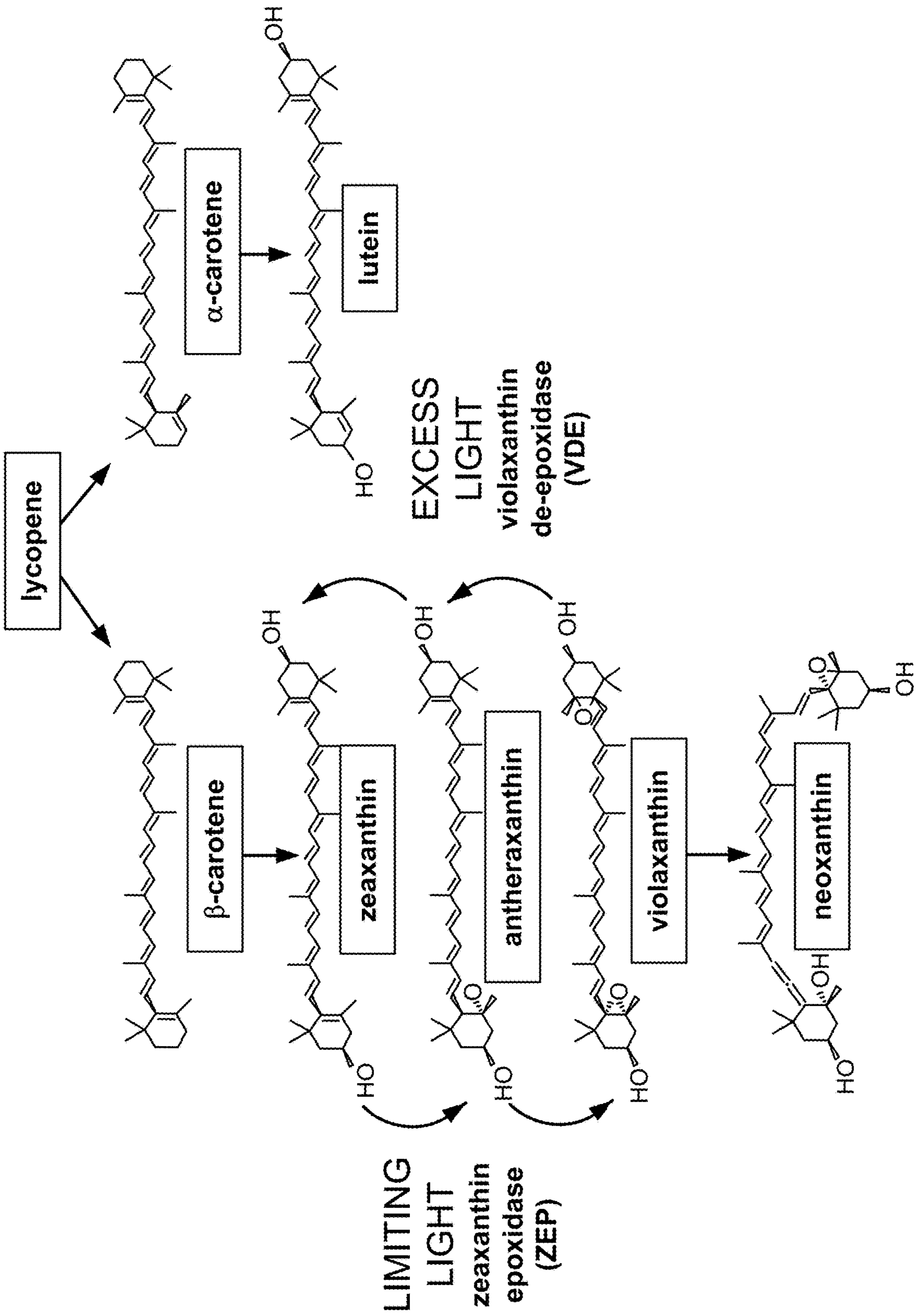
FIG. 17. NPQ components (qE, qZ, and qI) association with conversion of violaxanthin to zeaxanthin.

To evaluate the photo-protective efficiency in the VPZ lines relative to WT, seedlings were exposed to 2000 μmol $m^2$ $s^{-1}$ of blue light for one and two hours. The contrasting effects of photoinhibition and NPQ on Fo' after the high light treatment were used to calculate a photo-protection index (FIG. 5), in which a value of 1 equals complete protection from photo-inhibitory damage. One hour of high light exposure resulted in significant induction of photo-inhibition, which was slightly higher in WT seedlings than in the VPZ lines (FIG. 5A). Photo-protective efficiency after two hours pared to wild type. FIG. 14 shows increased NPQ kinetics, quantum yield and $CO_2$ fixation in transgenic lines VPZ-56, VPZ-23 and VPZ-34. These results show an increase in quantum yield and $CO_2$ fixation at various light intensities, after prior exposure of the leaf to 2000 μmol $m^{-2}$ $s^{-1}$ PFD. 1, 2 and 3 show the progression of this increase in time after exposure.

FIG. 16 shows that the time constants of NPQ in the first induction/relaxation are similar, but subsequent light cycles lead to slower build up (independent of amplitude, these are time constants) and faster relaxation of NPQ in transgenic plants, and faster recovery of quantum yield in dark relaxation. These comparative results are entirely consistent with reduced build up of zeaxanthin in the transgenic lines. Levels of NPQ in VPZ lines at high light are similar or higher than WT. Levels of qE in VPZ lines estimated by dA532 nm are higher than WT, most likely associated with PsbS overexpression. Repeated high light exposure shows higher time constants of NPQ increase, and lower time constants of NPQ relaxation in VPZ lines. VPZ lines show 5-10% improved quantum yield at low PFD during rapid switches in PFD, due to faster rate of NPQ relaxation.

Combined overexpression of VDE, ZEP and PsbS leads to modified kinetics of build-up and relaxation of NPQ in seedlings and fully grown plants, higher quantum yield under fluctuating light conditions in seedlings and fully grown plants, no significant differences in steady state gas exchange in fully grown plants, higher gross assimilation rate under fluctuating conditions in fully grown plants, and approximately 10% increase in growth in greenhouse.

Example 11. Materials and Methods

Transformation

*N. tabacum* cv. 'Petite Havana' was transformed using the *Agrobacterium*-mediated leaf disc protocol according to Clemente, *Agrobacterium* Protocols (ed Wang K.), pp. 143-154. Humana Press Inc., Totowa. The binary plasmid contained coding sequences of three genes from *A. thaliana*: violaxanthin de-epoxidase (AtVDE), AtPsbS and zeaxanthin epoxidase (AtZEP) as well as the bar gene encoding resistance for bialaphos (Thompson et. al. Journal of Agricultural and Food Chemistry 35, 361-365, 1987). 20 independent $T_0$ transformants were generated and T-DNA copy number was determined using digital droplet PCR (ddPCR) analysis of genomic DNA according to Glowacka et al Plant Cell and Environment doi: 10.1111/pce.12693, 2015. Two lines with a single copy (VPZ-34 and 56) and one line with two copies (VPZ-23) of the T-DNA were used to generate $T_1$ progeny in which homozygous plants were identified by ddPCR according to Glowacka et al and self-pollinated to obtain homozygous $T_2$ offspring for further analysis.

Propagation of Plant Material $T_2$ seeds of VPZ lines and WT seeds from the same harvest date were germinated on growing medium (LC1 Sunshine mix, Sun Gro Horticulture, Agawam, MA, USA) in a controlled environment walk-in growing chamber (Environmental Growth Chambers, Chagrin Falls, Ohio, USA) with 12 h day (23° C.)/12 h night (18° C.) cycle under 150 μmol quanta $m^{-2}$ $s^{-1}$. Five days after germination, seedlings were transplanted to 8×12 potting trays (812 series, Hummert International, Earth City, MO, USA) for chlorophyll fluorescence imaging or 9×4 potting trays (3600 series, Hummert International) and grown until two true leaves had emerged. Seedlings to be used in gas exchange and biomass analyses were moved to the greenhouse after the first transplant.

Transcription and Protein Expression

Five leaf discs (total 2.9 cm2) were sampled from the youngest fully expanded leaves from five plants per line, from the position of the leaf where gas exchange was also performed. Protein and mRNA were extracted from the same leaf sample (NucleoSpin RNA/Protein kit, REF740933, Macherey-Nagel). Extracted mRNA was treated by DNase (Turbo DNA-free kit; AM1907, Thermo Fisher Scientific, Waltham, MA, USA) and transcribed to cDNA using Superscript III First-Strand Synthesis System for RT-PCR (18080-051; Thermo Fisher Scientific). RT-qPCR was used to quantify expression levels of the transgenes AtZEP, AtPsbS and AtVDE, and the native genes NtZEP, NtPsbS and NtVDE relative to NtActin and NtTubulin (primer sequences provided supplemental materials).

After quantification of total protein concentration (protein quantification assay ref740967.50, Macherey-Nagel), 4 μg protein was separated by SDS-PAGE electrophoresis, blotted to membrane (Immobilon-P, IPVH00010, Millipore, USA) using semi-dry blotting (Trans-Blot SD, Bio-Rad) and immuno-labelled with primary antibodies raised against AtPsbS (AS09533, Agrisera, Vännäs, Sweden), AtZEP (AS08289, Agrisera) and AtVDE (AS153091, Agrisera) followed by incubation with secondary antibodies (Promega W401B). Chemiluminescence was detected using a scanner (ImageQuant LAS-4010, Fuji,) and densitometry was performed using ImageJ (version 1.47v, National Institute of Health, USA) to estimate protein concentrations Wild-type protein concentrations were used for normalization.

NPQ and PSII Operating Efficiency in Young Seedlings

Non-photochemical quenching (NPQ) was determined in 18 seedlings simultaneously, using a chlorophyll fluorescence imager (CF Imager, Technologica, Colchester, UK). Seedlings were first dark adapted for 20 minutes after which the dark-adapted minimal fluorescence (Fo) and maximal fluorescence (Fm) were imaged using a 800 ms pulse of saturating light intensity (6000 μmol quanta $m^{-2}$ $s^{-1}$, λmax=470 nm). Subsequently, seedlings were subjected to either 10 minutes of 1000 μmol quanta $m^{-2}$ $s^{-1}$ followed by 10 minutes of darkness or six cycles of three minutes 2000 μmol quanta $m^{-2}$ $s^{-1}$ followed by two minutes of 200 μmol quanta $m^{-2}$ $s^{-1}$. Saturating flashes were provided at regular intervals to image variable fluorescence (F') and the maximum fluorescence under illuminated conditions (Fm'). Average NPQ per seedling was then calculated from these measurements according to Eq.1, assuming the Stern-Volmer quenching model:

$$NPQ=Fm/Fm'-1 \quad \text{Eq.1}$$

Maximal or operating PSII efficiency were estimated from the fluorescence measurements according to equation 2 and 3, following Genty et al. *Biochimica et Biophysica Acta* 990, 87-921989, 1989.

$$\text{Maximal PSII efficiency}=(Fm-Fo)/Fm \quad \text{Eq.2}$$

$$\text{PSII operating efficiency}=(Fm'-F')/Fm' \quad \text{Eq.3}$$

Time Constants of NPQ Adjustment to Changes in Light Intensity

Seedlings were dark-adapted and chlorophyll fluorescence was determined using a chlorophyll fluorescence imager as described above. Maximal fluorescence was measured every 30 seconds while light intensity was changed every 3 min from 2000 to 200, 2000, 200, 2000 and finally 0 μmol quanta $m^{-2}$ $s^{-1}$. The final relaxation in darkness lasted 10 minutes. Six sets of 18 seedlings of three VPZ transformed lines and wild-type were measured accordingly, whereby a 5 second frameshift was created between fluorescence measurements and light intensity changes between each set. NPQ was computed according to Eq. 1, normalized against the highest value within each set after which all six sets were compiled as a function of time to generate time-series of normalized NPQ with a resolution of 5 seconds. Time constants in a double exponential function for induction or relaxation of NPQ were fitted to the compiled time-series after each change in light intensity. For the final recovery in darkness, time constants were also fitted for PSII operating efficiency (estimated using equation 3).

Photo Protection Efficiency

Seedlings were dark-adapted for 20 min after which dark-adapted maximal PSII efficiency (Fv/Fm) was determined using the chlorophyll fluorescence imager as described above. Subsequently, seedlings were exposed to 2000 μmol quanta $m^{-2}$ $s^{-1}$ for a duration of 60 min or 120 min. After the exposure, seedlings were allowed to recover in darkness for 10 min to allow relaxation of qE, after which minimal fluorescence (Fo') and maximal fluorescence (Fm') without full dark-adaptation were measured. The measurement of Fo' was compared to a derived value which considers exclusively the effect of NPQ on Fo' (Oxborough and Baker, *Photosynthesis Research* 54: 135-142, 1997). The difference between PSII efficiency using either measured or derived Fo' was then used to determine the efficiency of photo-protection.

Gas Exchange and Linear Electron Transport in Fully Expanded Leaves

For gas exchange analyses, seedlings were transplanted from trays to 3.8 L pots (400C, Hummert International) filled with growing medium (LC1 Sunshine mix, supplemented with 10 g granulated fertilizer per pot (Osmocote Plus 15/9/12, The Scotts Company LLC, Marysville, Ohio, USA). Pots were randomized and spaced 30 cm apart on greenhouse tables. Plants were watered and plant positions were changed randomly every two days, until the fifth leaf was fully expanded. Gas exchange measurements were performed using an open gas exchange system (LI6400XT, LI-COR, Lincoln, Nebraska, USA) equipped with a 2 cm2 leaf chamber fluorometer. All gas exchange measurements were corrected for diffusive leaks between cuvette and surrounding atmosphere, using dark measurements at various $CO_2$ concentrations according to Gong et al. *Plant, Cell and Environment* 38, 2417-24322015).

To determine the light dose response curves of net assimilation rate and linear electron transport in fully expanded leaves, gas exchange and pulse amplitude modulated chlorophyll fluorescence were measured at a range of light intensities. All chlorophyll fluorescence measurements were performed using the multiphase flash routine (Loriaux et al. 2013). Youngest fully expanded leaves (n=6) were clamped in the cuvette with block temperature set at 25° C. and [$CO_2$] in the airstream controlled at 1500 ppm. After 30 min of dark adaptation, minimal fluorescence (Fo) and maximal fluorescence (Fm) were determined. Subsequently, light intensity was varied in two different ways. The first experiment consisted of slowly increasing the light intensity from 0 to 50, 80, 110, 140, 170, 200, 400, 600, 800, 1000, 1200, 1500 and 2000 μmol $m^{-2}$ $s^{-1}$, trying to keep induction of NPQ at each light intensity to an absolute minimum. When steady state was reached, gas exchange parameters were logged and baseline fluorescence (F') and light-adapted maximal fluorescence (Fm') were measured to estimate NPQ (Eq.1) and PSII operating efficiency (Eq.3). In the second experiment leaves were allowed to reach steady state gas exchange at 2000 μmol $m^{-2}$ $s^{-1}$. Subsequently, light intensity was changed from 2000 to 1500, 1000, 800, 600, 400, 200, 170, 140, 110, 80 and 50, each step lasted 4 minutes and was preceded by 4 minutes of 2000 μmol $m^{-2}$ $s^{-1}$. At each light intensity, F' and Fm' and gas exchange parameters were determined after 60 s, 140 s and 220 s. Average values of these three measurements were used for subsequent analysis to reconstruct light response curves with intermittent high PFD.

Leaf absorptance of incident irradiance was measured on the same spot used for gas exchange analysis, using an integrating sphere (LI1800, LI-COR, USA) connected to a spectrometer (USB-2000, Ocean Optics Inc, Dunedin, Florida, USA). Rates of linear electron transport (J) were determined for both experiments according to:

$$J\text{=Leaf absorptance*PSII operating efficiency*}PFD\text{*0.5} \quad \text{Eq.4}$$

Light intensity dose response curves for linear electron transport and gas exchange from both experiments were adjusted to constant leaf temperature according to equations in Sharkey et al. (2007) and fitted to a descriptive non-rectangular hyperbola model (Von Caemmerer, Biochemical models of leaf photosynthesis. Collingwood, Australia: CSIRO Publishing 2000), yielding estimates for initial slope, convexity and asymptote.

To analyze the $CO_2$ dose response curve of net assimilation rate, leaves were clamped in the cuvette with block temperature controlled at 25° C. and light intensity set to 2000 μmol $m^{-2}$ $s^{-1}$. $CO_2$ concentration in the airstream was controlled at 400, 300, 200, 100, 75, 400, 400, 500, 600, 700, 800, 1200 and 1600 ppm and gas exchange parameters were logged when steady state was reached. The model for leaf photosynthesis by Farquhar et al. Planta 149, 78-90.1980 assuming infinite mesophyll conductance, with temperature corrections according to Sharkey et al. Plant Cell Environ. 30, 1035-1040, 2007 was fitted to derive the maximal carboxylation rate (Vcmax), electron transport rate at 2000 μmol $m^{-2}$ $s^{-1}$ (J), triose phosphate utilization rate (TPU) and mitochondrial respiration rate not associated with photo-respiration (Rd).

Xanthophyll Cycle Pigment Concentrations

Leaves were clamped in the leaf cuvette of an open gas exchange system and dark-adapted as described above. Subsequently, $CO_2$ and $H_2O$ exchange were either allowed to reach steady state at 0, 400 and 2000 μmol $m^{-2}$ $s^{-1}$ or subjected to a series of changes in light intensity (three cycles of 3 min 2000/3 min 200 μmol $m^{-2}$ $s^{-1}$), immediately after which leaf discs (0.58 cm2) were sampled from the enclosed leaf spot, snap-frozen in liquid nitrogen and stored at −80° C. until extraction. Pigment analysis took place at the Horn Point Laboratory (University of Maryland Center for Environmental Science, Cambridge, MD, USA). Frozen samples were macerated in 90% acetone using an ultrasonic probe and the crude extract was filtered (0.45 μm). Pigments were separated by HPLC using a Zorbax Eclipse XDB-C8 column (963967-906, Agilent Technologies, Santa Clara, CA, USA) and quantified according to the protocol by Van Heukelem and Thomas (2001).

Growth and Final Biomass Accumulation

To evaluate the effects of VPZ overexpression on growth, two independent greenhouse experiments were performed from May 25-Jun. 29, 2015 (using WT, VPZ-23 and VPZ-34) and from October 9-Nov. 13, 2015 (using WT, VPZ-23, VPZ-34 and VPZ-56). Seedlings were propagated as specified above (paragraph plant propagation) and transplanted from trays to 14.5 L pots (2000C, Hummert International) filled with growing medium (LC1 Sunshine mix, Sun Gro Horticulture) supplemented with 30 g slow release granulated fertilizer per pot (Osmocote Plus 15/9/12, The Scotts Company LLC). Pots were randomized and placed on greenhouse tables with 30 cm spacing. Plants were watered and plant positions were changed randomly every two days. Light intensity at leaf level was logged with a quantum sensor (LI-190R, LI-COR, USA) at the center of the greenhouse table, which was mounted on a tripod and adjusted daily to maintain a position of 10 cm above the youngest leaves. Air temperature, relative humidity and [$CO_2$] were measured approximately 1 m above the plant canopy, using a combined temperature and humidity sensor (HMP60-L, Vaisala Oyj, Helsinki, Finland) and an infrared gas analyzer (SBA-5, PPsystems, Amesbury, MA, USA). All climate data was logged every 30 min using a datalogger (CR1000, Campbell Scientific Inc, Logan, UT, USA). Temperature in the greenhouse was generally kept between 28° C. (day) and 18° C. (night), using a combination of ventilation, evaporative cooling and gas heaters. Light intensity varied with incoming irradiance, with midday peaks reaching approximately 1800 μmol $m^{-2}$ $s^{-1}$ in the first experiment and 1000-1500 μmol $m^2$ $s^{-1}$ in the second experiment. [$CO_2$] was not controlled and varied between 360 ppm (day) and 430 ppm (night). After the first flower had opened, stem length and the number of leaves per plant were determined and total leaf area per plant was measured with a conveyor-belt scanner (LI-3100C Area Meter, LI-COR, USA). Plants were subsequently separated into leaf, stem and root fractions and dried to constant weight at 70° C.

Statistical Analysis

All statistical analyses were performed using SAS (version 9.3, SAS Institute Inc., Cary, NC, USA). Data was tested for homogeneity of variance using Brown-Forsythe's test and normality using Shapiro-Wilk's test. One-way analysis of variance was applied to fitted gas exchange parameters, transcription levels and protein expression. Datasets of chlorophyll fluorescence imaging of NPQ in young seedlings were analyzed by two-way (photo-protection), or repeated measures one-way (10 min on/off) or two-way (high/low light) analysis of variance. Analysis of the two replicated greenhouse trials was performed using a mixed model with two fully randomized blocks. In all cases, significant effects in ANOVA were followed by Dunnett's multiple comparison test of line means against WT control ($\alpha$=0.05). Fitted time constants of NPQ induction and relaxation were compared based on 95% confidence intervals.

Example 12. Transgenic Maize (Prophetic)

This invention can also provide for a maize line with improved photosynthesis and growth as compared to a phenotype in parental units of said maize line. The maize line can be created by generating a population of transgenic plants comprising heterologous nucleotide sequences encoding polypeptides selected from PsbS, ZEP and VDE as described herein. Each transgenic event comprises introducing into the genome of a parent plant at least one nucleotide construct comprising a promoter operably linked to heterologous nucleotide as described herein. The nucleotide construct is introduced into the parental genome in sufficient quantity to produce transgenic cells which can be cultured into plants of transgenic maize having said enhanced phenotype. The transgenic cells are cultured into transgenic plants producing progeny transgenic seed. The population of transgenic plants is screened for observable phenotypes. Seed is collected from transgenic plants which are selected as having an unexpected enhanced phenotype. Optionally, the method comprises repeating a cycle of germinating transgenic seed, growing subsequent generation plants from said transgenic seed, observing phenotypes of said subsequent generation plants and collecting seeds from subsequent generation plants having an enhanced phenotype. In another aspect, the method a large population is screened by employing at least one heterologous nucleotide sequences encoding polypeptides selected from PsbS, ZEP and VDE. Other preferred aspects of the method employ nucleotide construct where the heterologous DNA is operably linked to a selected promoter, e.g. the 5' end of a promoter region. The DNA construct may be introduced into a random location in the genome or into a preselected site in the genome.

An example of maize transformation protocol is described herein.

Initiate *Agrobacterium* Culture

1. Streak AGL1 carrying a simple binary vector (e.g., pZY102) from ~80° C. stock on ABC agar plates with appropriate antibiotics (for the vector and strain illustrated here, 100 mg/liter spectinomycin and 30 mg/liter rifampin), preparing a dilution series in order to obtain single colonies. Incubate the plates in the dark for 3 days at 28° C.

2. Select a single colony and streak it on YEP agar plates containing appropriate antibiotics (for the vector and strain illustrated here, 100 mg/liter spectinomycin and 30 mg/liter rifampin). Incubate the plates in the dark for 3 days at 20° C.

3. Add 5 ml of sterile PHI-A (inoculation medium) to a 15-ml conical centrifuge tube.

4. Transfer two full loops of AGL1 from the YEP plate to the tube prepared in step 3. After 2 to 3 min, shake the tube to thoroughly suspend bacterial cells.

5. Remove 1 ml of this suspension and place it in a spectrophotometer cuvette to check the optical density at 550 nm (OD550). Adjust the cell suspension to an OD550 of 0.35 (0.5×109 cfu/ml) at room temperature (e.g., 24° C.) by either adding more *Agrobacterium* cells or diluting the culture with more PHI-A.

6. Shake the culture in a shaker at 100 rpm for 4 to 5 hr at room temperature (e.g., 24° C.).

7. Aliquot 1 ml of the suspension into 2-ml sterile microcentrifuge tube.

Embryo Isolation, Inoculation, and Co-Cultivation

8. Remove the husks and silk from ears which were harvested 10 to 13 days post-pollination (with embryo size of 1.5 mm; see Support Protocol). Insert a pair of forceps into one end of the ear.

9. Completely submerge the fresh Hi-II ears in a solution containing 0.5 liters of 30% commercial bleach with a few drops of Tween 20 (in a sterile 1-liter wide-mouth bottle) for 20 min.

10. Wash ears three times with sterile water (making sure ears are completely submerged in the water each time), and let the ear stand upright on a sterile 150×15-mm petri dish.

11. Remove top half of the kernels from each ear with a sterile #11 razor blade.

12. Isolate 1.5-mm immature embryos from the sterile ear with a sterile microspatula and transfer 50 to 100 embryos per 1.7- to 2.0-ml microcentrifuge tube. Wash the embryos with 1 ml PHI-A solution three times to remove debris and starch.

13. Immediately afterwards, add 1 ml of the *Agrobacterium* suspension to the tube containing the immature embryos, allow the tube to stand 5 min in the sterile hood, then pour the entire contents including all of the embryos onto PHI-B (co-cultivation medium) agar plate.

14. Draw off *Agrobacterium* suspension using a pipet with a fine tip, then spread the embryos evenly across the plate and place embryos with scutellum face up and flat side face down on the medium.

15. Seal the plate with parafilm and incubate in the dark at 20° C. for 3 days.

Resting

16. Transfer the embryos with a spatula to a plate of PHI-C (resting medium). Avoid damaging the embryos.

17. Seal the plate with parafilm and incubate in the dark at 28° C. for 7 days.

Selection

18. Transfer embryos with spatula or forceps to a plate of PHI-D1 (selection medium I). Place 25 embryos per plate and seal the plate. Incubate the embryos in the dark at 28° C. for the first 2-week selection.

19. Transfer calli with forceps from the PHI-D1 plate to a plate of PHI-D2 (selection medium II). Subculture the calli every 2 weeks onto fresh PHI-D2 medium for a total of 2 months using the incubation conditions in step 18.

20. Bulk up the herbicide-resistant calli by growing them on fresh PHI-D2 medium for another 2 weeks under the same conditions as in steps 18 and 19, until the diameter of the calli is about 1.0 cm.

Maturation and Regeneration

21. Using forceps, transfer each entire callus mass containing opaque embryos onto PHI-E (maturation medium) in 20×100 mm petri plates (wrapped with 3 M porous tape) and place culture plates in the dark at 28° C. for two 2 to 3 weeks to allow somatic embryos to mature.

22. Transfer ivory-white calli onto PHI-F (regeneration medium) and incubate at 25° C. under 16-hr photoperiod until shoots and roots develop.

23. Transfer each small plantlet to a 25×150-mm tube containing PHI-F (regeneration medium), and grow at 25° C. under 16-hr photoperiod for 2 to 3 weeks.

24. Transfer the plants to small plastic pots with soil mixture, e.g., Promix BX soil, in a light incubator or culture room at 24° C. with an 18 hr/light, 6 hr/dark cycle.

Example 13. Transgenic Sorghum (Prophetic)

This invention can also provide for a sorghum line with improved photosynthesis and growth as compared to a phenotype in parental units of said sorghum line. The sorghum line can be created by generating a population of transgenic plants comprising heterologous nucleotide sequences encoding polypeptides selected from PsbS, ZEP and VDE as described herein. Each transgenic event comprises introducing into the genome of a parent plant at least one nucleotide construct comprising a promoter operably linked to heterologous nucleotide as described herein. The nucleotide construct is introduced into the parental genome in sufficient quantity to produce transgenic cells which can be cultured into plants of transgenic sorghum having said enhanced phenotype. The transgenic cells are cultured into transgenic plants producing progeny transgenic seed. The population of transgenic plants is screened for observable phenotypes. Seed is collected from transgenic plants which are selected as having an unexpected enhanced phenotype. Optionally, the method comprises repeating a cycle of germinating transgenic seed, growing subsequent generation plants from said transgenic seed, observing phenotypes of said subsequent generation plants and collecting seeds from subsequent generation plants having an enhanced phenotype. In another aspect, the method a large population is screened by employing at least one heterologous nucleotide sequences encoding polypeptides selected from PsbS, ZEP and VDE. Other preferred aspects of the method employ nucleotide construct where the heterologous DNA is operably linked to a selected promoter, e.g. the 5' end of a promoter region. The DNA construct may be introduced into a random location in the genome or into a preselected site in the genome.

Examples of sorghum transformation protocol are described in Guo et al., Methods Mol Biol 1223, 181-188, 2015, as well as Howe et al., Plant Cell Rep 25(8): 784-791, 2006.

Example 14. Transgenic Soybean (Prophetic)

This invention can also provide for a soybean line with improved photosynthesis and growth as compared to a phenotype in parental units of said soybean line. The soybean line can be created by generating a population of transgenic plants comprising heterologous nucleotide sequences encoding polypeptides selected from PsbS, ZEP and VDE as described herein. Each transgenic event comprises introducing into the genome of a parent plant at least one nucleotide construct comprising a promoter operably linked to heterologous nucleotide as described herein. The nucleotide construct is introduced into the parental genome in sufficient quantity to produce transgenic cells which can be cultured into plants of transgenic soybean having said enhanced phenotype. The transgenic cells are cultured into transgenic plants producing progeny transgenic seed. The population of transgenic plants is screened for observable phenotypes. Seed is collected from transgenic plants which are selected as having an unexpected enhanced phenotype. Optionally, the method comprises repeating a cycle of germinating transgenic seed, growing subsequent generation plants from said transgenic seed, observing phenotypes of said subsequent generation plants and collecting seeds from subsequent generation plants having an enhanced phenotype. In another aspect, the method a large population is screened by employing at least one heterologous nucleotide sequences encoding polypeptides selected from PsbS, ZEP and VDE. Other preferred aspects of the method employ nucleotide construct where the heterologous DNA is operably linked to a selected promoter, e.g. the 5' end of a promoter region. The DNA construct may be introduced into a random location in the genome or into a preselected site in the genome.

An example of soybean transformation protocol is described herein.

Cotyledonary explants are prepared from the 5-day-old soybean seedlings by making a horizontal slice through the hypocotyl region, approximately 3-5 mm below the cotyledon. A subsequent vertical slice is made between the cotyledons, and the embryonic axis is removed. This manipulation generates 2 cotyledonary node explants. Approximately 7-12 vertical slices are made on the adaxial surface of the ex-plant about the area encompassing 3 mm above the cotyledon/hypocotyl junction and 1 mm below the cotyledon/hypocotyl junction. Explant manipulations are conducted with a No. 15 scalpel blade.

Explants are immersed in the *Agrobacterium* inoculum for 30 min and then co-cultured on 100×15 mm Petri plates containing the *Agrobacterium* resuspension medium solidified with 0.5% purified agar (BBL Cat #11853). The co-cultivation plates are overlaid with a piece of Whatman #1 filter paper (Mullins et al., 1990; Janssen and Gardner, 1993; Zhang et al., 1997). The explants (5 per plate) are cultured adaxial side down on the co-cultivation plates, that are overlaid with filter paper, for 3 days at 24° C., under an 18/6 hour light regime with an approximate light intensity of 80 μmol s-1 m-2(F17T8/750 cool white bulbs, Litetronics). The co-cultivation plates are wrapped with Parafilm.

Following the co-cultivation period explants are briefly washed in B5 medium supplemented with 1.67 mg 1-1 BAP, 3% sucrose, 500 mg 1-1 ticarcillin and 100 mg 1-1 cefotaxime. The medium is buffered with 3 mM MES, pH 5.6. Growth regulator, vitamins and antibiotics are filter sterilized post autoclaving. Following the washing step, explants are cultured (5 per plate) in 100×20 mm Petri plates, adaxial side up with the hypocotyl imbedded in the medium, containing the washing medium solidified with 0.8% purified agar (BBL Cat #11853) amended with either 3.3 or 5.0 mg 1-1 glufosinate (AgrEvo USA). This medium is referred to as shoot initiation medium (SI). Plates are wrapped with 3M pressure sensitive tape (Scotch™, 3M, USA) and cultured under the environmental conditions used during the seed germination step.

After 2 weeks of culture, the hypocotyl region is excised from each of the explants, and the remaining explant, cotyledon with differentiating node, is subsequently sub-cultured onto fresh SI medium. Following an additional 2 weeks of culture on SI medium, the cotyledons are removed from the differentiating node. The differentiating node is sub-cultured to shoot elongation medium (SE) composed of Murashige and Skoog (MS) (1962) basal salts, B5 vitamins, 1 mgl-1 zeatin-riboside, 0.5 mg 1-1 GA3 and 0.1 mg 1-1 IAA, 50 mg 1-1 glutamine, 50 mg 1-1 asparagine, 3% sucrose and 3 mM MES, pH 5.6. The SE medium is amended with either 1.7 or 2.0 mg 1-1 glufosinate. The explants are sub-cultured biweekly to fresh SI medium until shoots reached a length greater than 3 cm. The elongated shoots are rooted on Murashige and Skoog salts with B5 vitamins, 1% sucrose, 0.5 mg 1-1 NAA without further selection in either Magenta boxes or Sundae cups (Industrial Soap Company, St. Louis MO).

Example 15. Transgenic Rice (Prophetic)

This invention can also provide for a rice line with improved photosynthesis and growth as compared to a phenotype in parental units of said rice line. The rice line can be created by generating a population of transgenic plants comprising heterologous nucleotide sequences encoding polypeptides selected from PsbS, ZEP and VDE as described herein. Each transgenic event comprises introducing into the genome of a parent plant at least one nucleotide construct comprising a promoter operably linked to heterologous nucleotide as described herein. The nucleotide construct is introduced into the parental genome in sufficient quantity to produce transgenic cells which can be cultured into plants of transgenic rice having said enhanced phenotype. The transgenic cells are cultured into transgenic plants producing progeny transgenic seed. The population of transgenic plants is screened for observable phenotypes. Seed is collected from transgenic plants which are selected as having an unexpected enhanced phenotype. Optionally, the method comprises repeating a cycle of germinating transgenic seed, growing subsequent generation plants from said transgenic seed, observing phenotypes of said subsequent generation plants and collecting seeds from subsequent generation plants having an enhanced phenotype. In another aspect, the method a large population is screened by employing at least one heterologous nucleotide sequences encoding polypeptides selected from PsbS, ZEP and VDE. Other preferred aspects of the method employ nucleotide construct where the heterologous DNA is operably linked to a selected promoter, e.g. the 5' end of a promoter region. The DNA construct may be introduced into a random location in the genome or into a preselected site in the genome.

An example of rice transformation protocol is described herein.

Infection and Co-Cultivation

Transfer the callus into sterile tea strainer and incubate the tea strainer in the *agrobacterium* suspension by very gently and intermittently shaking the strainer for 15 min, then blot dry strainer on top of stacked Whatmann 1 sterile filter paper in a sterile Petri dish to remove excess bacteria. Transfer the callus onto sterile filter paper placed on top of MSG4K medium, and culture in the dark at 25° C. for 48 h.

Resting and Bialaphos (Basta) Selection

Transfer the co-cultivated callus to a sterile 50 ml tube and wash them with sterile water for 5 times and once with liquid co-cultivation medium containing timentin 200 mg/l. Blot the callus dry in sterile Whatman filter paper and transfer them to MSG2K "rest" medium containing plates. Culture the callus plates in the dark at 25° C. for 7 days. Transfer the callus to MSG2K bialaphos selection medium. Culture the plates in the dark at 25° C. for 3 weeks. Repeat the process for additional 5 weeks subculturing into fresh medium in every 3 weeks.

Callus Desiccation, Shoot Regeneration and Rooting

After 8 weeks in selection medium with 3-4 rounds of selection, transfer the callus to sterile Petri dishes stacked with 2 layers of sterile Whatman #1 filter paper in sterile hood. Wrap it with 3M surgical tapes and leave in the hood as such undisturbed in dark for 24 h. The plates need to wrapped in aluminum foil to ensure the darkness for the callus. This partial desiccation of callus step is absolutely necessary to induce shoots in shoot regeneration medium. After 48 h, transfer the callus to MSG75K shoot regeneration medium and incubate in dark for 3 weeks. Transfer the proliferating callus with somatic embryos to same medium and incubate under low light, approximately 20 to 30 μE m-2s-1 with 12 h/8 h dark cycle. Shoots will start appearing after 10 days in light and most of callus will become green. Continue to culture the green callus along embryos in MSG75K shoot regeneration medium under same light regime until satisfied amount of shoots were obtained. Meanwhile, when shoots reaches above 5 cm in length dissect them in the base and transfer to Greiner Bio-One plant culture containers (#968161-82051-508-container with lid, 330 ml, sterile, 68 Dia.×110 H mm) with MSG100K rooting medium.

Example 16. Transgenic Wheat (Prophetic)

This invention can also provide for a wheat line with improved photosynthesis and growth as compared to a phenotype in parental units of said wheat line. The wheat line can be created by generating a population of transgenic plants comprising heterologous nucleotide sequences encoding polypeptides selected from PsbS, ZEP and VDE as described herein. Each transgenic event comprises introducing into the genome of a parent plant at least one nucleotide construct comprising a promoter operably linked to heterologous nucleotide as described herein. The nucleotide construct is introduced into the parental genome in sufficient quantity to produce transgenic cells which can be cultured into plants of transgenic wheat having said enhanced phenotype. The transgenic cells are cultured into transgenic plants producing progeny transgenic seed. The population of transgenic plants is screened for observable phenotypes. Seed is collected from transgenic plants which are selected as having an unexpected enhanced phenotype. Optionally, the method comprises repeating a cycle of germinating transgenic seed, growing subsequent generation plants from said transgenic seed, observing phenotypes of said subsequent generation plants and collecting seeds from subsequent generation plants having an enhanced phenotype. In another aspect, the method a large population is screened by employing at least one heterologous nucleotide sequences encoding polypeptides selected from PsbS, ZEP and VDE. Other preferred aspects of the method employ nucleotide construct where the heterologous DNA is operably linked to a selected promoter, e.g. the 5' end of a promoter region. The DNA construct may be introduced into a random location in the genome or into a preselected site in the genome.

An example of wheat transformation protocol is described in Medvecká E, Harwood W A. Wheat (*Triticum aestivum* L.) Transformation Using Mature Embryos. *Agrobacterium* Protocols: Volume 1. 2015:199-209.

Example 17. Transgenic Cowpea

Figure 27:
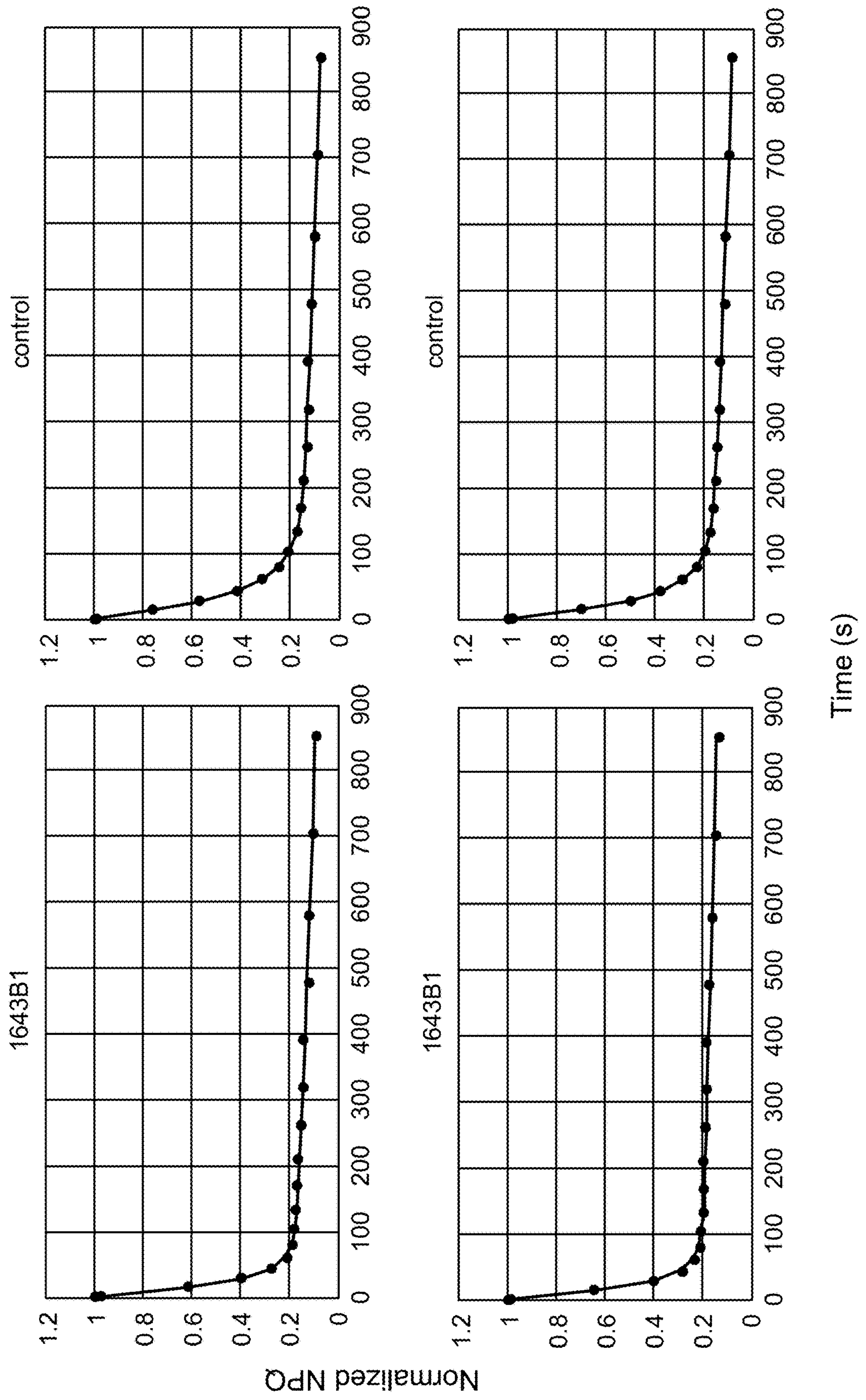
FIG. 27. NPQ relaxation kinetics in transgenic cowpea 1643B1. X-axis is time in seconds. Y-axis is normalized NPQ.
Figure 28:
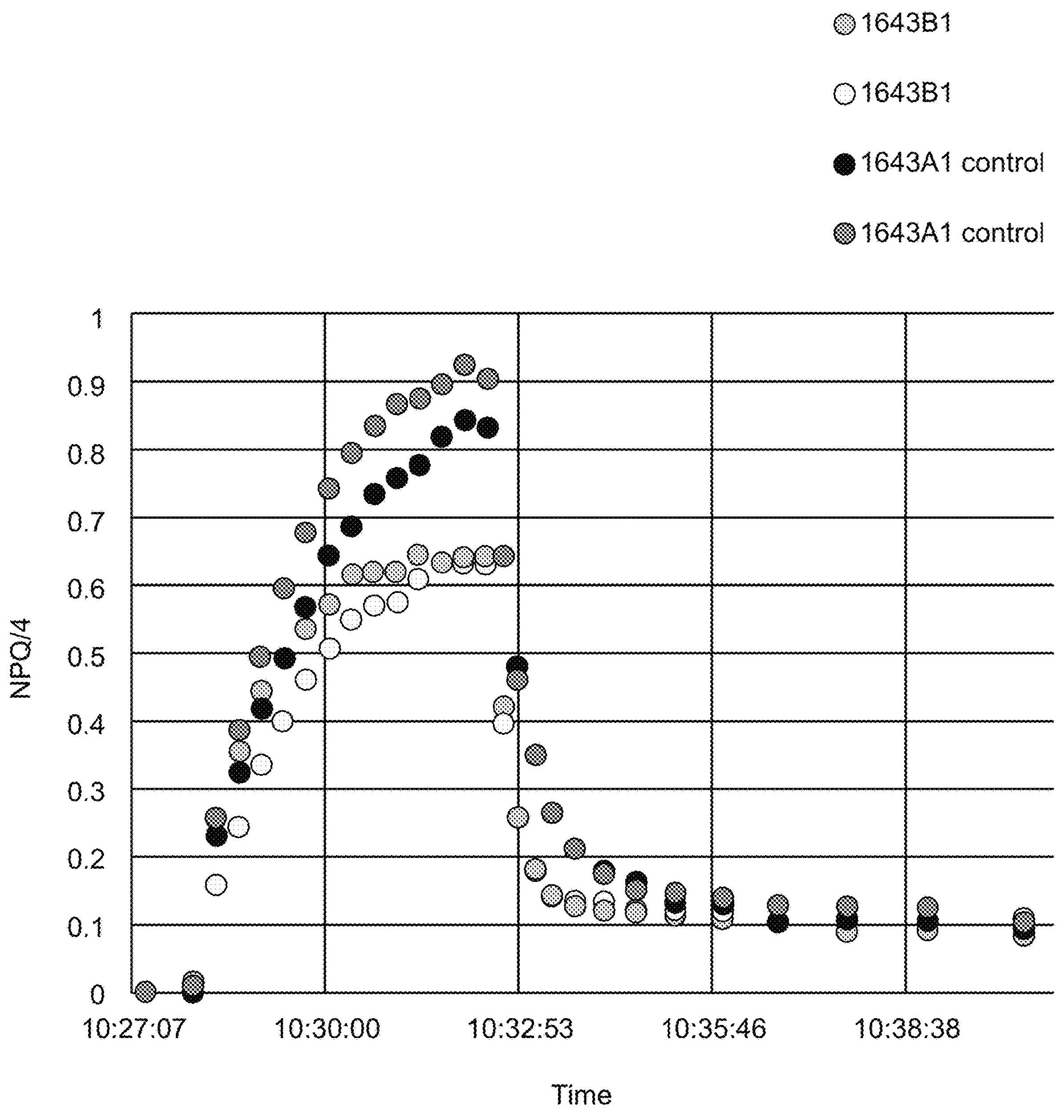
FIG. 28. NPQ induction and relaxation kinetics in transgenic cowpea 1643B1. X-axis is time. Y-axis is NPQ divided by 4.
Figure 29:
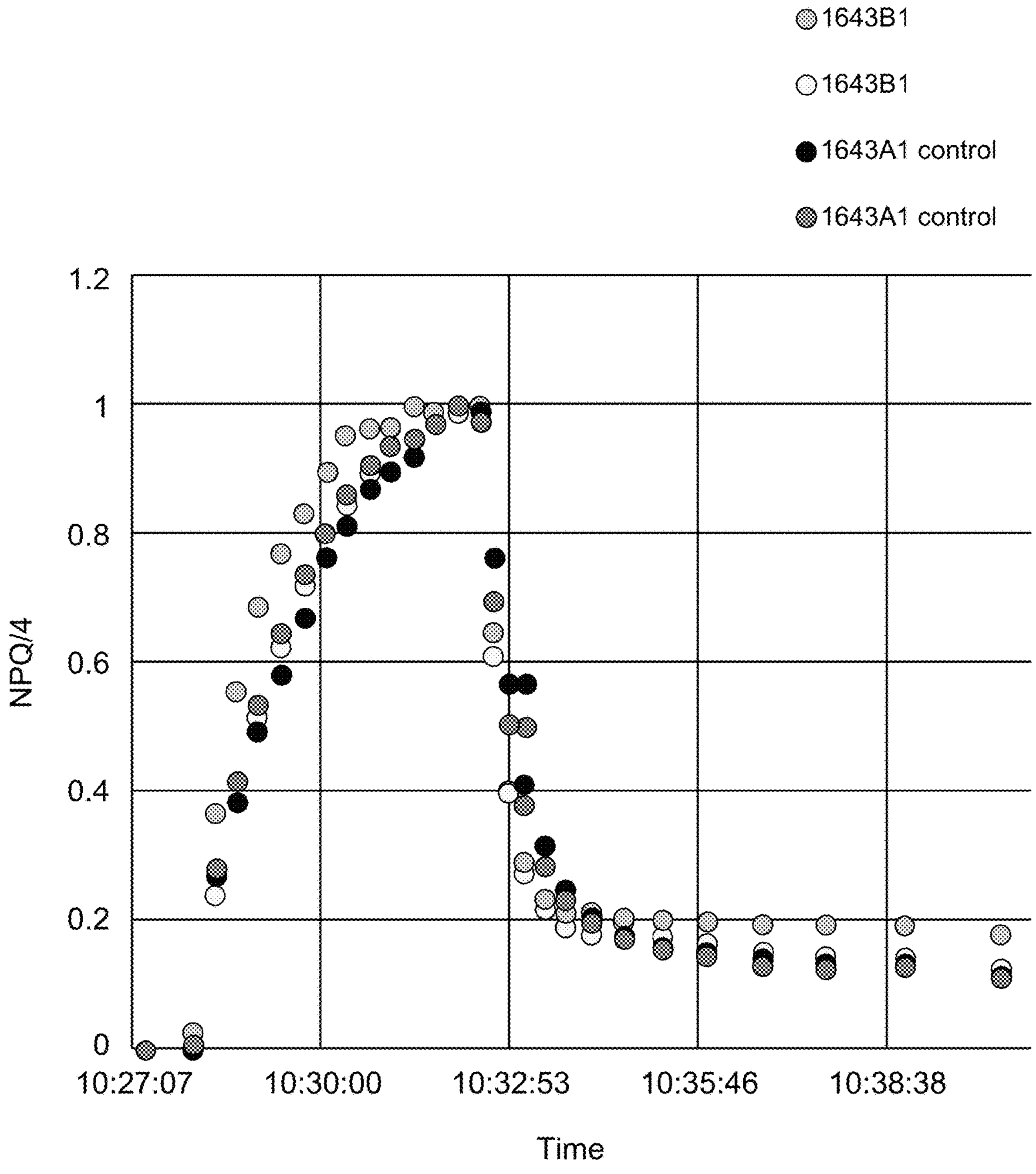
FIG. 29. Normalized NPQ induction and relaxation kinetics under fluctuating light in transgenic cowpea 1643B1. X-axis is time. Y-axis is NPQ divided by 4. Data is normalized to the highest NPQ within each set.
Figure 30:
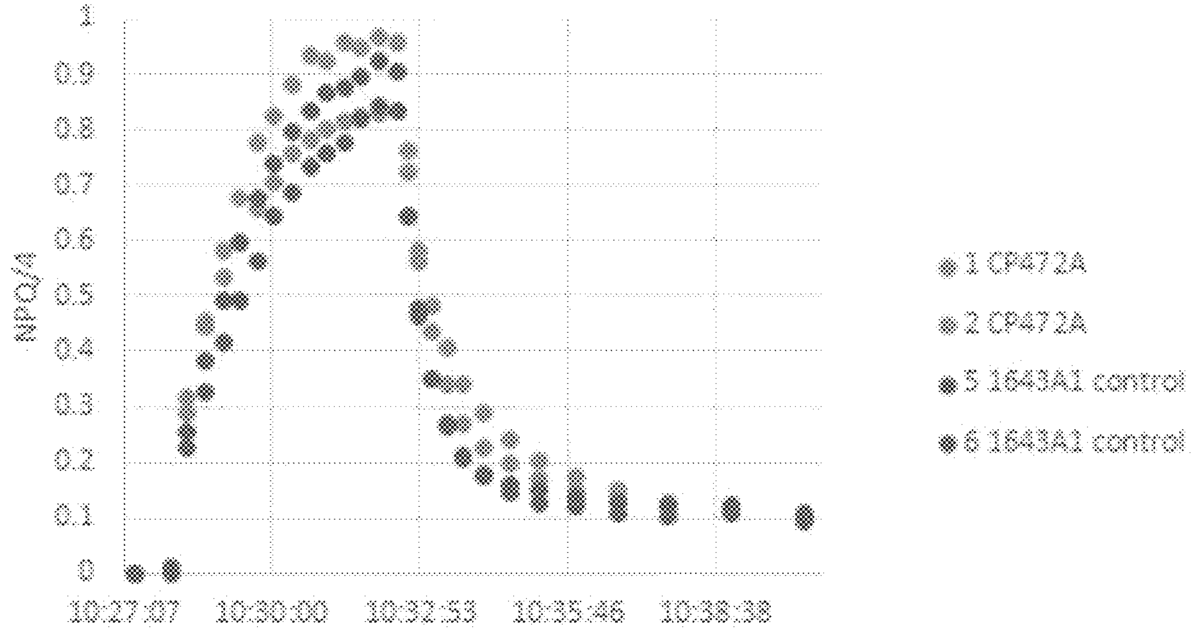
FIG. 30. NPQ induction and relaxation kinetics in transgenic cowpea CP472A. X-axis is time. Y-axis is NPQ divided by 4.

Cowpea plants were transformed with a T-DNA construct containing nucleotide sequences encoding PsbS, ZEP and VDE, following the transformation protocol as described in Higgins et al., Innovative research along the cowpea value chain. Ibadan, Nigeria: International Institute of Tropical Agriculture, pp. 133-139, 2013. To compare the kinetics of dynamic NPQ adjustment, a double exponential model was fitted to dark relaxation of NPQ in $T_0$ transgenic cowpea after exposure to fluctuating light. As shown in Table 4, the qE relaxation (τ1) was noticeably faster in the transformant line 164381A as compared to the control, with measurements of 20.5 s and 19.7 s versus 35.9 s and 29.7 s. The qZ phase of NPQ relaxation (τ2) was slower in the transformant line 1643B1 as compared to the control, likely caused by the limitation that the measurements were taken on $T_0$ transgenic plants. As is known in the art, transgenic plants from $T_1$ or $T_2$ generations are usually preferred over $T_0$ for phenotypic measurements. One reason is that in $T_0$ transgenic plants, stress from the transformation and tissue culture processes can interfere with normal plant physiology and affect phenotypic measurements. Another reason is that molecular characterization of a transgene cannot be complete until in the $T_1$ or $T_2$ generation and transgenic characteristics such as copy number and insertion location in the genome can have significant effects on the transgene expression. As shown in FIG. 27, FIG. 28 and FIG. 29, NPQ relaxed faster in the transformant line 1643B1 than in the control plant. As shown in FIG. 30, NPQ relaxed slower in the transformant line CP472A (orange dots) than in the control plant (blue dots), which is likely caused by the limitation that measurements were taken on $T_0$ transgenic plants as discussed above.

TABLE 4

Time constants of NPQ relaxation in transgenic cowpea.

| | 1643B1 | | Control | |
|---|---|---|---|---|
| | Measurement 1 | Measurement 2 | Measurement 1 | Measurement 2 |
| Time constant τ1 (s) | 20.5 | 19.7 | 35.9 | 29.7 |
| Time constant τ2 (s) | 1220.8 | 2272.0 | 1099.2 | 1043.0 |

Example 18. Transgenic Cassava (Prophetic)

This invention can also provide for a cassava line with improved photosynthesis and growth as compared to a phenotype in parental units of said cassava line. The cassava line can be created by generating a population of transgenic plants comprising heterologous nucleotide sequences encoding polypeptides selected from PsbS, ZEP and VDE as described herein. Each transgenic event comprises introducing into the genome of a parent plant at least one nucleotide construct comprising a promoter operably linked to heterologous nucleotide as described herein. The nucleotide construct is introduced into the parental genome in sufficient quantity to produce transgenic cells which can be cultured into plants of transgenic cassava having said enhanced phenotype. The transgenic cells are cultured into transgenic plants producing progeny transgenic seed. The population of transgenic plants is screened for observable phenotypes. Seed is collected from transgenic plants which are selected as having an unexpected enhanced phenotype. Optionally, the method comprises repeating a cycle of germinating transgenic seed, growing subsequent generation plants from said transgenic seed, observing phenotypes of said subsequent generation plants and collecting seeds from subsequent generation plants having an enhanced phenotype. In another aspect, the method a large population is screened by employing at least one heterologous nucleotide sequences encoding polypeptides selected from PsbS, ZEP and VDE. Other preferred aspects of the method employ nucleotide construct where the heterologous DNA is operably linked to a selected promoter, e.g. the 5' end of a promoter region. The DNA construct may be introduced into a random location in the genome or into a preselected site in the genome.

An example of cassava transformation protocol is described in Chetty et al., New Biotechnology 30.2: 136-143, 2013.

Example 19. Transgenic Poplar (Prophetic)

This invention can also provide for a poplar line with improved photosynthesis and growth as compared to a phenotype in parental units of said poplar line. The poplar line can be created by generating a population of transgenic plants comprising heterologous nucleotide sequences encoding polypeptides selected from PsbS, ZEP and VDE as described herein. Each transgenic event comprises introducing into the genome of a parent plant at least one nucleotide construct comprising a promoter operably linked to heterologous nucleotide as described herein. The nucleotide construct is introduced into the parental genome in sufficient quantity to produce transgenic cells which can be cultured into plants of transgenic poplar having said enhanced phenotype. The transgenic cells are cultured into transgenic plants producing progeny transgenic seed. The population of transgenic plants is screened for observable phenotypes. Seed is collected from transgenic plants which are selected as having an unexpected enhanced phenotype. Optionally, the method comprises repeating a cycle of germinating transgenic seed, growing subsequent generation plants from said transgenic seed, observing phenotypes of said subsequent generation plants and collecting seeds from subsequent generation plants having an enhanced phenotype. In another aspect, the method a large population is screened by employing at least one heterologous nucleotide sequences encoding polypeptides selected from PsbS, ZEP and VDE. Other preferred aspects of the method employ nucleotide construct where the heterologous DNA is operably linked to a selected promoter, e.g. the 5' end of a promoter region. The DNA construct may be introduced into a random location in the genome or into a preselected site in the genome.

An example of poplar transformation protocol is described in Movahedi et al., International Journal of Molecular Science 15.6: 10780-10793, 2014.

Example 20. Transgenic Eucalyptus (Prophetic)

This invention can also provide for a eucalyptus line with improved photosynthesis and growth as compared to a phenotype in parental units of said eucalyptus line. The eucalyptus line can be created by generating a population of transgenic plants comprising heterologous nucleotide sequences encoding polypeptides selected from PsbS, ZEP and VDE as described herein. Each transgenic event comprises introducing into the genome of a parent plant at least one nucleotide construct comprising a promoter operably linked to heterologous nucleotide as described herein. The nucleotide construct is introduced into the parental genome in sufficient quantity to produce transgenic cells which can be cultured into plants of transgenic eucalyptus having said enhanced phenotype. The transgenic cells are cultured into transgenic plants producing progeny transgenic seed. The population of transgenic plants is screened for observable phenotypes. Seed is collected from transgenic plants which are selected as having an unexpected enhanced phenotype. Optionally, the method comprises repeating a cycle of germinating transgenic seed, growing subsequent generation plants from said transgenic seed, observing phenotypes of said subsequent generation plants and collecting seeds from subsequent generation plants having an enhanced phenotype. In another aspect of the method a large population is screened by employing at least one heterologous nucleotide sequences encoding polypeptides selected from PsbS, ZEP and VDE. Other preferred aspects of the method employ nucleotide constructs where the heterologous DNA is operably linked to a selected promoter, e.g. the 5' end of a promoter region. The DNA construct may be introduced into a random location in the genome or into a preselected site in the genome.

An example of eucalyptus transformation protocol is described in Diwakar et al., Plant Tissue Culture: Propagation, Conservation and Crop Improvement, 219-244, 2016.

Example 21. Sequence Identity Analysis of NPQ Genes

To identify amino acid sequences that are homologous to the *Arabidopsis* PsbS, ZEP and VDE, BLAST protein searches was performed with the BLASTX program. Percentage of sequence similarity by BLAST is presented in Table 5 for PsbS, Table 6 for ZEP, and Table 7 for VDE, where top 100 hits of sequences ordered by descending percentage of sequence identity to the *Arabidopsis* homologue are listed.

To compare the sequence identity and/or similarity of the amino acid sequences that are homologous to the *Arabidopsis* PsbS, ZEP and VDE, alignment of sequences was performed with the CLUSTAL OMEGA program. FIG. 24 illustrates the amino acid sequence similarity through CLUSTAL O for (A) PsbS, (B) ZEP and (C) VDE, respectively.

TABLE 5

Percentage of sequence identity for PsbS.

| Description | Query cover | E value | Identity | Accession |
|---|---|---|---|---|
| Chlorophyll A-B binding family protein [*Arabidopsis thaliana*] | 100% | 0 | 100% | NP_175092.1 |
| unknown protein [*Arabidopsis thaliana*] | 100% | 0 | 99% | AAK95290.1 |
| hypothetical protein ARALYDRAFT_891398 [*Arabidopsis lyrata* subsp. *lyrata*] | 100% | 0 | 98% | XP_002891292.1 |
| PREDICTED: photosystem II 22 kDa protein, chloroplastic-like [*Camelina sativa*] | 100% | 2.00E−178 | 97% | XP_010500150.1 |
| PREDICTED: photosystem II 22 kDa protein, chloroplastic isoform X1 [*Camelina sativa*] | 100% | 3.00E−178 | 97% | XP_010479050.1 |
| PREDICTED: photosystem II 22 kDa protein, chloroplastic-like [*Camelina sativa*] | 100% | 2.00E−177 | 97% | XP_010461444.1 |
| hypothetical protein CARUB_v10010031mg [*Capsella rubella*] | 100% | 8.00E−176 | 96% | XP_006304103.1 |
| Photosystem II 22 kDa protein, chloroplastic [*Noccaea caerulescens*] | 100% | 3.00E−156 | 95% | JAU12851.1 |
| PREDICTED: photosystem II 22 kDa protein, chloroplastic [*Raphanus sativus*] | 100% | 8.00E−151 | 95% | XP_018447609.1 |
| PREDICTED: photosystem II 22 kDa protein, chloroplastic [*Brassica rapa*] | 100% | 1.00E−149 | 95% | XP_009107479.1 |
| hypothetical protein EUTSA_v10011718mg [*Eutrema salsugineum*] | 99% | 3.00E−148 | 94% | XP_006393723.1 |
| PREDICTED: photosystem II 22 kDa protein, chloroplastic-like [*Brassica napus*] | 100% | 4.00E−148 | 95% | XP_013681211.1 |
| PREDICTED: photosystem II 22 kDa protein, chloroplastic [*Raphanus sativus*] | 100% | 5.00E−148 | 95% | XP_018467982.1 |
| PREDICTED: photosystem II 22 kDa protein, chloroplastic [*Brassica oleracea* var. *oleracea*] | 100% | 6.00E−148 | 95% | XP_013592876.1 |
| PREDICTED: photosystem II 22 kDa protein, chloroplastic-like [*Brassica oleracea* var. *oleracea*] | 100% | 3.00E−147 | 94% | XP_013599587.1 |
| PREDICTED: photosystem II 22 kDa protein, chloroplastic [*Brassica rapa*] | 99% | 4.00E−147 | 95% | XP_009123055.1 |
| PREDICTED: photosystem II 22 kDa protein, chloroplastic [*Cucumis melo*] | 99% | 6.00E−125 | 78% | XP_008466710.1 |
| Chlorophyll A-B binding family protein [*Arabidopsis thaliana*] | 96% | 1.00E−124 | 100% | NP_973971.1 |
| PREDICTED: photosystem II 22 kDa protein, chloroplastic [*Cucumis sativus*] | 99% | 3.00E−122 | 76% | XP_004150442.1 |

TABLE 5-continued

| Percentage of sequence identity for PsbS. | | | | |
|---|---|---|---|---|
| Description | Query cover | E value | Identity | Accession |
| PREDICTED: photosystem II 22 kDa protein, chloroplastic [*Phoenix dactylifera*] | 97% | 2.00E−121 | 77% | XP_008783427.1 |
| Photosystem II protein, chloroplastic [*Anthurium amnicola*] | 99% | 5.00E−121 | 76% | JAT63827.1 |
| PREDICTED: photosystem II 22 kDa protein, chloroplastic isoform X1 [*Beta vulgaris* subsp. *vulgaris*] | 99% | 2.00E−120 | 77% | XP_010692414.1 |
| hypothetical protein TSUD_300570 [*Trifolium subterraneum*] | 99% | 1.00E−119 | 71% | GAU40978.1 |
| Chloroa_b-bind domain-containing protein [*Cephalotus follicularis*] | 100% | 3.00E−119 | 74% | GAV71974.1 |
| PsbS [*Pisum sativum*] | 99% | 5.00E−119 | 71% | AKG94171.1 |
| PREDICTED: photosystem II 22 kDa protein, chloroplastic [*Elaeis guineensis*] | 88% | 5.00E−119 | 84% | XP_010911871.1 |
| PREDICTED: photosystem II 22 kDa protein, chloroplastic [*Camelina sativa*] | 96% | 2.00E−118 | 96% | XP_010479049.1 |
| PREDICTED: photosystem II 22 kDa protein, chloroplastic [*Vitis vinifera*] | 99% | 3.00E−118 | 76% | XP_002285857.1 |
| PREDICTED: photosystem II 22 kDa protein, chloroplastic [*Tarenaya hasleriana*] | 99% | 2.00E−117 | 82% | XP_010544817.1 |
| RecName: Full = Photosystem II 22 kDa protein, chloroplastic; AltName: Full = CP22; Flags: Precursor | 82% | 2.00E−116 | 88% | Q02060.1 |
| PREDICTED: photosystem II 22 kDa protein, chloroplastic-like [*Gossypium raimondii*] | 99% | 7.00E−116 | 78% | XP_012447533.1 |
| PREDICTED: photosystem II 22 kDa protein, chloroplastic-like [*Gossypium hirsutum*] | 99% | 7.00E−116 | 78% | XP_016708802.1 |
| PREDICTED: photosystem II 22 kDa protein, chloroplastic-like [*Gossypium arboreum*] | 99% | 3.00E−115 | 78% | XP_017604982.1 |
| PREDICTED: photosystem II 22 kDa protein, chloroplastic-like [*Gossypium hirsutum*] | 99% | 5.00E−115 | 78% | XP_016687044.1 |
| Photosystem II 22 kDa, chloroplastic [*Gossypium arboreum*] | 99% | 5.00E−115 | 78% | KHG12586.1 |
| PREDICTED: photosystem II 22 kDa protein, chloroplastic [*Amborella trichopoda*] | 99% | 1.00E−114 | 73% | XP_006847012.1 |
| Chain A, Crystal Structure Of The Photoprotective Protein Psbs From Spinach | 80% | 1.00E−114 | 88% | 4RI2_A |
| hypothetical protein PRUPE_ppa009763mg [*Prunus persica*] | 100% | 2.00E−114 | 73% | XP_007222356.1 |
| PREDICTED: photosystem II 22 kDa protein, chloroplastic-like [*Lupinus angustifolius*] | 93% | 3.00E−114 | 77% | XP_019415222.1 |
| light-harvesting complex I chlorophyll A/B-binding protein [*Medicago truncatula*] | 99% | 3.00E−114 | 73% | XP_003602031.1 |
| unknown [*Lotus japonicus*] | 99% | 4.00E−114 | 75% | AFK43146.1 |
| PREDICTED: photosystem II 22 kDa protein, chloroplastic [*Ricinus communis*] | 99% | 6.00E−114 | 75% | XP_002513761.1 |
| PREDICTED: photosystem II 22 kDa protein, chloroplastic [*Fragaria vesca* subsp. *vesca*] | 99% | 8.00E−114 | 73% | XP_004290871.1 |
| PREDICTED: photosystem II 22 kDa protein, chloroplastic [*Prunus mume*] | 100% | 1.00E−113 | 73% | XP_008219642.1 |
| Chlorophyll A-B binding protein [*Corchorus capsularis*] | 99% | 2.00E−113 | 73% | OMO59479.1 |
| Chlorophyll A-B binding protein [*Corchorus olitorius*] | 99% | 8.00E−113 | 73% | OMP06543.1 |
| PREDICTED: photosystem II 22 kDa protein, chloroplastic [*Theobroma cacao*] | 99% | 2.00E−112 | 76% | XP_007019073.2 |
| PREDICTED: photosystem II 22 kDa protein, chloroplastic-like [*Malus domestica*] | 100% | 2.00E−112 | 74% | XP_008375547.1 |
| photosystem 11 22 kDa protein [*Pyrus x bretschneideri*] | 100% | 7.00E−112 | 73% | AHM26637.1 |
| Photosystem II 22 kDa family protein [*Populus trichocarpa*] | 99% | 3.00E−111 | 74% | XP_002300987.1 |
| hypothetical protein L484_004387 [*Morus notabilis*] | 100% | 8.00E−111 | 72% | XP_010106359.1 |
| PREDICTED: photosystem II 22 kDa protein, chloroplastic [*Oryza sativa* Japonica Group] | 99% | 1.00E−110 | 73% | XP_015621169.1 |
| PREDICTED: photosystem II 22 kDa protein, chloroplastic [*Nelumbo nucifera*] | 100% | 2.00E−110 | 75% | XP_010242794.1 |
| PREDICTED: photosystem II 22 kDa protein, chloroplastic [*Daucus carota* subsp. *sativus*] | 99% | 3.00E−110 | 76% | XP_017247379.1 |
| PREDICTED: photosystem II 22 kDa protein, chloroplastic [*Populus euphratica*] | 99% | 3.00E−110 | 74% | XP_011027529.1 |
| PREDICTED: photosystem II 22 kDa protein, chloroplastic-like [*Malus domestica*] | 79% | 3.00E−110 | 87% | XP_008352659.1 |

TABLE 5-continued

Percentage of sequence identity for PsbS.

| Description | Query cover | E value | Identity | Accession |
|---|---|---|---|---|
| PREDICTED: photosystem II 22 kDa protein, chloroplastic-like [*Gossypium arboreum*] | 100% | 5.00E−110 | 75% | XP_017613374.1 |
| PREDICTED: photosystem II 22 kDa protein, chloroplastic [*Cicer arietinum*] | 99% | 2.00E−109 | 70% | XP_004502468.1 |
| hypothetical protein B456_009G245800 [*Gossypium raimondii*] | 99% | 4.00E−109 | 76% | KJB59229.1 |
| unknown [*Picea sitchensis*] | 80% | 6.00E−109 | 83% | ABK20973.1 |
| PREDICTED: photosystem II 22 kDa protein, chloroplastic [*Jatropha curcas*] | 99% | 1.00E−108 | 76% | XP_012078240.1 |
| photosystem II 22 kDa protein, chloroplastic [*Dorcoceras hygrometricum*] | 99% | 4.00E−108 | 74% | KZV16554.1 |
| PREDICTED: photosystem II 22 kDa protein, chloroplastic [*Malus domestica*] | 100% | 5.00E−108 | 74% | XP_008378474.1 |
| chloroplast photosystem II subunit [*Sedum alfredii*] | 74% | 7.00E−108 | 88% | AEK26371.1 |
| predicted protein [*Hordeum vulgare* subsp. *vulgare*] | 99% | 2.00E−107 | 70% | BAJ90394.1 |
| PREDICTED: photosystem II 22 kDa protein, chloroplastic [*Juglans regia*] | 98% | 2.00E−107 | 74% | XP_018817122.1 |
| unknown [*Medicago truncatula*] | 95% | 2.00E−107 | 73% | ACJ84782.1 |
| putative photosystem II protein [*Gossypioides kirkii*] | 99% | 3.00E−107 | 76% | ACD56611.1 |
| Photosystem II, 22 kDa Protein [*Plantago major*] | 99% | 3.00E−107 | 72% | CAJ38395.1 |
| PREDICTED: photosystem II 22 kDa protein, chloroplastic [*Pyrus x bretschneideri*] | 100% | 6.00E−107 | 72% | XP_018501271.1 |
| PREDICTED: photosystem II 22 kDa protein, chloroplastic-like [*Musa acuminata* subsp. *malaccensis*] | 99% | 9.00E−107 | 75% | XP_009399195.1 |
| Photosystem II 22 kDa protein, chloroplastic [*Glycine soja*] | 100% | 4.00E−106 | 71% | KHN09207.1 |
| hypothetical protein CICLE_v10002099 mg [*Citrus Clementina*] | 99% | 2.00E−105 | 72% | XP_006434195.1 |
| putative photosystem II protein [*Gossypium hirsutum*] | 100% | 2.00E−105 | 75% | ABO41853.1 |
| PREDICTED: photosystem II 22 kDa protein, chloroplastic [*Arachis ipaensis*] | 99% | 3.00E−105 | 72% | XP_016163508.1 |
| PREDICTED: photosystem II 22 kDa protein, chloroplastic [*Citrus sinensis*] | 99% | 4.00E−105 | 72% | XP_006472781.1 |
| photosystem II 22 kDa protein, chloroplastic [*Cajanus cajan*] | 98% | 5.00E−105 | 70% | XP_020228501.1 |
| Chlorophyll A-B binding family protein [*Theobroma cacao*] | 99% | 2.00E−104 | 74% | EOY16298.1 |
| PREDICTED: photosystem II 22 kDa protein, chloroplastic [*Glycine max*] | 100% | 3.00E−104 | 69% | XP_003523444.1 |
| PREDICTED: photosystem II 22 kDa protein, chloroplastic [*Eucalyptus grandis*] | 100% | 3.00E−104 | 73% | XP_010065001.1 |
| unnamed protein product [*Coffea canephora*] | 98% | 5.00E−104 | 71% | CDP10910.1 |
| unknown [*Picea sitchensis*] | 80% | 6.00E−104 | 80% | ABK25763.1 |
| photosystem II 22 kDa protein, chloroplastic-like [*Glycine max*] | 100% | 1.00E−103 | 70% | NP_001276237.1 |
| PREDICTED: photosystem II 22 kDa protein, chloroplastic [*Ziziphus jujuba*] | 100% | 2.00E−103 | 71% | XP_015885664.1 |
| PREDICTED: photosystem II 22 kDa protein, chloroplastic [*Sesamum indicum*] | 99% | 3.00E−103 | 73% | XP_011074844.1 |
| PREDICTED: photosystem II 22 kDa protein, chloroplastic-like [*Gossypium raimondii*] | 90% | 4.00E−103 | 82% | XP_012467939.1 |
| unknown [*Glycine max*] | 100% | 5.00E−103 | 69% | ACU23291.1 |
| PREDICTED: photosystem II 22 kDa protein, chloroplastic [*Oryza sativa* Japonica Group] | 86% | 7.00E−103 | 80% | XP_015633953.1 |
| PREDICTED: photosystem II 22 kDa protein, chloroplastic like [*Oryza brachyantha*] | 83% | 8.00E−103 | 80% | XP_006653075.1 |
| PREDICTED: photosystem II 22 kDa protein, chloroplastic-like [*Gossypium hirsutum*] | 90% | 8.00E−103 | 82% | XP_016727785.1 |
| PREDICTED: photosystem II 22 kDa protein, chloroplastic-like [*Gossypium hirsutum*] | 90% | 1.00E−102 | 82% | XP_016732479.1 |
| B0518A01.1 [*Oryza sativa* Indica Group] | 100% | 1.00E−102 | 72% | CAH68096.1 |
| PsbS protein [*Phyllostachys edulis*] | 74% | 1.00E−102 | 86% | ACU33835.1 |
| PREDICTED: photosystem II 22 kDa protein, chloroplastic [*Nicotiana tomentosiformis*] | 99% | 1.00E−102 | 72% | XP_009623344.1 |
| PREDICTED: photosystem II 22 kDa protein, chloroplastic [*Oryza brachyantha*] | 74% | 2.00E−102 | 86% | XP_006645083.2 |
| OSJNBa0039K24.28 [*Oryza sativa* Japonica Group] | 86% | 2.00E−102 | 80% | CAE01809.2 |
| chloroplast photosystem II 22 kDa component [*Nicotiana benthamiana*] | 99% | 3.00E−102 | 71% | ABC59515.1 |
| PREDICTED: photosystem II 22 kDa protein, chloroplastic [*Nicotiana sylvestris*] | 99% | 3.00E−102 | 71% | XP_009771859.1 |

TABLE 5-continued

Percentage of sequence identity for PsbS.

| Description | Query cover | E value | Identity | Accession |
|---|---|---|---|---|
| Photosystem II subunit S [*Zostera marina*] | 99% | 5.00E−102 | 70% | KMZ60119.1 |
| hypothetical protein M569_10990 [*Genlisea aurea*] | 80% | 1.00E−101 | 84% | EPS63793.1 |

TABLE 6

Percentage of sequence identity for ZEP.

| Description | Query cover | E value | Identity | Accession |
|---|---|---|---|---|
| zeaxanthin epoxidase (ZEP) (ABA1) [*Arabidopsis thaliana*] | 100% | 0 | 100% | NP_851285.1 |
| AtABAI [*Arabidopsis thaliana*] | 100% | 0 | 99% | BAB11935.1 |
| zeaxanthin epoxidase [*Arabidopsis thaliana*] | 100% | 0 | 99% | AAF82390.1 |
| zeaxanthin epoxidase [*Arabidopsis thaliana*] | 100% | 0 | 99% | AAG17703.1 |
| hypothetical protein CARDB_v10026026 mg [*Capsella rubella*] | 100% | 0 | 93% | XP_006280131.1 |
| PREDICTED: zeaxanthin epoxidase, chloroplastic [*Camelina sativa*] | 100% | 0 | 94% | XP_010444704.1 |
| hypothetical protein ARALYDRAFT_ 496897 [*Arabidopsis lyrata* subsp. *lyrata*] | 100% | 0 | 95% | XP_002865032.1 |
| PREDICTED: zeaxanthin epoxidase, chloroplastic [*Camelina sativa*] | 100% | 0 | 93% | XP_010484561.1 |
| hypothetical protein EUTSA_v10003769 mg [*Eutrema salsugineum*] | 99% | 0 | 91% | XP_006393901.1 |
| zeaxanthin epoxidase [*Eutrema halophilum*] | 99% | 0 | 91% | AAV85824.1 |
| hypothetical protein EUTSA_v10003769 mg [*Eutrema salsugineum*] | 99% | 0 | 91% | XP_006393902.1 |
| hypothetical protein AALP_ AA8G503900 [*Arabis alpina*] | 100% | 0 | 90% | KFK28343.1 |
| Zeaxanthin epoxidase, chloroplastic [*Noccaea caerulescens*] | 100% | 0 | 90% | JAU06164.1 |
| Zeaxanthin epoxidase, chloroplastic [*Noccaea caerulescens*] | 100% | 0 | 90% | JAU34415.1 |
| Zeaxanthin epoxidase, chloroplastic [*Noccaea caerulescens*] | 100% | 0 | 90% | JAU86000.1 |
| BnaA07g12170D [*Brassica napus*] | 99% | 0 | 90% | CDY01444.1 |
| zeaxanthin epoxidase, chloroplastic [*Brassica napus*] | 99% | 0 | 90% | NP_001302817.1 |
| PREDICTED: zeaxanthin epoxidase, chloroplastic [*Brassica rapa*] | 99% | 0 | 90% | XP_009103460.1 |
| zeaxanthin epoxidase [*Brassica rapa* subsp. *pekinensis*] | 99% | 0 | 90% | ACM68704.1 |
| PREDICTED: zeaxanthin epoxidase, chloroplastic [*Raphanus sativus*] | 99% | 0 | 89% | XP_018441511.1 |
| zeaxanthin epoxidase [*Brassica napus*] | 100% | 0 | 90% | ADC29517.1 |
| PREDICTED: zeaxanthin epoxidase, chloroplastic-like isoform X2 [*Brassica napus*] | 100% | 0 | 89% | XP_013686243.1 |
| PREDICTED: zeaxanthin epoxidase, chloroplastic isoform X2 [*Brassica oleracea* var. *oleracea*] | 100% | 0 | 89% | XP_013597987.1 |
| PREDICTED: zeaxanthin epoxidase, chloroplastic-like isoform X1 [*Brassica napus*] | 100% | 0 | 89% | XP_013686242.1 |
| PREDICTED: zeaxanthin epoxidase, chloroplastic isoform X1[*Brassica oleracea* var. *oleracea*] | 100% | 0 | 89% | XP_013597986.1 |
| zeaxanthin epoxidase (ZEP) (ABA1) [*Arabidopsis thaliana*] | 91% | 0 | 96% | NP_201504.2 |
| PREDICTED: zeaxanthin epoxidase, chloroplastic [*Brassica oleracea* var. *oleracea*] | 100% | 0 | 85% | XP_013613157.1 |
| PREDICTED: zeaxanthin epoxidase, chloroplastic-like isoform X3 [*Raphanus sativus*] | 100% | 0 | 86% | XP_018457364.1 |
| BnaC09g07550D [*Brassica napus*] | 100% | 0 | 85% | CDX81344.1 |
| PREDICTED: zeaxanthin epoxidase, chloroplastic-like [*Brassica rapa*] | 100% | 0 | 84% | XP_009112352.1 |
| BnaA09g07610D [*Brassica napus*] | 100% | 0 | 84% | CDY18634.1 |

TABLE 6-continued

Percentage of sequence identity for ZEP.

| Description | Query cover | E value | Identity | Accession |
|---|---|---|---|---|
| PREDICTED: zeaxanthin epoxidase, chloroplastic-like isoform X4 [*Raphanus sativus*] | 95% | 0 | 86% | XP_018457365.1 |
| PREDICTED: zeaxanthin epoxidase, chloroplastic-like isoform X1 [*Raphanus sativus*] | 95% | 0 | 86% | XP_018457362.1 |
| PREDICTED: zeaxanthin epoxidase, chloroplastic-like isoform X2 [*Raphanus sativus*] | 95% | 0 | 86% | XP_018457363.1 |
| PREDICTED: zeaxanthin epoxidase, chloroplastic-like [*Tarenaya hasleriana*] | 100% | 0 | 80% | XP_010547517.1 |
| PREDICTED: zeaxanthin epoxidase, chloroplastic [*Tarenaya hasleriana*] | 100% | 0 | 79% | XP_010558547.1 |
| PREDICTED: zeaxanthin epoxidase, chloroplastic isoform X3 [*Brassica oleracea* var. *oleracea*] | 86% | 0 | 90% | XP_013597988.1 |
| zeaxanthin epoxidase precursor [*Arabidopsis thaliana*] | 74% | 0 | 100% | AAL91193.1 |
| PREDICTED: zeaxanthin epoxidase, chloroplastic [*Ricinus communis*] | 99% | 0 | 72% | XP_002523587.1 |
| PREDICTED: zeaxanthin epoxidase, chloroplastic [*Jatropha curcas*] | 99% | 0 | 72% | XP_012079233.1 |
| hypothetical protein COLO4_11419 [*Corchorus olitorius*] | 92% | 0 | 75% | OMP01999.1 |
| zeaxanthin epoxidase [*Vitis vinifera*] | 99% | 0 | 71% | NP_001268202.1 |
| PREDICTED: zeaxanthin epoxidase, chloroplastic-like [*Populus euphratica*] | 95% | 0 | 73% | XP_011043539.1 |
| unnamed protein product [*Vitis vinifera*] | 99% | 0 | 71% | CBI21425.3 |
| zeaxanthin epoxidase [*Vitis vinifera*] | 99% | 0 | 71% | AAR11195.1 |
| hypothetical protein JCGZ_12396 [*Jatropha curcas*] | 92% | 0 | 74% | KDP31935.1 |
| hypothetical protein Csa_2G277050 [*Cucumis sativus*] | 98% | 0 | 70% | KGN61963.1 |
| hypothetical protein CCACVL1_26372 [*Corchorus capsularis*] | 92% | 0 | 75% | OMO56663.1 |
| RecName: Full = Zeaxanthin epoxidase, chloroplastic; AltName: Full = PA-ZE; Flags: Precursor | 98% | 0 | 72% | 081360.1 |
| PREDICTED: zeaxanthin epoxidase, chloroplastic-like [*Vigna radiata* var. *radiata*] | 100% | 0 | 70% | XP_014509031.1 |
| zeaxanthin epoxidase, chloroplastic [*Cucumis sativus*] | 98% | 0 | 70% | NP_001292713.1 |
| PREDICTED: zeaxanthin epoxidase, chloroplastic [*Juglans regia*] | 97% | 0 | 73% | XP_018844974.1 |
| zeaxanthin epoxidase family protein [*Populus tomentosa*] | 94% | 0 | 73% | APR63737.1 |
| hypothetical protein PRUPE_ppa002248 mg [*Prunus persica*] | 98% | 0 | 72% | XP_007204247.1 |
| hypothetical protein PRUPE_7G133100 [*Prunus persica*] | 98% | 0 | 72% | ONH96498.1 |
| FHA domain-containing protein/FAD_ binding_3 domain-containing protein [*Cephalotus follicularis*] | 99% | 0 | 70% | GAV73676.1 |
| zeaxanthin epoxidase 1 [*Bixa orellana*] | 97% | 0 | 73% | AMJ39488.1 |
| PREDICTED: zeaxanthin epoxidase, chloroplastic isoform X2 [*Theobroma cacao*] | 96% | 0 | 73% | XP_007047261.2 |
| zeaxanthin epoxidase [*Camellia sinensis*] | 98% | 0 | 71% | AJB84624.1 |
| Zeaxanthin epoxidase (ZEP) (ABA1) isoform 2 [*Theobroma cacao*] | 96% | 0 | 73% | EOX91418.1 |
| zeaxanthin epoxidase, chloroplastic [*Cucumis melo*] | 98% | 0 | 70% | NP_001315402.1 |
| PREDICTED: zeaxanthin epoxidase, chloroplastic-like [*Vigna angularis*] | 97% | 0 | 71% | XP_017411486.1 |
| zeaxanthin epoxidase family protein [*Populus trichocarpa*] | 93% | 0 | 71% | XP_002307265.1 |
| PREDICTED: zeaxanthin epoxidase, chloroplastic [*Eucalyptus grandis*] | 98% | 0 | 70% | XP_010028248.1 |
| zeaxanthin epoxidase, chloroplastic-like isoform X1 [*Cajanus cajan*] | 98% | 0 | 71% | XP_020238178.1 |
| PREDICTED: zeaxanthin epoxidase, chloroplastic [*Prunus mume*] | 98% | 0 | 72% | XP_008241462.1 |
| hypothetical protein PHAVU_003G243800 g [*Phaseolus vulgaris*] | 98% | 0 | 71% | XP_007155924.1 |
| Zeaxanthin epoxidase (ZEP) (ABA1) isoform 3 [*Theobroma cacao*] | 96% | 0 | 72% | EOX91419.1 |

TABLE 6-continued

Percentage of sequence identity for ZEP.

| Description | Query cover | E value | Identity | Accession |
|---|---|---|---|---|
| PREDICTED: zeaxanthin epoxidase, chloroplastic isoform X1 [*Theobroma cacao*] | 96% | 0 | 72% | XP_007047260.2 |
| PREDICTED: zeaxanthin epoxidase, chloroplastic [*Ziziphus jujuba*] | 100% | 0 | 70% | XP_015890147.1 |
| PREDICTED: zeaxanthin epoxidase, chloroplastic-like [*Populus euphratica*] | 90% | 0 | 75% | XP_011005864.1 |
| Zeaxanthin epoxidase (ZEP) (ABA1) isoform 1 [*Theobroma cacao*] | 96% | 0 | 72% | EOX91417.1 |
| PREDICTED: zeaxanthin epoxidase, chloroplastic-like [*Arachis duranensis*] | 98% | 0 | 70% | XP_015955494.1 |
| hypothetical protein MANES_13G124100 [*Manihot esculenta*] | 98% | 0 | 72% | OAY33781.1 |
| zeaxanthin epoxidase [*Citrus unshiu*] | 99% | 0 | 70% | BAB78733.1 |
| zeaxanthin epoxidase [*Citrus unshiu*] | 99% | 0 | 70% | BAI79257.1 |
| hypothetical protein GLYMA_11G055700 [*Glycine max*] | 99% | 0 | 70% | KRH28470.1 |
| PREDICTED: zeaxanthin epoxidase, chloroplastic [*Citrus sinensis*] | 99% | 0 | 70% | XP_006466600.1 |
| hypothetical protein CISIN_1g005770 mg [*Citrus sinensis*] | 99% | 0 | 69% | KDO79210.1 |
| PREDICTED: zeaxanthin epoxidase, chloroplastic-like [*Citrus sinensis*] | 99% | 0 | 69% | XP_006494451.1 |
| hypothetical protein CICLE_v10025089 mg [*Citrus Clementina*] | 99% | 0 | 69% | XP_006425899.1 |
| zeaxanthin epoxidase, chloroplastic-like [*Glycine max*] | 97% | 0 | 71% | NP_001241348.1 |
| Zeaxanthin epoxidase, chloroplastic [*Glycine soja*] | 98% | 0 | 70% | KHN26473.1 |
| PREDICTED: zeaxanthin epoxidase, chloroplastic-like [*Pyrus x bretschneideri*] | 97% | 0 | 71% | XP_009343160.1 |
| PREDICTED: zeaxanthin epoxidase, chloroplastic-like [*Malus domestica*] | 100% | 0 | 69% | XP_008340140.1 |
| zeaxanthin epoxidase [*Citruilus lanatus*] | 98% | 0 | 69% | ADI56522.1 |
| PREDICTED: zeaxanthin epoxidase, chloroplastic [*Arachis ipaensis*] | 98% | 0 | 69% | XP_016185162.1 |
| zeaxanthin epoxidase [*Malus domestica*] | 98% | 0 | 69% | AHA61555.1 |
| PREDICTED: zeaxanthin epoxidase, chloroplastic [*Nicotiana sylvestris*] | 98% | 0 | 70% | XP_009767383.1 |
| zeaxanthin epoxidase [*Chrysanthemum x morifolium*] | 91% | 0 | 74% | BAE79556.1 |
| PREDICTED: zeaxanthin epoxidase, chloroplastic-like [*Cicer arietinum*] | 98% | 0 | 70% | XP_004511928.1 |
| PREDICTED: zeaxanthin epoxidase, chloroplastic-like [*Pyrus x bretschneideri*] | 98% | 0 | 70% | XP_018505293.1 |
| RecName: Full = Zeaxanthin epoxidase, chloroplastic; Flags: Precursor | 98% | 0 | 71% | Q40412.1 |
| zeaxanthin epoxidase [*Chrysanthemum boreale*] | 91% | 0 | 74% | AGU91434.1 |
| zeaxanthin epoxidase 1 isoform [*Bixa orellana*] | 93% | 0 | 74% | AMJ39489.1 |
| PREDICTED: zeaxanthin epoxidase, chloroplastic [*Nicotiana tabacum*] | 98% | 0 | 70% | XP_016476042.1 |
| PREDICTED: zeaxanthin epoxidase, chloroplastic [*Pyrus x bretschneideri*] | 98% | 0 | 70% | XP_009345968.1 |
| PREDICTED: zeaxanthin epoxidase, chloroplastic [*Beta vulgaris* subsp. *vulgaris*] | 99% | 0 | 67% | XP_010666612.1 |
| hypothetical protein CISIN_1g005770 mg [*Citrus sinensis*] | 99% | 0 | 68% | KDO79209.1 |
| PREDICTED: zeaxanthin epoxidase, chloroplastic isoform X1 [*Nelumbo nucifera*] | 98% | 0 | 69% | XP_010269709.1 |

TABLE 7

Percentage of sequence identity for VDE.

| Description | Query cover | E value | Identity | Accession |
|---|---|---|---|---|
| non-photochemical quenching 1 [*Arabidopsis thaliana*] | 100% | 0 | 100% | NP_172331.1 |
| non-photochemical quenching 1 [*Arabidopsis lyrata* subsp. *lyrata*] | 100% | 0 | 96% | XP_002889702.1 |
| hypothetical protein CARDB_v10009082 mg [*Capsella rubella*] | 100% | 0 | 95% | XP_006307456.1 |

TABLE 7-continued

Percentage of sequence identity for VDE.

| Description | Query cover | E value | Identity | Accession |
|---|---|---|---|---|
| PREDICTED: violaxanthin de-epoxidase, chloroplastic [*Camelina sativa*] | 100% | 0 | 93% | XP_010475655.1 |
| PREDICTED: violaxanthin de-epoxidase, chloroplastic [*Camelina sativa*] | 100% | 0 | 94% | XP_010458094.1 |
| PREDICTED: violaxanthin de-epoxidase, chloroplastic [*Camelina sativa*] | 100% | 0 | 94% | XP_010488996.1 |
| PREDICTED: violaxanthin de-epoxidase, chloroplastic [*Brassica napus*] | 100% | 0 | 88% | XP_013641072.1 |
| PREDICTED: violaxanthin de-epoxidase, chloroplastic [*Brassica rapa*] | 100% | 0 | 87% | XP_009148110.2 |
| BnaA06g04940D [*Brassica napus*] | 100% | 0 | 87% | CDX93554.1 |
| Violaxanthin de-epoxidase, chloroplastic [*Noccaea caerulescens*] | 100% | 0 | 87% | JAU20005.1 |
| Violaxanthin de-epoxidase, chloroplastic [*Noccaea caerulescens*] | 100% | 0 | 87% | JAU75731.1 |
| Violaxanthin de-epoxidase, chloroplastic [*Noccaea caerulescens*] | 100% | 0 | 87% | JAU51142.1 |
| violaxanthin de-epoxidase, chloroplastic-like [*Brassica napus*] | 100% | 0 | 87% | NP_001302836.1 |
| BnaC05g06200D [*Brassica napus*] | 100% | 0 | 87% | CDX95051.1 |
| hypothetical protein EUTSA_v10007587 mg [*Eutrema salsugineum*] | 100% | 0 | 88% | XP_006417674.1 |
| Violaxanthin de-epoxidase, chloroplastic [*Noccaea caerulescens*] | 100% | 0 | 87% | JAU77894.1 |
| PREDICTED: violaxanthin de-epoxidase, chloroplastic [*Tarenaya hasleriana*] | 100% | 0 | 74% | XP_010528777.1 |
| NPQ1 [*Arabidopsis thaliana*] | 72% | 0 | 100% | OAP18415.1 |
| PREDICTED: violaxanthin de-epoxidase, chloroplastic [*Eucalyptus grandis*] | 88% | 0 | 76% | XP_010043341.1 |
| PREDICTED: violaxanthin de-epoxidase, chloroplastic isoform X2 [*Gossypium arboreum*] | 89% | 0 | 74% | XP_017627747.1 |
| hypothetical protein MANES_09G144600 [*Manihot esculenta*] | 91% | 0 | 73% | OAY41983.1 |
| Non-photochemical quenching 1 isoform 1 [*Theobroma cacao*] | 91% | 0 | 73% | EOY10737.1 |
| PREDICTED: violaxanthin de-epoxidase, chloroplastic isoform X1 [*Gossypium arboreum*] | 82% | 0 | 79% | XP_017627745.1 |
| PREDICTED: violaxanthin de-epoxidase, chloroplastic-like [*Gossypium hirsutum*] | 82% | 0 | 79% | XP_016673034.1 |
| PREDICTED: violaxanthin de-epoxidase, chloroplastic [*Theobroma cacao*] | 91% | 0 | 72% | XP_007030235.2 |
| hypothetical protein PQPTR_0013s05000 g [*Populus trichocarpa*] | 83% | 0 | 78% | XP_002319136.2 |
| PREDICTED: violaxanthin de-epoxidase, chloroplastic isoform X3 [*Gossypium arboreum*] | 83% | 0 | 78% | XP_017627748.1 |
| PREDICTED: violaxanthin de-epoxidase, chloroplastic [*Jatropha curcas*] | 84% | 0 | 78% | XP_012092715.1 |
| chloroplast violaxanthin de-epoxidase [*Prunus humilis*] | 81% | 0 | 79% | AIZ75647.1 |
| PREDICTED: violaxanthin de-epoxidase, chloroplastic isoform X1 [*Pyrus x bretschneideri*] | 81% | 0 | 79% | XP_009379699.1 |
| PREDICTED: violaxanthin de-epoxidase, chloroplastic isoform X2 [*Pyrus x bretschneideri*] | 81% | 0 | 79% | XP_009379700.1 |
| violaxanthin de-epoxidase 1 [*Bixa orellana*] | 94% | 0 | 68% | AMJ39491.1 |
| hypothetical protein PRUPE_ppa005029 mg [*Prunus persica*] | 81% | 0 | 79% | XP_007207430.1 |
| PREDICTED: violaxanthin de-epoxidase, chloroplastic [*Vitis vinifera*] | 82% | 0 | 78% | XP_002267152.1 |
| PREDICTED: violaxanthin de-epoxidase, chloroplastic [*Prunus mume*] | 81% | 0 | 79% | XP_016651828.1 |
| hypothetical protein CICLE_v10019925 mg [*Citrus Clementina*] | 82% | 0 | 77% | XP_006443345.1 |
| hypothetical protein PRUPE_6G356100 [*Prunus persica*] | 81% | 0 | 79% | ONI05101.1 |
| hypothetical protein PRUPE_6G356100 [*Prunus persica*] | 81% | 0 | 79% | ONI05102.1 |
| unnamed protein product [*Vitis vinifera*] | 82% | 0 | 78% | CBI28686.3 |
| hypothetical protein CISIN_1g011550 mg [*Citrus sinensis*] | 82% | 0 | 77% | KDO45543.1 |
| PREDICTED: violaxanthin de-epoxidase, chloroplastic [*Malus domestica*] | 81% | 0 | 79% | XP_008388766.1 |
| violaxanthin de-epoxidase [*Citrus sinensis*] | 84% | 0 | 74% | NP_001275810.1 |
| violaxanthin de-epoxidase 1 [*Vitis vinifera*] | 82% | 0 | 78% | AFP28802.1 |

TABLE 7-continued

Percentage of sequence identity for VDE.

| Description | Query cover | E value | Identity | Accession |
|---|---|---|---|---|
| PREDICTED: violaxanthin de-epoxidase, chloroplastic isoform X2 [*Gossypium raimondii*] | 89% | 0 | 75% | XP_012492660.1 |
| hypothetical protein B456_007G268500 [*Gossypium raimondii*] | 89% | 0 | 75% | KJB44721.1 |
| PREDICTED: LOW QUALITY PROTEIN: violaxanthin de-epoxidase, chloroplastic-like [*Malus domestica*] | 81% | 0 | 78% | XP_008350656.1 |
| PREDICTED: violaxanthin de-epoxidase, chloroplastic [*Populus euphratica*] | 100% | 0 | 67% | XP_011034433.1 |
| VDE domain-containing protein [*Cephalotus follicularis*] | 81% | 0 | 82% | GAV86158.1 |
| PREDICTED: violaxanthin de-epoxidase, chloroplastic isoform X1 [*Gossypium raimondii*] | 82% | 0 | 79% | XP_012492659.1 |
| PREDICTED: violaxanthin de-epoxidase, chloroplastic isoform X3 [*Gossypium raimondii*] | 82% | 0 | 79% | XP_012492661.1 |
| PREDICTED: violaxanthin de-epoxidase, chloroplastic [*Fragaria vesca* subsp. *vesca*] | 84% | 0 | 73% | XP_004302125.1 |
| PREDICTED: violaxanthin de-epoxidase, chloroplastic [*Ziziphus jujuba*] | 90% | 0 | 76% | XP_015901670.1 |
| violaxanthin de-epoxidase [*Fragaria x ananassa*] | 84% | 0 | 72% | AFR11775.2 |
| hypothetical protein B456_007G268500 [*Gossypium raimondii*] | 82% | 0 | 79% | KJB44724.1 |
| Violaxanthin de-epoxidase, chloroplastic [*Gossypium arboreum*] | 89% | 0 | 72% | KHG25773.1 |
| RecName: Full = Violaxanthin de-epoxidase, chloroplastic; Flags: Precursor | 82% | 0 | 75% | Q9SM43.2 |
| PREDICTED: violaxanthin de-epoxidase, chloroplastic [*Phoenix dactylifera*] | 82% | 0 | 75% | XP_008810272.1 |
| Violaxanthin de-epoxidase [*Corchorus capsularis*] | 83% | 0 | 78% | OMO84679.1 |
| violaxanthin de-epoxidase [*Coffea arabica*] | 79% | 0 | 82% | ABB70816.1 |
| PREDICTED: violaxanthin de-epoxidase, chloroplastic isoform X2 [*Elaeis guineensis*] | 82% | 0 | 75% | XP_010913044.1 |
| PREDICTED: violaxanthin de-epoxidase, chloroplastic isoform X1 [*Elaeis guineensis*] | 82% | 0 | 75% | XP_010913041.1 |
| Violaxanthin de-epoxidase [*Morus notabilis*] | 85% | 0 | 72% | XP_010109315.1 |
| PREDICTED: violaxanthin de-epoxidase, chloroplastic [*Ricinus communis*] | 83% | 0 | 78% | XP_002525473.1 |
| violaxanthin de-epoxidase [*Coffea canephora*] | 79% | 0 | 82% | ABB70514.1 |
| PREDICTED: violaxanthin de-epoxidase, chloroplastic isoform X1 [*Nelumbo nucifera*] | 82% | 0 | 78% | XP_010247237.1 |
| PREDICTED: violaxanthin de-epoxidase, chloroplastic isoform X2 [*Nelumbo nucifera*] | 82% | 0 | 78% | XP_010247238.1 |
| violaxanthin de-epoxidase [*Camellia sinensis*] | 84% | 0 | 77% | AJB84625.1 |
| PREDICTED: violaxanthin de-epoxidase, chloroplastic [*Jugians regia*] | 84% | 0 | 76% | XP_018826961.1 |
| PREDICTED: violaxanthin de-epoxidase, chloroplastic [*Oryza brachyantha*] | 81% | 0 | 76% | XP_006652202.2 |
| violaxanthin deepoxidase [*Chrysanthemum x morifolium*] | 83% | 0 | 78% | BAE79554.1 |
| violaxanthin de-epoxidase [*Medicago truncatula*] | 79% | 0 | 79% | XP_003626506.2 |
| RecName: Full = Violaxanthin de-epoxidase, chloroplastic; Flags: Precursor | 79% | 0 | 81% | Q40251.1 |
| violaxanthin deepoxidase [*Chrysanthemum boreale*] | 83% | 0 | 79% | AGU91436.1 |
| violaxanthin de-epoxidase [*Camellia sinensis*] | 84% | 0 | 77% | AAL67858.2 |
| violaxanthin de-epoxidase [*Citrus limon*] | 81% | 0 | 75% | BAO18773.1 |
| violaxanthin de-epoxidase, chloroplastic [*Ananas comosus*] | 83% | 0 | 76% | XP_020111643.1 |
| violaxanthin de-epoxidase [*Citrus sinensis*] | 81% | 0 | 75% | BAO18772.1 |
| PREDICTED: violaxanthin de-epoxidase, chloroplastic-like isoform X5 [*Glycine max*] | 81% | 0 | 78% | XP_006576259.1 |
| PREDICTED: violaxanthin de-epoxidase, chloroplastic [*Amborella trichopoda*] | 79% | 0 | 79% | XP_006830529.1 |
| PREDICTED: violaxanthin de-epoxidase, chloroplastic [*Setaria italica*] | 81% | 0 | 77% | XP_004975369.1 |
| PREDICTED: violaxanthin de-epoxidase, chloroplastic-like [*Camelina sativa*] | 65% | 0 | 96% | XP_010462602.2 |
| violaxanthin de-epoxidase [*Citrus unshiu*] | 81% | 0 | 74% | BAN91498.1 |
| violaxanthin de-epoxidase, chloroplastic isoform X2 [*Cajanus cajan*] | 97% | 0 | 68% | XP_020213947.1 |
| PREDICTED: violaxanthin de-epoxidase, chloroplastic [*Oryza sativa* Japonica Group] | 82% | 0 | 75% | XP_015636342.1 |
| violaxanthin de-epoxidase, chloroplastic isoform X1 [*Cajanus cajan*] | 97% | 0 | 68% | XP_020213942.1 |
| PREDICTED: violaxanthin de-epoxidase, chloroplastic-like isoform X3 [*Glycine max*] | 81% | 0 | 78% | XP_014628869.1 |

TABLE 7-continued

Percentage of sequence identity for VDE.

| Description | Query cover | E value | Identity | Accession |
|---|---|---|---|---|
| PREDICTED: violaxanthin de-epoxidase, chloroplastic-like isoform X1 [*Glycine max*] | 81% | 0 | 78% | XP_014628868.1 |
| Violaxanthin de-epoxidase, chloroplastic [*Glycine soja*] | 81% | 0 | 78% | KHN35342.1 |
| PREDICTED: violaxanthin de-epoxidase, chloroplastic [*Beta vulgaris* subsp. *vulgaris*] | 84% | 0 | 75% | XP_010674199.1 |
| PREDICTED: violaxanthin de-epoxidase, chloroplastic-like isoform X2 [*Glycine max*] | 81% | 0 | 78% | XP_006576257.1 |
| violaxanthin de-epoxidase, chloroplastic-like precursor [*Glycine max*] | 81% | 0 | 78% | NP_001241404.1 |
| PREDICTED: violaxanthin de-epoxidase, chloroplastic isoform X1 [*Cicer arietinum*] | 81% | 0 | 79% | XP_004494767.1 |
| violaxanthin de-epoxidase precursor [*Oryza sativa* Japonica Group] | 82% | 0 | 75% | AAL09678.1 |
| OSJNBb0089B03.4 [*Oryza sativa* Japonica Group] | 82% | 0 | 75% | CAE03990.1 |
| violaxanthin de-epoxidase precursor [*Oryza sativa* Indica Group] | 81% | 0 | 76% | AAF97601.3 |
| PREDICTED: violaxanthin de-epoxidase, chloroplastic isoform X2 [*Cicer arietinum*] | 81% | 0 | 79% | XP_004494768.1 |
| hypothetical protein TSUD_347010 [*Trifolium subterraneum*] | 81% | 0 | 78% | GAU13597.1 |
| hypothetical protein LR48_Vigan10g159600 [*Vigna angularis*] | 79% | 0 | 79% | KOM55704.1 |
| violaxanthin de-epoxidase, chloroplastic-like [*Glycine max*] | 81% | 0 | 77% | NP_001240949.1 |
| PREDICTED: violaxanthin de-epoxidase, chloroplastic [*Vigna angularis*] | 79% | 0 | 78% | XP_017437597.1 |

Example 22. Greenhouse NPQ Expression Experiment

Figure 25:
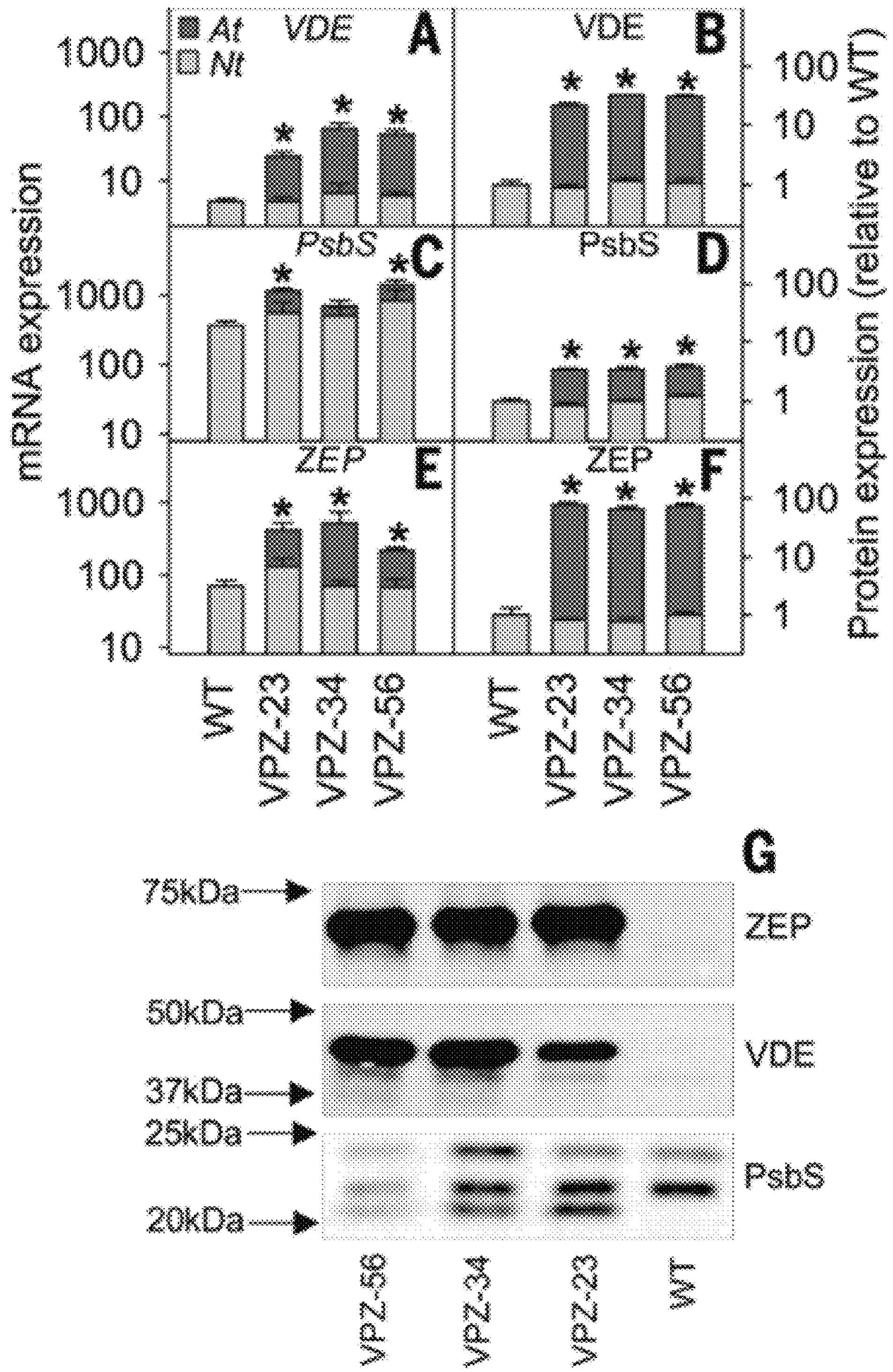
FIG. 25. Levels of mRNA and protein of VDE, PsbS, and ZEP in leaves of transgenic tobacco plants grown under greenhouse conditions. (A, C, and E) mRNA levels relative to actin and tubulin. (B, D, and F) Protein levels relative to wild type (WT), determined from densitometry on immunoblots. Error bars indicate standard error of measurement (SEM) (n=5 biological replicates), and asterisks indicate significant differences between VPZ lines and WT (α=0.05). (G) Representative immunoblots for VDE, PsbS, and ZEP.

*Nicotiana tabacum* was transformed with the coding sequences of *Arabidopsis* VDE, ZEP, and PsbS under the control of different promoters for expression in leaves. Two transformants with a single transfer DNA (T-DNA) integration (VPZ-34 and -56) and one transformant with two T-DNA insertions (VPZ-23) were selected based on a seedling NPQ screen and self-pollinated to obtain homozygous $T_2$ progeny for further investigation. These plants were then grown in a greenhouse. Levels of mRNA and protein of VDE, PsbS, and ZEP were measured (FIG. 25).

All three VPZ lines showed increases in total (transgenic plus native) transcript levels of VDE (10-fold), PsbS (threefold), and ZEP (sixfold) relative to those of WT (A, C, and E). For PsbS, the increase in transcript levels translated into an approximately fourfold-higher PsbS protein level (D), as exemplified in bands at 21 kDa (AtPsbS) and 24 kDa (NtPsbS) (G). For VDE and ZEP, the increase in transcript levels corresponded to 30-fold for VDE (45 kDa) (B and G) and 74-fold for ZEP (73 kDa) (F and G) increases over WT protein levels.

Example 23. Field NPQ Expression Experiment

Figure 26:
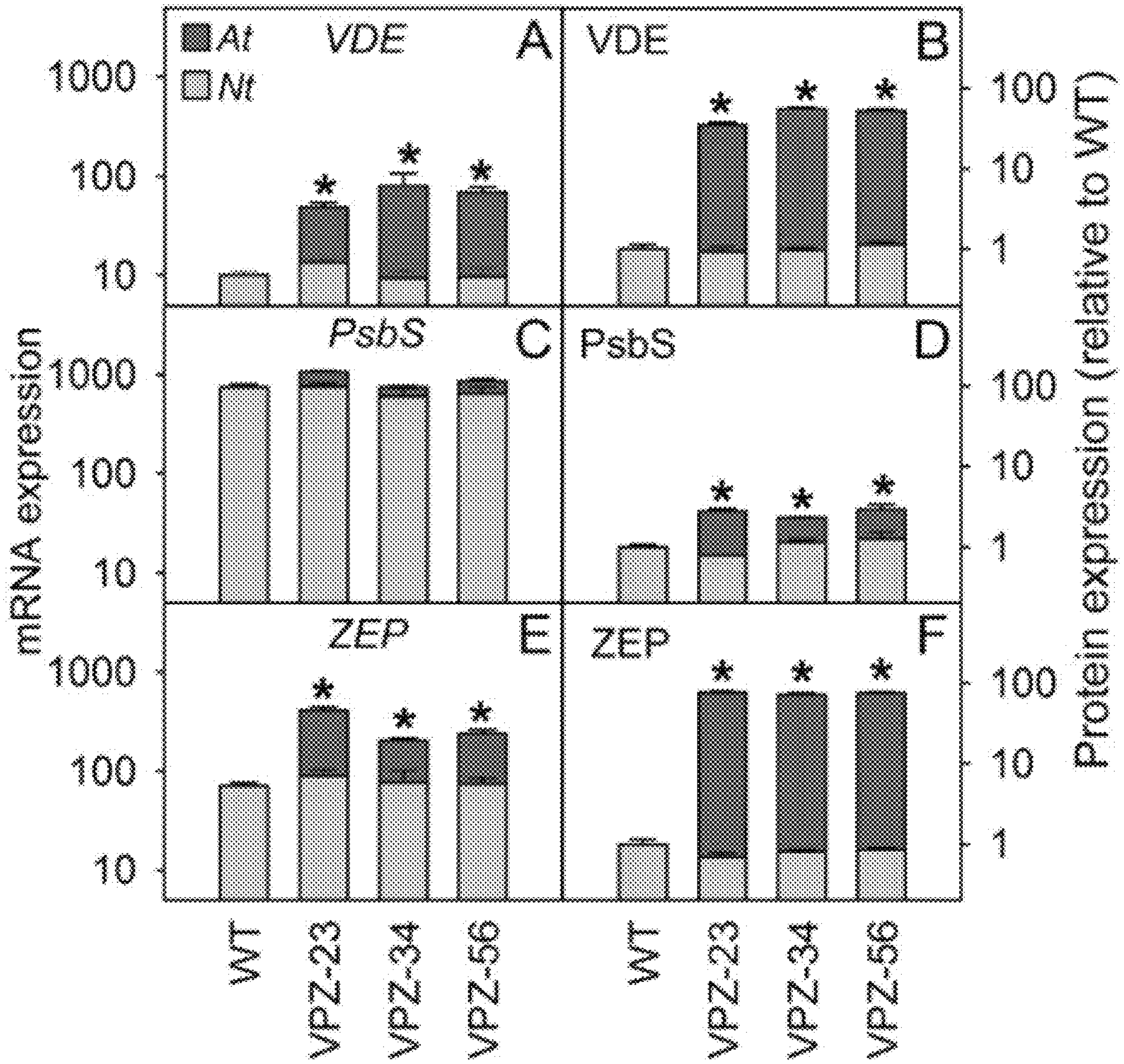
FIG. 26. Levels of mRNA and protein of VDE, PsbS, and ZEP in leaves of transgenic tobacco plants grown under field conditions. (A, C, E) mRNA levels relative to actin and tubulin. (B, D, F) Protein levels relative to wild type (WT), determined from densitometry on immunoblots. Error bars indicate SEM (n=4), and asterisk indicates significant differences between VPZ lines and WT (α=0.05).

*Nicotiana tabacum* was transformed with the coding sequences of *Arabidopsis* VDE, ZEP, and PsbS under the control of different promoters for expression in leaves. Two transformants with a single transfer DNA (T-DNA) integration (VPZ-34 and -56) and one transformant with two T-DNA insertions (VPZ-23) were selected based on a seedling NPQ screen and self-pollinated to obtain homozygous $T_2$ progeny for further investigation. These plants were then grown in a field. Levels of mRNA and protein of VDE, PsbS, and ZEP were measured (FIG. 26).

All three VPZ lines showed increases in total (transgenic plus native) transcript levels of VDE (4-fold), PsbS (1.2-fold), and ZEP (7-fold) relative to those of WT. All three VPZ lines also showed increases in total (transgenic plus native) protein levels of VDE (47-fold), PsbS (3-fold), and ZEP (75-fold) relative to those of the WT.

Example 24. Transgenic Rice Experiment

Figure 31:
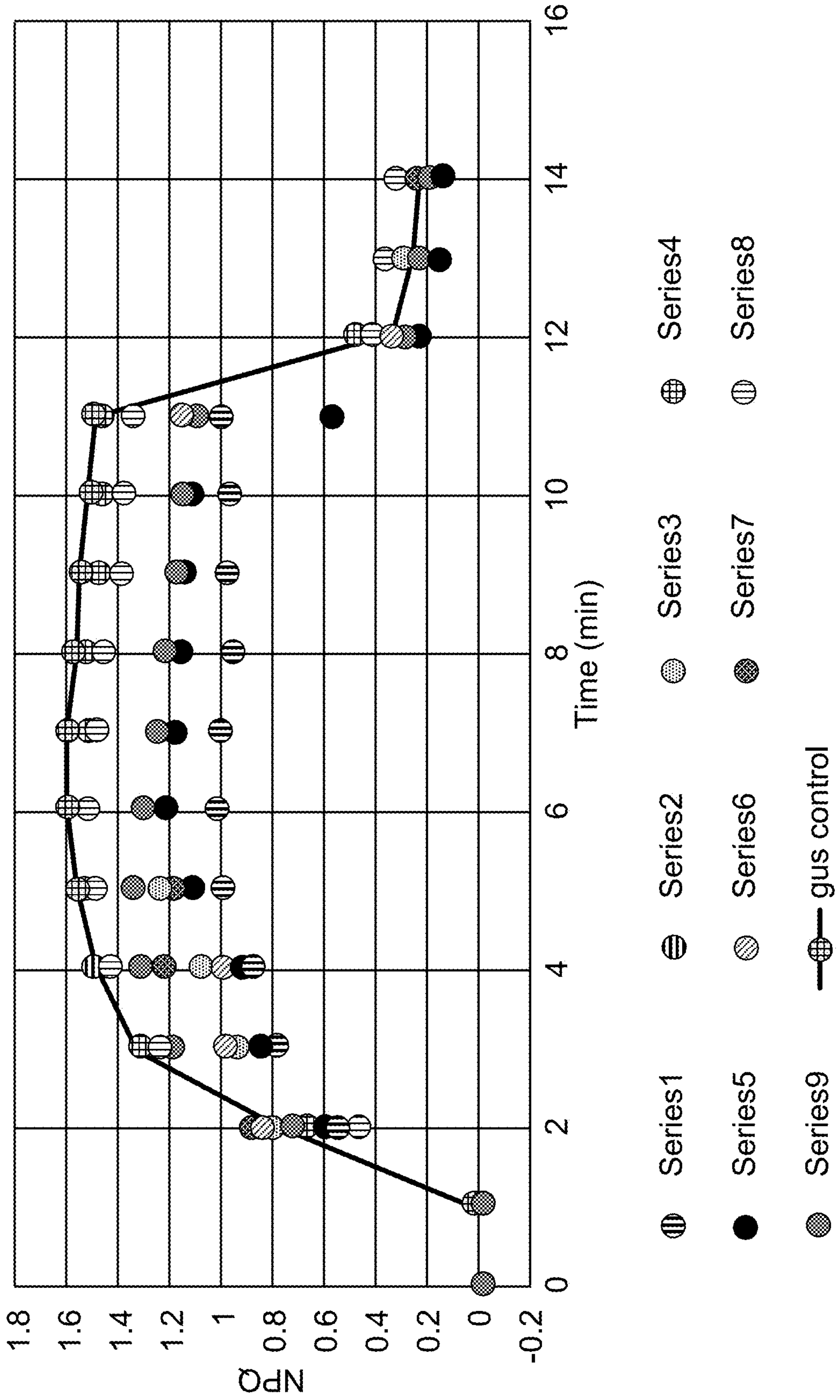
FIG. 31. NPQ induction and relaxation kinetics in nine transgenic rice lines.
Figure 32:
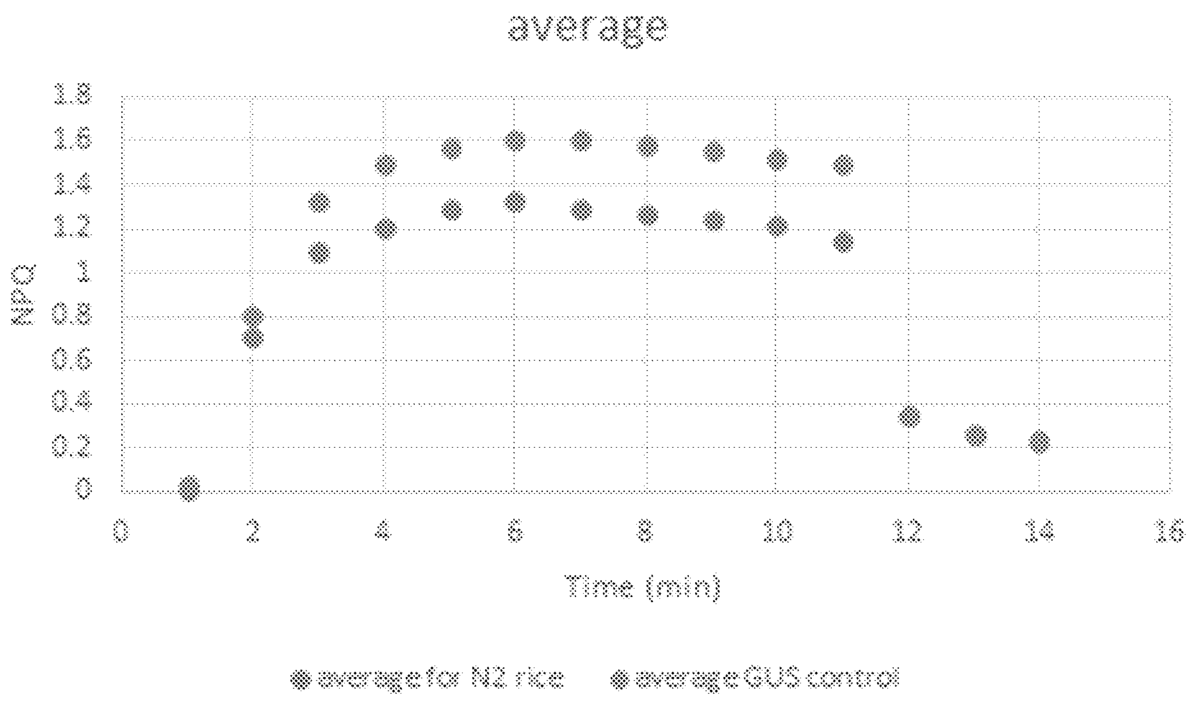
FIG. 32. Average NPQ induction and relaxation kinetics in transgenic rice.

Rice plants were transformed with a T-DNA construct containing nucleotide sequences encoding PsbS, ZEP and VDE, following the transformation protocol described in Example 15. The same expression construct used in the transgenic tobacco experiment was used in this experiment. Leaves of nine independent $T_0$ transformants and two GUS controls were dark adapted. Subsequently, NPQ was measured during 10 min of 1000 μmol m-2 s-1 light followed by 3 min of darkness. FIG. 31 shows the NPQ of the nine rice transformants (dots) and the control (line) over the course of 10 min of 1000 μmol m-2 s-1 light followed by 3 min of darkness. FIG. 32 shows the average of NPQ of the nine rice transformants (blue dot) and the control (orange dot) over the course of 10 min of 1000 μmol m-2 s-1 light followed by 3 min of darkness.

As shown in FIG. 31 and FIG. 32, NPQ amplitudes of these nine transformants were lower than the control during the 10 min of 1000 μmol m-2 s-1 light. This result is consistent with increased expression of ZEP in these transformants, which prevents zeaxanthin formation and thus reduces NPQ amplitude. An alternative explanation is that PsbS overexpression interferes with expression of native PsbS and thus reduces the NPQ amplitude. Results also showed that there was no significant difference in NPQ between the transformants and the control during the 3-min relaxation in the dark, due to the possible lack of zeaxanthin built up in this experiment.

The lack of change in NPQ kinetics in these transgenic rice plants is most plausibly ascribed to a limitation of the experimental design: in this experiment, the rice plants were transformed with an expression cassette constructed for tobacco transformation, which contains promoters designed for optimal gene expression in dicot plants. It is known in the art that dicot promoters do not work well in monocot plants. Therefore, expression of PsbS, ZEP and VDE in these transgenic rice plants was likely not optimally increased to the level that would be conducive to increase of NPQ relaxation rate.

Example 25. Additional Experiments

Figure 18:
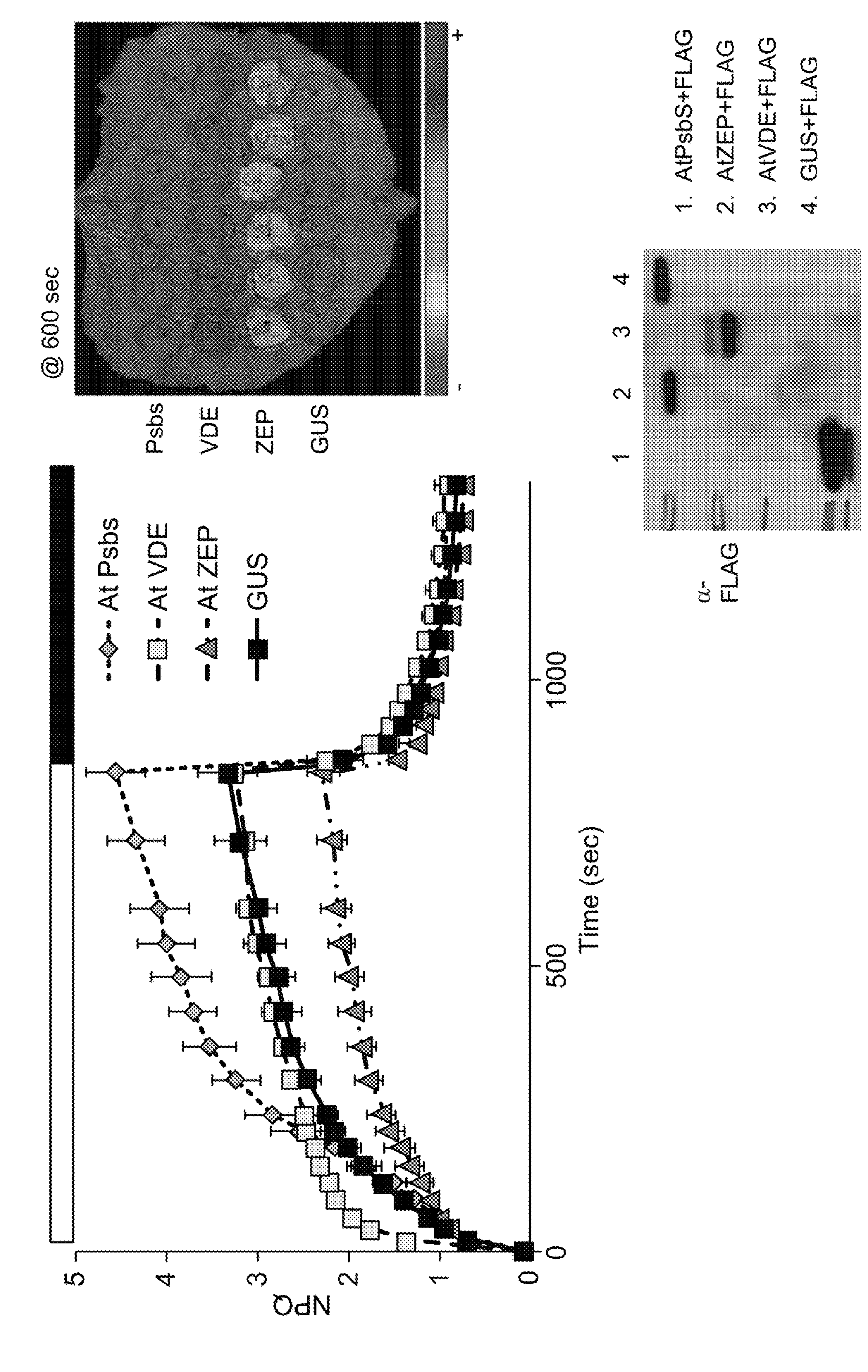
FIG. 18. Transient overexpression of NPQ-related genes in *Nicotiana benthamiana*. The upper left panel shows NPQ measurements on leaf spots overexpressing FLAG-tagged PsbS, VDE, ZEP, and GUS as a negative control, during 13 min illumination at 600 μmol photons m-2 s-1 (white bar), followed by 10 min of dark (black bar). Error bars represent standard deviation (n=6). The upper right panel shows the false-color image of NPQ of a leaf expressing PSBS, VDE, ZEP and GUS 10 min after high light exposure. Rainbow bar indicates relative amount of NPQ. The lower panel shows the immunoblot analysis of tissue collected from the leaf in the upper right panel and probed with anti-FLAG.

Transient overexpression of NPQ-related genes was conducted in *Nicotiana benthamiana*. Measurements of NPQ were taken on leaf spots overexpressing FLAG-tagged PsbS, VDE, ZEP, and GUS as a negative control, during 13 min illumination at 600 μmol photons m-2 s-1, followed by 10 min of dark. As shown in FIG. 18, results showed that overexpression of PsbS increased NPQ capacity relative to the GUS control. Overexpression of VDE sped up NPQ induction. Overexpression of ZEP sped up NPQ relaxation but negatively impacted NPQ induction and capacity.

Figure 19:
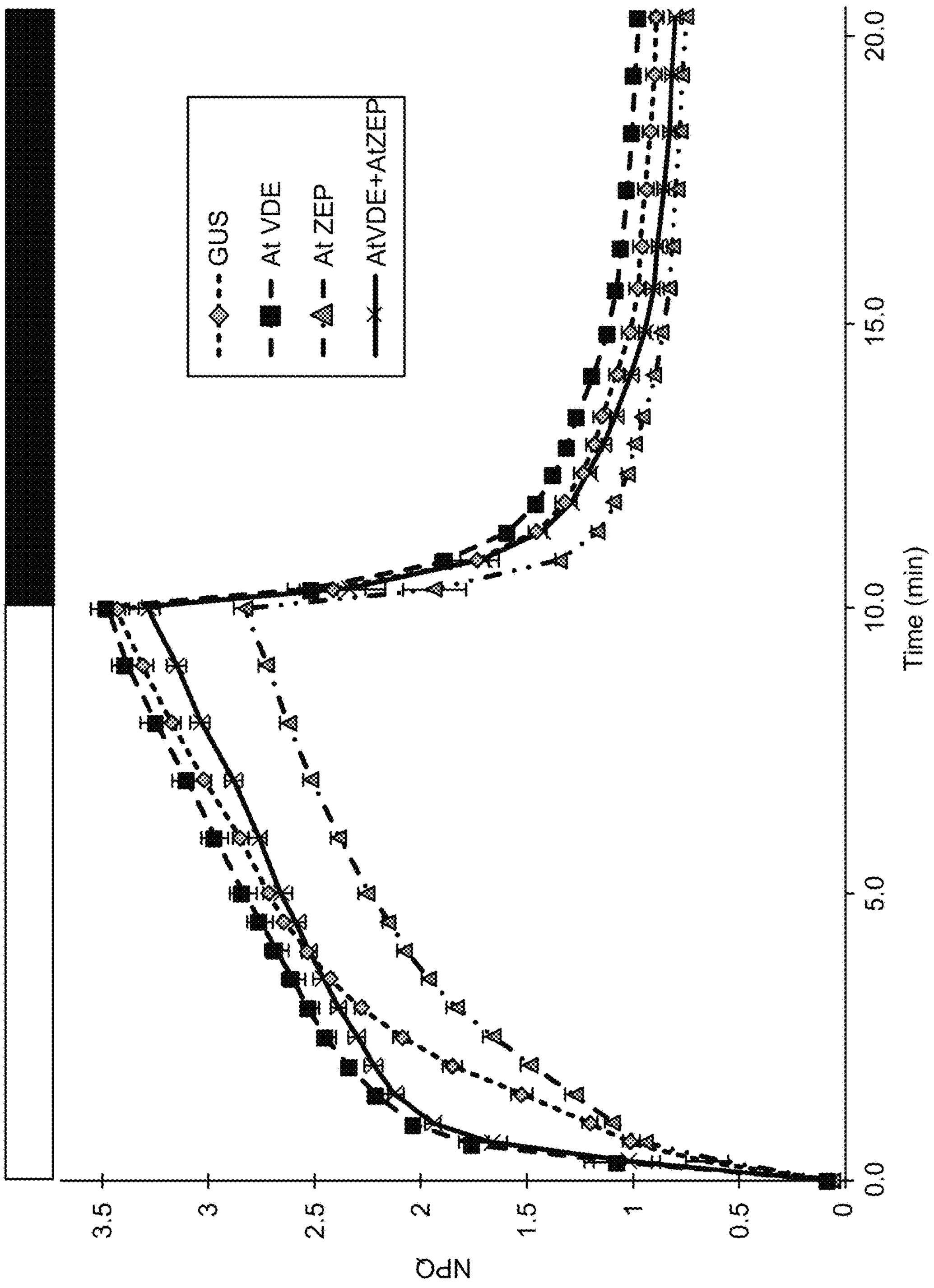
FIG. 19. Transient co-overexpression of VDE and ZEP in *Nicotiana benthamiana* speeds up NPQ induction and relaxation. Error bars represent standard error (n=4).

Transient co-overexpression of VDE and ZEP was conducted in *Nicotiana benthamiana*. Results showed an increased rate of NPQ induction and relaxation as seen in FIG. 19. Co-overexpression of VDE was shown necessary to balance overexpression of ZEP and prevent negative impact of ZEP overexpression on NPQ induction and capacity.

Figure 20:
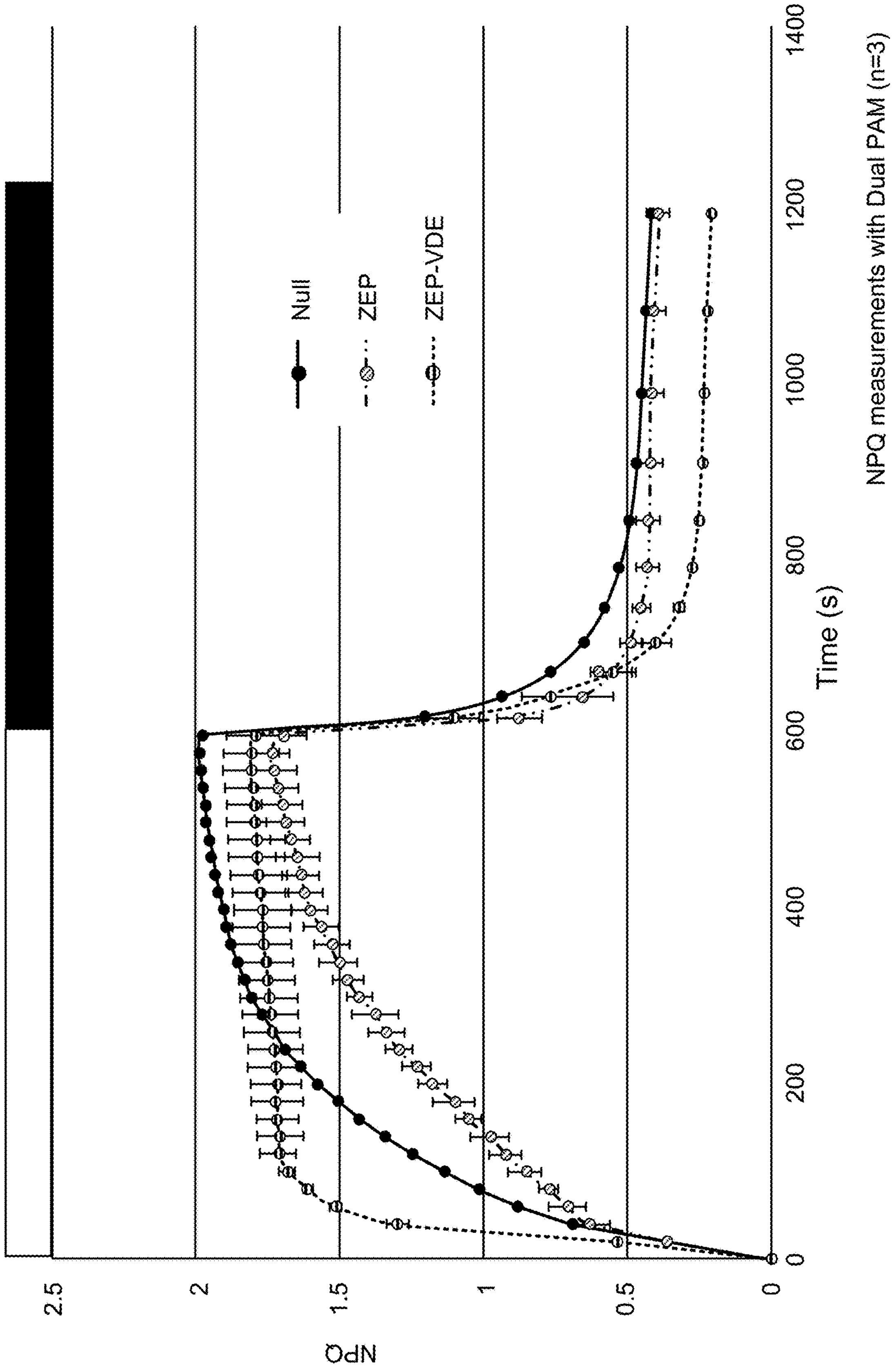
FIG. 20. NPQ kinetics of transgenic $T_1$ progeny. NPQ measurements with DUAL PAM were taken on the youngest fully developed leaf of $T_1$ adult plants for three different lines: one wild-type segregant (Null), one overexpressing ZEP (ZEP) and one overexpressing ZEP and VDE (ZEP-VDE), during 10 min illumination at 600 μmol photons m-2 s-1 (white bar), followed by 10 min of dark (black bar). Each curve corresponds to the average NPQ measurement of three different plants; error bars indicate standard error (n=3).

FIG. 20 shows the NPQ kinetics of stable transgenic $T_1$ plants of *Nicotiana tabacum* cv. Petite Havana. NPQ measurements with DUAL PAM were taken on the youngest fully developed leaf of $T_1$ adult plants for three different lines: one wild-type segregant (Null), one overexpressing ZEP (ZEP) and one overexpressing ZEP and VDE (ZEP-VDE), during 10 min illumination at 600 μmol photons m-2 s-1, followed by 10 min of dark. Results showed that the ZEP-VDE line showed faster NPQ induction and relaxation.

Figure 21:
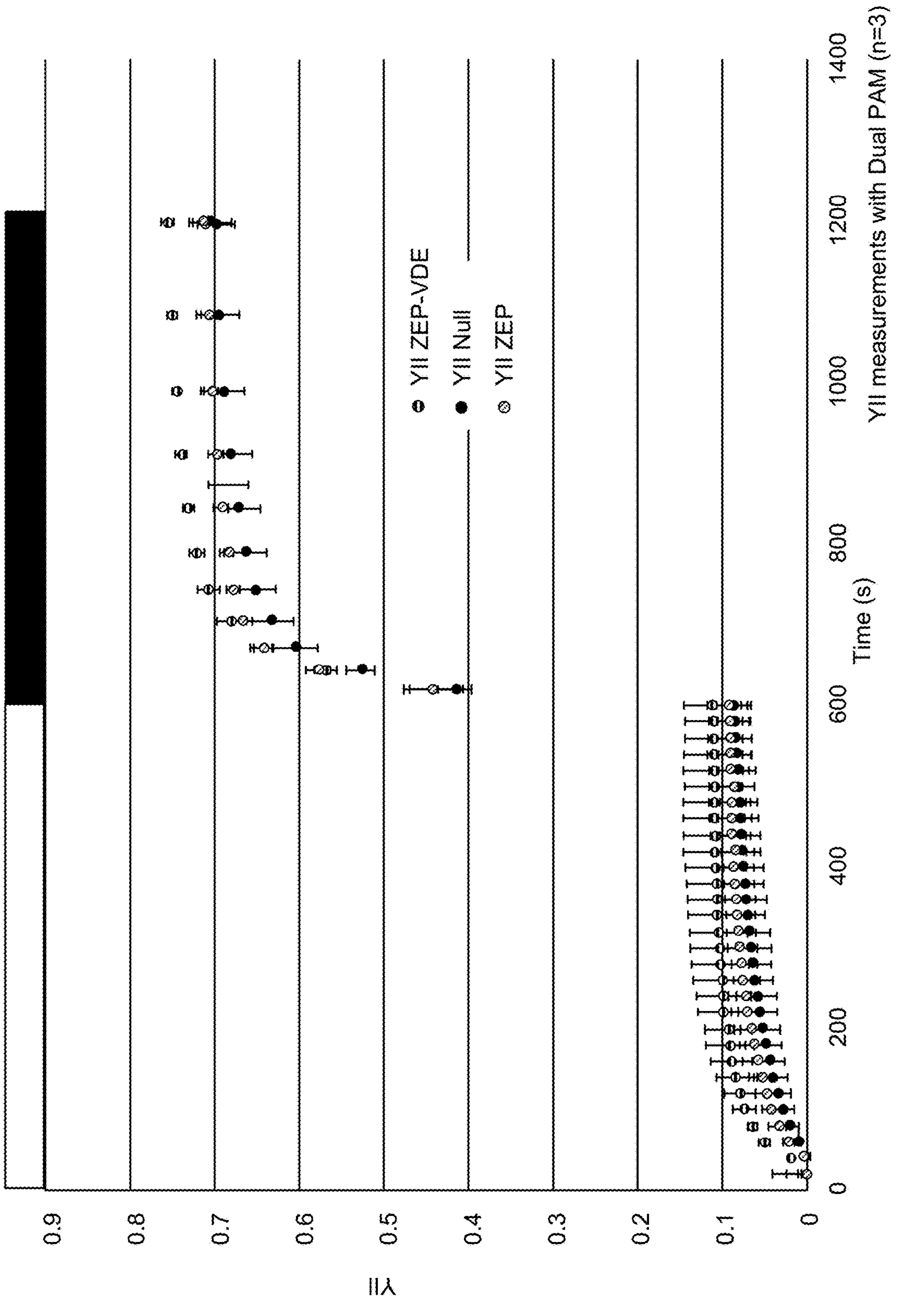
FIG. 21. Photosystem II quantum yield (YID of stable transgenic $T_1$ plants of *Nicotiana tabacum* cv. Petite Havana.

FIG. 21 shows the photosystem II quantum yield (YII) of stable transgenic $T_1$ plants of *Nicotiana tabacum* cv. Petite Havana. Measurements of YII performed simultaneously with NPQ measurements described in FIG. 20, were taken on the same plants and in the same conditions. During the dark recovery period, YII was higher for the line overexpressing ZEP-VDE compared to the one overexpressing ZEP or the Null.

Figure 22:
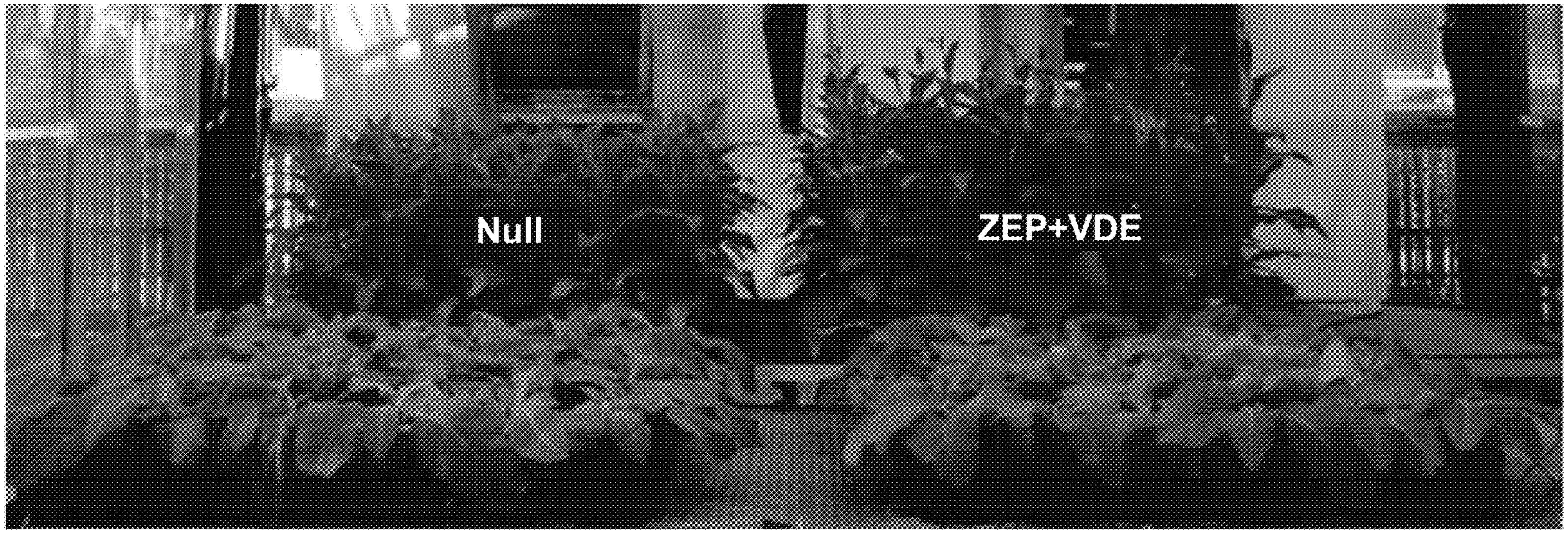
FIG. 22. Growth experiment in the greenhouse. Four sets of plants are shown in the figure, one per transgenic line. Each set contains 36 plants.

FIG. 22 shows the growth experiment in the greenhouse. Results demonstrated the increased size and biomass of stable transgenic $T_1$ plants of *Nicotiana tabacum* cv. Petite Havana that overexpress ZEP and VDE (ZEP-VDE), compared to wild type (Null). Lines overexpressing PsbS (PsbS) or ZEP and PSBS (ZEP-PsbS) showed a similar biomass to wild type. Four sets of plants are shown in the figure, one per transgenic line. Each set contains 36 plants. The aboveground biomass for each set was determined by the total wet weight and total dry weight of the harvest of the 36 plants, after 19 days of growth. The data represent the results of a single experiment.

SEQUENCE LISTING

```
Sequence total quantity: 68
SEQ ID NO: 1            moltype = DNA  length = 1059
FEATURE                 Location/Qualifiers
source                  1..1059
                        mol_type = other DNA
                        organism = Arabidopsis thaliana
SEQUENCE: 1
atcttttaat ctcttcactt ccacaacaca acacaaaaca catcactgat ccttctctca  60
tcctcagaaa gaatggctca aaccatgctg cttacttcag gcgtcaccgc cggccatttt  120
ttgaggaaca agagcccttt ggctcagccc aaagttcacc atctcttcct ctctggaaac  180
tctccggttg cactaccatc taggagacaa tcattcgttc ctctcgctct cttcaaaccc  240
aaaaccaaag ctgctcctaa aaaggttgag aagccgaaga gcaaggttga ggatggcatc  300
tttggaacgt ctggtgggat tggtttcaca aaggcgaatg agctattcgt tggtcgtgtt  360
gctatgatcg gtttcgctgc atcgttgctt ggtgaggcgt tgacgggaaa agggatatta  420
gctcagctga atctggagac agggataccg atttacgaag cagagccatt gcttctcttc  480
ttcatcttgt tcactctgtt gggagccatt ggagctctcg gagacagagg aaaattcgtc  540
gacgatcctc ccaccgggct cgagaaagcc gtcattcctc ccggcaaaaa cgtccgatct  600
gccctcggtc tcaaagaaca aggtccattg tttgggttca cgaaggcgaa cgagttattc  660
gtaggaagat tggcacagtt gggaatagca ttttcactga taggagagat tattaccggg  720
aaaggagcat tagctcaact caacattgag accggtatac caattcaaga tatcgaacca  780
cttgtcctct taaacgttgc tttcttcttc ttcgctgcca ttaatcctgg taatggaaaa  840
ttcatcaccg atgatggtga agaaagctaa attatcatgt acttaaattt agtagagagt  900
gtgtgacctt ctcttcatgt tgagacaaaa ggaaatggac agcttaaatt gttgtaatac  960
ttatatcctt ttgtttttaa cttggaattt tctgattata tatagtttta ttacacctaa  1020
gtgactaggt gattgatatc atctagcatc tcttaacag                        1059

SEQ ID NO: 2            moltype = DNA  length = 2385
FEATURE                 Location/Qualifiers
source                  1..2385
                        mol_type = other DNA
                        organism = Arabidopsis thaliana
SEQUENCE: 2
atttgcctcc ttcttcttca aaccaatttc ttcttcttct tctctcaggt ttgagtctga  60
ggcatcacaa cagataaagt cttgaacttt gatcaagaat tctaaacgga gtttttgctc  120
ttctcgtcgg tgaaagaaaa atcgagatgg gttcaactcc gttttgctac tctatcaatc  180
catctccatc aaagcttgat ttcacgagga cccatgtgtt tagtcctgtt tctaaacagt  240
tttacttaga tttatcatcg ttttccggaa aacccggagg agtatctggg tttaggagcc  300
gtcgagcttt gctcggagta aaggcggcga cggcgttagt tgagaaggag gagaagagag  360
aggcggtgac ggagaagaag aagaaatcga gggttttagt tgccggaggt ggaatcggag  420
gattggtgtt tgctttagcg gctaagaaga aaggattcga tgtgttagtg tttgagaaag  480
```

-continued

```
atttgagtgc tataagagga gaaggaaaat acagaggccc gattcaaata cagagcaacg  540
ctttagctgc tttggaagct attgatattg aagttgctga acaagttatg gaagctgggt  600
gtatcactgg tgatcggatt aacggtctcg ttgatggtat ctctggtact tggtatgtaa  660
agtttgatac tttcactcct gcggcgtcac ggggacttcc tgtgactaga gtaattagta  720
gaatgactct gcagcagatt ctagcacgtg cggttggaga agatgtgatt agaaacgaga  780
gtaatgttgt tgattttgaa gattctggag ataaggttac tgtggtactc gagaatggtc  840
aacgctatga aggtgatctg cttgtgggtg cagatggcat ttggtctaag gtgagaaata  900
atttgtttgg ccgtagtgaa gctacttatt caggctacac ttgttacacg ggattgcag   960
attttatacc agcggatatc gagtctgttg gctaccgggt tttcttggga cacaaacagt  1020
actttgtttc ttcggatgtt ggtggtggaa aaatgcaatg gtatgcattt cacgaggaac  1080
cagctggtgg ggctgatgct ccaaatggta tgaagaaaag gttgtttgaa atatttgacg  1140
gttggtgcga caatgtactc gacttgttgc atgcgactga ggaggaagcc attctgagaa  1200
gagatattta tgatagaagt cctggtttta cttggggtaa agggcgtgtt acgctgctcg  1260
gggattctat ccatgcgatg cagccaaata tgggtcaagg tggatgcatg gccattgagg  1320
atagttttca actagcattg gagcttgatg aagcatggaa acagagtgtt gaaacgacta  1380
cacctgttga tgttgtttcc tctttgaaaa gatatgagga atctagaaga ctgagagtcg  1440
ctattatcca tgcaatggcg aggatggctg caattatggc ttccacttac aaagcatact  1500
taggtgttgg gcttggtcct ctgtctttct tgacaaagtt tagagtacca catccaggaa  1560
gagttggtgg tagattcttc gttgacattg ctatgccatc gatgcttgac tgggtccttg  1620
gaggtaacag tgaaaaactc caaggaaggc cacctagttg cagactcact gacaaagccg  1680
atgaccggct tcgagagtgg tttgaagatg acgatgctct tgaacgtact ataaagggag  1740
aatggtatct aattccacac ggcgacgatt gttgcgtttc ggaaacatta tgtctaacca  1800
aagatgaaga tcaaccttgc atcgtcggaa gcgaaccaga tcaagatttt cctggaatgc  1860
gcattgtgat cccttcgtct caggtttcga agatgcatgc tcgtgtgatt tacaaagacg  1920
gagctttctt cttgatggat cttcgaagcg aacacggaac ctatgtgacc gataacgaag  1980
gaagaagata tagagcaaca ccgaatttc ccgcgcggtt tagatcgtcc gacatcatcg  2040
agtttggttc agataagaag gcggcgttta gggtgaaagt aatcaggaaa actccgaaat  2100
cgacgaggaa gaatgagagt aacaacgata aattacttca gacagcttga aataagtaaa  2160
ccgatggtga aattaagtaa ttttaatcgg tttggcagat aatttgagta gtaattttct  2220
caaaagaaaa aaaatctgct ttcagctatt ccttgcatga caatgtatat ataggtctga  2280
aacaaaatat aaattataca agacattaat cttcatttct tcaacttcca ggcaacaata  2340
atctaatttt gattactaaa aggtaattat attatcaaat tgttt                  2385
```

```
SEQ ID NO: 3            moltype = DNA  length = 1776
FEATURE                 Location/Qualifiers
source                  1..1776
                        mol_type = other DNA
                        organism = Arabidopsis thaliana
SEQUENCE: 3
gagatatttg ggtggagaaa acaaccgcct aggacaaaaa aaaattgtgg gtagaggagg  60
aggaggaggc tttgttcaca caccacacga cggaacattc tcttccgagt cttatccaaa  120
gcaaaatcat attttgctta aatatcttct tctccggctc tgtctctgtc tctcttcttc  180
ccgcggagct ttcagttttt gtttggtatt gcttggtgtg gggaagatta gatagtgtga  240
agaatggcag tagctacaca ttgtttcact tcaccttgtc atgaccgtat tcgatttttc  300
tcaagtgatg atggtattgg taggcttggc attacaagaa agaggatcaa tggcactttc  360
ttgctcaaga ttttacctcc aatccaaagt gctgatctca gaacaactgg tgggagatcc  420
tcacgtcctt tatctgcatt caggtcagga ttctctaagg ggatatttga cattgtgcca  480
ttaccatcaa agaatgagct gaaagagctg accgctccgc tgttgctaaa actcgtgggt  540
gttttagctt gcgcgttcct tattgttcca tctgcagatg cagttgatgc acttaaaact  600
tgtgcatgct tattgaaggg atgcaggata gaactcgcaa agtgcattgc caaccctgcc  660
tgtgcagcca atgtcgcgtg ccttcagacc tgcaataacc gtccagatga aaccgagtgc  720
cagattaaat gtggggatct gtttgagaac agtgttgttg atgagttcaa cgagtgtgct  780
gtgtcgagaa aaaagtgtgt tcctagaaaa tctgatctcg gagaatttcc tgccccagac  840
ccttctgttc ttgtacagaa cttcaacatc tcggacttta acgggaagtg gtacattaca  900
agtggcttga atccaacctt tgatgccttc gactgccagc tgcatgagtt ccacacagaa  960
ggtgacaaca agcttgttgg aaacatctct tggagaataa agaccctaga cagtggattc  1020
tttactaggt cagccgtaca aaaattcgtg caagatccta accaacctgg tgttctctac  1080
aatcatgaca acgagtacct tcactatcaa gatgactggt atatcctgtc atcaaagata  1140
gagaataaac ctgaagacta tatatttgta tactaccgtg ggcgaaacga tgcttgggat  1200
ggatatggtg gtgcagttgt atacacgaga agttctgtat tacccaatag cattatacca  1260
gaactcgaaa aagcagcaaa aagcataggc agagacttca gcacattcat tagaacggat  1320
aacacatgtg gtcctgaacc tgcgctcgtg gagagaattg agaagacagt ggaagaaggt  1380
gaaaggataa tcgtaaaaga ggttgaagag atagaagaag aggtagagaa ggaagtggag  1440
aaggtcggta ggactgagat gaccttgttc cagagattgg ctgaaggatt taatgaactg  1500
aagcaagacg aggagaattt cgtgagagag ttaagtaaag aagagatgga gtttttggat  1560
gagatcaaaa tggaagcaag tgaggttgaa aaattgtttg ggaaagcttt gccaatcagg  1620
aaggtcaggt agaaacaaga accaccattg ttgtacaaac tatattatac atactgtgtt  1680
cggttcatat aaagtaatat ttttgtacac agtcatcatc attccataac aattggatac  1740
agaaaacaca aggattaaac atcctttgag cgaaac                            1776
```

```
SEQ ID NO: 4            moltype = AA  length = 265
FEATURE                 Location/Qualifiers
source                  1..265
                        mol_type = protein
                        organism = Arabidopsis thaliana
SEQUENCE: 4
MAQTMLLTSG VTAGHFLRNK SPLAQPKVHH LFLSGNSPVA LPSRRQSFVP LALFKPKTKA  60
APKKVEKPKS KVEDGIFGTS GGIGFTKANE LFVGRVAMIG FAASLLGEAL TGKGILAQLN  120
LETGIPIYEA EPLLLFFILF TLLGAIGALG DRGKFVDDPP TGLEKAVIPP GKNVRSALGL  180
```

```
KEQGPLFGFT KANELFVGRL AQLGIAFSLI GEIITGKGAL AQLNIETGIP IQDIEPLVLL  240
NVAFFFFAAI NPGNGKFITD DGEES                                        265

SEQ ID NO: 5            moltype = AA  length = 667
FEATURE                 Location/Qualifiers
source                  1..667
                        mol_type = protein
                        organism = Arabidopsis thaliana
SEQUENCE: 5
MGSTPFCYSI NPSPSKLDFT RTHVFSPVSK QFYLDLSSFS GKPGGVSGFR SRRALLGVKA  60
ATALVEKEEK REAVTEKKKK SRVLVAGGGI GGLVFALAAK KKGFDVLVFE KDLSAIRGEG  120
KYRGPIQIQS NALAALEAID IEVAEQVMEA GCITGDRING LVDGISGTWY VKFDTFTPAA  180
SRGLPVTRVI SRMTLQQILA RAVGEDVIRN ESNVVDFEDS GDKVTVVLEN GQRYEGDLLV  240
GADGIWSKVR NNLFGRSEAT YSGYTCYTGI ADFIPADIES VGYRVFLGHK QYFVSSDVGG  300
GKMQWYAFHE EPAGGADAPN GMKKRLFEIF DGWCDNVLDL LHATEEEAIL RRDIYDRSPG  360
FTWGKGRVTL LGDSIHAMQP NMGQGGCMAI EDSFQLALEL DEAWKQSVET TTPVDVVSSL  420
KRYEESRRLR VAIIHAMARM AAIMASTYKA YLGVGLGPLS FLTKFRVPHP GRVGGRFFVD  480
IAMPSMLDWV LGGNSEKLQG RPPSCRLTDK ADDRLREWFE DDDALERTIK GEWYLIPHGD  540
DCCVSETLCL TKDEDQPCIV GSEPDQDFPG MRIVIPSSQV SKMHARVIYK DGAFFLMDLR  600
SEHGTYVTDN EGRRYRATPN FPARFRSSDI IEFGSDKKAA FRVKVIRKTP KSTRKNESNN  660
DKLLQTA                                                            667

SEQ ID NO: 6            moltype = AA  length = 462
FEATURE                 Location/Qualifiers
source                  1..462
                        mol_type = protein
                        organism = Arabidopsis thaliana
SEQUENCE: 6
MAVATHCFTS PCHDRIRFFS SDDGIGRLGI TRKRINGTFL LKILPPIQSA DLRTTGGRSS  60
RPLSAFRSGF SKGIFDIVPL PSKNELKELT APLLLKLVGV LACAFLIVPS ADAVDALKTC  120
ACLLKGCRIE LAKCIANPAC AANVACLQTC NNRPDETECQ IKCGDLFENS VVDEFNECAV  180
SRKKCVPRKS DLGEFPAPDP SVLVQNFNIS DFNGKWYITS GLNPTFDAFD CQLHEFHTEG  240
DNKLVGNISW RIKTLDSGFF TRSAVQKFVQ DPNQPGVLYN HDNEYLHYQD DWYILSSKIE  300
NKPEDYIFVY YRGRNDAWDG YGGAVVYTRS SVLPNSIIPE LEKAAKSIGR DFSTFIRTDN  360
TCGPEPALVE RIEKTVEEGE RIIVKEVEEI EEEVEKEVEK VGRTEMTLFQ RLAEGFNELK  420
QDEENFVREL SKEEMEFLDE IKMEASEVEK LFGKALPIRK VR                     462

SEQ ID NO: 7            moltype = AA  length = 36
FEATURE                 Location/Qualifiers
source                  1..36
                        mol_type = protein
                        organism = Arabidopsis thaliana
SEQUENCE: 7
QLNLETGIPI YEAEPLLLFF ILFTLLGAIG ALGDRG                            36

SEQ ID NO: 8            moltype = AA  length = 49
FEATURE                 Location/Qualifiers
source                  1..49
                        mol_type = protein
                        organism = Arabidopsis thaliana
SEQUENCE: 8
IGGLVFALAA KRKGFEVLVF EKDLSAVRGE GQYRGPIQIQ SNALAALEA              49

SEQ ID NO: 9            moltype = AA  length = 47
FEATURE                 Location/Qualifiers
source                  1..47
                        mol_type = protein
                        organism = Arabidopsis thaliana
SEQUENCE: 9
CAANIACLQT CNNRPDETEC QIKCGDLFEN NVVDEFNECA VSRKKCV                47

SEQ ID NO: 10           moltype = AA  length = 272
FEATURE                 Location/Qualifiers
source                  1..272
                        mol_type = protein
                        organism = Cucumis melo
SEQUENCE: 10
MAAQTMLLTS GVCVGHGVCL KRELSLRPNN NQFTRLFFNP LPNHSVSLPA RGFTPLAVFK  60
SRTKAPPKKV EKPKQKVEDG IFGTSGGIGF TKQNELFVGR VAMIGFAASL LGEAITGKGI  120
LAQLNLETGI PIYEAEPLLL FFILFTLLGA IGALGDRGKF IDDPEPATGL ERAVIPPGKS  180
FRSALGLKEG GPLFGFTKAN ELFVGRLAQL GFAFSLIGEI ITGKGALAQL NIETGVPINE  240
IEPLVLLNVV FFFIAAVNPG TGKFVTDEED DE                                272

SEQ ID NO: 11           moltype = AA  length = 272
FEATURE                 Location/Qualifiers
source                  1..272
                        mol_type = protein
                        organism = Cucumis sativus
SEQUENCE: 11
```

```
MAAQTMLLTS GVCVGHGVCL KRELSLRPNY TQFTRLFFNP LPSHSVSLPP RGFTTLAVFK  60
SRTKAPPKKV EKPKQKVEDG IFGTSGGIGF TKQNELFVGR VAMIGFAASI LGEAITGKGI  120
LAQLNLETGI PIYEAEPLLL FFILFTLLGA IGALGDRGKF IDDPEPATGL ERAVIPPGKS  180
FRSALGLKEG GPLFGFTKAN ELFVGRLAQL GFAFSLIGEI ITGKGALAQL NIETGVPINE  240
IEPLVLLNVV FFFIAAVNPG TGKFVTDEED DE                                272

SEQ ID NO: 12          moltype = AA  length = 267
FEATURE                Location/Qualifiers
source                 1..267
                       mol_type = protein
                       organism = Eutrema salsugineum
SEQUENCE: 12
MAQTMMLTSG VSANQFLRNK NPLAQPKVHH LFLSGNSPVV IPSRRQSLVP LALFKPKTKA  60
APKKVEKVKP KVEDGIFGTS GGIGFTKANE LFVGRVAMIG FAASLLGEAV TGKGILAQLN  120
LETGIPIYEA EPLLLFFILF TLLGAIGALG DRGKFVDDPP TPTGLEKAVI APGKNVRSAL  180
GLKEQGPLFG FTKANELFVG RLAQLGIAFS LIGEIITGKG ALAQLNIETG IPIQDIEPLV  240
LLNVAFFFFA AINPGNGKFI TDDGEDM                                      267

SEQ ID NO: 13          moltype = AA  length = 265
FEATURE                Location/Qualifiers
source                 1..265
                       mol_type = protein
                       organism = Arabidopsis thaliana
SEQUENCE: 13
MAQTMLLTSG VTAGHFLRNK SPLAQPKVHH LFLSGNSPVA LPSRRQSFVP LALFKPKTKA  60
APKKVEKPKS KVEDGIFGTS GGIGFTKANE LFVGRVAMIG FAASLLGEAL TGKGILAQLN  120
LETGIPIYEA EPLLLFFILF TLLGAIGALG DRGKFVDDPP TGLEKAVIPP GKNVRSALGL  180
KEQGPLFGFT KANELFVGRL AQLGIAFSLI GEIITGKGAL AQLNIETGIP IQDIEPLVLL  240
NVAFFFFAAI NPGNGKFITD DGEES                                        265

SEQ ID NO: 14          moltype = AA  length = 265
FEATURE                Location/Qualifiers
source                 1..265
                       mol_type = protein
                       organism = Arabidopsis lyrata
SEQUENCE: 14
MAQTMLLTSG VSAGQFLRNK SPLAQPKVHH LFLSGNSPVV LPSRRQSFVP LALFKPKTKA  60
APKKVEKPKK KVEDGIFGTS GGIGFTKANE LFVGRVAMIG FAASLLGEAL TGKGILAQLN  120
LETGIPIYEA EPLLLFFILF TLLGAIGALG DRGQFVDDPP TGLEKAVIPP GKNVRSALGL  180
KEQGPLFGFT KANELFVGRL AQLGIAFSLI GEIITGKGAL AQLNIETGIP IQDIEPLVLL  240
NVAFFFFAAI NPGNGKFITD DGEES                                        265

SEQ ID NO: 15          moltype = AA  length = 265
FEATURE                Location/Qualifiers
source                 1..265
                       mol_type = protein
                       organism = Camelina sativa
SEQUENCE: 15
MAQTMLLTSG VSAGQFLRNK NPLAQPKVHH LFLSGTSPVA LPSRRQSFVP LALFKPKTKA  60
APKKVVKPKD KVEDGIFGTS GGIGFTKANE LFVGRVAMIG FAASLLGEAL TGKGILAQLN  120
LETGIPIYEA EPLLLFFILF TLLGAIGALG DRGKFVDDPP TGLEKAVIPP GKGVRSALGL  180
KEQGPLFGFT KANELFVGRL AQLGIAFSLI GEIITGKGAL AQLNIETGIP IQDIEPLVLL  240
NVAFFFFAAI NPGNGKFITD DGEES                                        265

SEQ ID NO: 16          moltype = AA  length = 265
FEATURE                Location/Qualifiers
source                 1..265
                       mol_type = protein
                       organism = Capsella rubella
SEQUENCE: 16
MAQTMLLTSG VSAGQFLRNK NPLAQPKVHQ LFLSGTSPVA LPSRRQSFVP LALFKPKTKA  60
APKKVEKVKP KVEDGIFGTS GGIGFTKANE LFVGRVAMIG FAASLLGEGI TGKGILAQLN  120
LETGIPIYEA EPLLLFFILF TLLGAIGALG DRGKFVDDPP TGLEKAVIPP GKGVRSALGL  180
KEQGPLFGFT KANELFVGRL AQLGIAFSLI GEIITGKGAL AQLNIETGIP IQDIEPLVLL  240
NVAFFFFAAI NPGNGKFITD DGEES                                        265

SEQ ID NO: 17          moltype = AA  length = 265
FEATURE                Location/Qualifiers
source                 1..265
                       mol_type = protein
                       organism = Noccaea caerulescens
SEQUENCE: 17
MAQTMLLTSG VSANQFLRNK NPLAQPKIQH LFLSGNSPVA LPSRRPSFVP LALFKPKTKA  60
APKKVEKAKP KVEDGIFGTS GGIGFTKQNE LFVGRVAMIG FAASLLGEAL TGKGILAQLN  120
LETGIPIYEA EPLLLFFILF TLLGAIGALG DRGKFVDDPP TGLEKAVIPP GKSVRSALGL  180
KEQGPLFGFT KSNELFVGRL AQLGIAFSLI GEIITGKGAL AQLNIETGIP IQDIEPLVLL  240
NVAFFFFAAI NPGNGKFITD DGEES                                        265

SEQ ID NO: 18          moltype = AA  length = 265
```

```
FEATURE                Location/Qualifiers
source                 1..265
                       mol_type = protein
                       organism = Brassica napus
SEQUENCE: 18
MAQTMLLTSG ISANHFLRNK NPLAQPKVHH LFLSGNSPVT LPSRIPSLVP LAIFKPKTKA  60
APKKVEKVKP KVEDGIFGTS GGIGFTKQNE LFVGRVAMIG FAASLLGEAL TGKGILAQLN  120
LETGIPIYEA EPLLLFFILF TLLGAIGALG DRGKFVDDPP TGLEKAVIPP GKGVRSALGL  180
KEQGPLFGFT KANELFVGRL AQLGIAFSLI GEIITGKGAL AQLNIETGIP IQDIEPLVLL  240
NVAFFFAAAI NPGNGKFITD DGEES                                      265

SEQ ID NO: 19          moltype = AA  length = 265
FEATURE                Location/Qualifiers
source                 1..265
                       mol_type = protein
                       organism = Raphanus sativus
SEQUENCE: 19
MAQTMLLTSG ISANHFLRNK NPLAQPKVHH LFLSGNSPVT LPSRRPSLVP LAIFKPKTKA  60
APKKVEKVKP KVEDGIFGTS GGIGFTKQNE LFVGRVAMIG FAASLLGEAL TGKGILAQLN  120
LETGIPIYEA EPLLLFFILF TLLGAIGALG DRGKFVDDPP TGLEKAVIPP GKGVRSALGL  180
KEQGPLFGFT KANELFVGRL AQLGIAFSLI GEIITGKGAL AQLNIETGIP IQDIEPLVLL  240
NVAFFFFAAI NPGNGKFITD DGEES                                      265

SEQ ID NO: 20          moltype = AA  length = 265
FEATURE                Location/Qualifiers
source                 1..265
                       mol_type = protein
                       organism = Brassica rapa
SEQUENCE: 20
MAQTMLLTSG ISANHFLRNK NPLAQPKVHH LFLSGNSPVT LPSRRPSLVP LAIFKPKTKA  60
APKKVEKVKP KVEDGIFGTS GGIGFTKQNE LFVGRVAMIG FAASLLGEAL TGKGILAQLN  120
LETGIPIYEA EPLLLFFILF TLLGAIGALG DRGKFVDDPP TGLEKAVIPP GKGVRSALGL  180
KEQGPLFGFT KANELFVGRL AQLGIAFSLI GEIITGKGAL AQLNIETGIP IQDIEPLVLL  240
NVAFFFAAAI NPGNGKFITD DGEES                                      265

SEQ ID NO: 21          moltype = AA  length = 265
FEATURE                Location/Qualifiers
source                 1..265
                       mol_type = protein
                       organism = Raphanus sativus
SEQUENCE: 21
MAQTMLLTSG VSANTFLRNK NPLAQPKVHH LFLSGNSHVI LPSRRPSLVP LAIFKPKTKA  60
APKKVEKVKP KVEDGIFGTS GGIGFTKQNE LFVGRVAMIG FAASLLGEAL TGKGILAQLN  120
LETGIPIYEA EPLLLFFILF TLLGAIGALG DRGKFVDDPP TGLEKAVIPP GKGVRSALGL  180
KEQGPLFGFT KANELFVGRL AQLGIAFSLI GEIITGKGAL AQLNIETGIP IQDIEPLVLL  240
NVAFFFFAAI NPGNGKFITD DGEES                                      265

SEQ ID NO: 22          moltype = AA  length = 265
FEATURE                Location/Qualifiers
source                 1..265
                       mol_type = protein
                       organism = Brassica napus
SEQUENCE: 22
MAQTMLLTSG VSANQFLRNK NPLAQPKVHH FFLSGNSHVV LPSRRPSLVP LAIFKPKTKA  60
APKKVEKVKP KVEDGIFGTS GGIGFTKQNE LFVGRVAMIG FAASLLGEAL TGKGILAQLN  120
LETGIPIYEA EPLLLFFILF TLLGAIGALG DRGKFVDDPP TGLEKAVIPP GKGVRSALGL  180
KEQGPLFGFT KANELFVGRL AQLGIAFSLI GEIITGKGAL AQLNIETGIP IQDIEPLVLL  240
NVAFFFFAAI NPGNGKFITD DGEES                                      265

SEQ ID NO: 23          moltype = AA  length = 265
FEATURE                Location/Qualifiers
source                 1..265
                       mol_type = protein
                       organism = Brassica rapa
SEQUENCE: 23
MAQTMLLTSG VSANQFLRNK NPLAQPKVHH FFLSGNSHVV LPSRRPSLVP LAIFKPKTKA  60
APKKVEKVKP KVEDGIFGTS GGIGFTKQNE LFVGRVAMIG FAASLLGEAL TGKGILAQLN  120
LETGIPIYEA EPLLLFFILF TLLGAIGALG DRGKFVDDPP TGLEKAVIPP GKGVRSALGL  180
KEQGPLFGFT KANELFVGRL AQLGIAFSLI GEIITGKGAL AQLNIETGIP IQDIEPLVLL  240
NVAFFFFAAI NPGNGKFITD DGEER                                      265

SEQ ID NO: 24          moltype = AA  length = 274
FEATURE                Location/Qualifiers
source                 1..274
                       mol_type = protein
                       organism = Phoenix dactylifera
SEQUENCE: 24
MVHAVFTSGL GAHLPDSKRE PLLQSQLRRL RPTPFSHLLL SQPSHKQLPS PSYSSYTPVL  60
ALFKSKTKAP PKKVEKAKPK VEDGIFGTSG GIGFTKQNEL FVGRVAMIGF AASLLGEAIT  120
```

```
GKGILAQLNL ETGIPIYEAE PLLLFFILFT LLGAIGALGD RGRFVDDPPT GLDKAVIPPG  180
KGIRSALGLK EGGPLFGFTK SNELFVGRLA QLGIAFSIIG EIVTGKGALA QLNIETGVPI  240
NEIEPLVLFN VIFFFIAALN PGNGKFVTDV DEEE                              274

SEQ ID NO: 25          moltype = AA  length = 270
FEATURE                Location/Qualifiers
source                 1..270
                       mol_type = protein
                       organism = Anthurium amnicola
SEQUENCE: 25
MAQSMLMSSL GSRLVETKGE PLLQFQIRRL RPTPATHLLL PPPTRRHPLP PSYAPTLAAF  60
KSKTKAAPKK VEKGNFKVED GIFGTSGGIG FTKQNELFVG RVAMIGFAAS LLGEAITGKG  120
ILAQLNLETG IPIYEAEPLL LFFILFTLLG AIGALGDRGR FVDDPPTGLD KAVVPPGKGF  180
RSSLGLKEGG PLFGFTKSNE LFVGRLAQLG IAFSIIGEII TGKGALAQLN IETGVPISDI  240
EPLVLLNVVF FFLAALNPGT GQFVTDDGED                                   270

SEQ ID NO: 26          moltype = AA  length = 269
FEATURE                Location/Qualifiers
source                 1..269
                       mol_type = protein
                       organism = Trifolium subterraneum
SEQUENCE: 26
MAQTMLLMSS VSSTYSVELK KDPLLQLQCQ RLRSRISDVS FNPLSSNSKS LSSRTFTTLA  60
LFKSKTKAPA KVVKPKPKVE DGIFGTSGGF GFTKQNELFV GRVAMIGFAA SILGEALTGK  120
GILAQLNLET GIPIYEAEPL LLFFIIFTLL GAIGALGDRG KFVDDEPTTG GVIPPGKGFR  180
AALGLREGGP LFGFTKSNEL FVGRLAQLGF VFSLIGEIIT GKGALAQLNV ETGVPITEIE  240
PLVLFNVIFF FIAALNPGTG TFVTDEEED                                    269

SEQ ID NO: 27          moltype = AA  length = 270
FEATURE                Location/Qualifiers
source                 1..270
                       mol_type = protein
                       organism = Pisum sativum
SEQUENCE: 27
MAQTMLLMSS VSSTYSVPLN KDPLLQLQCQ RLKPRFSDIS FSPLSSNSKS FSSRTFKTLA  60
LFKSKTKAPA KVVPKQKPKV EDGVFGTSGG FGFTKQNELF VGRVAMIGFA ASILGEGITG  120
KGILSQLNLE TGIPIYEAEP LLLFFIIFTL LGAIGALGDR GKFVDDEPTT GGVIPPGKGF  180
RQALGLSEGG PLFGFTKSNE LFVGRLAQLG FAFSLIGEII TGKGALAQLN IETGVPINEI  240
EPLVLFNVAF FFIAALNPGT GKFVTDEEED                                   270

SEQ ID NO: 28          moltype = AA  length = 271
FEATURE                Location/Qualifiers
source                 1..271
                       mol_type = protein
                       organism = Beta vulgaris
SEQUENCE: 28
MAQAMLLMPS VSTTNTIDLK RNALLKIQIQ KIKPKSSSSH LFFSPLSSSS SSSSTFKTLA  60
LFKPKTKAPV KKVEKPKLKV EDGLFGTSGG IGFTKENELF VGRVAMIGFA ASLLGEGLTG  120
KGILAQLNLE TGIPIYEAEP LLLFFILFTL LGAIGALGDR GRFVDDPPTG LEKAVIPPGK  180
NVRSALGLRE GGPLFGFTKS NELFVGRLAQ LGFAFSLIGE IITGKGALAQ LNIETGVPVN  240
EIEPLVLLNV LFFFIAAINP GTGKFITDEE E                                 271

SEQ ID NO: 29          moltype = AA  length = 274
FEATURE                Location/Qualifiers
source                 1..274
                       mol_type = protein
                       organism = Cephalotus follicularis
SEQUENCE: 29
MAQTMLLMCG ISTSHVVDLR RDPLFHVQIQ KLRPKSFSHL FFNPLSNNGF SLAQKFNTLA  60
LFKSKTKAAP KKVATTAKPK VEDGLFGTSG GIGFTKQNEL FVGRVAMIGF AASLLGEAVT  120
GKGILSQLNL ETGIPIYEAE PLLLFFILFT LLGAIGALGD RGRFVDDEPT GLERAVIPPG  180
KGIRGALGLR EGGPLFGFTK SNELFVGRLA QLGIAFSLIG EIITGKGALA QLNIETGIPI  240
NEIEPLVLFN VIFFFFAALN PGTGKFVTDE EAED                              274

SEQ ID NO: 30          moltype = AA  length = 665
FEATURE                Location/Qualifiers
source                 1..665
                       mol_type = protein
                       organism = Tarenaya hassleriana
SEQUENCE: 30
MGSTLFCSPV NPSLSKLDFS RTHLLSPADK HFFLDLPSFM GKVRGKSSVM SRRRVVGVKA  60
TAAVEEERRE TAAEKEKLRV LVAGGGIGGL VFALAAKRKG FDVAVFEKDL SAIRGEGQYR  120
GPIQIQSNAL AALEAIDMGV AEEVMEAGCI TGDRINGLVD GVSGSWYVKF DTFTPAAERG  180
LPVTRVISRM TLQQILARAV GEDVIQNESN VVSFSESEDK VTVVLENGEC YQGDLLVGAD  240
GIWSKVRSQL FGHEEATYSG YTCYTGIADF VPADIESVGY RVFLGHKQYF VSSDVGGGKM  300
QWYAFHEEPA GGRDAPDGRK KRLLEIFQGW CDNVIDLLHA TEEDAILRRD IYDRTPSFTW  360
GKGRVTLLGD SIHAMQPNMG QGGCMAIEDS YQLAWELEHA WRRSVETDKP IDIVSSLRSY  420
EEARKLRVAI IHGMARMAAI MASTYKGYLG VGLGPLSFLT MLRIPHPGTV GGRFFIDVAM  480
PLMLNWVLGG NSSKLEGRLP CCRLSDKADD QLQRWFQDND ALERTVIGDW YLIPYGNDSI  540
```

```
VSETVRLDKD EDQPCIIGSE PDEDFPGMRI EIPSSQVSKV HARIIYKDGA FFVMDLRSEY  600
GTYITDNEGR RYRVTPNFPA RFRPSDIIEL GSDKKAAFRV KVIRKTPKMT RRDDRESSSK  660
LLQAA                                                              665

SEQ ID NO: 31          moltype = AA  length = 663
FEATURE                Location/Qualifiers
source                 1..663
                       mol_type = protein
                       organism = Arabis alpina
SEQUENCE: 31
MGSTPFCYTI NPSPSKLDFT KTHLAKQFYL DLSSFTGKSG AGLSGIKNRR GVVGVKASAT  60
ALVEEEKRET VTEKKKKSRV LVAGGGIGGL VFALAAKKKG FDVLVFEKDL SAIRGEGQYR  120
GPIQIQSNAL AALEAIDIAV AEEVMEAGCI TGDRINGLVD GVSGTWYVKF DTFTPAASRG  180
LPVTRVISRM TLQQILARAV GEEVIRNESN VVDFEDSGDK VTVVLENGQR YEGDLLVGAD  240
GIWSKVRNNL FGRSEATYSG YTCYTGIADF IPADIESVGY RVFLGHKQYF VSSDVGGGKM  300
QWYAFYEEPA GGVDAPNGMK KRLFDIFEGW CDNVLDLLHA TEEEAILRRD IYDRSPSFTW  360
GKGRVTLLGD SIHAMQPNMG QGGCMAIEDS YQLASELEDA WKQSVDTNRP VDVVSSLKRY  420
EESRRLRVAI IHGMARMAAI MASTYKAYLG VGLGPLSFLT KFRVPHPGRV GGRFFIDIAM  480
PLMLNWVLGG NSEKLEGRAP SCRLTDRADD RLREWFDDNE ALERTISGEW YLIPQGDDCC  540
VSETLCLTKD EDQPCIIGSE PDKDFPGMHI VIPSSQVSKM HARIIYKDGA FFVMDLRSEH  600
GTYVVDNEGG RYRATPNFPA RFRPSDILEF GSDKKAAFKV KVIRKTPKST SKNESNGKLL  660
QAA                                                                663

SEQ ID NO: 32          moltype = AA  length = 665
FEATURE                Location/Qualifiers
source                 1..665
                       mol_type = protein
                       organism = Camelina sativa
SEQUENCE: 32
MGSTPFCYSI NPSPSKLDFT RTHVFSPVSK QFYLDLSSFT GKSAGGGGGF RSRRALVGVK  60
AATALVEEKR ESGTEKKKKS RVLVAGGGIG GLVFALAAKK KGFDVLVFEK DLSAIRGEGQ  120
YRGPIQIQSN ALAALEAIDT DVAEQVMEAG CITGDRINGL VDGISGTWYV KFDTFTPAAS  180
RGLPVTRVIS RMTLQQILAR AVGEEVIRNE SNVVDFEDSG DKVTVVLENG ERYEGDLLVG  240
ADGIWSKVRN NLFGRSEASY SGYTCYTGIA DFIPADIESV GYRVFLGNKQ YFVSSDVGGG  300
KMQWYAFHEE PAGGADAPNG MKKRLFEIFD GWCDNVLDLL HATEEDAILR RDIYDRNPSF  360
TWGKGRVTLL GDSIHAMQPN MGQGGCMAIE DSFQLALELD EAWKQSVETK TPVDVVSSLK  420
RYEESRRLRV ALIHGMARMA AIMASTYKAY LGVGLGPLSF LTKFRVPHPG RVGGRFFIDI  480
AMPMMLNWVL GGNSEKLEGR SPSCRLTDKA DDRLREWFED DDALERTIKG EWYLIPHGDD  540
CCISETLCLT KDEDQPCIIG SEPDQDLPGK HIVIPSSQVS KMHARVIYKD GAFFLMDLRS  600
EHGTYVTDNE GRRYRATPNS PARFRTSDII EFGSDKKAAF RVKVIRTTPK STRKNESNDK  660
LLQAA                                                              665

SEQ ID NO: 33          moltype = AA  length = 668
FEATURE                Location/Qualifiers
source                 1..668
                       mol_type = protein
                       organism = Camelina sativa
SEQUENCE: 33
MGSTPFCYSI NPTPSKLDFT RTHVFSPVSK QFYLDLSSFT GKSGVGAGGF RSLRALVGVK  60
AATALVEEEQ KRESVTDKTK KKSRVLVAGG GIGGLVFALA AKKKGFDVLV FEKDLSAIRG  120
EGQYRGPIQI QSNALAALEA IDTDVAEQVM VAGCITGDRI NGLVDGISGT WYVKFDTFTP  180
AASRGLPVTR VISRMTLQQI LARAVGEELI RNESNVVDFE DSGDKVTVVL ENGERYEGDL  240
LVGADGIWSK VRNNLFGRSE ASYSGYTCYT GIADFIPADI ESVGYRVFLG NKQYFVSSDV  300
GGGKMQWYAF HEEPAGGADA PNGMKKRLFE IFDGWCDNVL DLLHATEEDA ILRRDIYDRN  360
PSFTWGKGRV TLLGDSIHAM QPNMGQGGCM AIEDSFQLAL ELDEAWKQSV KTKTPVDVVS  420
SLKRYEESRR LRVALIHGMA RMAAIMASTY KAYLGVGLGP LSFLTKFRVP HPGRVGGRFF  480
IDIAMPMMLN WVLGGNSEKL EGRSPSCRLT DKADDRLREW FEDDDALERT IKGEWYLIPH  540
GDECCISETL CLTKDEDQPC IIGSKPDQDL PGKHIVIPSS QVSKMHARVI YKDGAFFLMD  600
LRSEHGTYVT DNEGRRYRAT PNSPARFRTS DIIEFGSDKK AAFRVKVIRT TPKSTRKNES  660
NDKLLQAA                                                           668

SEQ ID NO: 34          moltype = AA  length = 669
FEATURE                Location/Qualifiers
source                 1..669
                       mol_type = protein
                       organism = Capsella rubella
SEQUENCE: 34
MGSTPFCYSI NPSPSKLDFT RTHVFSPVAK QFYLDLSSFT GKSGVGGGLS GFRSRRTLVG  60
VKAATALVEE EQKPGEVTER KKKSRVLVAG GGIGGLVFAL AAKKKGFDVL VFEKDLSAIR  120
GEGQYRGPIQ IQSNALAALE AIDNDVAEQV MEAGCITGDR INGLVDGVSG TWYVKFDTFT  180
PAASRGLPVT RVISRMTLQQ ILARAVGEEV IRNESNVVDF EDSGDKVTVV LENGQRYEGD  240
LLVGADGIWS KVRNNLFGRS EAEYSGYTCY TGIADFIPAD IESVGYRVFL GHKQYFVSSD  300
VGGGKMQWYA FHEEPAGGTD APNGMKKRLF EIFDGWCDNV LDLLHATEED AILRRDIYDR  360
SPSFTWGKGR VTLLGDSIHA MQPNMGQGGC MAIEDSFQLA LELEEAWKQS VETNTSVDVV  420
SSLKKYEESR RLRVAIIHGM ARMAAIMAST YKAYLGVGLG PLSFLTKFRV PHPGRVGGRF  480
FIDIAMPLML NWVLGGNSEK LEGRPPSCRL TDKADDRLRE WFENDDALER TINGEWYLIP  540
HGDECCVSET LCLTKDEDQP CIVGSEPDQD LPGKHIVIPS SQVSKMHARV IYKDGAFFLM  600
DLGSEHGTFV TDNEGRRYRA TPNFPGRFRS SDIIEFGSDK KAAFRVKVIR KTPKATRKNE  660
SNDKLLQAA                                                          669
```

```
SEQ ID NO: 35          moltype = AA  length = 667
FEATURE                Location/Qualifiers
source                 1..667
                       mol_type = protein
                       organism = Arabidopsis thaliana
SEQUENCE: 35
MGSTPFCYSI NPSPSKLDFT RTHVFSPVSK QFYLDLSSFS GKPGGVSGFR SRRALLGVKA  60
ATALVEKEEK REAVTEKKKK SRVLVAGGGI GGLVFALAAK KKGFDVLVFE KDLSAIRGEG  120
KYRGPIQIQS NALAALEAID IEVAEQVMEA GCITGDRING LVDGISGTWY VKFDTFTPAA  180
SRGLPVTRVI SRMTLQQILA RAVGEDVIRN ESNVVDFEDS GDKVTVVLEN GQRYEGDLLV  240
GADGIWSKVR NNLFGRSEAT YSGYTCYTGI ADFIPADIES VGYRVFLGHK QYFVSSDVGG  300
GKMQWYAFHE EPAGGADAPN GMKKRLFEIF DGWCDNVLDL LHATEEEAIL RRDIYDRSPG  360
FTWGKGRVTL LGDSIHAMQP NMGQGGCMAI EDSFQLALEL DEAWKQSVET TTPVDVVSSL  420
KRYEESRRLR VAIIHAMARM AAIMASTYKA YLGVGLGPLS FLTKFRVPHP GRVGGRFFVD  480
IAMPSMLDWV LGGNSEKLQG RPPSCRLTDK ADDRLREWFE DDDALERTIK GEWYLIPHGD  540
DCCVSETLCL TKDEDQPCIV GSEPDQDFPG MRIVIPSSQV SKMHARVIYK DGAFFLMDLR  600
SEHGTYVTDN EGRRYRATPN FPARFRSSDI IEFGSDKKAA FRVKVIRKTP KSTRKNESNN  660
DKLLQTA                                                           667

SEQ ID NO: 36          moltype = AA  length = 667
FEATURE                Location/Qualifiers
source                 1..667
                       mol_type = protein
                       organism = Arabidopsis lyrata
SEQUENCE: 36
MGSTLFCYSI NPSPSKLDFT RTHVVSPVAK QFYLDLSSFS GKSGGGLSGF RSRKTLVGVK  60
AATALVEKEE KREAVTEKKK KSRVLVAGGG IGGLVFALAA KKKGFDVVVF EKDLSAIRGE  120
GQYRGPIQIQ SNALAALEAI DTDVAEQVME AGCITGDRIN GLVDGVSGSW YVKFDTFTPA  180
ASRGLPVTRV ISRMTLQQIL ARAVGEDVIR NESNVVDFED SGDKVTVVLE NGQRYEGDLL  240
VGADGIWSKV RNNLFGRSEA TYSGYTCYTG IADFVPADIE SVGYRVFLGH KQYFVSSDVG  300
GGKMQWYAFH EEPAGGVDAP NGMKKRLFEI FDGWCDNVLD LLHATEEDAI LRRDIYDRSP  360
SFTWGKGRVT LLGDSIHAMQ PNMGQGGCMA IEDSFQLALE LEEAWKQSVG TNTPVDVVSS  420
LKRYEESRRL RVAIIHGMAR MAAIMASTYK AYLGVGLGPL SFLTKFRVPH PGRVGGRFFV  480
DIAMPLMLDW VLGGNSEKLE GRPPSCRLTD KADDRLREWF EDDDALERTI KGEWYLIPHG  540
EDCCVSETLC LTNDEDQPCI VGSEPDQDFP GMRIVIPSSQ VSKMHARVIY KDGVFFLMDL  600
RSEHGTYVTD NEGRRYRATP NFPARFRSSD IIEFGSDKKA AFRVKVIRKT PKSTRKNESN  660
DKLLQTA                                                           667

SEQ ID NO: 37          moltype = AA  length = 662
FEATURE                Location/Qualifiers
source                 1..662
                       mol_type = protein
                       organism = Raphanus sativus
SEQUENCE: 37
MGSSTLFCYS INPSPSKLDF TKTHVFSPVA KQFYLDFPSF AAGKLRLRKR RALVGAKAET  60
LLEEKRETVT EKKKKPRVLV AGGGIGGLVF ALAAKKKGFD VLVFEKDLSA IRGEGQYRGP  120
IQIQSNALAA LEAIDIGVAE EVMEAGCITG DRINGLVDGV SGTWYVKFDT FTPAASRGLP  180
VTRVISRMTL QQILARAVGE EIIRNESNVV DFQDSGDKVT VVLENGERYD GDLLVGADGI  240
WSKVRNNLFG RSEATYSGYT CYTGIADFVP ADIESVGYRV FLGHKQYFVS SDVGGGKMQW  300
YAFHEEAAGG VDAPNGMKKR LFDIFEGWCD NVLDLLQATE EEAILRRDIY DKSPSFTWGK  360
GRVTLLGDSI HAMQPNMGQG GCMAIEDSFQ LGLELEAAWK QSVETNTPVD VVSSLRRYEE  420
SRRLRVAIIH GMARMAAIMA STYKAYLGVG LGPLSFLTKF RVPHPGRVGG RFFIDIAMPL  480
MLNWVLGGNS EKLEGRPPSC RLTDKADDRL REWFEDDEAL ERTINGEWYL IPHGNECSVS  540
ETLRLTKDEE QPCIVGSEPD QDFPGTHIVI PSPQVSKMHA RVIYKDGAFF LMDLRSEHGT  600
YLTDNEGGKY RVTPNFPTRF RSSDIIEFGS DKKAAFRVKV IRTTPKLTRR DEKSDGKLLQ  660
AA                                                                662

SEQ ID NO: 38          moltype = AA  length = 687
FEATURE                Location/Qualifiers
source                 1..687
                       mol_type = protein
                       organism = Brassica napus
SEQUENCE: 38
MKCTSHIKLP LRASRIEMGS STPFCYSINP SPSKLDFTRT HAFSPVAKQF YLDLPSFAGK  60
SGGGLSGLRK RRTLIGVKAA AATLVAEEEK RETVTESKKK PRVLVAGGGI GGLVFALAAK  120
KKGFDVLVFE KDLSAIRGEG QYRGPIQIQS NALAALEAID IGVAEEVMEA GCITGDRING  180
LVDGVSGTWY VKFDTFTPAA SRGLPVTRVI SRMTLQQILA RAVGEEIIRN ESNVVDFEDS  240
GDKVTVVLEN GQRYDGDLLV GADGIWSKVR NNLFGRSEAT YSGYTCYTGI ADFVPADIES  300
VGYRVFLGHK QYFVSSDVGG GKMQWYAFHE EAAGGVDAPN GMKKRLFDIF EGWCDNVLDL  360
LQATEEEAIL RRDIYDRSPS FTWGKGRVTL LGDSIHAMQP NMGQGGCMAI EDSFQLGLEL  420
EQAWKQSVET NTPVDVVSSL RRYEESRRLR VAIIHGMARM AAIMASTYKA YLGVGLGPLS  480
FLTKFRVPHP GRVGGRFFID IAMPLMLNWV LGGNSEKLEG RPPSCRLTDK ADDRLREWFE  540
DDEALERTIN GEWYLIPHGN ECSVSETLRL TKDEDQPCIV GSEPDQDFPG MHIVIPSPQV  600
SKMHARVIYK DGAFFVMDLR SEHGTYLTDN EGGKYRVTPN FPARFRPSDI IEFGSDKKAA  660
FRVKVIRTTP KLTRRDEKSD GKLLQAA                                     687

SEQ ID NO: 39          moltype = AA  length = 668
FEATURE                Location/Qualifiers
```

```
source                  1..668
                        mol_type = protein
                        organism = Brassica rapa
SEQUENCE: 39
MGCSTPFCYS INPSPSKLDF TKTHAFSPVA KQFYLDLPSF AGKSGGGLSG LRKRRALVGV  60
KAATLLAEEE KRETVTESKK KPRVLVAGGG IGGLVFALAA KKKGFDVLVF EKDLSAIRGE  120
GQYRGPIQIQ SNALAALEAI DIGVAEEVME AGCITGDRIN GLVDGVSGTW YVKFDTFTPA  180
ASRGLPVTRV ISRMTLQQIL ARAVGEEIIR NESNVVDFED SGDKVTVVLE NGQRYDGDLL  240
VGADGIWSKV RNNLFGRSEA TYSGYTCYTG IADFVPADIE SVGYRVFLGH KQYFVSSDVG  300
GGKMQWYAFH EEAAGGVDAP NGMKKRLFDI FEGWCDNVLD LLQATEEEAI LRRDIYDRSP  360
SFTWGKGRVT LLGDSIHAMQ PNMGQGGCMA IEDSFQLGLE LEQAWKQSVE TNTPVDVVSS  420
LRRYEESRRL RVAIIHGMAR MAAIMASTYK AYLGVGLGPL SFLTKFRVPH PGRVGGRFFI  480
DIAMPLMLNW VLGGNSEKLE GRPPSCRLTD KADDRLREWF EDDEALERTI NGEWYLIPHG  540
NECSVSETLR LTKDEEQPCI VGSEPDQDFP GTHIVIPSPQ VSKMHARVIY KDGAFFVMDL  600
RSEHGTYLTD NEGGKYRVTP NFPARFRPSD IIEFGSDKKA AFRVKVIRTT PKLTRRDEKS  660
DGKLLQAA                                                          668

SEQ ID NO: 40           moltype = AA  length = 668
FEATURE                 Location/Qualifiers
source                  1..668
                        mol_type = protein
                        organism = Brassica rapa
SEQUENCE: 40
MGCSTPFCYS INPSPSKLDF TKTHAFSPVA KQFYLDLPSF AGKSGGGLSG LRKRRALVGV  60
KAATLLAEEE KRETVTESKK KPRVLVAGGG IGGLVFALAA KKKGFDVLVF EKDLSAIRGE  120
GQYRGPIQIQ SNALAALEAI DIGVAEEVME AGCITGDRIN GLVDGVSGTW YVKFDTFTPA  180
ASRGLPVTRV ISRMTLQQIL ARAVGEEIIR NESNVVDFED SGDKVTVVLE NGQRYDGDLL  240
VGADGIWSKV RNNLFGRSEA TYSGYTCYTG IADFVPADIE SVGYRVFLGH KQYFVSSDVG  300
GGKMQWYAFH EEAAGGVDAP NGMKKRLFDI FEGWCDNVLD LLQATEEEAI LRRDIYDRSP  360
SFTWGKGRVT LLGDSIHAMQ PNMGQGGCMA IEDSFQLGLE LEQAWKQSVE TNTPVDVVSS  420
LRRYEESRRL RVAIIHGMAR MAAIMASTYK AYLGVGLGPL SFLTKFRVPH PGRVGGRFFI  480
DIAMPLMLNW VLGSNSEKLE GRPPSCRLTD KADDRLREWF EDDEALERTI NGEWYLIPHG  540
NECSVSETLR LTKDEEQPCI VGSEPDQDFP GTHIVIPSPQ VSKMHARVIY KDGAFFVMDL  600
RSEHGTYLTD NEGGKYRVTP NFPARFRPSD IIEFGSDKKA AFRVKVIRTT PKLTRRDEKS  660
DGKLLQAA                                                          668

SEQ ID NO: 41           moltype = AA  length = 667
FEATURE                 Location/Qualifiers
source                  1..667
                        mol_type = protein
                        organism = Noccaea caerulescens
SEQUENCE: 41
MGSTPFCYST NPSPSKLDFT RTHAFSPLAK QFYLDLSSLA GKSGGGLSGF RSPRTLVGVK  60
AAAATALVEE EKREVVAEKK KSRVLVAGGG IGGLVFALAA KKKGFDVLVF EKDLSAIRGE  120
GQYRGPIQIQ SNALAALEAI DTDVAEEVME AGCITGDRIN GLVDGVSGTW YVKFDTFTPA  180
ASRGLPVTRV ISRMTLQQIL ARAVGEEIIR NESNVVDFED SGDKVTVVLE NGERYEGDLL  240
VGADGIWSKV RNNLFGRSEA TYSGYTCYTG IADFVPADIE SVGYRVFLGH KQYFVSSDVG  300
GGKMQWYAFH EEPAGGVDPP NGMKKRLFDI FEGWCDNVLD LLHATEEDAI LRRDIYDRTP  360
SFTWGKGRVT LLGDSIHAMQ PNMGQGGCMA IEDSYQLAME LEGAWKQSVE TNTPVDVVSS  420
LKKYEESRRL RVAIIHGMAR MAAIMASTYK AYLGVGLGPL SFLTKFRVPH PGRVGGRFFI  480
DIAMPLMLNW VLGGNSEKLE GRSPSCRLTD KADDRLREWF EDNDALERTI NGEWYLIPHG  540
DDSSVKETIS LTKDEDQPCI IGSEPDQDLP GMHIVIPSSQ VSKMHARVTY KDGAFFLMDL  600
GSEHGTYVVD NEGRRYRASP NYPARFRSSD IIEFGSDKKA AFRVKVIRTT PKSTSKNESN  660
GKLLQAA                                                           667

SEQ ID NO: 42           moltype = AA  length = 666
FEATURE                 Location/Qualifiers
source                  1..666
                        mol_type = protein
                        organism = Eutrema salsugineum
SEQUENCE: 42
MGSTPFCYSI NPSPSKLDFT RTHVFSPVAK QFYLDLSSCA GKSGGGLSGF RSRRALVGVR  60
AATALVEEEK REIAKEKKKP RVLVAGGGIG GLVFALAAKK KGFDVLVFEK DLSAIRGEGQ  120
YRGPIQIQSN ALAALEAIDI DVAEEVMEAG CITGDRINGL VDGVSGTWYV KFDTFTPAAS  180
RGLPVTRVIS RMTLQQILAR AVGEEVIRNE SNVVDFEDSG DKVTVVLENG ERYEGDLLVG  240
ADGIWSKVRN NLFGRSEATY SGYTCYTGIA DFVPADIESV GYRVFLGHKQ YFVSSDVGGG  300
KMQWYAFHEE PAGGVDAPNG MKKRLFDIFE GWCDNVLDLL HATEEEAILR RDIYDRTPSF  360
NWGKGRVTLL GDSIHAMQPN MGQGGCMAIE DSYQLALELE EAWERSVETN APVDVVSSLR  420
RYEESRRLRV AIIHGMARMA AIMASTYKAY LGVGLGPLSF LTKFRVPHPG RVGGRFFIDI  480
AMPLMLNWVL GGNSEKLEGR PPSCRLTDKA DDRLREWFED DDALERTING EWYLIPYGNE  540
CSVSETLCLT KDEDQPCIIG SEPDQDFPGM HIVIPAPQVS KMHARVTYKD GAFFLMDLRS  600
EHGTYVTDNE GRRYRVTPNF PARFRSSDII EFGSDKKAAF RVKVIRTTPK STSKNKESNG  660
KLLQAV                                                            666

SEQ ID NO: 43           moltype = AA  length = 666
FEATURE                 Location/Qualifiers
SITE                    492
                        note = MISC_FEATURE - Xaa = Any Amino Acid
source                  1..666
```

```
                        mol_type = protein
                        organism = Eutrema halophilum
SEQUENCE: 43
MGSTPFCYSI NPSPSKLDFT RTHVFSPVAK QFYLDLSSCA GKSGGGLSGF RSRRALVGVR  60
AATALVEEEK REIAKEKKKP RVLVAGGGIG GLVFALAAKK KGFDVLVFEK DLSAIRGEGQ  120
YRGPIQIQSN ALAALEAIDI DVAEEVMEAG CITGDRINGL VDGVSGTWYV KFDTFTPAAS  180
RGLPVTRVIS RMTLQQILAR AVGEEVIRNE SNVVDFEDSG DKVTVVLENG ERYEGDLLVG  240
ADGIWSKVRN NLFGRSEATY SGYTCYTGIA DFVPADIESV GYRVFLGHKQ YFVSSDVGGG  300
KMQWYAFHEE PAGGVDAPNG MKKRLFDIFE GWCDNVLDLL HATEEEAILR RDIYDRTPSF  360
NWGKGRVTLL GDSIHAMQPN MGQGGCMAIE DSYQLALELE EAWERSVETN APVDVVSSLR  420
RYEESRRLRV AIIHGMARMA AIMASTYKAY LGVGLGPLSF LTKFRVPHPG RVGGRFFIDI  480
AMPLMLNWVL GXNSEKLEGR PPSCRLTDKA DDRLREWFED DDALERTING EWYLIPYGNE  540
CSVSETLCLT KDEDQPCIIG SEPDQDFPGM HIVIPAPQVS KMHARVTYKD GAFFLMDLRS  600
EHGTYVTDNE GRRYRVTPNF PARFRSSDII EFGSDKKAAF RVKVIRTTPK STSKNKESNG  660
KLLQAV                                                            666

SEQ ID NO: 44           moltype = AA  length = 665
FEATURE                 Location/Qualifiers
source                  1..665
                        mol_type = protein
                        organism = Cucumis sativus
SEQUENCE: 44
MALTRFHNPF NLSSSSLSRT CFPVPAFREY LVEISPCQRI GCNFGGKSAC GRRKKLTQVK  60
AAVTEAPPAE GAAGEISRSL PTKNVRILVA GGGIGGLVFA LAAKRKGFDV VVFEKDISAI  120
RGEGQYRGPI QIQSNALAAL EAIDLDVAEE VMRVGCITGD RINGLVDGVS GNWYIKFDTF  180
TPAAERGLPV TRVISRMSLQ QILAARAVGDD VIINDSNVVD FEDSGEKVKV TLENGQQHEG  240
DLLVGADGIW SKVRKNLFGH SEAVYSGYTC YTGIADFIPA DIETVGYRVF LGHKQYFVSS  300
DVGAGKMQWY AFHKEPPGGA DAPNGKKERL FKIFEGWCDN VTDLIQATDE DSVLRRDIYD  360
RTPIFTWGKG RVTLLGDSVH AMQPNMGQGG CMAIEDGYQL ALELDKAWNE SVASGSPIDI  420
VSSLKSYESS RRIRVAVIHG MARMAALMAS TYKAYLGVGL GPLSFLTQFR IPHPGTFGGR  480
FFIDLAMPLM LNWVLGGNSS KLEGRPPACR LSDKANDQLR KWFEDDDALE RAINGDWFLL  540
PQGGEASVSQ PICLRKDENQ PCLIGSVEKE VDSGLSVAIP LPQVSEKHAR IYYKDGAFFL  600
TDLRSEHGTW LSDHEGRRYR APPNFPVRFH QSDLIEFGSD KKARFRVKVI RSSVENDREK  660
VEMNS                                                             665

SEQ ID NO: 45           moltype = AA  length = 658
FEATURE                 Location/Qualifiers
source                  1..658
                        mol_type = protein
                        organism = Vitis vinifera
SEQUENCE: 45
MASAVFYSSV QPSIFSRTHI PIPISKDSFE EFGHSINYKH YFRSNPCGQK KRVAQVKATL  60
AEATPAPPAP SLPSKKVRIL VAGGGIGGLV LALAAKKKGF DVVVFEKDMS AIRGEGQYRG  120
PIQIQSNALA ALEAVDMEVA EEVMRAGCIT GDRINGLVDG VSGDWYVKFD TFTPAAERGL  180
PVTRVISRMT LQQILARAVG EDIIMNGSNV VDFEDDGNKV TVILENGQRY EGDLLIGADG  240
IWSKVRKSLF GPKEATYSGY TCYTGIADFV PADIDSVGYR VFLGHKQYFV SSDVGAGKMQ  300
WYAFYNEPAG GVDGPEGKKE RLLKIFGGWC DNVIDLILAT DEEAILRRDI YDRTPTFTWG  360
RGRVTLLGDS VHAMQPNMGQ GGCMAIEDSY QLAMELDKAW EQSIKSGTPI DVVSCLKSYE  420
KARRIRVAVI HGMARMAAIM ASTYKAYLGV GLGPLSFLTK LRIPHPGRVG GRFFIDIAMP  480
LMLSWVLGGN SSKLEGRPPS CRLSDKANDQ LRRWFEDDDA LERAIGGEWF LLPSGESGLQ  540
PICLSKDENK PCIIGSVSHT DFPGISTVIP SPKVSKMHAR ISCKDGAFFL TDLQSEHGTW  600
ITDNVGRRQR VSPNFPTRFH PSEVIDFGSE KASFRVKVVR TPPDNAAKNE ESKLFQAV   658

SEQ ID NO: 46           moltype = AA  length = 664
FEATURE                 Location/Qualifiers
source                  1..664
                        mol_type = protein
                        organism = Corchorus olitorius
SEQUENCE: 46
MATTLFQNPS TFFTGTQFPV SIPKYVPTES SACLHCNYHF RGKASKQKKR FLQVKATVAG  60
TQSDSKSDEK NKVDANQQEK KKARILVAGG GIGGLVFALA AKNKGFDVVV FEKDLSAIRG  120
EGQYRGPIQI QSNALAALEA IDMEVAEKVM EAGCITGDRI NGLVDGVSGS WYIKFDTFTP  180
AAERGLPVTR VISRMTLQQI LARAVGEDII FNESNVVDFE DDGNKVSVVL ENGKRFEGDL  240
LVGADGIWSK VRKNLFGPKD AVYSGYTCYT GIADFVPADI DSVGYRVFLG HKQYFVSSDV  300
GGGKMQWYAF HKEPAGGVDT QGKKERLLKI FEGWCDNVID LLLATDEEAI LRRDIYDRTP  360
SLTWGKGRVT LLGDSIHAMQ PNLGQGGCMA IEDGYQLALE LDKAWKQSVE SGTPIDVVSS  420
LRSYESARRL RVAIIHGMAR MAAIMASTYK AYLGVGLGPL SFLTKYRIPH PGRVGGRFFI  480
DIAMPLMLSW VLGGNSSKLE GRSLTCRLSD KASDQLREWF EDNDALERAI SGEWFLFPAG  540
DGVSSQPICL SRDENNPFMI GSEKKEDFPG TSVVIPSSQV SKTHAQITYK DGAFFVTDLQ  600
SEHGTYIINQ EGKKSRVTPN VPTRIRPSDV IEFGSDKKAA FRVKAIKSAP KIAEKEGSGV  660
LQAA                                                              664

SEQ ID NO: 47           moltype = AA  length = 661
FEATURE                 Location/Qualifiers
source                  1..661
                        mol_type = protein
                        organism = Populus euphratica
SEQUENCE: 47
MASSTLFGNT LTAVSSRTHF PTPIFNNSLE LLSSTHSNYN FKTKTSTSAK KLKVEAVVTE  60
```

```
TPAVSKSEGK QSEQRKLKVL VAGGGIGGLV FALAAKNKGF DVMVFEKDLS AVRGEGQYRG  120
PIQIQSNALA ALEAIDLDVA EEVMRAGCIT GDRINGLVDG ISGTWYVKFD TFTPAAERGL  180
PVTRVISRMT LQQILARSVG DDTILNDSNV VSFQDDGDKV TVVLENGQQY EGDLLVGADG  240
IWSKVRKNLF GPKEAVYSGY TCYTGIADFV PVDIETVGYR VFLGHKQYFV SSDVGAGKMQ  300
WYAFHKESPG GMDAPHGKKD RLLKIFEGWC DNVIDLLLTT DEDSILRRDI YDREPIITWG  360
KGRVTLLGDS VHAMQPNMGQ GGCMAIEDSY QLASELERAW KQSIESGTPV DVLSSLRSYE  420
NARRLRVAII HGMARMAAIM ASTYKAYLGV GLGPLSFLTN FRIPHPGRVG GRFFIDIAMP  480
VMLDWVLGGN SSKLEGRSLS CRLSDKASDQ LRRWFVDDDA LERSLNGEWF LLPCGNDAVA  540
SQPIGLSRDE NKPCVVGSVS QEDFPGMSIV IPAPQVSKTH ARITCKDGAF YLIDLRSEHG  600
TFITDIEGRR YRAPPNFPTR FHPSDMIEFG SDKKVIFRVK VMRSPPKISE KKDEGQVLQS  660
V                                                                 661

SEQ ID NO: 48          moltype = AA  length = 665
FEATURE                Location/Qualifiers
source                 1..665
                       mol_type = protein
                       organism = Ricinus communis
SEQUENCE: 48
MASSAFFCNS INPSTSVFSR THFSFPIFST STVEFSSFAQ YNFHFKTKKS DHQNKRFTQV  60
KAVVTESPTV AESNGKLSEQ KKLRILVAGG GIGGLVFALA AKRKGFEVLV FEKDLSAIRG  120
EGQYRGPIQV QSNALAALEA IDLEVAEEVM RAGCITGDRI NGLVDGVSGT WYCKFDTFTP  180
AAERGLPVTR VISRMTLQQI LACAVGEDVI MNASNVINFQ DNEDKVTVTL ENGQQFEGDL  240
LVGADGIWSK VRKNLFGPKE ATYSGYTCYT GIADFVPVDI ESVGYRVFLG HKQYFVSSDV  300
GAGKMQWYAF HNEPPGGVDS PNGKKERLLK IFEGWCDNVI DLLHATDEDA ILRRDIYDRE  360
PVFTWGKGRV TLLGDSIHAM QPNMGQGGCM AIEDSYQLAL ELDKAWKQSI ESGTPVDVVS  420
SLKSYERTRR LRVAIIHGMA RMAAIMASTY KAYLGVGLGP LSFLTKYRIP HPGRVGGRFF  480
IDIAMPVMLN WVLGGNSSKL EGRPLSCRLS DKASDQLQTW FEDDNALERA LNGEWFLLPF  540
GDDAVQEPIC LSRDENIPCM VGSESQEDFP GKSIVISSPQ VSKMHARISY KDGGFYVIDL  600
QSEHGTFITD NDGRRSRVPP NFPTLFHPSE AIEFGSAGKA KFRVKVMKSP AKIKEKGGNE  660
ILQSV                                                             665

SEQ ID NO: 49          moltype = AA  length = 665
FEATURE                Location/Qualifiers
source                 1..665
                       mol_type = protein
                       organism = Jatropha curcas
SEQUENCE: 49
MASSTLFCNL INPSISVFSR THLPFPIVSS SSMELSSSAH CNFHFRSKKS EQNKKLTQVK  60
AVVTESTSVA QSDEKQPEQR KPRILVAGGG IGGLVFALAA KRKGFEVLVF EKDLSAVRGE  120
GQYRGPIQIQ SNALAALEAI DLEVAEEVME AGCITGDRIN GLVDGVSGTW YVKFDTFTPA  180
AERGLPVTRV ISRMTLQQIL ALAVGEDVIR NESNVVSFQD DGDKVTVTLE NGQHFEGDLL  240
VGADGIWSKV RKNLFGPKDA TYSDYTCYTG IADFVPADIE SVGYRVFLGH KQYFVSSDVG  300
AGKMQWYAFH KEPPGGVDRP NGKKERLLKI FEGWCDNVID LLLATDEDAI LRRDIYDRTP  360
TLTWGRGRVT LLGDSVHAMQ PNMGQGGCMA IEDGYQLALE IEKAWKQSIE SGTPIDIVSS  420
LKSYERARRL RVAIIHGMAR MAAIMASTYK AYLGVGLGPL SFLTKYRIPH PGRVGGRFFI  480
DIAMPVMLSW VLGGNSSKLE GRSQCCRLSD KASDQLRTWF EDDDALERAL NAEWFLLPLG  540
NKVVVSEPIC LSRNENTPCV VGKVSHKDFP GMSIVIPSPQ VSEMHARISY KDGAFYVIDL  600
QSEHGTYISD ADGRRYRVPQ NSPTRFHPSD VIEFGSDEKA KFRVKVMKSP SRIKEKEGSE  660
ILQSV                                                             665

SEQ ID NO: 50          moltype = AA  length = 480
FEATURE                Location/Qualifiers
source                 1..480
                       mol_type = protein
                       organism = Eucalyptus grandis
SEQUENCE: 50
MASMAAGSIC LFRDESIGAA SIAVTILANR SSHMAKLLCY RGKARATMWM GIKTTRRLAM  60
KCSLESHCRS ESSCSGFPLP RKEEVTSSRG SRSGVPKVTE SAREIFHLVR EWSQRRVIQL  120
AALAACTFLI IPSADAVDAL KTCACLLKEC RIELAKCVAN PSCAANVACL QTCNNRPDET  180
ECQIKCGDLF ENSVVDEFNE CAVSRKKCVP RKSDVGEFPV PDPAVLVKSF NMADFTGKWF  240
ISSGLNPTFD TFDCQLHEFH TESNKLMGNL TWRIRTPDSG FFTRTAVQRF VQDPEQPGIL  300
YNHDNEYLHY QDDWYILSSK TENKPDDYVF VYYRGRNDAW DGYGGAVVYT RSAVLPDSIV  360
PELERAAKSV GRDFKDFIRT DNTCGPEPPL VERIEKTVEE GEKTIVREVE QIEDEVQKVG  420
KTEMTLFQRL TEGFRELRQD EENFLRRLSQ EEMEVLNELK MEATEVEKLF GRALPIRKLR  480

SEQ ID NO: 51          moltype = AA  length = 458
FEATURE                Location/Qualifiers
source                 1..458
                       mol_type = protein
                       organism = Tarenaya hassleriana
SEQUENCE: 51
MAVAVQSFSS PCYRDTQFIS GNRSNRKLLR KRMVDSDTIV LVKICSGARG KIHCSLKARF  60
SSPSSGYKSG LSKGRPPFEA LTLWNKLKEQ SRQSLLKLVG ILACTFLIVP SVDAVDALKT  120
CACLLKECRI ELAKCISNPS CAANVACLQT CNNRPDETEC QIKCGDLFEN SVVDEFNECA  180
VSRKKCVPRK SDLGEFPAPD PAVLVKRFNI GDFSGKWYIS SGLNPTFDTF DCQLHEFHTE  240
SDKLVGNLSW RIRTPDGGFF TRSTVQKFVQ DPNQPGILYN HDNEYLHYQD DWYILSSKVE  300
NGPDDYVFVY YRGRNDAWDG YGGAVVYTRS AVLPNNIVPE LERAAKSVGR DFSKFIRTDN  360
TCGPEPPLVE RIEKTVEEGE RTIIREVEQI EGEVAKVGET EMTLLQRLVE GFKELKQDEE  420
NFLQGLNKEE MELLSELKME ASEVEKLFGK ALPIRKLR                          458
```

```
SEQ ID NO: 52           moltype = AA  length = 461
FEATURE                 Location/Qualifiers
source                  1..461
                        mol_type = protein
                        organism = Camelina sativa
SEQUENCE: 52
MAVATHCFTS PCHDRIRFFS SDDGIGRLGI SRKRINGTFL VKILPPIQNV DLRTNGRSSR  60
PLSAFRSGIS KGVFDILSLP SKDELKELST PLLLKLVGVF ACAFLIVPSA EAVDALKTCA  120
CLLKGCRIEL AKCISNPACA ANIACLQTCN NRPDETECQI KCGDIFENKV VDEFNECAVT  180
RKKCVPKKSD LGEFPAPDPS VLVQNFNIGD FSGKWYITSG LNPTFDAFDC QLHEFHTEGE  240
NKLVGNISWR IKTLDSGFFT RSAVQTFVQD PNQPGVLYNH DNEYLHYQDD WYILSSKIEN  300
KPEDYIFVYY RGRNDAWDGY GGAVVYTRSS VLPNSIVPEL EKAAKSIGRD FSTFIRTDNT  360
CGPEPPLVER LEKTVEEGER IIVKDFEEIE EEVEKEVEKV GKTEMTLFQR LAEGFNELRK  420
DEENFVRELS KEEMEFLDEI KMEANEVEKL FGKALPIRKV R                      461

SEQ ID NO: 53           moltype = AA  length = 461
FEATURE                 Location/Qualifiers
source                  1..461
                        mol_type = protein
                        organism = Capsella rubella
SEQUENCE: 53
MAVATHCFTS PCHDRIRFFS SDDGIARLGI SRKRINGTFL VKILSPIQSA DLRTSGRSSR  60
PLSAFRSGFS KRVFDIVSLP SKNELKELST PLLLKLVGVL ACAFLIVPSA EAVDALKTCA  120
CLLEGCRIEL AKCIANPACA ANVACLQTCN NRPDETECQI KCGDLFENSV VDEFNECAVS  180
RKKCVPRKSD LGEFPAPDPS VLVQNFNIGD FNGKWYITSG LNPTFDAFDC QLHEFHTEGD  240
NKLVGNISWR IKTLDSGFFT RSAVQTFVQD PNQPGVLYNH DNAYLHYQDD WYILSSKIEN  300
KPEDYIFVYY RGRNDAWDGY GGAVVYTRSS VLPNSIVPEL EKAAKSIGRD FSTFIKTDNT  360
CGPEPPLVER LEKTVEEGER IIVKEVEEIE EEVEKEVEKV GKTEMTLFQR LAEGFNELKQ  420
DEENFVRELS KEEMEFLDEI KMEASEVEKL FGKALPIRKV R                      461

SEQ ID NO: 54           moltype = AA  length = 462
FEATURE                 Location/Qualifiers
source                  1..462
                        mol_type = protein
                        organism = Arabidopsis thaliana
SEQUENCE: 54
MAVATHCFTS PCHDRIRFFS SDDGIGRLGI TRKRINGTFL LKILPPIQSA DLRTTGGRSS  60
RPLSAFRSGF SKGIFDIVPL PSKNELKELT APLLLKLVGV LACAFLIVPS ADAVDALKTC  120
ACLLKGCRIE LAKCIANPAC AANVACLQTC NNRPDETECQ IKCGDLFENS VVDEFNECAV  180
SRKKCVPRKS DLGEFPAPDP SVLVQNFNIS DFNGKWYITS GLNPTFDAFD CQLHEFHTEG  240
DNKLVGNISW RIKTLDSGFF TRSAVQKFVQ DPNQPGVLYN HDNEYLHYQD DWYILSSKIE  300
NKPEDYIFVY YRGRNDAWDG YGGAVVYTRS SVLPNSIIPE LEKAAKSIGR DFSTFIRTDN  360
TCGPEPALVE RIEKTVEEGE RIIVKEVEEI EEEVEKEVEK VGRTEMTLFQ RLAEGFNELK  420
QDEENFVREL SKEEMEFLDE IKMEASEVEK LFGKALPIRK VR                     462

SEQ ID NO: 55           moltype = AA  length = 455
FEATURE                 Location/Qualifiers
source                  1..455
                        mol_type = protein
                        organism = Arabidopsis lyrata
SEQUENCE: 55
MAVATHCFTS PCHGRIRFFS SDDGRLGITR KRINGTFLLK ILPPIQNAGG RSSRPISAFR  60
SGFSKGIFDI VALPSKNELK ELTTPLLLKL VGVLACAFLI VPSADAVDAL KTCACLLKGC  120
RIELAKCIAN PACAANVACL QTCNNRPDET ECQIKCGDLF ENSVVDEFNE CAVSRKKCVP  180
RKSDLGEFPA PDPSVLVQNF NISDFNGKWY ITSGLNPTFD AFDCQVHEFH TEGDNKLVGN  240
ISWRIKTLDS GFFTRSAVQK FVQDPNQPGV LYNHDNEYLH YQDDWYILSS KIENKPDDYI  300
FVYYRGRNDA WDGYGGAVVY TRSSVLPNSI IPELEKAAKS IGRDFSTFIR TDNTCGPEPP  360
LVERIEKTVE EGERIIVKEV EEIEEEVEKE VEKVGKTEMT LFQRLAEGFN ELKQDEENFV  420
REFSKEEMEF LDEIKMEASE IEKLFGKALP IRKVR                             455

SEQ ID NO: 56           moltype = AA  length = 457
FEATURE                 Location/Qualifiers
source                  1..457
                        mol_type = protein
                        organism = Brassica napus
SEQUENCE: 56
MSVSTHCFTS PCHDRTRFFS GDDGNKLLRK RIKGTFLVKI LPSSQNAYLR ITAKSSRPLS  60
GFRSGISKGV FDIVALTSKN ALKELTTPLM LKLVGVVACA FLIVPSADAV DALKTCACLL  120
KGCRIELAKC IANPSCAANV ACLQTCNNRP DETECQIKCG DLFENSVVDE FNECAVSRKK  180
CVPRKSDLGE FPAPDPSVLV KNFNINDFDG KWYITSGLNP TFDAFDCQLH EFHTEDGKLV  240
GNISWRIKTP DSGFFTRSTV QKFVQDPNQP AVFYNHDNEY LHYQDDWYIL SSKIENKPED  300
YIFVYYRGRN DAWDGYGGAV VYTRSASLPN TIVPELEKAA KSIGREFSTF IKTDNTCGPE  360
PPLVERLEKT VEEGEKIIVK EVEEIEEEVE KEVEKVGKTE MTLFQRLAEG FEELKQDEEN  420
FLRGLSKEEM ELLDELKMEA NEVEKLFGKA LPIRKFR                           457

SEQ ID NO: 57           moltype = AA  length = 491
FEATURE                 Location/Qualifiers
source                  1..491
```

```
                        mol_type = protein
                        organism = Brassica rapa
SEQUENCE: 57
MSYPKGISSH PYISLFLFSL YLPPLLPAEL SVSSMSVSTH CFTSPCHDRT RFFSGDDGNK  60
LLRKRIKGTF LVKILPSSQN AYLRVTAKSS RPLSGFRSGI SKGVFDIVAL TSKNALKELS  120
TPLMLKLVGV VACAFLIVPS ADAVDALKTC ACLLKGCRIE LAKCIANPSC AANVACLQTC  180
NNRPDETECQ IKCGDLFENS VVDEFNECAV SRKKCVPRKS DLGEFPAPDP SVLVKNFNVK  240
DFDGKWYITS GLNPTFDAFD CQLHEFHTED GKLVGNISWR IKTPDSGFFT RSTVQKFVQD  300
PNQPAVFYNH DNEYLHYQDD WYILSSKIEN KPEDYIFVYY RGRNDAWDGY GGAVVYTRSA  360
SLPNTIVPEL EKAAKSIGRE FSTFIKTDNT CGPEPPLVER LEKTVEEGEK IIVKEVEEIE  420
EEVEKEVEKV GKTEMTLFQR LAEGFEELKQ DEENFLRGLS KEEMELLDEL KMEANEVEKL  480
FGKALPIRKF R                                                     491

SEQ ID NO: 58           moltype = AA  length = 493
FEATURE                 Location/Qualifiers
source                  1..493
                        mol_type = protein
                        organism = Noccaea caerulescens
SEQUENCE: 58
LSLSLSLSLS LSLLPAELSI FGIASGRLAT ESMSVATHCF TSPTCHDRIR FFSRITSDDG  60
RLVRKRINGT FLLKILPPSQ NAHLRTTLRS SRPLSAGFRS GISKGVIDIV ALTSRNALKE  120
LSTPLLLKLV GVLACAFLIV PSADAVDALK TCACLLKECR IELAKCIANP SCAANVACLQ  180
TCNNRPDETE CQIKCGDLFA NSVVDEFNEC AVSRKKCVPR KSDLGEFPVP DPSALVKNFN  240
IQDFNGKWYI TSGLNPTFDI FDCQLHEFHV QGNKLVGNIS WRIKTPDTGF FTRSAVQTFK  300
QDPNQPAVLY NHDNEYLHYQ DDWYILSSKI ENKPEDYIFV YYRGRNDAWD GYGGAVVYTR  360
SNVLPNSIVP ELEKAAKSIG RDFNTFVRTD NTCGPEPPLV ERLEKTVEEG EKMIEKEVEE  420
IEEEVEKEVE KVGKTEMTLF QRLAEGFNEL KQDEENFLRG LSEEEMALLD ELKMEAGEVE  480
KLFGKALPIR KFR                                                   493

SEQ ID NO: 59           moltype = AA  length = 459
FEATURE                 Location/Qualifiers
source                  1..459
                        mol_type = protein
                        organism = Eutrema salsugineum
SEQUENCE: 59
MAVATYCFTS PCHDRIRFFS GVTSFDGRLL RKRINGTFLV KILPPSQNAD LRTTSRSSRP  60
LSGFRSGTSK GVFDIVALTS RNALKELSTP MVLKLVGVLA CAFLIVPSAD AVDALKTCAC  120
LLKGCRIELA KCIANPSCAA NVACLQTCNN RPDETECQIK CGDLFENKVV DEFNECAVSR  180
KKCVPQKSDL GEFPVPDPSV LVKNFNISDF NGKWYITSGL NPTFDTFDCQ RHEFHADGDK  240
LVGNISWRIK TLDSGFFTRS AVQKFVQDPN QPAILYNHDN EYLHYQDDWY ILSSKVENKP  300
DDYIFVYYRG RNDAWDGYGG AVVYTRSAVL PNSIVPELEK AAKSIGRDFS TFVRTDNTCG  360
PEPPLVERFE KTVEEGEKII VKEVEEIEEE VEKEVEKVGK TEMTLFQRLA EGFNELKQDE  420
ENFLRGLSEE EMELLNELKM EASEVEKLFG KSLPIRKVR                        459

SEQ ID NO: 60           moltype = AA  length = 481
FEATURE                 Location/Qualifiers
source                  1..481
                        mol_type = protein
                        organism = Prunus humilis
SEQUENCE: 60
MALAGRSIFL SHNDSIGNTC IRLGITSDEG FQKRRMVGFH VVVKFPSNRR KSRYSQFIRS  60
KRNFCVLGSK CSSLLSSKTE EAFSKCSTRT SEPEMKRVIS FLLEEASSCI KEWSQLHFMK  120
VAGLLACTFM IMPSANAADA LKTCACLLKE CRVELAKCIG NPSCAANIAC LQTCNNRPDE  180
TECQIKCGDL FENSVVDEFN ECAVSRKKCV PKKSDVGEFP IPDPAVLVKS FDIEKFNGKW  240
FITSGLNPTF DAFDCQLHEF HTESSKLVGN LSWRIRTPDG GFFTRSAVQK FVQDPNQPGI  300
LYNHDNDYLH YQDDWYILSS KMENKPDDYI FVYYRGRNDA WDGYGGAVIY TRSSVLPASI  360
VPDLEKAAAS VGRDFSKFIR TDNTCGPEPP LVERLEKTLE EGERNIIEEV KQIEGEVEKV  420
EQTELTLLQK LAEGFNELKQ DEENFLRGLS KEEMDILSEL KMEAGEVEKL FGQTLPLRKL  480
R                                                                481

SEQ ID NO: 61           moltype = AA  length = 481
FEATURE                 Location/Qualifiers
source                  1..481
                        mol_type = protein
                        organism = Pyrus x bretschneideri
SEQUENCE: 61
MAFAGRSVFL SHKESIGNAC IRLGLKSDER LQKGRMVGFH VVVKFSSQRR KSRYCQFISA  60
KRNFSGLGSK RSSLLSSRTE EAFSERSTKT SEPEMGRAID LMIEEVLSVI KEWSQLHFMK  120
VAGLLLCTFM VMPSANAVDA LKTCACLLKE CRVELAKCIG NPSCAANIAC LQTCNNRPDE  180
TECQIKCGDL FENKVVDEFN ECAVSRKKCV PMKSDVGEFP IPDPAALVKS FDMSKFNGKW  240
FITSGLNPTF DVFDCQLHEF HTESSKLVGN LSWRIKTPDG GFFTRSAVQK FVQDPNQPGI  300
LYNHDNEYLH YQDDWYILSS KIENTPEDYI FVYYRGRNDA WDGYGGAVVY TRSSVLPESI  360
VPELERAAKS VGRDFSKFIR TDNTCGPEPP LVERLEKTIE EGERTIIEEV KQIEGEVEKV  420
EQTELTLFQK LLEGFNVLKQ DEENFLRGLS KEEMDLLSEL KMEAGEVGKL FGKTLPLRKL  480
R                                                                481

SEQ ID NO: 62           moltype = AA  length = 471
FEATURE                 Location/Qualifiers
source                  1..471
```

```
                         mol_type = protein
                         organism = Bixa orellana
SEQUENCE: 62
MALAPHSTHF SELTGRRFLS RKVVHLHGMV LLRIQSSDRK SRYSKSINPY RNHIVSKLRC  60
SDQLSEGTHN ISSTCSSNTR RKHEAKEGFE FVVPNLPNIL RKWSQLQIMK VAGVLACALL  120
VIPSASAVDA LKTCTCLLKE CRIELAKCIA NPSCAANVAC LQTCNNRPDE TECQIKCGDL  180
FENSVVDVFN ECAVSRKKCV PQKSDVGEFA VPDPSVLVKN FNIADFSGKW YISSGLNPSF  240
DTFDCQLHEF HTESNKLVGN LSWRIRTPDG GFFTRSTLQK FVQDPKQPGI LYNHDNEYLH  300
YQDDWYILSS KIENKQDDYV FVYYRGRNDA WDGYGGAVVY TRSAVLPESI VPELERAAKC  360
VGRDFNKFIK TDNTCGPEPP LVERLEKKVE EGEETIIREV EQLEGQVEKV GKTEMTLFQK  420
LAEGFKELQK DEENFLEELS KEEMDVLSEL KMEAREVEKL FGGALPLRKL R           471

SEQ ID NO: 63            moltype = AA  length = 487
FEATURE                  Location/Qualifiers
source                   1..487
                         mol_type = protein
                         organism = Theobroma cacao
SEQUENCE: 63
MAQAARSLCF SHDKSVQVPC RTSGLTSNER FHRRQIAHFH GIMLVKIQSS GRKARYSQLN  60
KSNPNYSASD LRCSNQLSRR KDRNFSSCSC NRRRPKAEEA FAFLVPTISN VLKEWSQSKI  120
VKVVGLLACA YLVIPSASAV DALKTCTCLL KECRIELAKC IANPSCAANI ACLQTCNDRP  180
DETECQIKCG DLFENSVVDE FNECAVSRKK CVPQKSDIGE FPVPSPAVLV KNFNIADFSG  240
KWFISSGLNP TFDTFDCQLH EFHTEAGKLV GNLSWRIGTP DGGFFTRSTL QRFVQDPNYP  300
GILYNHDNEY LHYQDDWYII SSKIENKQDD YIFVYYQGRN DAWDGYGGAV VYTRSAVLPE  360
SIVPELEKAA KNVGRDFNKF IRTDNTCGPE PPLVERLEKK VEEGEQTLIR EVKEIEGEVE  420
KEVKRVEKTE MTLFQKLAEG FKELQQDEEN FLRGLSKEEM GLLNELKMEA SEVEKLFGEA  480
LPLRKLR                                                           487

SEQ ID NO: 64            moltype = AA  length = 479
FEATURE                  Location/Qualifiers
source                   1..479
                         mol_type = protein
                         organism = Gossypium arboreum
SEQUENCE: 64
MAEAARLICF SHGKSVKVPC RTSGFTRKER FHRRLVAHFH GMMLLKLQSS CRNSRYSQLI  60
KPNMNYSASK LRCSHQLSRR KERKFSSSSS NERTPKIPTI SNLLEQWSQS QTVKLVGLLA  120
CAYLVIPSAA AVDALKTCTC LLKECRIELA KCIANPSCAA NVACLQTCND RPDETECQIK  180
CGDLFENSVV DEFNECAVSR KKCVPQKSDI GEFPVPDPAV LVENFNIADF TGKWFISSGL  240
NPTFDTFDCQ LHEFHIEGGK LVGNLSWRIR TPDGGFFTRS ATQRFVQDPN HPGILYNHDN  300
EYLHYQDDWY IISSKIENKP DDYVFVYYRG RNDAWDGYGG AVVYTRSAVL PETIVPELKR  360
AAQNVGRNFN KFIRTDNSCG PEPPLVERLE KKVEEGEQTL IREVEQIEGE VEKGVEKVEK  420
TEQTLFQRLA EGFKELQQDE ENFLRGLSKE EMELLNDLKM EASEVEKLFG EALPIRKLR   479

SEQ ID NO: 65            moltype = AA  length = 487
FEATURE                  Location/Qualifiers
source                   1..487
                         mol_type = protein
                         organism = Gossypium hirsutum
SEQUENCE: 65
MAEAARLICF SHGKSVKVPC RTSGFTRKER FHRRLVAHFH GMMLLKLQSS CRNSRYSQLI  60
KPNMNYSASK LRCSHQFSRR KERKFSSSSS NERTPKAEEV FSFQIPTISN LLEQWSQSQT  120
VKLVGLLACA YLVIPSAAAV DALKTCTCLL KECRIELAKC IANPSCAANV ACLQTCNDRP  180
DETECQIKCG DLFENSVVDE FNECAVSRKK CVPQKSDIGE FPVPDPAVLV ENFNIADFTG  240
KWFISSGLNP TFDTFDCQLH EFHIEGGKLV GNLSWRIRTP DGGFFTRSAT QRFLQDPNHP  300
GILYNHDNEY LHYQDDWYII SSKIENKPDD YVFVYYRGRN DAWDGYGGAV VYTRSAVLPE  360
TIVPELKRAA QNVGRNFNKF IRTDNSCGPE PPLVERLEKK VEEGEQTLIR EVEQIEGEVE  420
KGVEKVEKTE QTLFQRLAEG FKELQQDEEN FLRGLSKEEM ELLNDLKMEA SEVEKLFGEA  480
LPIRKLR                                                           487

SEQ ID NO: 66            moltype = AA  length = 489
FEATURE                  Location/Qualifiers
source                   1..489
                         mol_type = protein
                         organism = Populus trichocarpa
SEQUENCE: 66
MALAANPFCL SQEQYIISSS SVAKSGLASD GRFHRRQRLH FHGAVLSQFW PNSRKLRYIQ  60
SIRSHRHHYG GVIRCSNQLS DWTKKFSSLC SSSSRSMPKA IERLNFVVLS VTNALKERNN  120
LECLKLAGIL LCALLVIPSA DAVDALKTCT CLLKECRLEL AKCIANPSCA ANVACLQTCN  180
NRPDETECQA SSIKCGDLFE NSVVDEFNEC AVSRKKCVPR KSDVGEFPVP DPAVLVENFN  240
MADFSGKWFI TSGLNPTFDT FDCQLHEFHT ESNKLVGNLS WRIKTPDTGF FTRSAVQRFV  300
QDPVHPGILY NHDNEYLHYQ DDWYILSSKI ENKQDDYVFV YYQGRNDAWD GYGGAVVYTR  360
SAVLPESIVP ELEKAAKSVG RDFSKFIRTD NTCGPEPPLV ERLEKTVEEG EKTIIKEVEE  420
IEQKVEKAGK TELSLFQRLT EGFKEIQKDE ENFLRELSKE ETDLLNDLRM EAGEVEKLFG  480
RALPIRKLR                                                         489

SEQ ID NO: 67            moltype = AA  length = 483
FEATURE                  Location/Qualifiers
source                   1..483
                         mol_type = protein
```

-continued

```
                        organism = Manihot esculenta
SEQUENCE: 67
MAISANSVCL SHEESICSSY FRPGIASYER IHGRRGLNYQ SIVVLNFWPN SRKSRYVQLM  60
RTHKNYHGIK LRCSHGFSGW TKKFSSFCRT GANVTKAKEV LNFLMFSVSN NLKEKSHLQF  120
LKVASILACV LLFIPSADAV DALKTCTCLL KECRLELAKC IANPACAANI ACLQTCNNRP  180
DETECQIKCG DLFENTVVDE FNECAVSRKK CVPKKSDVGE FPVPDPAVLV KSFNIADFNG  240
KWYITRGLNP TFDTFDCQLH EFHVESNKLV GNISWRIRTP DSGFFTRSTV QRFVQDPMQP  300
GILYNHDNEY LHYQDDWYIL SSKVENKSDD YIFVYYRGRN DAWDGYGGAV VYTRSSVLPE  360
SIAPELERAA KSVGRDFSKF IRTDNTCGPE PPLVERLEKT VEEGEKSIIR EVQEIEGEVE  420
KVGKTEMTLF QRLAEGFKEL QQDEEILLRK LSKEEMELFN DLKMEASEVE KLFGGALPLR  480
KLR                                                              483

SEQ ID NO: 68           moltype = AA  length = 481
FEATURE                 Location/Qualifiers
source                  1..481
                        mol_type = protein
                        organism = Jatropha curcas
SEQUENCE: 68
MALAANSIYL SHEESISSSY IKSGIERFHG RKGLHFRSIV VLKILPNSRK SRRHVQLIRS  60
YRNYCGLVLR CSHQFSGWTN KFPSFSSTAA SINKAKEVLN FLMLSVSNNL KEKGQLQFLK  120
VAGILACALL VIPSADAVDA LKTCACLLKE CRLELAKCIA NPACAANIAC LQTCNNRPDE  180
TECQIKCGDL FENNVVDEFN ECAVSRKKCV PKKSDVGEFP VPDPAVLVKS FNIADFSGKW  240
FITSGLNPTF DTFDCQLHDF HRESNRLVGN LSWRIRTPDG GFFTRSTVQK FVQDPLQPGI  300
LYNHDNEYLH YQDDWYILSS KLENSENDYI FVYYRGRNDA WDGYGGAVVY TRSAVLPESI  360
IPELETAAKK VGRDFNKFII TDNTCGPEPP LAERIEKTVE EGEKTIIREV EEIEGNVEKV  420
GKTEMALFQR LAEGFKELQQ DEEFFVRELS KEEMDILNDL KMEAGEVEKL FGEALPLRKL  480
R                                                                481
```

The invention claimed is:

1. A genetically modified higher plant comprising genetic modifications that increase expression of both a zeaxanthin epoxidase (ZEP) polypeptide and a violaxanthin de-epoxidase (VDE) polypeptide as compared to expression of the ZEP polypeptide and the VDE polypeptide in a control plant without the genetic modifications grown under the same conditions, wherein the genetically modified higher plant is a tracheophyte, wherein the genetically modified plant comprises at least endogenous levels of an endogenous photosystem II subunit S (PsbS) polypeptide, wherein the expression of the VDE polypeptide is increased by expressing a transfected nucleotide sequence encoding the VDE polypeptide in the genetically modified plant and/or by a genetic modification in a promoter of a nucleotide sequence encoding the VDE polypeptide, and wherein the expression of the ZEP polypeptide is increased by expressing a transfected nucleotide sequence encoding the ZEP polypeptide in the genetically modified plant and/or by a genetic modification in a promoter of a nucleotide sequence encoding the ZEP polypeptide.

2. The genetically modified higher plant of claim 1, wherein the expression of the VDE polypeptide is increased by expressing the transfected nucleotide sequence encoding the VDE polypeptide, and wherein the transfected nucleotide sequence is operably linked to at least one expression control sequence; and wherein the expression of the ZEP polypeptide is increased by expressing the transfected nucleotide sequence encoding the ZEP polypeptide, and wherein the transfected nucleotide sequence is operably linked to at least one expression control sequence.

3. The genetically modified higher plant of claim 1, wherein one or both of the transfected nucleotide sequences are derived from a dicot or a monocot.

4. The genetically modified higher plant of claim 3, wherein the dicot is selected from *Arabidopsis thaliana, Beta vulgaris* (sugar beet), *Glycine max* (soybean), *Vigna unguiculata* (cowpea), and *Manihot esculenta* (cassava), or wherein the monocot comprises *Saccharum officinarum* (sugarcane).

5. The genetically modified higher plant of claim 1, wherein:

(a) the ZEP polypeptide is encoded by a nucleotide sequence having at least 70% identity to SEQ ID NO: 2;

the ZEP polypeptide has an amino acid sequence having at least 70% identity to SEQ ID NO: 5, KRH28470.1, NP_001241348.1, or XP_010666612.1; or the ZEP polypeptide comprises an amino acid sequence having at least 70% identity to SEQ ID NO: 8; and/or (b) the VDE polypeptide is encoded by the nucleotide sequence having at least 70% identity to SEQ ID NO: 3 or a conserved domain thereof;

the VDE polypeptide has an amino acid sequence having at least 70% identity to SEQ ID NO: 6, SEQ ID NO: 67 (XP_021623226.1), XP_006576259.1, XP_014628869.1, XP_014628868.1, NP_001241404.1, NP_001240949.1, XP_006576257.1, XP_010674199.1, or a conserved domain thereof; or the VDE polypeptide comprises a conserved domain having at least 70% identity to SEQ ID NO: 9 or a conserved domain thereof.

6. The genetically modified higher plant of claim 5, wherein:

(a) the ZEP is encoded by the nucleotide sequence having at least 80%, 90%, or 100% identity to SEQ ID NO: 2;

the ZEP polypeptide has an amino acid sequence having at least 80%, 90%, or 100% identity to SEQ ID NO: 5, KRH28470.1, NP_001241348.1, or XP_010666612.1; or the ZEP polypeptide comprises an amino acid sequence having at least 80%, 90%, or 100% identity to SEQ ID NO: 8; and/or (b) the VDE polypeptide is encoded by the nucleotide sequence having at least 80%, 90%, or 100% identity to SEQ ID NO: 3 or a conserved domain thereof;

the VDE polypeptide has an amino acid sequence having at least 80%, 90%, or 100% identity to SEQ ID NO: 6, SEQ ID NO: 67 (XP_021623226.1), XP_006576259.1, XP_014628869.1, XP_014628868.1, NP_001241404.1, NP_001240949.1, XP_006576257.1, XP_010674199.1, or a conserved domain thereof; or the VDE polypeptide comprises a conserved domain having at least 80%, 90%, or 100% identity to SEQ ID NO: 9 or a conserved domain thereof.

7. The genetically modified higher plant of claim 1, wherein:

the ZEP is encoded by a nucleotide sequence of SEQ ID NO: 2, and the VDE polypeptide is encoded by a nucleotide sequence of SEQ ID NO: 3;

the ZEP polypeptide is encoded by a nucleotide sequence having at least 90% identity to SEQ ID NO: 2, and the VDE polypeptide is encoded by a nucleotide sequence having at least 90% identity to SEQ ID NO: 3;

the ZEP polypeptide is encoded by a nucleotide sequence having at least 70% identity to SEQ ID NO: 2, and the VDE polypeptide is encoded by a nucleotide sequence having at least 70% identity to SEQ ID NO: 3;

the ZEP polypeptide has an amino acid sequence of SEQ ID NO: 5, and the VDE polypeptide has an amino acid sequence of SEQ ID NO: 6;

the ZEP polypeptide has an amino acid sequence at least 90% identical to SEQ ID NO: 5, and the VDE polypeptide has an amino acid sequence at least 90% identical to SEQ ID NO: 6;

the ZEP polypeptide has an amino acid sequence at least 70% identical to SEQ ID NO: 5, and the VDE polypeptide has an amino acid sequence at least 70% identical to SEQ ID NO: 6; and/or the ZEP polypeptide comprises the amino acid sequence of SEQ ID NO: 8, and the VDE polypeptide comprises a conserved domain of SEQ ID NO: 9.

8. The genetically modified higher plant of claim 1, wherein:

the ZEP polypeptide has the amino acid sequence of KRH28470.1 or NP_001241348.1, and the VDE polypeptide has the amino acid sequence of XP_006576259.1, XP_014628869.1, XP_014628868.1, NP_001241404.1, NP_001240949.1, or XP_006576257.1;

the ZEP polypeptide has an amino acid sequence at least 90% identical to KRH28470.1 or NP 001241348.1, and the VDE polypeptide has an amino acid sequence at least 90% identical to XP_006576259.1, XP_014628869.1, XP_014628868.1, NP_001241404.1, NP_001240949.1, or XP 006576257.1;

the ZEP polypeptide has an amino acid sequence at least 70% identical to KRH28470.1 or NP 001241348.1, and the VDE polypeptide has an amino acid sequence at least 70% identical to XP 006576259.1, XP_014628869.1, XP_014628868.1, NP_001241404.1, NP_001240949.1, or XP 006576257.1;

the ZEP polypeptide comprises the amino acid sequence of KRH28470.1 or NP_001241348.1, and the VDE polypeptide comprises a conserved domain of XP_006576259.1, XP_014628869.1, XP_014628868.1, NP_001241404.1, NP_001240949.1, or XP_006576257.1;

the ZEP polypeptide has the amino acid sequence of XP_010666612.1, and the VDE polypeptide has the amino acid sequence of XP_010674199.1;

the ZEP polypeptide has an amino acid sequence at least 90% identical to XP_010666612.1, and the VDE polypeptide has an amino acid sequence at least 90% identical to XP_010674199.1;

the ZEP polypeptide has an amino acid sequence at least 70% identical to XP_010666612.1 or NP_001241348.1, and the VDE polypeptide has an amino acid sequence at least 70% identical to XP 010674199.1;

the ZEP polypeptide comprises the amino acid sequence of XP_010666612.1, and the VDE polypeptide comprises a conserved domain of XP_010674199.1;

the VDE polypeptide has the amino acid sequence of SEQ ID NO: 67;

the VDE polypeptide has an amino acid sequence at least 90% identical to SEQ ID NO: 67;

the VDE polypeptide has an amino acid sequence at least 70% identical to SEQ ID NO: 67; and/or the VDE polypeptide comprises a conserved domain of SEQ ID NO: 67.

9. The genetically modified higher plant of claim 8, further comprising a genetic modification that increases expression of a photosystem II subunit S (PsbS) polypeptide as compared to expression of the endogenous PsbS polypeptide in a control plant without the genetic modification grown under the same conditions, wherein the expression of the PsbS polypeptide is increased by expressing a transfected nucleotide sequence encoding the PsbS polypeptide in the genetically modified plant and/or by a genetic modification in a promoter of a nucleotide sequence encoding the endogenous PsbS polypeptide, and wherein the PsbS polypeptide is encoded by the nucleotide sequence of SEQ ID NO: 1;

the PsbS polypeptide is encoded by a nucleotide sequence at least 90% identical to SEQ ID NO: 1;

the PsbS polypeptide is encoded by a nucleotide sequence at least 70% identical to SEQ ID NO: 1;

the PsbS polypeptide has the amino acid sequence of SEQ ID NO: 4;

the PsbS polypeptide has an amino acid sequence at least 90% identical to SEQ ID NO: 4;

the PsbS polypeptide has an amino acid sequence at least 70% identical to SEQ ID NO: 4; and/or the PsbS polypeptide comprises a conserved domain of SEQ ID NO: 1, SEQ ID NO: 4, or SEQ ID NO: 7; the PsbS polypeptide has an amino acid sequence of XP_003523444.1, NP_001276237.1, or ACU23291.1;

the PsbS polypeptide has an amino acid sequence at least 90% identical to XP_003523444.1, NP_001276237.1, or ACU23291.1;

the PsbS polypeptide has an amino acid sequence at least 70% identical to XP_003523444.1, NP_001276237.1, or ACU23291.1;

the PsbS polypeptide comprises a conserved domain of SEQ ID NO: 4, XP_003523444.1, NP_001276237.1, or ACU23291.1;

the PsbS polypeptide has an amino acid sequence of SEQ ID NO: 28;

the PsbS polypeptide has an amino acid sequence at least 90% identical to SEQ ID NO: 28;

the PsbS polypeptide has an amino acid sequence at least 70% identical to SEQ ID NO: 28; and/or the PsbS polypeptide comprises a conserved domain of SEQ ID NO: 28.

10. The genetically modified higher plant of claim 9, wherein the expression of the PsbS polypeptide is increased by expressing the transfected nucleotide sequence encoding the PsbS polypeptide, and wherein the transfected nucleotide sequence is operably linked to at least one expression control sequence.

11. The genetically modified higher plant of claim 1, wherein the plant is a crop plant, a model plant, a monocotyledonous plant, a dicotyledonous plant, a plant with Crassulacean acid metabolism (CAM) photosynthesis, a plant with C3 photosynthesis, a plant with C4 photosynthesis, an annual plant, a greenhouse plant, a horticultural flowering plant, a perennial plant, a switchgrass plant, a maize plant, a biomass plant, or a sugarcane plant.

12. The genetically modified higher plant of claim 1, wherein the plant is selected from the group of tobacco, corn, rice, sorghum, soybean, cowpea, poplar, eucalyptus, cassava, barley, potato, sugarcane, alfalfa, sugar beet, or wherein the plant is selected from the group consisting of switchgrass, Miscanthus, Medicago, sweet sorghum, grain sorghum, sugarcane, energy cane, elephant grass, maize, cassava, cowpea, wheat, barley, oats, rice, soybean, sugar beet, oil palm, safflower, sesame, tobacco, flax, cotton, sunflower, Camelina, *Brassica napus, Brassica carinata, Brassica juncea*, pearl millet, foxtail millet, other grain, rice, oilseed, a vegetable crop, a forage crop, an industrial crop, a woody crop and a biomass crop.

13. The genetically modified higher plant of claim 12, wherein the plant is:

sugar beet, the ZEP polypeptide has an amino acid sequence at least 70% identical to XP 010666612.1 or NP_001241348.1, the VDE polypeptide has an amino acid sequence at least 70% identical to XP_010674199.1;

soybean, the ZEP polypeptide has an amino acid sequence at least 70% identical to KRH28470.1 or NP_001241348.1, the VDE polypeptide has an amino acid sequence at least 70% identical to XP_006576259.1, XP_014628869.1, XP_014628868.1, NP_001241404.1, NP_001240949.1, or XP_006576257.1;

cassava and the VDE polypeptide has an amino acid sequence at least 70% identical to SEQ ID NO: 67;

cowpea; or sugarcane.

14. The genetically modified higher plant of claim 1, wherein:

the plant has improved growth under fluctuation light conditions as compared to the control plant grown under the same fluctuating light conditions;

the plant has increased photosynthetic efficiency under fluctuating light conditions as compared to the control plant grown under the same fluctuating light conditions;

the plant has improved photoprotection efficiency under fluctuating light conditions as compared to the control plant grown under the same fluctuating light conditions;

the plant has an increased rate of relaxation of non-photochemical quenching (NPQ) under fluctuating light conditions as compared to the control plant grown under the same fluctuating light conditions; and/or the plant has improved quantum yield and $CO_2$ fixation under fluctuating light conditions as compared to the control plant grown under the same fluctuating light conditions.

15. The genetically modified higher plant of claim 1, wherein the plant further comprises expression of at least one additional polypeptide that provides herbicide resistance, insect or pest resistance, disease resistance, modified fatty acid metabolism, and/or modified carbohydrate metabolism.

16. The genetically modified higher plant of claim 1, wherein:

the transcript level of the VDE polypeptide is increased 3-fold as compared to the control plant, and wherein the transcript level of the ZEP polypeptide is increased 8-fold as compared to the control plant;

the transcript level of the VDE polypeptide is increased 10-fold as compared to the control plant, and wherein the transcript level of the ZEP polypeptide is increased 6-fold as compared to the control plant;

the transcript level of the VDE polypeptide is increased 4-fold as compared to the control plant, and wherein the transcript level of the ZEP polypeptide is increased 7-fold as compared to the control plant;

the protein level of the VDE polypeptide is increased 16-fold as compared to the control plant, and wherein the protein level of the ZEP polypeptide is increased 80-fold as compared to the control plant;

the protein level of the VDE polypeptide is increased 30-fold as compared to the control plant, and wherein the protein level of the ZEP polypeptide is increased 74-fold as compared to the control plant;

the protein level of the VDE polypeptide is increased 47-fold as compared to the control plant, and wherein the protein level of the ZEP polypeptide is increased 75-fold as compared to the control plant;

the increase of transcript level as compared to the control plant between the VDE polypeptide and the ZEP polypeptide has a ratio selected from the group consisting of 3:8, 10:6, and 4:7;

the increase of protein level as compared to the control plant between the VDE polypeptide and the ZEP polypeptide has a ratio selected from the group consisting of 16:80, 30:74, and 47:75;

the increase of transcript level of the VDE polypeptide as compared to the control plant is from about 3-fold to about 10-fold, and wherein the increase of transcript level of the ZEP polypeptide as compared to the control plant is from about 6-fold to about 8-fold; or the increase of protein level of the VDE polypeptide as compared to the control plant is in from about 16-fold to about 47-fold, and wherein the increase of protein level of the ZEP polypeptide as compared to the control plant is from about 74-fold to about 80-fold.

17. The genetically modified higher plant of claim 5, further comprising a genetic modification that increases expression of a photosystem II subunit S (PsbS) polypeptide as compared to expression of the endogenous PsbS polypeptide in a control plant without the genetic modification grown under the same conditions, wherein the expression of the PsbS polypeptide is increased by expressing a transfected nucleotide sequence encoding the PsbS polypeptide in the genetically modified plant and/or by a genetic modification in a promoter of a nucleotide sequence encoding the endogenous PsbS polypeptide, wherein the PsbS polypeptide:

(i) is encoded by a nucleotide sequence having at least 70% identity to SEQ ID NO: 1 or a conserved domain thereof;

(ii) has an amino acid sequence having at least 70% identity to SEQ ID NO: 4, XP_003523444.1, NP_001276237.1, ACU23291.1, SEQ ID NO: 28 (XP_010692414.1), or a conserved domain thereof; or (iii) comprises a conserved domain having at least 70% identity to SEQ ID NO: 7 or a conserved domain thereof.

18. The genetically modified higher plant of claim 17, wherein the PsbS polypeptide:

(i) is encoded by a nucleotide sequence having at least 80%, 90%, or 100% identity to SEQ ID NO: 1 or a conserved domain thereof;

(ii) has an amino acid sequence having at least 80%, 90%, or 100% identity to SEQ ID NO: 4, XP_003523444.1, NP_001276237.1, ACU23291.1, SEQ ID NO: 28 (XP_010692414.1), or a conserved domain thereof; or (iii) comprises a conserved domain having at least 80%, 90%, or 100% identity to SEQ ID NO: 7 or a conserved domain thereof.

19. The genetically modified higher plant of claim 13, wherein the plant is sugar beet, and wherein the plant further comprises a genetic modification that increases expression of a PsbS polypeptide as compared to expression of the endogenous PsbS polypeptide in a control plant without the genetic modification grown under the same conditions, wherein the expression of the PsbS polypeptide is increased by expressing a transfected nucleotide sequence encoding the PsbS polypeptide in the genetically modified plant and/or by a genetic modification in a promoter of a nucleotide sequence encoding the endogenous PsbS polypeptide, and the PsbS polypeptide has an amino acid sequence at least 70% identical to SEQ ID NO: 28.

20. The genetically modified higher plant of claim 13, wherein the plant is soybean, and wherein the plant further comprises a genetic modification that increases expression of a PsbS polypeptide as compared to expression of the endogenous PsbS polypeptide in a control plant without the genetic modification grown under the same conditions, wherein the expression of the PsbS polypeptide is increased by expressing a transfected nucleotide sequence encoding the PsbS polypeptide in the genetically modified plant and/or by a genetic modification in a promoter of a nucleotide sequence encoding the endogenous PsbS polypeptide, and the PsbS polypeptide has an amino acid sequence at least 70% identical to XP_003523444.1, NP_001276237.1, or ACU23291.1.

* * * * *